United States Patent
Katoh et al.

(10) Patent No.: US 10,696,898 B2
(45) Date of Patent: Jun. 30, 2020

(54) REVERSE PHOTOCHROMIC COMPOUND

(71) Applicants: FUJIFILM Wako Pure Chemical Corporation, Osaka-shi, Osaka (JP); NIHON UNIVERSITY, Tokyo (JP)

(72) Inventors: Ryuzi Katoh, Tokyo (JP); Masami Enoki, Tokyo (JP); Kazuki Nemoto, Tokyo (JP); Katsufumi Suzuki, Saitama (JP); Tetsuji Murase, Saitama (JP); Shigeaki Imazeki, Saitama (JP)

(73) Assignees: FUJIFILM Wako Pure Chemical Corporation, Tokyo (JP); NIHON UNIVERSITY, Tokyo (JP)

( * ) Notice: Subject to any disclaimer, the term of this patent is extended or adjusted under 35 U.S.C. 154(b) by 0 days.

(21) Appl. No.: 16/477,469

(22) PCT Filed: Jan. 31, 2018

(86) PCT No.: PCT/JP2018/003112
§ 371 (c)(1),
(2) Date: Jul. 11, 2019

(87) PCT Pub. No.: WO2018/143239
PCT Pub. Date: Aug. 9, 2018

(65) Prior Publication Data
US 2019/0382654 A1 Dec. 19, 2019

(30) Foreign Application Priority Data
Jan. 31, 2017 (JP) .................................. 2017-016253

(51) Int. Cl.
*C09K 9/02* (2006.01)
*C07D 405/06* (2006.01)
(Continued)

(52) U.S. Cl.
CPC .............. *C09K 9/02* (2013.01); *C07D 405/06* (2013.01); *C08F 20/36* (2013.01); *C08G 65/34* (2013.01)

(58) Field of Classification Search
CPC ........... C09K 9/02; C08G 65/34; C08F 20/36; C07D 405/06
See application file for complete search history.

(56) References Cited

U.S. PATENT DOCUMENTS

| 5,919,608 | A | 7/1999 | Haque et al. |
| 2013/0102775 | A1 | 4/2013 | Horino et al. |

FOREIGN PATENT DOCUMENTS

| JP | 7-206858 | 8/1995 |
| JP | 9-124654 | 5/1997 |

(Continued)

OTHER PUBLICATIONS

International Search Report issued in International Application No. PCT/JP2018/003112, dated May 1, 2018, 4 pages.
(Continued)

*Primary Examiner* — Bijan Ahvazi
(74) *Attorney, Agent, or Firm* — Hamre, Schumann, Mueller & Larson, P.C.

(57) ABSTRACT

A reverse photochromic compound of the related art has difficulty in sensing light with a wavelength of 600 nm or greater in a visible light region which has been used for medical applications. Therefore, an object of the present invention is to provide a reverse photochromic compound and a polymer which have a high sensitivity to light having a wavelength of 600 nm or greater. The present invention relates to a compound and the like represented by the following general formula (1).

(Continued)

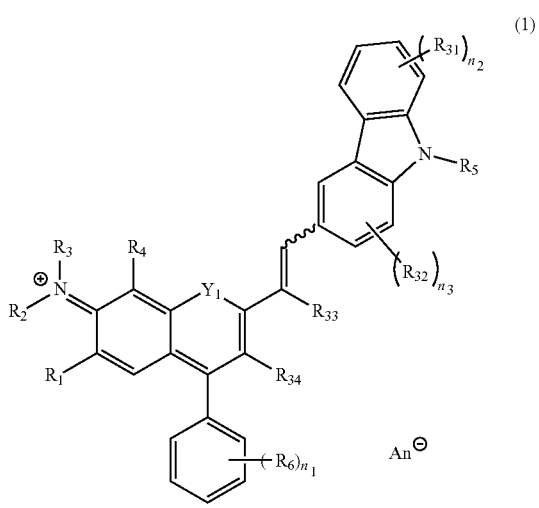

(1)

In the formula, $R_1$ and $R_4$ each independently represent a hydrogen atom or the like, $R_2$, $R_3$, and $R_5$ each independently represent an alkyl group or the like, $R_6$ represents a group having a polymerizable unsaturated group, a carboxy group, or an alkoxycarbonyl group, $R_{31}$ and $R_{32}$ each independently represent an alkoxy group or the like, $R_{33}$ and $R_{34}$ each independently represent a hydrogen atom or the like, $Y_1$ represents an oxygen atom or a sulfur atom, $An^-$ represents an anion, $n_1$ to $n_3$ represent a specific integer, and $R_1$ and $R_2$, $R_3$ and $R_4$, and/or $R_{33}$ and $R_{34}$ may form an alkylene group.

14 Claims, 5 Drawing Sheets

(51) Int. Cl.
*C08F 20/36* (2006.01)
*C08G 65/34* (2006.01)

(56) References Cited

FOREIGN PATENT DOCUMENTS

| | | |
|---|---|---|
| JP | 2000-219687 | 8/2000 |
| JP | 2001-115154 | 4/2001 |
| JP | 2012-017442 | 1/2012 |

OTHER PUBLICATIONS

Yuan, et al., "A unique Class of Near-Infrared Functional Fluorescent Dyes with Carboxylic-Acid-Modulated Fluorescence On/Off Switching: Rational Design, Synthesis, Optical Properties, Theoretical Calculations, and Applications for Fluorescence Imaging in Living Animals", J. Am. Chem. Soc., 2012, 134, 1200-1211.

Tolmachev, et al., "Synthesis, electronic structure, and absorption specta of the merocyanines derived from pyranes and benzopyranes", Dyes and Pigments 74 (2007) 348-356.

Harris, et al., "Dual-use chromophores for photorefractive and irreversible photochromic applications" Applied Optics, Jun. 10, 2001, vol. 40, No. 17, 2895-2901.

Garcia-Amoros, et al., "Plasmonic Activation of a Fluorescent Carbazole-Oxazine Switch", Chem. Eur. J. 2014, 20, 10276-10284.

REVERSE PHOTOCHROMIC COMPOUND

TECHNICAL FIELD

The present invention relates to a new compound used in a reverse photochromic material, and a polymer having a monomer unit derived from the compound.

BACKGROUND ART

A photochromic material has a function of reversibly changing the color or the transparency by being irradiated with light and is used as a light modulation material such as an eyeglass lens or window glass whose color changes depending on the brightness or a sensor material such as an ultraviolet checker or an X-ray sensor. In addition, the applied research to recording media such as optical memories and electronic paper has progressed.

The photochromism is largely classified into positive photochromism and negative photochromism. The former indicates a phenomenon in which a single colorless chemical species is reversely colored with recombination of chemical bonds by irradiation with light. The latter indicates a phenomenon in which a single colored chemical species reversibly changes into colorless by irradiation with light, and development for a reverse photochromic material has been in progress.

Known examples of representative photochromic compounds exhibiting photochromism include a diarylethene-based compound, a spiropyran-based compound, an azobenzene-based compound, a bisimidazole-based compound, and a fulgide compound.

Several examples such as indoline-based spiropyran derivatives (Patent Literature 1) and biimidazole derivatives (Patent Literature 2) have been reported as compounds exhibiting reverse photochromism.

Meanwhile, compounds (Non-Patent Literature 1) useful for fluorescence imaging have been reported as compounds having a merocyanine structure.

CITATION LIST

Patent Literature

Patent Literature 1 JP1997-124654A (JP-H09-124654A)
Patent Literature 2 JP2012-017442A

Non-Patent Literature

Journal of the American chemical Society (2012), 134 (2), 1200

SUMMARY OF INVENTION

Technical Problem

Reverse photochromic compounds of the related art have a high sensitivity to light with a wavelength of 600 nm or less in a visible light region, but compounds having a high sensitivity to light with a wavelength of 600 nm or greater which have been used for medical applications are rare. Therefore, an object of the present invention is to provide a reverse photochromic compound also having a sensitivity to light with a wavelength of 600 nm or greater in a visible light region.

Solution to Problem

As the result of intensive research conducted by the present inventors under the circumstances described above, it was found that a compound having a specific merocyanine structure is a reverse photochromic compound having a high sensitivity to light with a wavelength of 600 nm or greater.

In other words, the present invention contains the following inventions [i-i] to [i-xiv] in a first aspect.

[i-i]

A compound represented by the following general formula (1) (hereinafter, also referred to as a compound of the present invention),

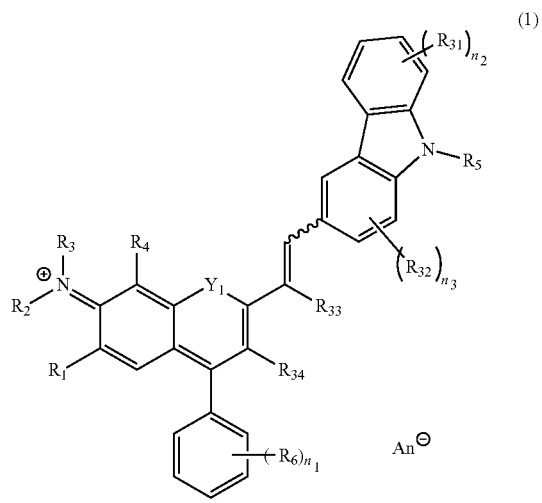

(in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, $An^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted or may form an unsubstituted phenylene group.).

[i-ii]

The compound according to the invention [i-i], in which $Y_1$ represents an oxygen atom.

[i-iii]

The compound according to the invention [i-i] or [i-ii], in which $n_1$ represents 1, and $n_2$ and $n_3$ represent 0 or 1.

[i-iv]

The compound according to any one of the inventions [i-i] to [i-iii], in which $R_2$, $R_3$, and $R_5$ represent an alkyl group having 1 to 6 carbon atoms or an unsubstituted phenyl group.

[i-v]

The compound according to any one of the inventions [i-i] to [i-iv], in which $R_{33}$ and $R_{34}$ form an unsubstituted linear alkylene group having 2 to 4 carbon atoms.

[i-vi]

The compound according to any one of the inventions [i-i] to [i-v], which fades in a case of being irradiated with light having a wavelength of 600 to 750 nm.

[i-vii]

A polymer comprising: a monomer unit derived from a compound represented by the following general formula (3) (hereinafter, also referred to as a polymer of the present invention),

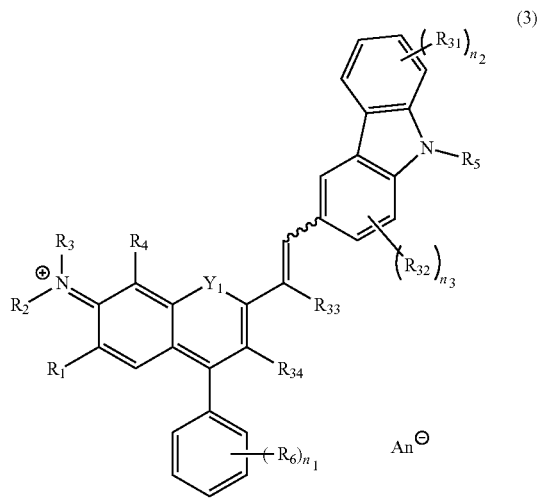

(3)

(in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, $An^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted or may form an unsubstituted phenylene group, where at least one of $R_2$, $R_3$, $R_5$, or $n_1$ pieces of $R_6$'s represents a group having a polymerizable unsaturated group.).

[i-viii]

The polymer according to the invention [i-vii], in which $Y_1$ represents an oxygen atom.

[i-ix]

The polymer according to the invention [i-vii] or [i-viii], in which $n_1$ represents 1, and $n_2$ and $n_3$ represent 0 or 1.

[i-x]

The polymer according to any one of the inventions [i-vii] to [i-ix], in which $R_2$, $R_3$, and $R_5$ represent an alkyl group having 1 to 6 carbon atoms or an unsubstituted phenyl group.

[i-xi]

The compound according to any one of the inventions [i-vii] to [i-x], in which $R_{33}$ and $R_{34}$ form an unsubstituted linear alkylene group having 2 to 4 carbon atoms.

[i-xii]

The polymer according to any one of the inventions [i-vii] to [i-xi], which fades in a case of being irradiated with light having a wavelength of 600 to 750 nm.

[i-xiii]

The polymer according to any one of the inventions [i-vii] to [i-xii], in which the polymer is a copolymer.

[i-xiv]

The polymer according to the invention [i-xiii], wherein the copolymer has one or two kinds of monomer units derived from a compound represented by the following general formula (4), (5), (6), or (7) and a monomer unit derived from a compound represented by the general formula (3) as constituent components,

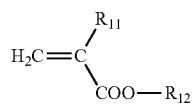

(4)

[in the formula, $R_{11}$ represents a hydrogen atom or a methyl group, and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms together with an oxygen atom, a dialkylaminoalkyl group having 3 to 9 carbon atoms, a fluoroalkyl group having 1 to 18 carbon atoms, a N-alkylenephthalimide group having 9 to 14 carbon atoms, a group represented by the following general formula (4-1)

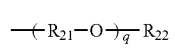

(4-1)

(in the formula, q pieces of $R_{21}$'s each independently represent an alkylene group having 1 to 3 carbon atoms which has a hydroxy group as a substituent or is unsubstituted, $R_{22}$ represents a phenyl group which has a hydroxy group as a substituent or is unsubstituted or an alkyl group having 1 to 3 carbon atoms, and q represents an integer of 1 to 3.), a group represented by the following general formula (4-2)

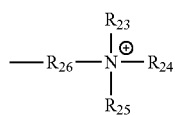

(4-2)

(in the formula, $R_{23}$ to $R_{25}$ each independently represent an alkyl group having 1 to 3 carbon atoms, and $R_{26}$ represents an alkylene group having 1 to 3 carbon atoms.), or a group represented by the following general formula (4-3)

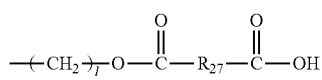

(4-3)

(in the formula, l represents an integer of 1 to 6, and $R_{27}$ represents a phenylene group or a cyclohexylene group.).],

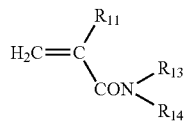

(5)

(in the formula, $R_{11}$ has the same definition as described above, $R_{13}$ represents a hydrogen atom or an alkyl group having 1 to 3 carbon atoms, $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms, and $R_{13}$ and $R_{14}$ may form a morpholino group together with a nitrogen atom adjacent to these.),

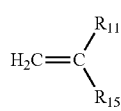

(6)

(in the formula, $R_{15}$ represents a phenyl group or a pyrrolidino group, and $R_{11}$ has the same definition as described above.), and

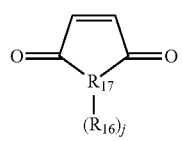

(7)

(in the formula, $R_{17}$ represents a nitrogen atom or an oxygen atom, j represents 0 in a case where $R_{17}$ represents an oxygen atom and represents 1 in a case where $R_{17}$ represents a nitrogen atom, and $R_{16}$ represents a hydrogen atom, an alkyl group having 1 to 20 carbon atoms, a hydroxyalkyl group having 1 to 10 carbon atoms, a haloalkyl group having 1 to 10 carbon atoms, an aryl group having 6 to 10 carbon atoms, or an aryl group having 6 to 10 carbon atoms which has an alkyl group having 1 to 6 carbon atoms or a halogeno group as a substituent.).

In addition, the present invention contains the following inventions [ii-i] to [ii-xiv] in a second aspect.

[ii-i]

A compound represented by the following general formula (1),

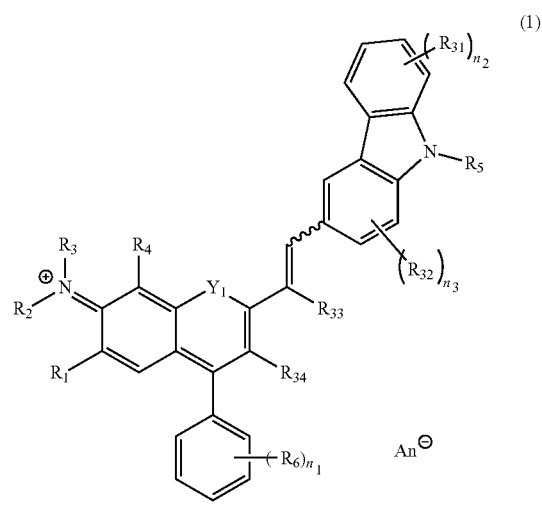

(1)

(in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, or an acyl group having 2 to 21 carbon atoms, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, $An^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted.).

[ii-ii]
The compound according to the invention [ii-i], in which $Y_1$ represents an oxygen atom.

[ii-iii]
The compound according to the invention [ii-i] or [ii-ii], in which $n_1$ represents 1, and $n_2$ and $n_3$ represent 0 or 1.

[ii-iv]
The compound according to any one of the inventions [ii-i] to [ii-iii], in which $R_2$, $R_3$, and $R_5$ represent an alkyl group having 1 to 6 carbon atoms.

[ii-v]
The compound according to any one of the inventions [ii-i] to [ii-iv], in which $R_{33}$ and $R_{34}$ form an unsubstituted linear alkylene group having 2 to 4 carbon atoms.

[ii-vi]
The compound according to any one of the inventions [ii-i] to [ii-v], which fades in a case of being irradiated with light having a wavelength of 600 to 750 nm.

[ii-vii]
A polymer comprising: a monomer unit derived from a compound represented by the following general formula (3),

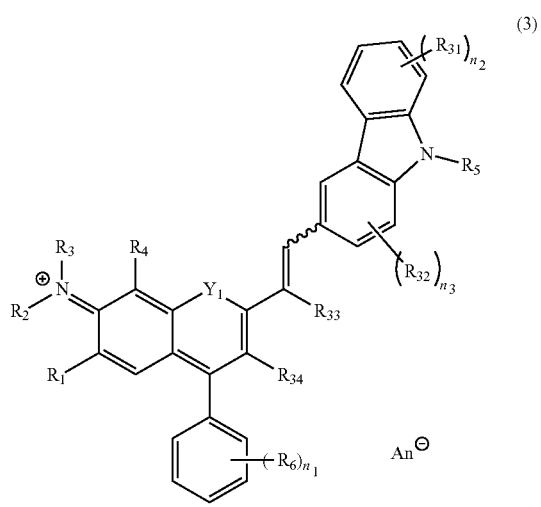

(in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, or an acyl group having 2 to 21 carbon atoms, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, $An^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted, where at least one of $R_2$, $R_3$, $R_5$, or $n_1$ pieces of $R_6$'s represents a group having a polymerizable unsaturated group.).

[ii-viii]
The polymer according to the invention [ii-vii], in which $Y_1$ represents an oxygen atom.

[ii-ix]
The polymer according to the invention [ii-vii] or [ii-viii], in which $n_1$ represents 1, and $n_2$ and $n_3$ represent 0 or 1.

[ii-x]
The polymer according to any one of the inventions [ii-vii] to [ii-ix], in which $R_2$, $R_3$, and $R_5$ represent an alkyl group having 1 to 6 carbon atoms.

[ii-xi]
The compound according to any one of the inventions [ii-vii] to [ii-x], in which $R_{33}$ and $R_{34}$ form an unsubstituted linear alkylene group having 2 to 4 carbon atoms.

[ii-xii]
The polymer according to any one of the inventions [ii-vii] to [ii-xi], which fades in a case of being irradiated with light having a wavelength of 600 to 750 nm.

[ii-xiii]
The polymer according to any one of the inventions [ii-vii] to [ii-xii], in which the polymer is a copolymer.

[ii-xiv]
The polymer according to the invention [ii-xiii], wherein the copolymer has one or two kinds of monomer units derived from a compound represented by the following general formula (4), (5), (6), or (7) and a monomer unit derived from a compound represented by the general formula (3) as constituent components,

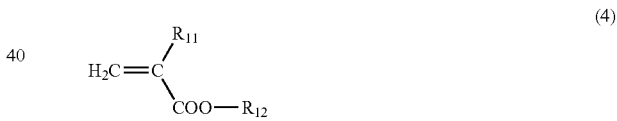

[in the formula, $R_{11}$ represents a hydrogen atom or a methyl group, and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms together with an oxygen atom, a dialkylaminoalkyl group having 3 to 9 carbon atoms, a fluoroalkyl group having 1 to 18 carbon atoms, a N-alkylenephthalimide group having 9 to 14 carbon atoms, a group represented by the following general formula (4-1)

(in the formula, q pieces of $R_{21}$'s each independently represent an alkylene group having 1 to 3 carbon atoms which has a hydroxy group as a substituent or is unsubstituted, $R_{22}$ represents a phenyl group which has a hydroxy group as a substituent or is unsubstituted or an alkyl group having 1 to 3 carbon atoms, and q represents an integer of 1 to 3.), a group represented by the following general formula (4-2)

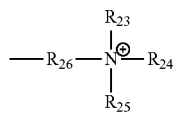

(4-2)

(in the formula, $R_{23}$ to $R_{25}$ each independently represent an alkyl group having 1 to 3 carbon atoms, and $R_{26}$ represents an alkylene group having 1 to 3 carbon atoms.), or a group represented by the following general formula (4-3)

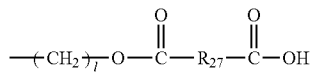

(4-3)

(in the formula, 1 represents an integer of 1 to 6, and $R_{27}$ represents a phenylene group or a cyclohexylene group.).],

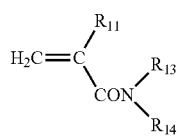

(5)

(in the formula, $R_{11}$ has the same definition as described above, $R_{13}$ represents a hydrogen atom or an alkyl group having 1 to 3 carbon atoms, $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms, and $R_{13}$ and $R_{14}$ may form a morpholino group together with a nitrogen atom adjacent to these.),

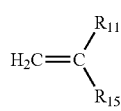

(6)

(in the formula, $R_{15}$ represents a phenyl group or a pyrrolidino group, and $R_{11}$ has the same definition as described above.), and

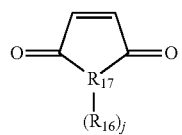

(7)

(in the formula, $R_{17}$ represents a nitrogen atom or an oxygen atom, j represents 0 in a case where $R_{17}$ represents an oxygen atom and represents 1 in a case where $R_{17}$ represents a nitrogen atom, and $R_{16}$ represents a hydrogen atom, an alkyl group having 1 to 20 carbon atoms, a hydroxyalkyl group having 1 to 10 carbon atoms, a haloalkyl group having 1 to 10 carbon atoms, an aryl group having 6 to 10 carbon atoms, or an aryl group having 6 to 10 carbon atoms which has an alkyl group having 1 to 6 carbon atoms or a halogeno group as a substituent.).

Advantageous Effects of Invention

The compound of the present invention or the polymer of the present invention exhibits an effect of also having a high sensitivity to light with a wavelength of 600 nm or greater in a visible light region, which is unlikely to be sensed by a reverse photochromic compound of the related art. Therefore, the compound of the present invention or the polymer of the present invention can be used for forming colored pixels of a color filter and the like used in a liquid crystal display device (LCD) or a solid-state imaging element (CCD, CMOS, or the like) and can also be used for printing inks, ink jet inks, and paints. The compound of the present invention or the polymer of the present invention is particularly suitable for a color filter of a liquid crystal display device. Further, the compound of the present invention or the polymer of the present invention can be molded into a sheet, a film, a bottle, a cup, or the like according to a known molding method of the related art and can also be used as a colored resin molded product. Accordingly, the compound of the present invention or the polymer of the present invention can be used for applications such as glasses, and color contact lenses, or the like, and can also be used for the same applications as described above by means of forming a multilayer structure using a known resin. In addition, the compound of the present invention or the polymer of the present invention can also be used for applications such as optical films, hair coloring agents, labeling substances for compounds and biological substances, materials for organic solar cells, or the like.

In addition, a compound which has a specific anion as a counter anion, among the compounds of the present invention, exhibits an effect of having a high solubility in various organic solvents and a high compatibility with respect to a resin and the like in addition to the effects. Further, the polymer of the present invention also exhibits an effect of having high elution resistance with respect to a solvent in addition to the effects.

BRIEF DESCRIPTION OF DRAWINGS

In FIG. 1, the broken line shows the measurement result before irradiation with light, the one dot chain line shows the measurement result immediately after irradiation with light for 1 minute, and the solid line shows the measurement result after storage in a dark place for 310 minutes after the irradiation with light.

In FIG. 2, the broken line shows the measurement result before irradiation with light, the one dot chain line shows the measurement result immediately after irradiation with light for 5 minutes, and the solid line shows the measurement result after storage in a dark place for a night after the irradiation with light.

In FIG. 3, the broken line shows the measurement result before irradiation with light, the one dot chain line shows the measurement result immediately after irradiation with light for 5 minutes, and the solid line shows the measurement result after storage in a dark place for a night after the irradiation with light.

In FIG. 4, the broken line shows the measurement result before irradiation with light, the one dot chain line shows the measurement result immediately after irradiation with light for 5 minutes, and the solid line shows the measurement result after storage in a dark place for a night after the irradiation with light.

In FIG. 5, "♦" shows the measurement result at the time of using methanol as a solvent, "□" shows the measurement result at the time of using toluene as a solvent, "∆" shows the measurement result at the time of using acetonitrile as a solvent, "x" shows the measurement result at the time of using chloroform as a solvent, "■" shows the measurement result at the time of using o-dichlorobenzene as a solvent, "●" shows the measurement result at the time of using 2-propanol as a solvent, and "+" shows the measurement result at the time of using chlorobenzene as a solvent.

In FIG. 6, "♦" shows the measurement result at the time of setting the temperature to 20° C., "■" shows the measurement result at the time of setting the temperature to 40° C., and "▲" shows the measurement result at the time of setting the temperature to 60° C.

In FIG. 8, the broken line shows the measurement result before irradiation with light, the one dot chain line shows the measurement result immediately after irradiation with light for 1 minute, and the solid line shows the measurement result after storage in a dark place for 10 minutes after the irradiation with light.

In FIG. 9, the broken line shows the measurement result before irradiation with light, the one dot chain line shows the measurement result immediately after irradiation with light for 2 minutes, and the solid line shows the measurement result after storage in a dark place for 138 hours after the irradiation with light.

In FIG. 10, the broken line shows the measurement result before irradiation with light, the one dot chain line shows the measurement result immediately after irradiation with light for 2 minutes, and the solid line shows the measurement result after storage in a dark place for 1 hour after the irradiation with light.

DESCRIPTION OF EMBODIMENTS

Figure 1:
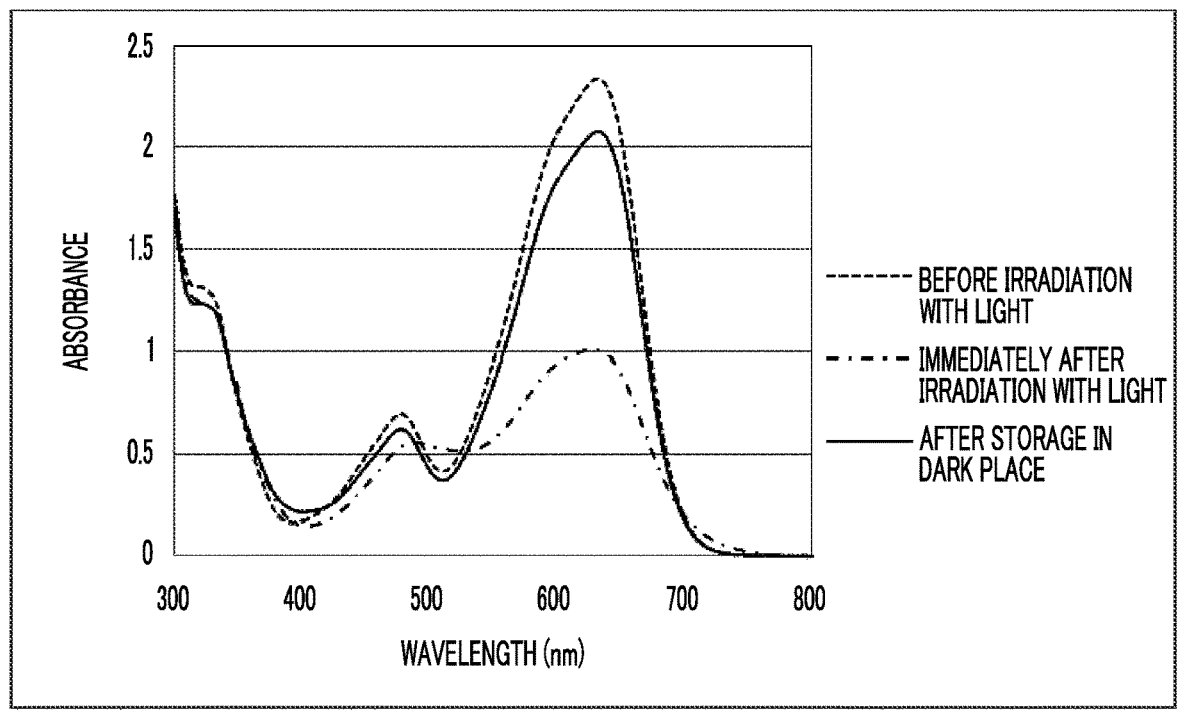
FIG. 1 is a graph showing the results obtained from measurement of the absorbance of a compound (a monomer having a polymerizable unsaturated group: compound 8) according to the embodiment of the present invention, which is obtained in Experiment Example 1.

Compound According to Embodiment of Present Invention

A compound according to the embodiment of the present invention is represented by the general formula (1).

The general formula (1) shows a compound having a plurality of conjugated structures, and delocalized electrons on the general formula (1) can freely move on the general formula (1) along the conjugated structures. For example, the general formula (1) can also be described as the following general formula (1') by moving the delocalized electrons on the general formula (1).

In addition, the same applies to specific examples and specific preferred examples of the general formula (1) described below.

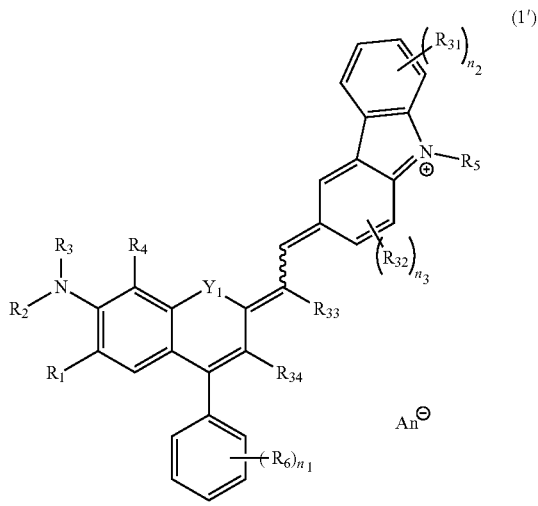

(1')

(In the formula, $R_1$ to $R_6$, $R_{31}$ to $R_{34}$, $Y_1$, $An^-$, and $n_1$ to $n_3$ each have the same definition as described above.)

Group Having Polymerizable Unsaturated Group in Compound According to Embodiment of Present Invention As the group having a polymerizable unsaturated group as $R_2$, $R_3$, $R_5$, and $R_6$ in the general formula (1), a group having a polymerizable unsaturated group at the terminal of a functional group may be exemplified. Examples of the polymerizable unsaturated group include an acryloyl group, a methacryloyl group, a vinylaryl group, a vinyloxy group, and an allyl group. Among these, an acryloyl group or a methacryloyl group is preferable.

Among examples of the group having a polymerizable unsaturated group as $R_6$ in the general formula (1), specific preferred examples thereof include a group represented by the following general formula (2).

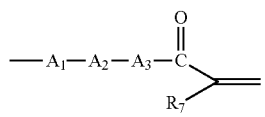
(2)

{In the formula, $R_7$ represents a hydrogen atom or a methyl group, $A_1$ represents —COO—, —NHCO—, —CONH—, —NHCONH—, or a group represented by the following general formula (2-1), $A_2$ represents an alkylene group having 1 to 21 carbon atoms which has at least one group selected from —O—, —OCO—, —COO—, —NHCO—, —CONH—, —NHCONH—, or an arylene group in the chain; an alkylene group having 1 to 21 carbon atoms which has at least one group selected from —O—, —OCO—, —COO—, —NHCO—, —CONH—, —NHCONH—, or an arylene group in the chain and has a hydroxy group as a substituent; an alkylene group having 1 to 21 carbon atoms which has a hydroxy group as a substituent; or an alkylene group having 1 to 21 carbon atoms, $A_3$ represents —NR$_{10}$— or —O—, and $R_{10}$ represents a hydrogen atom or an alkyl group having 1 to 12 carbon atoms,

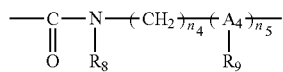
(2-1)

[In the formula, $R_8$ represents an alkyl group having 1 to 12 carbon atoms or a group represented by the following general formula (2-4),

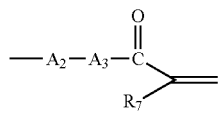
(2-4)

(In the formula, $R_7$, $A_2$, and $A_3$ each have the same definition as described above.)

$R_9$ represents a hydrogen atom or an alkyl group having 1 to 12 carbon atoms, and $A_4$ represents a nitrogen atom or a group represented by the following general formula (2-2).

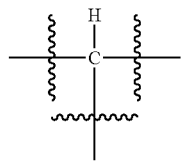
(2-2)

$n_4$ represents an integer of 0 to 3, $R_8$ and $R_9$ may form a 5- or 6-membered cyclic structure together with —N—(CH$_2$)$_{n4}$-(A$_4$)$_{n5}$- bonded to these, and in a case where $R_8$, $R_9$, and —N—(CH$_2$)$_{n4}$-(A$_4$)$_{n5}$- form a 5- or 6-membered cyclic structure, n5 represents 1, and in a case where a 5- or 6-membered cyclic structure is not formed, n5 represents 0 or 1.].)

It is preferable that $R_7$ in the general formula (2) represents a methyl group.

$A_1$ in the general formula (2) represents preferably —COO—, —CONH—, or a group represented by the general formula (2-1), more preferably —COO— or —CONH—, and still more preferably —COO—.

The alkylene group having 1 to 21 carbon atoms in the "alkylene group having 1 to 21 carbon atoms which has at least one group selected from —O—, —OCO—, —COO—, —NHCO—, —CONH—, —NHCONH—, or an arylene group in the chain", the "alkylene group having 1 to 21 carbon atoms which has at least one group of —O—, —OCO—, —COO—, or an arylene group in the chain and has a hydroxy group as a substituent", the "alkylene group having 1 to 21 carbon atoms which has a hydroxy group as a substituent", and the "alkylene group having 1 to 21 carbon atoms" as $A_2$ in the general formula (2) may be any of linear, branched, or cyclic. Among these, the alkylene group is preferably linear or branched and more preferably linear. In addition, among alkylene groups having 1 to 21 carbon atoms, an alkylene group having 1 to 12 carbon atoms is preferable, an alkylene group having 1 to 6 carbon atoms is more preferable, and an alkylene group having 1 to 3 carbon atoms is still more preferable. Specific examples thereof include a methylene group, an ethylene group, a trimethylene group, a propylene group, a tetramethylene group, a 1-methyltrimethylene group, a 2-methyltrimethylene group, a 1,2-dimethylethylene group, a 1,1-dimethylethylene group, an ethylethylene group, a pentamethylene group, a 1-methyltetramethylene group, a 2-methyltetramethylene group, a 1,2-dimethyltrimethylene group, a 1-ethyltrimethylene group, a hexamethylene group, a methylpentamethylene group, an n-heptylene group, an n-octylene group, an n-nonylene group, an n-decylene group, an n-undecylene group, an n-dodecylene group, an n-tridecylene group, an n-tetradecylene group, an n-pentadecylene group, an n-hexadecylene group, an n-heptadecylene group, an n-octadecylene group, an n-nonadecylene group, an n-icosylene group, an n-henicosylene group, a —C$_4$H$_6$—CH$_2$— group, a —C$_5$H$_8$—CH$_2$— group, a —C$_6$H$_{10}$—CH$_2$— group, —C$_6$H$_{10}$—C$_2$H$_4$— group, a —C$_6$H$_{10}$—C$_3$H$_6$— group, and a —C$_7$H$_{12}$—CH$_2$— group. Among these, the methylene group, the ethylene group, the trimethylene group, the tetramethylene group, the pentamethylene group, the hexamethylene group, the —C$_6$H$_{10}$—CH$_2$— group, the —C$_6$H$_{10}$—C$_2$H$_4$— group, or the —C$_6$H$_{10}$—C$_3$H$_6$— group is preferable, the methylene group, the ethylene group, the trimethylene group, the tetramethylene group, the pentamethylene group, or the hexamethylene group is more preferable, the methylene group, the ethylene group, or the trimethylene group is still more preferable, and the ethylene group is particularly preferable.

Examples of the "arylene group having 1 to 21 carbon atoms which has at least one group selected from —O—, —OCO—, —COO—, —NHCO—, —CONH—, —NHCONH—, or an arylene group in the chain" and the "alkylene group having 1 to 21 carbon atoms which has at least one group selected from —O—, —OCO—, —COO—, —NHCO—, —CONH—, —NHCONH—, or an arylene group in the chain and has a hydroxy group as a substituent" as $A_2$ in the general formula (2) include an arylene group having 6 to 10 carbon atoms, and specific examples thereof include a phenylene group and a naphthylene group. Among these, the phenylene group is preferable.

Examples of the "alkylene group having 1 to 21 carbon atoms which has at least one group selected from —O—, —OCO—, —COO—, —NHCO—, —CONH—, —NHCONH—, or an arylene group in the chain" as $A_2$ in the general formula (2) include groups represented by the following general formulae (21-1) to (21-5).

$$-(R_{51}-O-)_{h1}-R_{52}- \quad (21\text{-}1)$$

(In the formula, $R_{51}$ and $R_{52}$ each independently represent a linear or branched alkylene group having 1 to 4 carbon atoms, and $h_1$ represents an integer of 1 to 9. Here, the total number of carbon atoms in the formula is in a range of 2 to 21.)

$$-(CH_2)_{h2}-OCO-(CH_2)_{h3}- \quad (21\text{-}2)$$

(In the formula, $h_2$ and $h_3$ each independently represent an integer of 1 to 10.)

$$-(CH_2)_{h4}-OCO-R_{53}-COO-(CH_2)_{h5}- \quad (21\text{-}3)$$

(In the formula, $R_{53}$ represents a phenylene group or an alkylene group having 1 to 7 carbon atoms, and $h_4$ and $h_5$ each independently represent an integer of 1 to 3.)

$$-(CH_2)_{h6}\text{-}A_5\text{-}(CH_2)_{h7}- \quad (21\text{-}4)$$

(In the formula, $A_5$ represents —NHCO—, —CONH—, or —NHCONH—, and $h_6$ and $h_7$ each independently represent an integer of 1 to 10.)

$$-(CH_2)_{h8}-O-CONH-(CH_2)_{h9}- \quad (21\text{-}5)$$

(In the formula, $h_8$ and $h_9$ each independently represent an integer of 1 to 10.)

Specific examples of the linear or branched alkylene group having 1 to 4 carbon atoms as $R_{51}$ and $R_{52}$ in the general formula (21-1) include a methylene group, an ethylene group, a trimethylene group, a propylene group, a tetramethylene group, a 1-methyltrimethylene group, a 2-methyltrimethylene group, a 1,2-dimethylethylene group, a 1,1-dimethylethylene group, and an ethylethylene group. Among these, the ethylene group or the propylene group is preferable.

$h_2$ in the general formula (21-2) represents preferably an integer of 1 to 3 and more preferably 2.

It is preferable that $h_3$ in the general formula (21-2) represents 2.

Specific examples of the alkylene group having 1 to 7 carbon atoms as $R_{53}$ in the general formula (21-3) include a methylene group, an ethylene group, a trimethylene group, a tetramethylene group, a pentamethylene group, a hexamethylene group, an n-heptylene group, a cyclobutylene group, a cyclopentylene group, a cyclohexylene group, and a cycloheptylene group.

As $h_4$ and $h_5$ in the general formula (21-3), it is preferable that $h_4$ and $h_5$ are the same as each other. In addition, $h_4$ and $h_5$ represent preferably an integer of 1 to 3 and more preferably 2.

It is preferable that $A_5$ in the general formula (21-4) represents —NHCONH—.

As $h_6$ and $h_7$ in the general formula (21-4), it is preferable that $h_6$ and $h_7$ are the same as each other. In addition, it is preferable that $h_6$ and $h_7$ represent 2.

As $h_8$ and $h_9$ in the general formula (21-5), it is preferable that $h_8$ and $h_9$ are the same as each other. In addition, it is preferable that $h_8$ and $h_9$ represent an integer of 1 to 4.

Specific examples of the group represented by the general formula (21-1) include —$CH_2CH_2$—O—$CH_2CH_2$—, —($CH_2CH_2$—O$)_2$—$CH_2CH_2$—, —($CH_2CH_2$—O$)_3$—$CH_2CH_2$—, —($CH_2CH_2$—O$)_4$—$CH_2CH_2$—, —($CH_2CH_2$—O$)_5$—$CH_2CH_2$—, —($CH_2CH_2$—O$)_6$—$CH_2CH_2$—, —($CH_2CH_2$—O$)_7$—$CH_2CH_2$—, —($CH_2CH_2$—O$)_8$—$CH_2CH_2$—, —($CH_2CH_2$—O$)_9$—$CH_2CH_2$—, —$CH_2CH(CH_3)$—O—$CH_2CH(CH_3)$—, —($CH_2CH(CH_3)$—O$)_2$—$CH_2CH(CH_3)$—, —($CH_2CH(CH_3)$—O$)_3$—$CH_2CH(CH_3)$—, —($CH_2CH(CH_3)$—O$)_4$—$CH_2CH(CH_3)$—, —($CH_2CH(CH_3)$—O$)_5$—$CH_2CH(CH_3)$—, —($CH_2CH(CH_3)$—O$)_6$—$CH_2CH(CH_3)$—, —$CH(CH_3)CH_2$—O—$CH(CH_3)CH_2$—, —($CH(CH_3)CH_2$—O$)_2$—$CH(CH_3)CH_2$—, —($CH(CH_3)CH_2$—O$)_3$—$CH(CH_3)CH_2$—, —($CH(CH_3)CH_2$—O$)_4$—$CH(CH_3)CH_2$—, —($CH(CH_3)CH_2$—O$)_5$—$CH(CH_3)CH_2$—, —($CH(CH_3)CH_2$—O$)_6$—$CH(CH_3)CH_2$—, and —$CH(CH_3)CH_2$—O—$CH_2CH(CH_3)$—.

Specific examples of the group represented by the general formula (21-2) include —$CH_2$—O—CO—$(CH_2)_2$—, —$(CH_2)_2$—O—CO—$(CH_2)_2$—, and —$(CH_2)_3$—O—CO—$(CH_2)_2$—.

Specific examples of the group represented by the general formula (21-3) include —$CH_2$—O—CO—$CH_2$—CO—O—$CH_2$—, —$CH_2$—O—CO—$(CH_2)_2$—CO—O—$CH_2$—, —$CH_2$—O—CO—$(CH_2)_3$—CO—O—$CH_2$—, —$CH_2$—O—CO—$(CH_2)_4$—CO—O—$CH_2$—, —$CH_2$—O—CO—$(CH_2)_5$—CO—O—$CH_2$—, —$CH_2$—O—CO—$(CH_2)_6$—CO—O—$CH_2$—, —$CH_2$—O—CO—$(CH_2)_7$—CO—O—$CH_2$—, —$(CH_2)_2$—O—CO—$CH_2$—CO—O—$(CH_2)_2$—, —$(CH_2)_2$—O—CO—$(CH_2)_2$—CO—O—$(CH_2)_2$—, —$(CH_2)_2$—O—CO—$(CH_2)_3$—CO—O—$(CH_2)_2$—, —$(CH_2)_2$—O—CO—$(CH_2)_4$—CO—O—$(CH_2)_2$—, —$(CH_2)_2$—O—CO—$(CH_2)_5$—CO—O—$(CH_2)_2$—, —$(CH_2)_2$—O—CO—$(CH_2)_6$—CO—O—$(CH_2)_2$—, —$(CH_2)_2$—O—CO—$(CH_2)_7$—CO—O—$(CH_2)_2$—, —$(CH_2)_3$—O—CO—$CH_2$—CO—O—$(CH_2)_3$—, —$(CH_2)_3$—O—CO—$(CH_2)_2$—CO—O—$(CH_2)_3$—, —$(CH_2)_3$—O—CO—$(CH_2)_3$—CO—O—$(CH_2)_3$—, —$(CH_2)_3$—O—CO—$(CH_2)_4$—CO—O—$(CH_2)_3$—, —$(CH_2)_3$—O—CO—$(CH_2)_5$—CO—O—$(CH_2)_3$—, —$(CH_2)_3$—O—CO—$(CH_2)_6$—CO—O—$(CH_2)_3$—, —$(CH_2)_3$—O—CO—$(CH_2)_7$—CO—O—$(CH_2)_3$—, —$CH_2$—O—CO—$C_6H_4$—CO—O—$CH_2$—, —$(CH_2)_2$—O—CO—$C_6H_4$—CO—O—$(CH_2)_2$—, —$(CH_2)_3$—O—CO—$C_6H_4$—CO—O—$(CH_2)_3$—, —$CH_2$—O—CO—$C_6H_{10}$—CO—O—$CH_2$—, —$(CH_2)_2$—O—CO—$C_6H_{10}$—CO—O—$(CH_2)_2$—, and —$(CH_2)_3$—O—CO—$C_6H_{10}$—CO—O—$(CH_2)_3$—. Among these, —$CH_2$—O—CO—$CH_2$—CO—O—$CH_2$—, —$CH_2$—O—CO—$(CH_2)_2$—CO—O—$CH_2$—, —$CH_2$—O—CO—$(CH_2)_3$—CO—O—$CH_2$—, —$CH_2$—O—CO—$(CH_2)_4$—CO—O—$CH_2$—, —$CH_2$—O—CO—$(CH_2)_5$—CO—O—$CH_2$—, —$CH_2$—O—CO—$(CH_2)_6$—CO—O—$CH_2$—, —$CH_2$—O—CO—$(CH_2)_7$—CO—O—$CH_2$—, —$(CH_2)_2$—O—CO—$CH_2$—

CO—O—(CH$_2$)$_2$—, —(CH$_2$)$_2$—O—CO—(CH$_2$)$_2$—CO—O—(CH$_2$)$_2$—, —(CH$_2$)$_2$—O—CO—(CH$_2$)$_3$—CO—O—(CH$_2$)$_2$—, —(CH$_2$)$_2$—O—CO—(CH$_2$)$_4$—CO—O—(CH$_2$)$_2$—, —(CH$_2$)$_2$—O—CO—(CH$_2$)$_5$—CO—O—(CH$_2$)$_2$—, —(CH$_2$)$_2$—O—CO—(CH$_2$)$_6$—CO—O—(CH$_2$)$_2$—, —(CH$_2$)$_2$—O—CO—(CH$_2$)$_7$—CO—O—(CH$_2$)$_2$—, —(CH$_2$)$_3$—O—CO—CH$_2$—CO—O—(CH$_2$)$_3$—, —(CH$_2$)$_3$—O—CO—(CH$_2$)$_2$—CO—O—(CH$_2$)$_3$—, —(CH$_2$)$_3$—O—CO—(CH$_2$)$_3$—CO—O—(CH$_2$)$_3$—, —(CH$_2$)$_3$—O—CO—(CH$_2$)$_4$—CO—O—(CH$_2$)$_3$—, —(CH$_2$)$_3$—O—CO—(CH$_2$)$_5$—CO—O—(CH$_2$)$_3$—, —(CH$_2$)$_3$—O—CO—(CH$_2$)$_6$—CO—O—(CH$_2$)$_3$—, or —(CH$_2$)$_3$—O—CO—(CH$_2$)$_7$—CO—O—(CH$_2$)$_3$— is preferable; —(CH$_2$)$_2$—O—CO—CH$_2$—CO—O—(CH$_2$)$_2$—, —(CH$_2$)$_2$—O—CO—(CH$_2$)$_2$—CO—O—(CH$_2$)$_2$—, —(CH$_2$)$_2$—O—CO—(CH$_2$)$_3$—CO—O—(CH$_2$)$_2$—, —(CH$_2$)$_2$—O—CO—(CH$_2$)$_4$—CO—O—(CH$_2$)$_2$—, —(CH$_2$)$_2$—O—CO—(CH$_2$)$_5$—CO—O—(CH$_2$)$_2$—, —(CH$_2$)$_2$—O—CO—(CH$_2$)$_6$—CO—O—(CH$_2$)$_2$—, or —(CH$_2$)$_2$—O—CO—(CH$_2$)$_7$—CO—O—(CH$_2$)$_2$— is more preferable; and —(CH$_2$)$_2$—O—CO—(CH$_2$)$_2$—CO—O—(CH$_2$)$_2$— is particularly preferable.

Specific examples of the group represented by the general formula (21-4) include —CH$_2$—NHCO—CH$_2$—, —(CH$_2$)$_2$—NHCO—(CH$_2$)$_2$—, —(CH$_2$)$_3$—NHCO—(CH$_2$)$_3$—, —(CH$_2$)$_4$—NHCO—(CH$_2$)$_4$—, —CH$_2$—CONH—CH$_2$—, —(CH$_2$)$_2$—CONH—(CH$_2$)$_2$—, —(CH$_2$)$_3$—CONH—(CH$_2$)$_3$—, —(CH$_2$)$_4$—CONH—(CH$_2$)$_4$—, —CH$_2$—NHCONH—CH$_2$—, —(CH$_2$)$_2$—NHCONH—(CH$_2$)$_2$—, —(CH$_2$)$_3$—NHCONH—(CH$_2$)$_3$—, —(CH$_2$)$_4$—NHCONH—(CH$_2$)$_4$—, —(CH$_2$)$_5$—NHCONH—(CH$_2$)$_5$—, —(CH$_2$)$_6$—NHCONH—(CH$_2$)$_6$—, —(CH$_2$)$_7$—NHCONH—(CH$_2$)$_7$—, —(CH$_2$)$_8$—NHCONH—(CH$_2$)$_8$—, —(CH$_2$)$_9$—NHCONH—(CH$_2$)$_9$—, and —(CH$_2$)$_{10}$—NHCONH—(CH)$_{10}$—. Among these, —CH$_2$—NHCONH—CH$_2$—, —(CH$_2$)$_2$—NHCONH—(CH$_2$)$_2$—, —(CH$_2$)$_3$—NHCONH—(CH$_2$)$_3$—, —(CH$_2$)$_4$—NHCONH—(CH$_2$)$_4$—, —(CH$_2$)$_5$—NHCONH—(CH$_2$)$_5$—, —(CH$_2$)$_6$—NHCONH—(CH$_2$)$_6$—, —(CH$_2$)$_7$—NHCONH—(CH$_2$)$_7$—, —(CH$_2$)$_8$—NHCONH—(CH$_2$)$_8$—, —(CH$_2$)$_9$—NHCONH—(CH$_2$)$_9$—, or —(CH$_2$)$_{10}$—NHCONH—(CH$_2$)$_{10}$— is preferable; and —(CH$_2$)$_2$—NHCONH—(CH$_2$)$_2$— is more preferable.

Specific examples of the group represented by the general formula (21-5) include —CH$_2$—O—CONH—CH$_2$—, —(CH$_2$)$_2$—O—CONH—(CH$_2$)$_2$—, —(CH$_2$)$_3$—O—CONH—(CH$_2$)$_3$—, and —(CH$_2$)$_4$—O—CONH—(CH$_2$)$_4$—.

In the present specification, the "alkylene group having 1 to 21 carbon atoms which has at least one group selected from —O—, —OCO—, —COO—, —NHCO—, —CONH—, —NHCONH—, or an arylene group in the chain and has a hydroxy group as a substituent" indicates that at least one hydrogen atom in the chain has been substituted with a hydroxy group, and specific examples thereof include a group in which at least one hydrogen atom in the chain arylene group or the alkylene group having 1 to 21 carbon atoms has been substituted with a hydroxy group.

Examples of the "alkylene group having 1 to 21 carbon atoms which has at least one group selected from —O—, —OCO—, —COO—, —NHCO—, —CONH—, —NHCONH—, or an arylene group in the chain and has a hydroxy group as a substituent" as A$_2$ in the general formula (2) include groups represented by the following general formulae (22-1) and (22-2).

$$—R_{54}—(CH_2)_{h10}— \quad (22\text{-}1)$$

(In the formula, R$_{54}$ represents an arylene group having 6 to 10 carbon atoms which has a hydroxy group as a substituent, and h$_{10}$ represents an integer of 1 to 4.)

$$—R_{55}\text{-}A_6\text{-}(CH_2)_{h11}— \quad (22\text{-}2)$$

(In the formula, R$_{55}$ represents an alkylene group having 1 to 7 carbon atoms which has a hydroxy group as a substituent or an arylene group having 6 to 10 carbon atoms which has a hydroxy group as a substituent, A$_6$ represents —O—, —OCO—, —COO—, —NHCO—, —CONH—, or —NHCONH—, and h$_1$ represents an integer of 2 to 4.)

Examples of the arylene group having 6 to 10 carbon atoms which has a hydroxy group as a substituent and is represented by R$_{54}$ in the general formula (22-1) include a hydroxyphenylene group, a dihydroxyphenylene group, a hydroxynaphthylene group, and a dihydroxynaphthylene group.

Examples of the alkylene group having 1 to 7 carbon atoms which has a hydroxy group as a substituent and is represented by R$_{55}$ in the general formula (22-2) include a hydroxymethylene group, a hydroxyethylene group, a hydroxytrimethylene group, a hydroxytetramethylene group, a hydroxypentamethylene group, a hydroxyhexamethylene group, a hydroxyheptylene group, a hydroxycyclobutylene group, a hydroxycyclopentylene group, a hydroxycyclohexylene group, and a hydroxycycloheptylene group.

Examples of the arylene group having 6 to 10 carbon atoms which has a hydroxy group as a substituent and is represented by R$_{55}$ in the general formula (22-2) are the same as those exemplified as the arylene group having 6 to 10 carbon atoms which has a hydroxy group as a substituent and is represented by R$_{54}$ in the general formula (22-1).

Specific preferred examples of the group represented by the general formula (22-1) include —C$_6$H$_3$(OH)—CH$_2$—, —C$_6$H$_3$(OH)—(CH$_2$)$_2$—, —C$_6$H$_3$(OH)—(CH$_2$)$_3$—, —C$_6$H$_3$(OH)—(CH$_2$)$_4$—, —C$_6$H$_2$(OH)$_2$—CH$_2$—, —C$_6$H$_2$(OH)$_2$—(CH$_2$)$_2$—, —C$_6$H$_2$(OH)$_2$—(CH$_2$)$_3$—, and —C$_6$H$_2$(OH)$_2$—(CH$_2$)$_4$—.

Specific preferred examples of the group represented by the general formula (22-2) include —CH(OH)—CH$_2$—O—(CH$_2$)$_2$—, —CH(OH)—CH$_2$—O—(CH$_2$)$_3$—, —CH(OH)—CH$_2$—O—(CH$_2$)$_4$—, —CH(OH)—CH$_2$—OCO—(CH$_2$)$_2$—, —CH(OH)—CH$_2$—OCO—(CH$_2$)$_3$—, —CH(OH)—CH$_2$—OCO—(CH$_2$)$_4$—, —CH(OH)—CH$_2$—COO—(CH$_2$)$_2$—, —CH(OH)—CH$_2$—COO—(CH$_2$)$_3$—, —CH(OH)—CH$_2$—COO—(CH$_2$)$_4$—, —CH(OH)—CH$_2$—NHCO—(CH$_2$)$_2$—, —CH(OH)—CH$_2$—NHCO—(CH$_2$)$_3$—, —CH(OH)—CH$_2$—NHCO—(CH$_2$)$_4$—, —CH(OH)—CH$_2$—CONH—(CH$_2$)$_2$—, —CH(OH)—CH$_2$—CONH—(CH$_2$)$_3$—, —CH(OH)—CH$_2$—CONH—(CH$_2$)$_4$—, —CH(OH)—CH$_2$—NHCONH—(CH$_2$)$_2$—, —CH(OH)—CH$_2$—NHCONH—(CH$_2$)$_3$—, and —CH(OH)—CH$_2$—NHCONH—(CH$_2$)$_4$—.

Examples of the "alkylene group having 1 to 21 carbon atoms which has a hydroxy group as a substituent" as A$_2$ in the general formula (2) include a group represented by the following general formula (23-1).

$$—R_{56}—(CH_2)_{h12}— \quad (23\text{-}1)$$

(In the formula, R$_{56}$ represents an alkylene group having 1 to 7 carbon atoms which has a hydroxy group as a substituent, and h$_{12}$ represents an integer of 1 to 4.)

Examples of the alkylene group having 1 to 7 carbon atoms which has a hydroxy group as a substituent and is represented by R$_{56}$ in the general formula (23-1) are the same as those exemplified as the alkylene group having 1 to 7 carbon atoms which has a hydroxy group as a substituent and is represented by $R_{55}$ in the general formula (22-2).

Specific examples of the group represented by the general formula (23-1) include —$C_6H_9$(OH)—$CH_2$—, —$C_6H_9$(OH)—$(CH_2)_2$—, —$C_6H_9$(OH)—$(CH_2)_3$—, —$C_6H_9$(OH)—$(CH_2)_4$—, —CH(OH)—$CH_2$—, —CH(OH)—$(CH_2)_2$—, —CH(OH)—$(CH_2)_3$—, and —CH(OH)—$(CH_2)_4$—.

In a case where $A_1$ in the general formula (2) represents —COO—, —NHCO—, —NHCONH—, or a group represented by the general formula (2-1), an alkylene group having 1 to 21 carbon atoms is preferable as $A_2$ in the general formula (2). Among examples, a methylene group, an ethylene group, a trimethylene group, a tetramethylene group, a pentamethylene group, or a hexamethylene group is preferable, a methylene group, an ethylene group, or a trimethylene group is more preferable, and an ethylene group is particularly preferable.

In a case where $A_1$ in the general formula (2) represents —CONH—, $A_2$ in the general formula (2) represents preferably an alkylene group having 1 to 21 carbon atoms or an alkylene group having 1 to 21 carbon atoms which has at least one group selected from —O—, —OCO—, —COO—, —NHCO—, —CONH—, —NHCONH—, or an arylene group in the chain and more preferably an alkylene group having 1 to 21 carbon atoms which has at least one group selected from —O—, —OCO—, —COO—, —NHCO—, —CONH—, —NHCONH—, or an arylene group in the chain. Among these, a group represented by the general formula (21-3) or (21-4) is preferable; —$(CH_2)_2$—O—CO—$CH_2$—CO—O—$(CH_2)_2$—, —$(CH_2)_2$—O—CO—$(CH_2)_2$—CO—O—$(CH_2)_2$—, —$(CH_2)_2$—O—CO—$(CH_2)_3$—CO—O—$(CH_2)_2$—, —$(CH_2)_2$—O—CO—$(CH_2)_4$—CO—O—$(CH_2)_2$—, —$(CH_2)_2$—O—CO—$(CH_2)_5$—CO—O—$(CH_2)_2$—, —$(CH_2)_2$—O—CO—$(CH_2)_6$—CO—O—$(CH_2)_2$—, —$(CH_2)_2$—O—CO—$(CH_2)_7$—CO—O—$(CH_2)_2$—, —$CH_2$—NHCONH—$CH_2$—, —$(CH_2)_2$—NHCONH—$(CH_2)_2$—, —$(CH_2)_3$—NHCONH—$(CH_2)_3$—, —$(CH_2)_4$—NHCONH—$(CH_2)_4$—, —$(CH_2)_5$—NHCONH—$(CH_2)_5$—, —$(CH_2)_6$—NHCONH—$(CH_2)_6$—, —$(CH_2)_7$—NHCONH—$(CH_2)_7$—, —$(CH_2)_8$—NHCONH—$(CH_2)_8$—, —$(CH_2)_9$—NHCONH—$(CH_2)_9$—, or —$(CH_2)_{10}$—NHCONH—$(CH_2)_{10}$— is more preferable, and —$(CH_2)_2$—O—CO—$(CH_2)_2$—CO—O—$(CH_2)_2$— or —$(CH_2)_2$—NHCONH—$(CH_2)_2$— is particularly preferable.

The alkyl group having 1 to 12 carbon atoms as $R_{10}$ in $A_3$ in the general formula (2) may be any of linear, branched, or cyclic. Among these, the alkylene group is preferably linear or branched and more preferably linear. In addition, among examples of the alkyl group having 1 to 12 carbon atoms, an alkylene group having 1 to 6 carbon atoms is preferable and an alkylene group having 1 to 4 carbon atoms is more preferable. Specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-methylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a cyclohexylmethyl group, a 1-cyclohexylethyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-tert-butylcyclohexyl group, a 1-adamantyl group, and a 2-adamantyl group. Among these, the methyl group, the ethyl group, the n-propyl group, the isopropyl group, the n-butyl group, the isobutyl group, the sec-butyl group, or the tert-butyl group is preferable, and the methyl group or the ethyl group is more preferable.

It is preferable that $R_{10}$ in $A_3$ in the general formula (2) represents a hydrogen atom or an alkyl group having 1 to 4 carbon atoms. Among examples, a hydrogen atom, a methyl group, or an ethyl group is more preferable and a hydrogen atom is particularly preferable.

It is preferable that $A_3$ in the general formula (2) represents —O—.

Examples of the alkyl group having 1 to 12 carbon atoms as $R_8$ in the general formula (2-1) include the same as those exemplified as the alkyl group having 1 to 12 carbon atoms as $R_{10}$ in $A_3$ in the general formula (2), and the preferred examples thereof are the same as described above.

Specific preferred examples of the group represented by the general formula (2-4) include a group represented by the following general formula (2-4').

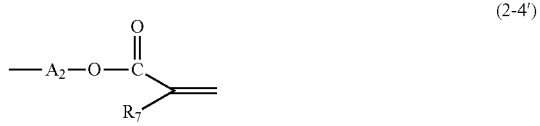

(2-4')

(In the formula, $R_7$ and $A_2$ each have the same definition as described above.)

Specific preferred examples of the group represented by the general formula (2-4') include a group represented by the following general formula (2-4").

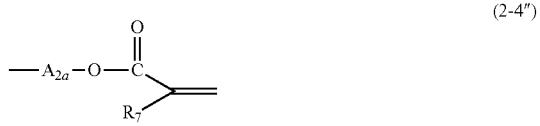

(2-4")

(In the formula, $A_{2a}$ represents an alkylene group having 1 to 21 carbon atoms, and $R_7$ has the same as described above.)

Examples of the alkylene group having 1 to 21 carbon atoms as $A_{2a}$ in the general formula (2-4") include the same as those exemplified as the alkylene group having 1 to 21 carbon atoms as $A_2$ in the general formula (2), and the preferred examples thereof are the same as described above.

Specific preferred examples of the group represented by the general formula (2-4") include a group represented by the following general formula (2-5).

(2-5)

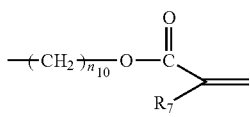

(In the formula, $n_{10}$ represents an integer of 1 to 12, and $R_7$ has the same definition as described above.)

$n_{10}$ in the general formula (2-5) represents preferably an integer of 1 to 6, more preferably an integer of 1 to 3, and still more preferably 2.

Specific preferred examples of the group represented by the general formula (2-5) include the following groups.

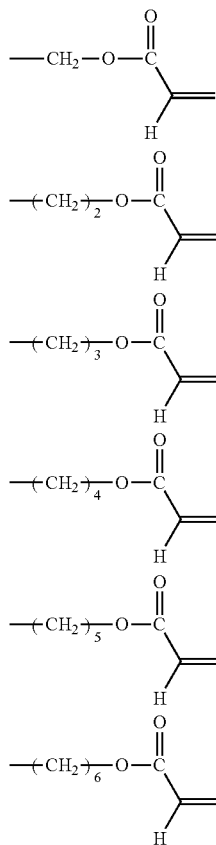
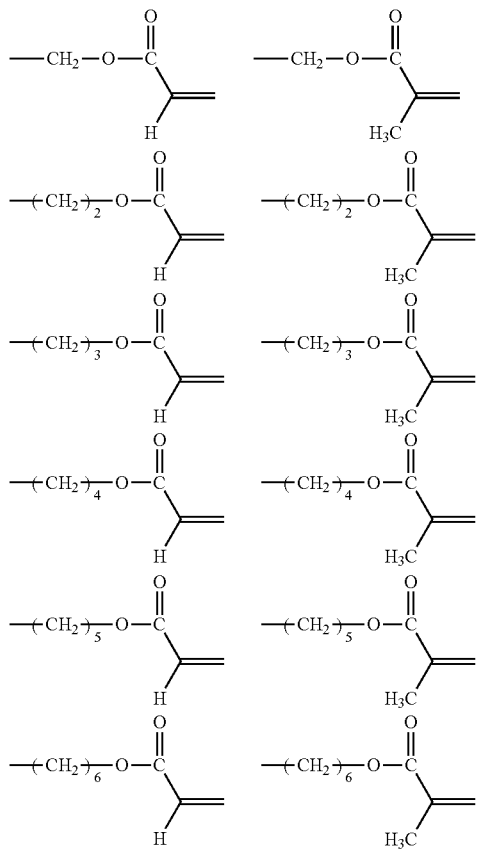

Among the specific examples, a group represented by the following general formula (2-5-1) or (2-5-2) is preferable.

(2-5-1)

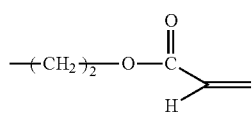

(2-5-2)

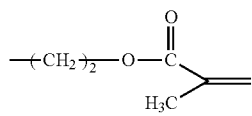

Examples of the alkyl group having 1 to 12 carbon atoms as $R_9$ in the general formula (2-1) are the same as those exemplified as the alkyl group having 1 to 12 carbon atoms as $R_{10}$ in $A_3$ in the general formula (2), and the preferred examples thereof are the same as described above.

In a case where $R_8$ and $R_9$ in the general formula (2-1) form a 5- or 6-membered cyclic structure together with —N—$(CH_2)_{n4}$-$(A_4)_{n5}$- bonded to these, $n_5$ represents 1, and the cyclic structure is represented by the following general formula (2-3).

(2-3)

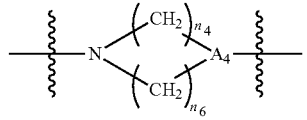

(In the formula, $n_6$ represents an integer of 0 to 4, $A_4$ and $n_4$ each have the same definition as described above. Here, $n_4+n_6$ is an integer of 3 to 4.)

It is preferable that $n_6$ in the general formula (2-3) represents 2.

The cyclic structure represented by the general formula (2-3) indicates a 5- or 6-membered ring, and a 6-membered ring is preferable between these.

Specific examples of the cyclic structure represented by the general formula (2-3) are as follows.

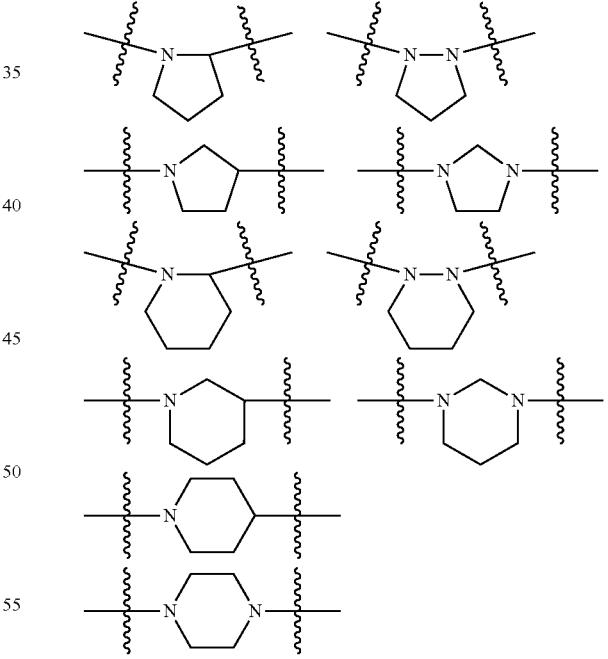

Among the specific example, the following structure is preferable.

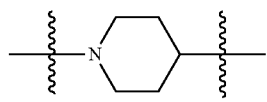

-continued

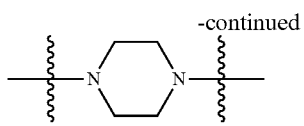

$R_8$ in the general formula (2-1) represents preferably an alkyl group having 1 to 6 carbon atoms or a group represented by the general formula (2-4") and preferably an alkyl group having 1 to 4 carbon atoms or a group represented by the general formula (2-5). Specific examples thereof include a methyl group, an ethyl group, an n-propyl group, an isopropyl group, an n-butyl group, an isobutyl group, a sec-butyl group, a tert-butyl group, and a group represented by any of the following formulae. Among these, a methyl group, an ethyl group, or a group represented by the general formula (2-5-1) or (2-5-2) is preferable.

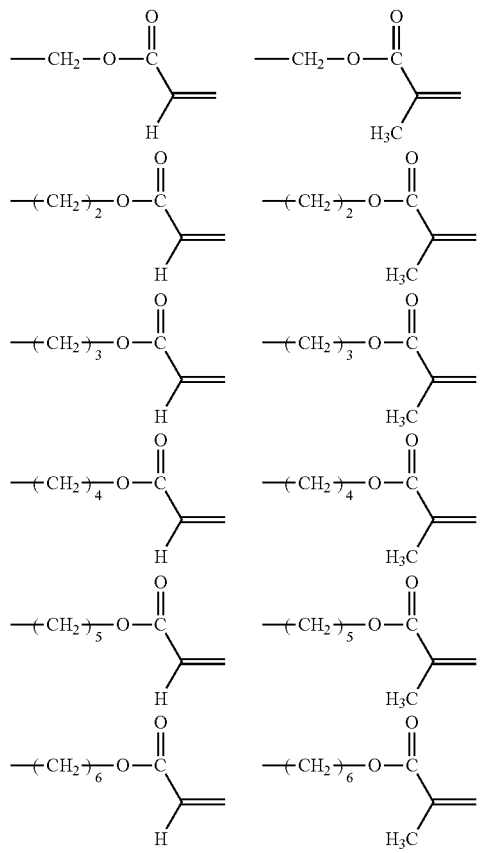

It is preferable that $R_9$ in the general formula (2-1) represents a hydrogen atom or an alkyl group having 1 to 4 carbon atoms, and specific examples thereof include a hydrogen atom, a methyl group, an ethyl group, an n-propyl group, an isopropyl group, an n-butyl group, an isobutyl group, a sec-butyl group, and a tert-butyl group. Among these, the hydrogen atom, the methyl group, or the ethyl group is preferable, and the hydrogen atom is more preferable.

It is preferable that $A_4$ in the general formula (2-1) represents a group represented by the general formula (2-2).

It is preferable that $n_4$ in the general formula (2-1) represents 2 in a case where a cyclic structure represented by the general formula (2-3) is formed and represents 0 in a case where a cyclic structure represented by the general formula (2-3) is not formed.

It is preferable that $n_5$ in the general formula (2-1) represents 1 in a case where a cyclic structure represented by the general formula (2-3) is formed and represents 0 in a case where a cyclic structure represented by the general formula (2-3) is not formed.

Specific preferred examples of the group represented by the general formula (2) include a group represented by the following general formula (2').

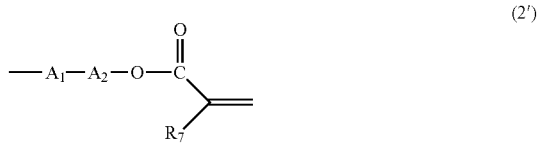

(In the formula, $R_7$, $A_1$, and $A_2$ each have the same definition as described above.)

Specific examples of the group represented by the following general formula (2') include groups represented by the following general formulae (2'a) to (2'd).

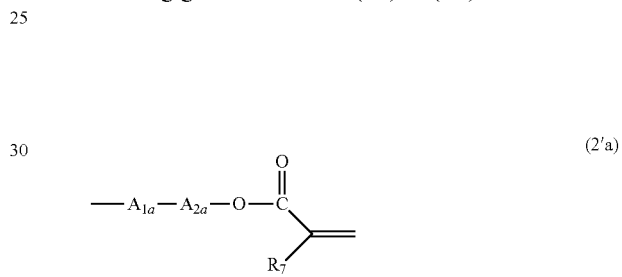

(In the formula, $A_{1a}$ represents —COO—, —NHCO—, or —NHCONH—, and $R_7$ and $A_{2a}$ each have the same definition as described above.)

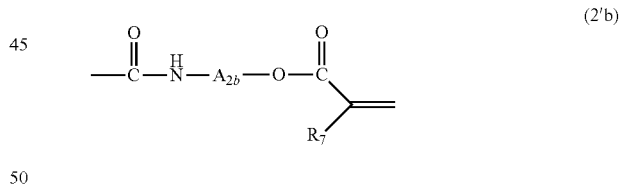

(In the formula, $A_{2b}$ represents an alkylene group having 1 to 21 carbon atoms which has at least one group selected from —O—, —OCO—, —COO—, —NHCO—, —CONH—, —NHCONH—, or an arylene group in the chain, and $R_7$ has the same definition as described above.)

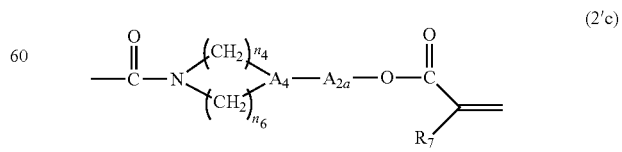

(In the formula, $R_7$, $A_{2a}$, $A_4$, $n_4$, and $n_6$ each have the same definition as described above.)

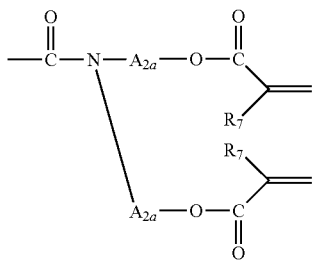

(2'd)

(In the formula, $R_7$ and $A_{2a}$ each have the same definition as described above, and two pieces of $R_7$'s may be the same as or different from each other, and two pieces of $A_{2a}$'s may be the same as or different from each other.)

It is preferable that $A_{1a}$ in the general formula (2'a) represents —COO—.

Examples of the an alkylene group having 1 to 21 carbon atoms which has at least one group selected from —O—, —OCO—, —COO—, —NHCO—, —CONH—, —NHCONH—, or an arylene group in the chain as $A_{2b}$ in the general formula (2'b) are the same as those exemplified as the alkylene group having 1 to 21 carbon atoms which has at least one group selected from —O—, —OCO—, —COO—, —NHCO—, —CONH—, —NHCONH—, or an arylene group in the chain as $A_2$ in the general formula (2), and the preferred examples thereof are the same as described above.

As $R_7$ in the general formula (2'd), it is preferable that two pieces of $R_7$'s are the same as each other.

As $A_{2a}$ in the general formula (2'd), it is preferable that two pieces of $A_{2a}$'S are the same as each other.

Specific preferred examples of the groups represented by the general formulae (2'a) to (2'd) include groups represented by the following general formulae (2"a) to (2"d).

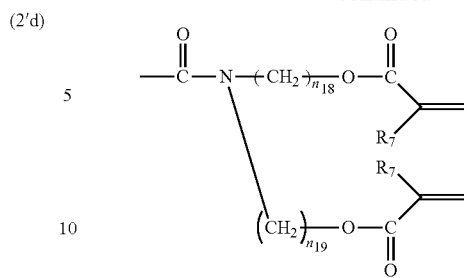

(2"d)

(In the formulae, $n_{11}$, $n_{18}$, and $n_{19}$ each independently represent an integer of 1 to 12, $n_{12}$ to $n_{17}$ each independently represent an integer of 1 to 6, and $R_7$ and $A_4$ each have the same definition as described above.)

$n_{11}$ in the general formula (2"a) represents preferably an integer of 1 to 6, more preferably an integer of 1 to 3, and still more preferably 2.

As $n_{12}$ and $n_{13}$ in the general formula (2"b-1), it is preferable that $n_{12}$ and $n_{13}$ are the same as each other, and $n_{12}$ and $n_{13}$ represent preferably an integer of 1 to 3 and more preferably 2.

As $n_{14}$ to $n_{16}$ in the general formula (2"b-2), it is preferable that all of $n_{14}$ to $n_{16}$ are the same as one another, and $n_{14}$ to $n_{16}$ represent preferably an integer of 1 to 3 and more preferably 2.

$n_{17}$ in the general formula (2"c) represents preferably an integer of 1 to 3 and more preferably 2.

As $n_{18}$ and $n_{19}$ in the general formula (2"d), it is preferable that $n_{18}$ and $n_{19}$ are the same as each other, and $n_{18}$ and $n_{19}$ represent preferably an integer of 1 to 6, more preferably an integer of 1 to 3, and still more preferably 2.

Specific preferred examples of the group represented by the general formula (2"a) are as follows.

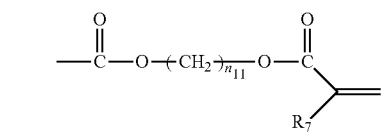

(2"a)

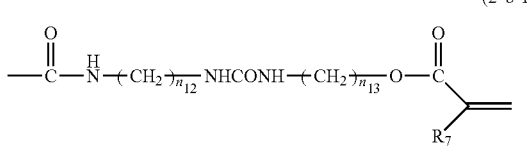

(2"b-1)

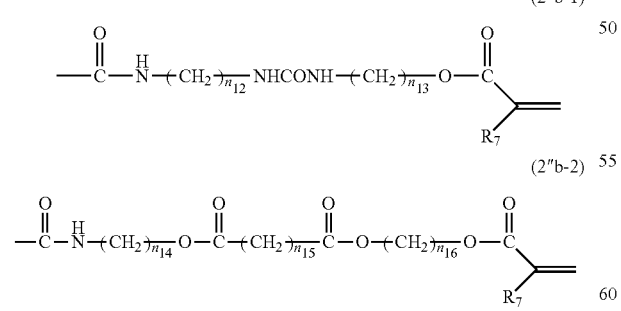

(2"b-2)

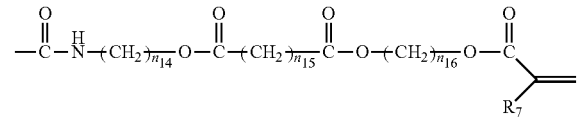

(2"c)

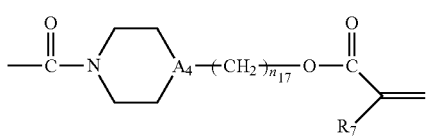

-continued

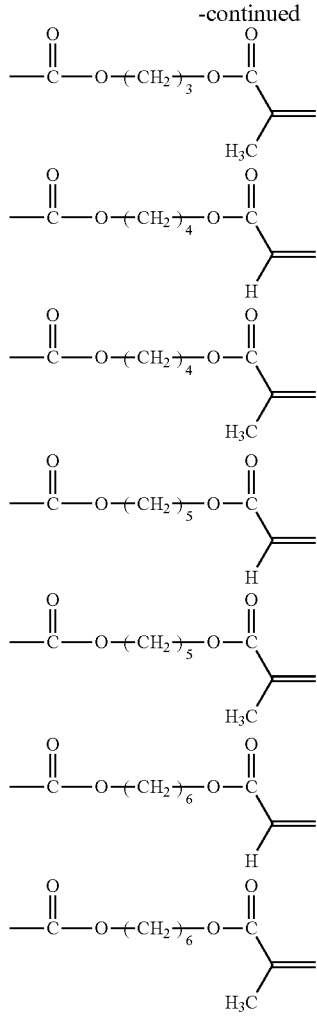

Among the specific examples, a group represented by the following general formula (2″-1) or (2″-2) is preferable.

(2″-1)

(2″-2)

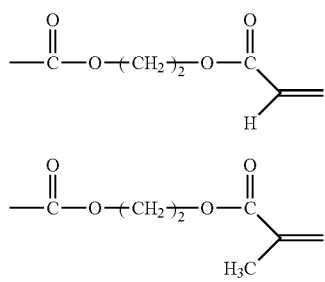

Specific preferred examples of the group represented by the general formula (2″b-1) are as follows.

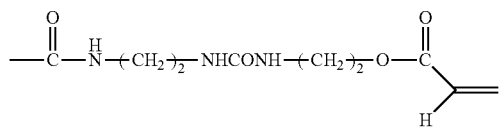

-continued

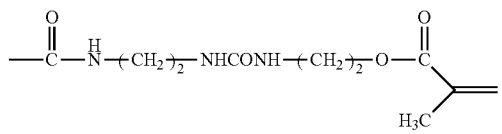

Specific preferred examples of the group represented by the general formula (2″b-2) are as follows.

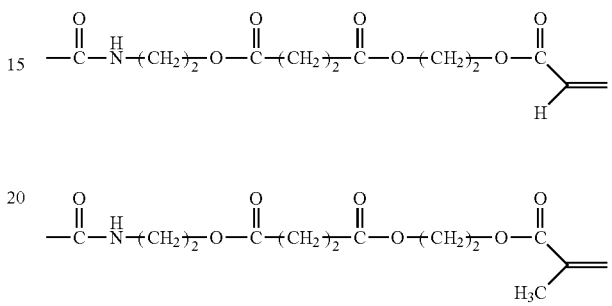

Specific preferred examples of the group represented by the general formula (2″c) are as follows.

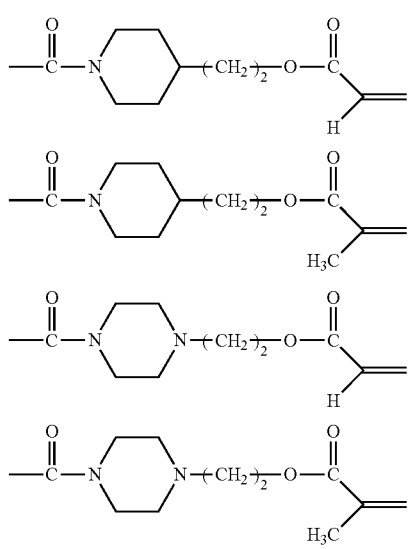

Specific preferred examples of the group represented by the general formula (2″d) are as follows.

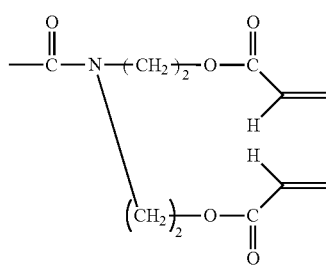

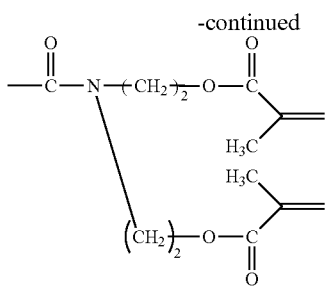

Among the groups represented by the general formulae (2″a) to (2″d), the group represented by the general formula (2″a), (2″b-1), or (2″b-2) is preferable, and the group represented by the general formula (2″a) is more preferable.

In a case where $R_6$ in the general formula (1) represents a group having a polymerizable unsaturated group, a group represented by the general formula (2) is preferable, a group represented by the general formula (2′) is more preferable, a group represented by any of the general formulae (2′a) to (2′d) is more preferable, and a group represented by any of the general formulae (2″a) to (2″d) is still more preferable. Among these, the group represented by the general formula (2″a) is particularly preferable. Specifically, those exemplified as the specific preferred examples of the groups represented by the general formulae (2″a) to (2″d) are preferable, and the following groups are particularly preferable.

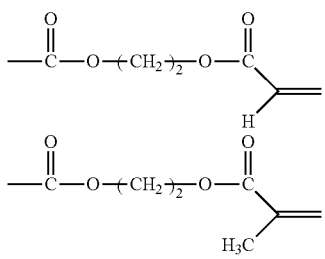

As the group having a polymerizable unsaturated group as $R_2$, $R_3$, and $R_5$ in the general formula (1), a group represented by the general formula (2-4) is preferable, a group represented by the general formula (2-4′) is more preferable, a group represented by the general formula (2-4″) is still more preferable, and a group represented by the general formula (2-5) is particularly preferable. Specifically, those exemplified as the specific preferred examples of the group represented by the general formula (2-5) are preferable, and the following groups are particularly preferable.

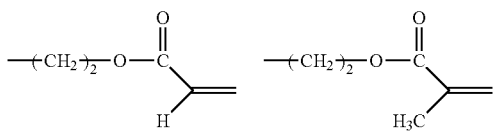

Functional Group Other than Polymerizable Unsaturated Group in Compound According to Embodiment of Present Invention The alkyl group having 1 to 6 carbon atoms as $R_1$ and $R_4$ in the general formula (1) may be any of linear, branched, or cyclic. Among these, the alkyl group is preferably linear or branched and more preferably linear. In addition, among examples of the alkyl group having 1 to 6 carbon atoms, an alkyl group having 1 to 4 carbon atoms is preferable. Specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, a isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, and a cyclohexyl group. Among these, the methyl group, the ethyl group, the n-propyl group, the isopropyl group, the n-butyl group, the isobutyl group, the sec-butyl group, or the tert-butyl group is preferable, and the methyl group or the ethyl group is more preferable.

The alkyl group having 1 to 20 carbon atoms as $R_2$ and $R_3$ in the general formula (1) may be any of linear, branched, or cyclic. Among these, the alkyl group is preferably linear or branched and more preferably linear. In addition, among examples of the alkyl group having 1 to 20 carbon atoms, an alkyl group having 1 to 12 carbon atoms is preferable, an alkyl group having 1 to 6 carbon atoms is more preferable, and an alkyl group having 1 to 4 carbon atoms is still more preferable. Specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-methylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, an n-tridecyl group, an isotridecyl group, an n-tetradecyl group, an isotetradecyl group, an n-pentadecyl group, an isopentadecyl group, an n-hexadecyl group, an isohexadecyl group, an n-heptadecyl group, an isoheptadecyl group, an n-octadecyl group, an isooctadecyl group, an n-nonadecyl group, an isononadecyl group, an n-icosyl group, an isoicosyl group, a cyclohexylmethyl group, a 1-cyclohexylethyl group, a 2-methylcyclohexyl group, a 3-methylcyclohexyl group, a 4-methylcyclohexyl group, a 2,6-dimethylcyclohexyl group, a 2,4-dimethylcyclohexyl group, a 3,5-dimethylcyclohexyl group, a 2,5-dimethylcyclohexyl group, a 2,3-dimethylcyclohexyl group, a 3,3,5-trimethylcyclohexyl group, a 4-tert-butylcyclohexyl group, a 1-adamantyl group, a 2-adamantyl group, a 1-methylcyclopentyl group, a 1-ethylcyclopentyl group, a 1-n-propylcyclopentyl group, a 1-methylcyclohexyl group, a 1-ethylcyclohexyl group, a 1-n-propylcyclopentyl group, a 1-n-butylcyclohexyl group, a 1-methylcycloheptyl group, a 1-ethylcycloheptyl group, a 1-n-propylcycloheptyl group, a 1-methylcyclooctyl group, and a 1-ethylcyclooctyl group. Among these, the methyl group, the ethyl group, the n-propyl group, the isopropyl group, the n-butyl group, the isobutyl group, the sec-butyl group, the tert-butyl group, the n-pentyl group, the isopentyl group, the sec-pentyl group, the tert-pentyl group, the neopentyl group, the 2-methylbutyl group, the 1,2-dimethylpropyl group, the 1-ethylpropyl group, the n-hexyl group, the isohexyl group, the sec-hexyl group, the tert-hexyl group, the neohexyl group, the 2-methylpentyl group, the 1,2-dimethylbutyl group, the 2,3-dimethylbutyl group, the 1-ethylbutyl group, the n-heptyl group, the n-octyl group, the n-nonyl group, the n-decyl group, the n-undecyl group, or the n-dodecyl group is preferable; the methyl group, the ethyl group, the n-propyl group, the isopropyl group, the n-butyl group, the isobutyl group, the sec-butyl group, the tert-butyl group, the n-pentyl group, the isopentyl group, or the n-hexyl group is more preferable; the methyl group, the ethyl group, the n-propyl group, the isopropyl group, the n-butyl group, the isobutyl group, the sec-butyl group, or the tert-butyl group is still more preferable; the methyl group or the ethyl group is even still more preferable; and the ethyl group is particularly preferable.

Examples of the aryl group having 6 to 14 carbon atoms of the "aryl group having 6 to 14 carbon atoms which has a substituent or is unsubstituted" as $R_2$ and $R_3$ in the general formula (1) include a phenyl group, a naphthyl group, and an anthracenyl group. Among these, the phenyl group is preferable.

The aryl group having 6 to 14 carbon atoms which has a substituent as $R_2$ and $R_3$ in the general formula (1) has typically 1 to 5 substituents, preferably 1 to 3 substituents, and more preferably one substituent. An alkyl group or the like having 1 to 20 carbon atoms is exemplified as the substituent. It should be noted that "1 to 20 carbon atoms" in this case indicates the number of carbon atoms in one alkyl group. For example, in a case where two alkyl groups as the substituents are present on an aryl group, the number of carbon atoms in each alkyl group is in a range of 1 to 20, the total number of carbon atoms in the substituents (two alkyl groups) is in a range of 2 to 40, and the total number of carbon atoms in the functional group (the aryl group having 6 to 14 carbon atoms which has two alkyl groups) is in a range of 8 to 54.

Examples of the alkyl group having 1 to 20 carbon atoms in the substituent of the "aryl group having 6 to 14 carbon atoms which has a substituent" as $R_2$ and $R_3$ in the general formula (1) are the same as those exemplified as the alkyl group having 1 to 20 carbon atoms as $R_2$ and $R_3$ in the general formula (1), and the preferred examples thereof are the same as described above.

Examples of the aryl group having 6 to 14 carbon atoms which has a substituent as $R_2$ and $R_3$ in the general formula (1) include an aryl group having 6 to 14 carbon atoms which has an alkyl group having 1 to 20 carbon atoms. Among examples, a phenyl group which has an alkyl group having 1 to 20 carbon atoms, a naphthyl group, or an anthracenyl group is preferable, a phenyl group which has an alkyl group having 1 to 12 carbon atoms is more preferable, a phenyl group which has an alkyl group having 1 to 6 carbon atoms is still more preferable, and a phenyl group which has an alkyl group having 1 to 3 carbon atoms is particularly preferable. Specific examples thereof include an o-tolyl group (methylphenyl group), an m-tolyl group, a p-tolyl group, an o-ethylphenyl group, an m-ethylphenyl group, a p-ethylphenyl group, an o-propylphenyl group, an m-propylphenyl group, a p-propylphenyl group, an o-butylphenyl group, an m-butylphenyl group, a p-butylphenyl group, an o-pentylphenyl group, an m-pentylphenyl group, a p-pentylphenyl group, an o-hexylphenyl group, an m-hexylphenyl group, a p-hexylphenyl group, a 2,3-xylyl group (2,3-dimethylphenyl group), a 2,4-xylyl group, a 2,5-xylyl group, a 2,6-xylyl group, a 3,4-xylyl group, a 3,5-xylyl group, and a mesityl group (2,4,6-trimethylphenyl group). Among these, the p-tolyl group, the p-ethylphenyl group, the p-propylphenyl group, the p-butylphenyl group, the p-pentylphenyl group, the p-hexylphenyl group, the 2,4-xylyl group, the 2,6-xylyl group, the 3,5-xylyl group, or the mesityl group is preferable, and the p-tolyl group, the p-ethylphenyl group, or the p-propylphenyl group is more preferable. It should be noted that the alkyl group in the specific examples is not limited to a normal-form and includes all branched forms such as a sec-form, a tert-form, an iso-form, and a neo-form. Among these, a normal-form is preferable.

In the general formula (1), the alkylene group having 2 to 4 carbon atoms in a case where $R_1$ and $R_2$ form an alkylene group having 2 to 4 carbon atoms and $R_3$ and $R_4$ form an alkylene group having 2 to 4 carbon atoms may be linear or branched, but is preferably linear. Specific examples thereof include an ethylene group, a trimethylene group, a propylene group, a 1,1-dimethylmethylene group, a tetramethylene group, a 1-methyltrimethylene group, a 2-methyltrimethylene group, a 1,2-dimethylethylene group, a 1,1-dimethylethylene group, and an ethylethylene group. Among these, the ethylene group, the trimethylene group, or the tetramethylene group is preferable, and the trimethylene group is more preferable.

In the general formula (1), specific examples of the general formula (1) in the case where $R_1$ and $R_2$ form an alkylene group having 2 to 4 carbon atoms and/or $R_3$ and $R_4$ form an alkylene group having 2 to 4 carbon atoms include the following general formulae (8-1) to (8-9).

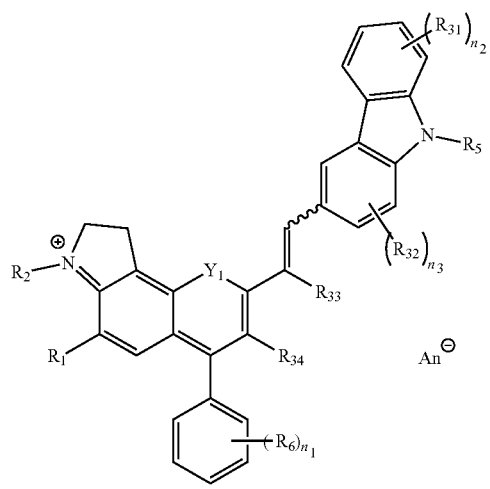

(8-1)

-continued
(8-2)
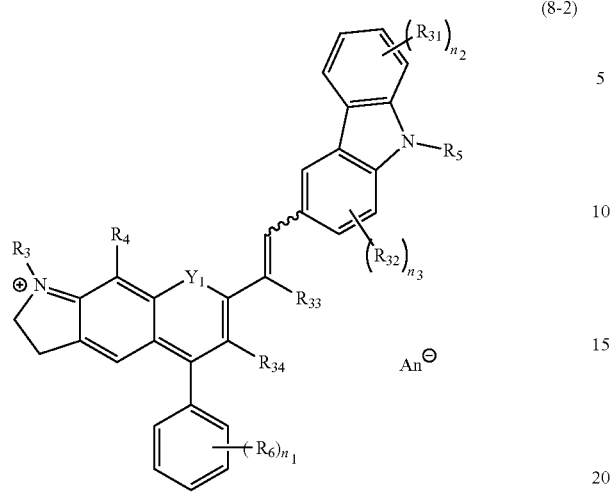
(8-3)
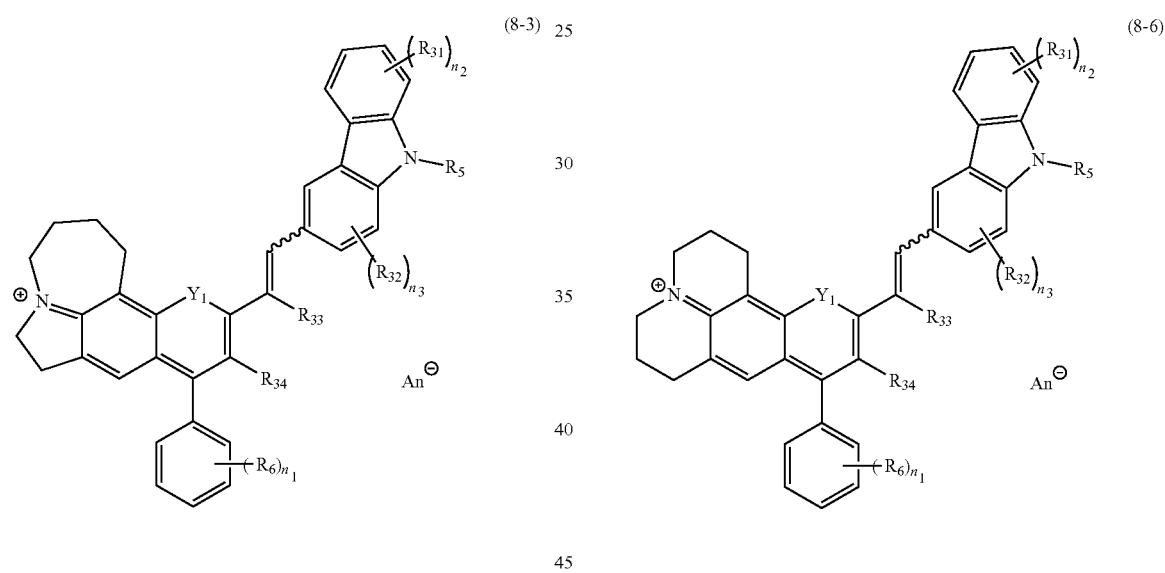
(8-4)
-continued
(8-5)
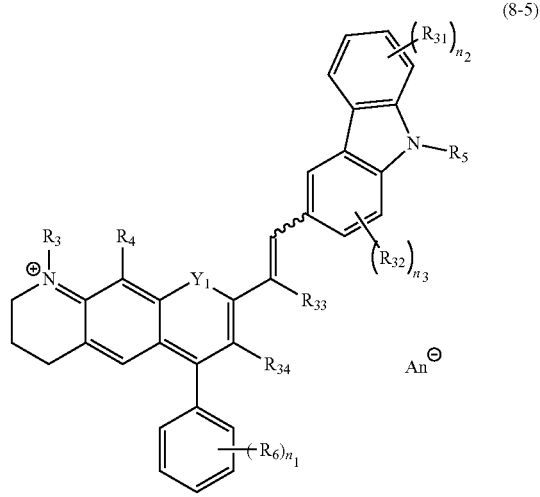
(8-6)
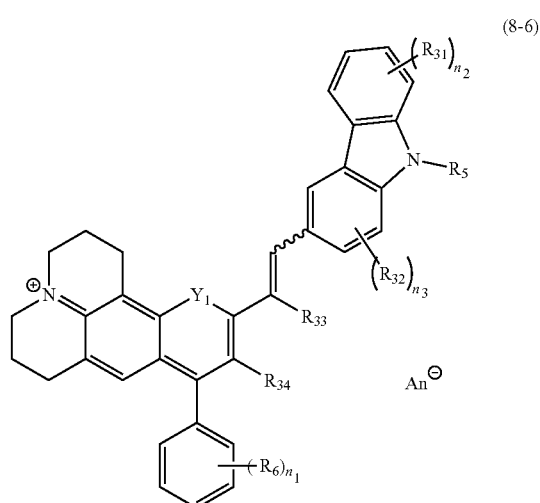
(8-7)
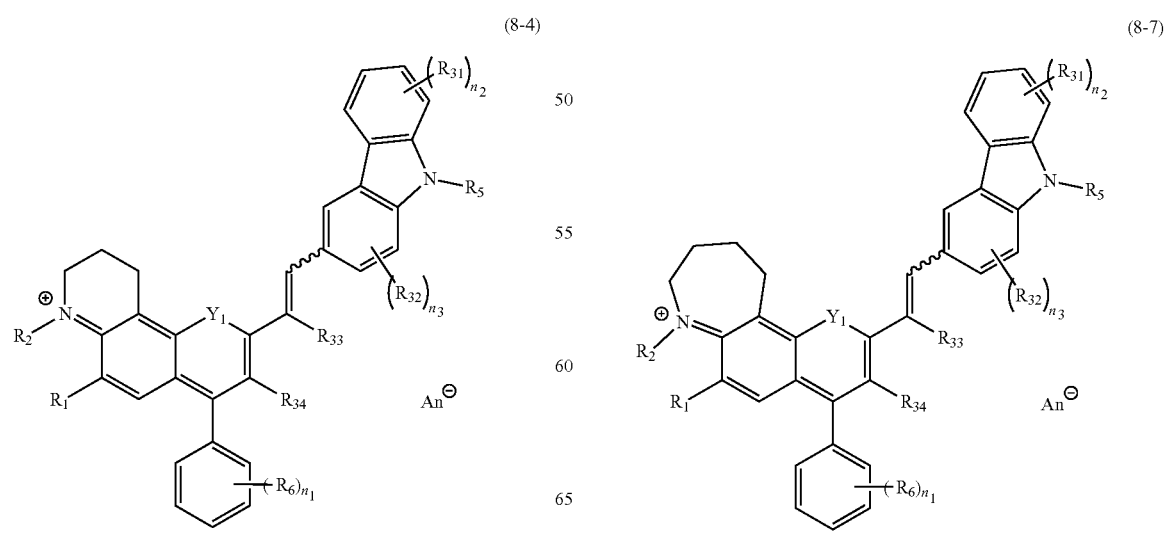

-continued (8-8)

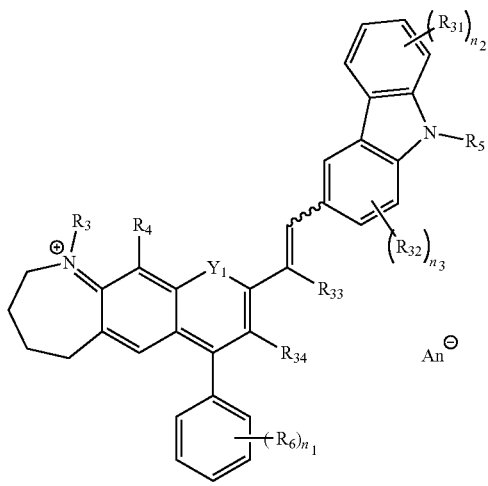

(8-9)

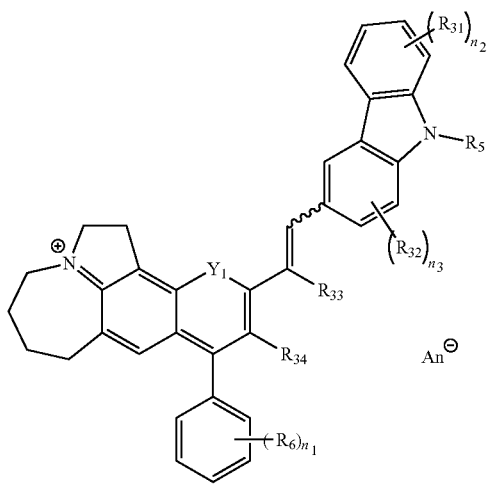

(In the formulae, $R_1$ to $R_6$, $R_{31}$ to $R_{34}$, $Y_1$, $An^-$, and $n_1$ to $n_3$ each have the same definition as described above.)

Among the specific examples, the general formulae (8-4) to (8-6) are preferable, and the general formula (8-6) is more preferable.

$R_1$ in the general formula (1) represents preferably a hydrogen atom, an alkyl group having 1 to 4 carbon atoms, or a linear alkylene group having 2 to 4 carbon atoms formed by $R_1$ and $R_2$, more preferably a hydrogen atom or a trimethylene group formed by $R_1$ and $R_2$, and still more preferably a hydrogen atom. Specific examples thereof include a hydrogen atom, a methyl group, an ethyl group, an n-propyl group, an isopropyl group, an n-butyl group, an isobutyl group, a sec-butyl group, a tert-butyl group, an ethylene group formed by $R_1$ and $R_2$, a trimethylene group formed by $R_1$ and $R_2$, and a tetramethylene group formed by $R_1$ and $R_2$. Among these, the hydrogen atom, the methyl group, the ethyl group, or the trimethylene group formed by $R_1$ and $R_2$ is preferable, the hydrogen atom or the trimethylene group formed by $R_1$ and $R_2$ is more preferable, and the hydrogen atom is still more preferable.

$R_2$ in the general formula (1) represents preferably a group represented by the general formula (2-4), an alkyl group having 1 to 12 carbon atoms, a phenyl group which has an alkyl group having 1 to 6 carbon atoms or is unsubstituted, or a linear alkylene group having 2 to 4 carbon atoms formed by $R_1$ and $R_2$; more preferably a group represented by the general formula (2-5), an alkyl group having 1 to 6 carbon atoms, a phenyl group which has an alkyl group having 1 to 3 carbon atoms or is unsubstituted, or a linear alkylene group having 2 to 4 carbon atoms formed by $R_1$ and $R_2$; still more preferably an alkyl group having 1 to 6 carbon atoms or a trimethylene group formed by $R_1$ and $R_2$; and particularly preferably an alkyl group having 1 to 6 carbon atoms. Specific examples thereof include a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, an ethylene group formed by $R_1$ and $R_2$, a trimethylene group formed by $R_1$ and $R_2$, a tetramethylene group formed by $R_1$ and $R_2$, and groups represented by the following formulae. It should be noted that the alkyl group in the specific examples is not limited to a normal-form and includes all branched forms such as a sec-form, a tert-form, an iso-form, and a neo-form. Among these, the normal-form or the iso-form is preferable, and the normal-form is more preferable.

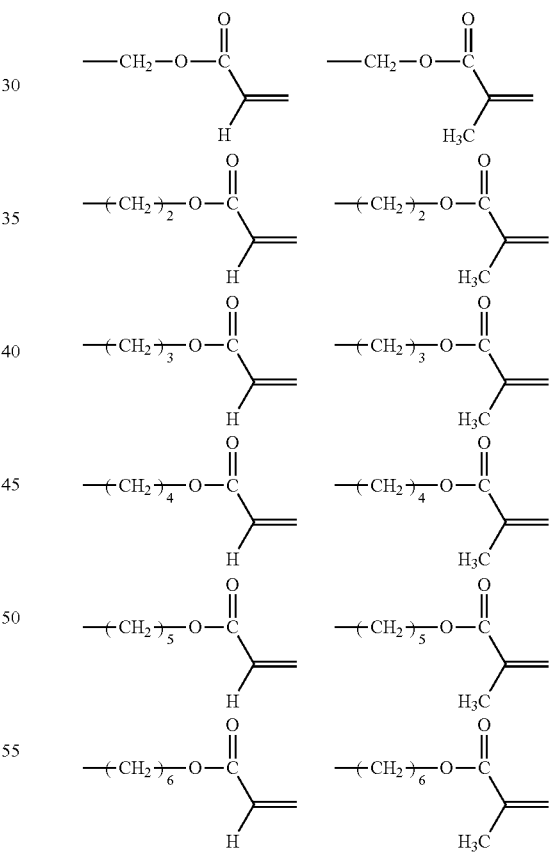

Among the specific examples, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_1$ and $R_2$, a trimethylene group formed by $R_1$ and $R_2$, a tetramethylene group formed by $R_1$ and $R_2$, a group represented by the general formula (2-5-1), or a group represented by the general formula (2-5-2) is preferable; the methyl group, the ethyl group, the n-propyl group, the isopropyl group, the n-butyl group, the isobutyl group, the sec-butyl group, the tert-butyl group, or the trimethylene group formed by $R_1$ and $R_2$ is more preferable; the methyl group, the ethyl group, or the trimethylene group formed by $R_1$ and $R_2$ is still more preferable; and the ethyl group is particularly preferable.

$R_3$ in the general formula (1) represents preferably a group represented by the general formula (2-4), an alkyl group having 1 to 12 carbon atoms, a phenyl group which has an alkyl group having 1 to 6 carbon atoms or is unsubstituted, or a linear alkylene group having 2 to 4 carbon atoms formed by $R_3$ and $R_4$; more preferably a group represented by the general formula (2-5), an alkyl group having 1 to 6 carbon atoms, a phenyl group which has an alkyl group having 1 to 3 carbon atoms or is unsubstituted, or a linear alkylene group having 2 to 4 carbon atoms formed by $R_3$ and $R_4$; still more preferably an alkyl group having 1 to 6 carbon atoms or a trimethylene group formed by $R_3$ and $R_4$; and particularly preferably an alkyl group having 1 to 6 carbon atoms. Specific examples thereof include a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, an ethylene group formed by $R_3$ and $R_4$, a trimethylene group formed by $R_3$ and $R_4$, a tetramethylene group formed by $R_3$ and $R_4$, and groups represented by the following formulae. It should be noted that the alkyl group in the specific examples is not limited to a normal-form and includes all branched forms such as a sec-form, a tert-form, an iso-form, and a neo-form. Among these, the normal-form or the iso-form is preferable, and the normal-form is more preferable.

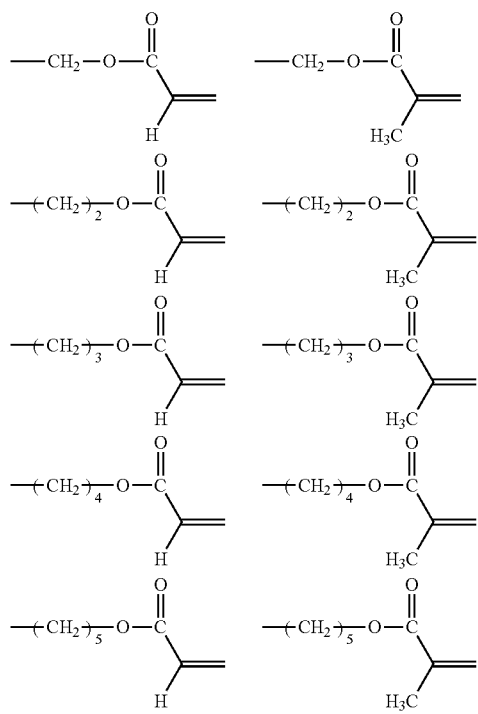

-continued

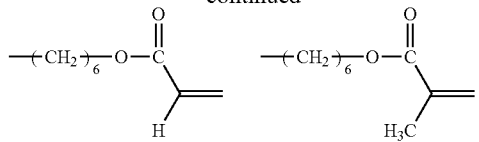

Among the specific examples, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_3$ and $R_4$, a trimethylene group formed by $R_3$ and $R_4$, a tetramethylene group formed by $R_3$ and $R_4$, a group represented by the general formula (2-5-1), or a group represented by the general formula (2-5-2) is preferable; the methyl group, the ethyl group, the n-propyl group, the isopropyl group, the n-butyl group, the isobutyl group, the sec-butyl group, the tert-butyl group, or the trimethylene group formed by $R_3$ and $R_4$ is more preferable; the methyl group, the ethyl group, or the trimethylene group formed by $R_3$ and $R_4$ is still more preferable; and the ethyl group is particularly preferable.

$R_4$ in the general formula (1) represents preferably a hydrogen atom, an alkyl group having 1 to 4 carbon atoms, or a linear alkylene group having 2 to 4 carbon atoms as $R_3$ and $R_4$; more preferably a hydrogen atom or a trimethylene group formed by $R_3$ and $R_4$; and still more preferably a hydrogen atom. Specific examples thereof include a hydrogen atom, a methyl group, an ethyl group, an n-propyl group, an isopropyl group, an n-butyl group, an isobutyl group, a sec-butyl group, a tert-butyl group, an ethylene group formed by $R_3$ and $R_4$, a trimethylene group formed by $R_3$ and $R_4$, and a tetramethylene group formed by $R_3$ and $R_4$. Among these, the hydrogen atom, the methyl group, the ethyl group, or the trimethylene group formed by $R_3$ and $R_4$ is preferable, the hydrogen atom or the trimethylene group formed by $R_3$ and $R_4$ is more preferable, and the hydrogen atom is still more preferable.

Examples of the alkyl group having 1 to 20 carbon atoms as $R_5$ in the general formula (1) are the same as those exemplified as the alkyl group having 1 to 20 carbon atoms as $R_2$ and $R_3$ in the general formula (1), and the preferred examples thereof are the same as described above.

The haloalkyl group having 1 to 20 carbon atoms as $R_5$ in the general formula (1) may be any of linear, branched, or cyclic. Among these, the haloalkyl group is preferably linear or branched and more preferably linear. In addition, among examples of the haloalkyl group having 1 to 20 carbon atoms, a haloalkyl group having 1 to 12 carbon atoms is preferable, a haloalkyl group having 1 to 6 carbon atoms is more preferable, and a haloalkyl group having 1 to 3 carbon atoms is still more preferable. Specific examples thereof include a chloroalkyl group such as a chloromethyl group, a trichloromethyl group, a 2-chloroethyl group, a 2,2,2-trichloroethyl group, a pentachloroethyl group, a 2-chloropropyl group, a 3-chloropropyl group, a 2-chloro-2-propyl group, or a heptachloropropyl group; a bromoalkyl group such as a bromomethyl group, a tribromomethyl group, a 2-bromoethyl group, a 2,2,2-tribromoethyl group, a pentabromoethyl group, a 2-bromopropyl group, a 3-bromopropyl group, a 2-bromo-2-propyl group, or a heptabromopropyl group; an iodoalkyl group such as an iodomethyl group, a triiodomethyl group, a 2-iodoethyl group, a 2,2,2-triiodoethyl group, a pentaiodomethyl group, a 2-iodopropyl group, a 3-iodopropyl group, a 2-iodo-2-propyl group, or a heptaiodopropyl group; and a fluoroalkyl group such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group, or a heptafluoropropyl group. Among these, a perhalogenoalkyl group such as a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, a trifluoromethyl group, a pentafluoroethyl group, or a heptafluoropropyl group is preferable; a perfluoroalkyl group such as a trifluoromethyl group, a pentafluoroethyl group, or a heptafluoropropyl group is more preferable; and a trifluoromethyl group is still more preferable.

In the present specification, the "acyl group having 2 to 21 carbon atoms" indicates a carbonyl group to which an alkyl group having 1 to 20 carbon atoms is bonded. Examples of the alkyl group having 1 to 20 carbon atoms are the same as those exemplified as the alkyl group having 1 to 20 carbon atoms as $R_2$ and $R_3$ in the general formula (1).

The acyl group having 2 to 21 carbon atoms as $R_5$ in the general formula (1) may be any of linear, branched, or cyclic. Among these, the acyl group is preferably linear or branched and more preferably linear. In addition, among examples of the acyl group having 2 to 21 carbon atoms, an acyl group having 2 to 13 carbon atoms is preferable, an acyl group having 2 to 7 carbon atoms is more preferable, and an acyl group having 2 to 5 carbon atoms is still more preferable. Specific examples thereof include an acetyl group, a propionyl group, an n-butyryl group, an isobutyryl group, an n-pentanoyl group, an isopentanoyl group, a sec-pentanoyl group, a tert-pentanoyl group, a cyclopentanoyl group, an n-hexanoyl group, a cyclohexanoyl group, an n-heptanoyl group, a cycloheptanoyl group, an n-octanoyl group, a cyclooctanoyl group, an n-nonanoyl group, an n-decanoyl group, an n-undecanoyl group, an n-dodecanoyl group, an n-tridecanoyl group, an n-tetradecanoyl group, an n-pentadecanoyl group, an n-hexadecanoyl group, an n-heptadecanoyl group, an n-octadecanoyl group, an n-nonadecanoyl group, an n-icosanoyl group, and an n-henicosanoyl group. Among these, the acetyl group, the propionyl group, the n-butyryl group, the isobutyryl group, the n-pentanoyl group, the isopentanoyl group, the sec-pentanoyl group, the tert-pentanoyl group, the n-hexanoyl group, or the n-heptanoyl group is preferable; the acetyl group, the propionyl group, the n-butyryl group, or the n-pentanoyl group is more preferable; and the acetyl group or a propionyl group is still more preferable.

Examples of the unsubstituted aryl group having 6 to 14 carbon atoms of the "aryl group having 6 to 14 carbon atoms which has a substituent or is unsubstituted" as $R_5$ in the general formula (1) include a phenyl group, a naphthyl group, and an anthracenyl group. Among these, the phenyl group is preferable.

Examples of the aryl group having 6 to 14 carbon atoms which has a substituent of the "aryl group having 6 to 14 carbon atoms which has a substituent or is unsubstituted" as $R_5$ in the general formula (1) are the same as those exemplified as the aryl group having 6 to 14 carbon atoms which has a substituent as $R_2$ and $R_3$ in the general formula (1), and the preferred examples thereof are the same as described above.

$R_5$ in the general formula (1) represents preferably a group represented by the general formula (2-4), a formyl group, an alkyl group having 1 to 12 carbon atoms, a haloalkyl group having 1 to 6 carbon atoms, an acyl group having 2 to 7 carbon atoms, an alkyl group having 1 to 6 carbon atoms, or an unsubstituted phenyl group; more preferably a group represented by the general formula (2-5), a formyl group, an alkyl group having 1 to 6 carbon atoms, a haloalkyl group having 1 to 3 carbon atoms, an acyl group having 2 to 5 carbon atoms, or a phenyl group which has an alkyl group having 1 to 3 carbon atoms or is unsubstituted; still more preferably an alkyl group having 1 to 6 carbon atoms or an unsubstituted phenyl group; and particularly preferably an alkyl group having 1 to 6 carbon atoms. Specific examples thereof include a formyl group, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a trifluoromethyl group, a pentafluoroethyl group, a heptafluoropropyl group, an acetyl group, a propionyl group, an n-butyryl group, an n-pentanoyl group, a p-tolyl group, an p-ethylphenyl group, a p-n-propylphenyl group, a p-isopropylphenyl group, a phenyl group, a group represented by the general formula (2-5-1), and a group represented by the general formula (2-5-2). Among these, the methyl group, the ethyl group, the n-propyl group, the isopropyl group, the n-butyl group, the isobutyl group, the sec-butyl group, the tert-butyl group, or the phenyl group is preferable, the methyl group, the ethyl group, or the phenyl group is more preferable, and the ethyl group is particularly preferable.

The alkoxycarbonyl group having 2 to 21 carbon atoms as $R_1$ in the general formula (1) may be any of linear, branched, or cyclic. Among these, the alkoxycarbonyl group is preferably linear or branched and more preferably linear. In addition, among examples of the alkoxycarbonyl group having 2 to 21 carbon atoms, an alkoxycarbonyl group having 2 to 13 carbon atoms is preferable, an alkoxycarbonyl group having 2 to 7 carbon atoms is more preferable, and an alkoxycarbonyl group having 2 to 5 carbon atoms is still more preferable. Specific examples thereof include a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, a cyclobutoxycarbonyl group, an n-pentyloxycarbonyl group, a cyclopentyloxycarbonyl group, an n-hexyloxycarbonyl group, a cyclohexyloxycarbonyl group, an n-heptyloxycarbonyl group, a cycloheptyloxycarbonyl group, an n-octyloxycarbonyl group, an n-nonyloxycarbonyl group, an n-decyloxycarbonyl group, an n-undecyloxycarbonyl group, an n-dodecyloxycarbonyl group, an n-tridecyloxycarbonyl group, an n-tetradecyloxycarbonyl group, an n-pentadecyloxycarbonyl group, an n-hexadecyloxycarbonyl group, an n-heptadecyloxycarbonyl group, an n-octadecyloxycarbonyl group, an n-nonadecyloxycarbonyl group, and an n-icosyloxycarbonyl group. Among these, the methoxycarbonyl group, the ethoxycarbonyl group, the n-propoxycarbonyl group, the isopropoxycarbonyl group, the n-butoxycarbonyl group, the isobutoxycarbonyl group, the sec-butoxycarbonyl group, the tert-butoxycarbonyl group, the n-pentyloxycarbonyl group, or the n-hexyloxycarbonyl group is preferable; the methoxycarbonyl group, the ethoxycarbonyl group, the n-propoxycarbonyl group, the isopropoxycarbonyl group, the n-butoxycarbonyl group, the isobutoxycarbonyl group, the sec-butoxycarbonyl group, or the tert-butoxycarbonyl group is more preferable; the methoxycarbonyl group or the ethoxycarbonyl group is still more preferable.

In the present specification, the "monoalkylaminocarbonyl group having 2 to 21 carbon atoms" indicates a functional group in which one alkyl group having 1 to 20 carbon atoms is bonded to the N-terminal of an aminocarbonyl group. Examples of the alkyl group having 1 to 20 carbon atoms are the same as those exemplified as the alkyl group having 1 to 20 carbon atoms as $R_2$ and $R_3$ in the general formula (1).

The monoalkylaminocarbonyl group having 2 to 21 carbon atoms as $R_6$ in the general formula (1) may be any of linear, branched, or cyclic. Among these, the monoalkylaminocarbonyl group is preferably linear or branched and more preferably linear. In addition, among examples of the monoalkylaminocarbonyl group having 2 to 21 carbon atoms, a monoalkylaminocarbonyl group having 2 to 13 carbon atoms is preferable, a monoalkylaminocarbonyl group having 2 to 7 carbon atoms is more preferable, and a monoalkylaminocarbonyl group having 2 to 5 carbon atoms is still more preferable. Specific examples thereof include a methylaminocarbonyl group, an ethylaminocarbonyl group, an n-propylaminocarbonyl group, an isopropylaminocarbonyl group, an n-butylaminocarbonyl group, an isobutylaminocarbonyl group, a sec-butylaminocarbonyl group, a tert-butylaminocarbonyl group, a cyclobutylaminocarbonyl group, an n-pentylaminocarbonyl group, a cyclopentylaminocarbonyl group, an n-hexylaminocarbonyl group, a cyclohexylaminocarbonyl group, an n-heptylaminocarbonyl group, a cycloheptylaminocarbonyl group, an n-octylaminocarbonyl group, an n-nonylaminocarbonyl group, an n-decylaminocarbonyl group, an n-undecylaminocarbonyl group, an n-dodecylaminocarbonyl group, an n-tridecylaminocarbonyl group, an n-tetradecylaminocarbonyl group, an n-pentadecylaminocarbonyl group, an n-hexadecylaminocarbonyl group, an n-heptadecylaminocarbonyl group, an n-octadecylaminocarbonyl group, an n-nanodecylaminocarbonyl group, and an n-icosylaminocarbonyl group. Among these, the methylaminocarbonyl group, the ethylaminocarbonyl group, the n-propylaminocarbonyl group, the isopropylaminocarbonyl group, the n-butylaminocarbonyl group, the isobutylaminocarbonyl group, the sec-butylaminocarbonyl group, the tert-butylaminocarbonyl group, the n-pentylaminocarbonyl group, or the n-hexylaminocarbonyl group is preferable; the methylaminocarbonyl group, the ethylaminocarbonyl group, the n-propylaminocarbonyl group, the n-butoxyaminocarbonyl group is more preferable; and the methylaminocarbonyl group or the ethylaminocarbonyl group is still more preferable.

In the present specification, the "dialkylaminocarbonyl group having 3 to 41 carbon atoms" indicates a functional group in which two alkyl groups having 1 to 20 carbon atoms are bonded to the N-terminal of an aminocarbonyl group. Examples of the alkyl group having 1 to 20 carbon atoms are the same as those exemplified as the alkyl group having 1 to 20 carbon atoms as $R_2$ and $R_3$ in the general formula (1).

In the dialkylaminocarbonyl group having 3 to 41 carbon atoms as $R_6$ in the general formula (1), two alkyl groups at the N-terminal may be any of linear, branched, or cyclic. Among these, it is preferable that at least one alkyl group is linear and more preferable that two alkyl groups are linear. In addition, among examples of the dialkylaminocarbonyl group having 3 to 41 carbon atoms, a dialkylaminocarbonyl group having 3 to 13 carbon atoms is preferable, a dialkylaminocarbonyl group having 3 to 9 carbon atoms is more preferable, and a dialkylaminocarbonyl group having 3 to 5 carbon atoms is still more preferable. Specific examples thereof include a N,N-dimethylaminocarbonyl group, a N,N-diethylaminocarbonyl group, a N,N-di(n-propyl)aminocarbonyl group, a N,N-di(n-butyl)aminocarbonyl group, a N,N-di(n-pentyl)aminocarbonyl group, a N,N-di(n-hexyl)aminocarbonyl group, a N,N-di(n-heptyl)aminocarbonyl group, a N,N-di(n-octyl)aminocarbonyl group, a N,N-di(n-nonyl)aminocarbonyl group, a N,N-di(n-decyl)aminocarbonyl group, a N,N-di(n-undecyl)aminocarbonyl group, a N,N-di(n-dodecyl)aminocarbonyl group, a N,N-ethylmethylaminocarbonyl group, a N,N-methyl-n-propylaminocarbonyl group, a N,N-isopropylmethylaminocarbonyl group, a N,N-methyl-n-butylaminocarbonyl group, a N,N-isobutylmethylaminocarbonyl group, a N,N-methyl-sec-butylaminocarbonyl group, a N,N-methyl-tert-butylaminocarbonyl group, a N,N-cyclobutylmethylaminocarbonyl group, a N,N-methyl-n-pentylaminocarbonyl group, a N,N-cyclopentylmethylaminocarbonyl group, a N,N-methyl-n-hexylaminocarbonyl group, a N,N-cyclohexylmethylaminocarbonyl group, a N,N-methyl-n-heptylaminocarbonyl group, a N,N-cycloheptylmethylaminocarbonyl group, a N,N-methyl-n-octylaminocarbonyl group, a N,N-methyl-n-nonylaminocarbonyl group, a N,N-methyl-n-decylaminocarbonyl group, a N,N-methyl-n-undecylaminocarbonyl group, a N,N-methyl-n-dodecylaminocarbonyl group, a N,N-methyl-n-tridecylaminocarbonyl group, a N,N-methyl-n-tetradecylaminocarbonyl group, a N,N-methyl-n-pentadecylaminocarbonyl group, a N,N-methyl-n-hexadecylaminocarbonyl group, a N,N-methyl-n-heptadecylaminocarbonyl group, a N,N-methyl-n-octadecylaminocarbonyl group, a N,N-methyl-n-nonadecylaminocarbonyl group, a N,N-methyl-n-icosylaminocarbonyl group, a N,N-ethyl-n-propylaminocarbonyl group, a N,N-ethylisopropylaminocarbonyl group, a N,N-ethyl-n-butylaminocarbonyl group, a N,N-ethylisobutylaminocarbonyl group, a N,N-ethyl-sec-butylaminocarbonyl group, a N,N-ethyl-tert-butylaminocarbonyl group, a N,N-cyclobutylethylaminocarbonyl group, a N,N-ethyl-n-pentylaminocarbonyl group, a N,N-cyclopentylethylaminocarbonyl group, a N,N-ethyl-n-hexylaminocarbonyl group, a N,N-cyclohexylethylaminocarbonyl group, a N,N-ethyl-n-heptylaminocarbonyl group, a N,N-cycloheptylethylaminocarbonyl group, a N,N-ethyl-n-octylaminocarbonyl group, a N,N-ethyl-n-nonylaminocarbonyl group, a N,N-ethyl-n-decylaminocarbonyl group, a N,N-ethyl-n-undecylaminocarbonyl group, a N,N-ethyl-n-dodecylaminocarbonyl group, a N,N-ethyl-n-tridecylaminocarbonyl group, a N,N-ethyl-n-tetradecylaminocarbonyl group, a N,N-ethyl-n-pentadecylaminocarbonyl group, a N,N-ethyl-n-hexadecylaminocarbonyl group, a N,N-ethyl-n-heptadecylaminocarbonyl group, a N,N-ethyl-n-octadecylaminocarbonyl group, a N,N-ethyl-n-nonadecylaminocarbonyl group, and a N,N-ethyl-n-icosylaminocarbonyl group. Among these, the N,N-dimethylaminocarbonyl group, the N,N-diethylaminocarbonyl group, the N,N-di(n-propyl)aminocarbonyl group, the N,N-di(n-butyl)aminocarbonyl group, the N,N-ethylmethylaminocarbonyl group, the N,N-methyl-n-propylaminocarbonyl group, the N,N-methyl-n-butylaminocarbonyl group, the N,N-ethyl-n-propylaminocarbonyl group, or the N,N-ethyl-n-butylaminocarbonyl group is preferable, and the N,N-dimethylaminocarbonyl group, the N,N-diethylaminocarbonyl group, or the N,N-ethylmethylaminocarbonyl group is more preferable.

The alkylcarbonylamino group having 2 to 21 carbon atoms as $1_6$ in the general formula (1) may be any of linear, branched, or cyclic. Among these, the alkylcarbonylamino group is preferably linear or branched and more preferably linear. In addition, among examples of the alkylcarbonylamino group having 2 to 21 carbon atoms, an alkylcarbonylamino group having 2 to 13 carbon atoms is preferable, an alkylcarbonylamino group having 2 to 7 carbon atoms is more preferable, and an alkylcarbonylamino group having 2 to 5 carbon atoms is still more preferable. Specific examples thereof include a methylcarbonylamino group, an ethylcarbonylamino group, an n-propylcarbonylamino group, an isopropylcarbonylamino group, an n-butylcarbonylamino group, an isobutylcarbonylamino group, a sec-butylcarbonylamino group, a tert-butylcarbonylamino group, a cyclobutylcarbonylamino group, an n-pentylcarbonylamino group, a cyclopentylcarbonylamino group, an n-hexylcarbonylamino group, a cyclohexylcarbonylamino group, an n-heptylcarbonylamino group, a cycloheptylcarbonylamino group, an n-octylcarbonylamino group, an n-nonylcarbonylamino group, an n-decylcarbonylamino group, an n-undecylcarbonylamino group, an n-dodecylcarbonylamino group, an n-tridecylcarbonylamino group, an n-tetradecylcarbonylamino group, an n-pentadecylcarbonylamino group, an n-hexadecylcarbonylamino group, an n-heptadecylcarbonylamino group, an n-octadecylcarbonylamino group, an n-nonadecylcarbonylamino group, and an n-icosylcarbonylamino group. Among these, the methylcarbonylamino group, the ethylcarbonylamino group, the n-propylcarbonylamino group, the isopropylcarbonylamino group, the n-butylcarbonylamino group, the isobutylcarbonylamino group, the sec-butylcarbonylamino group, the tert-butylcarbonylamino group, the n-pentylcarbonylamino group, or the n-hexylcarbonylamino group is preferable; the methylcarbonylamino group, the ethylcarbonylamino group, the n-propylcarbonylamino group, the n-butoxycarbonylamino group is more preferable; and the methylcarbonylamino group or the ethylcarbonylamino group is still more preferable.

The bonding position for R % in the general formula (1) may be any of I- to V-positions in the following general formula (1-1). R % is positioned preferably at the I-position, the III-position, or the V-position and more preferably at the I-position or the V-position in a case where $n_1$ represents 1; R % is positioned preferably at the I-position and the III-position or the III-position and the V-position in a case where $n_1$ represents 2; R % is positioned preferably at the I-position, the III-position, and the V-position in a case where $n_1$ represents 3; $R_6$ is positioned preferably at the I- to IV-positions or the II- to V-positions in a case where $n_1$ represents 4; and $R_6$ is positioned at all the I- to V-positions in a case where $n_1$ represents 5.

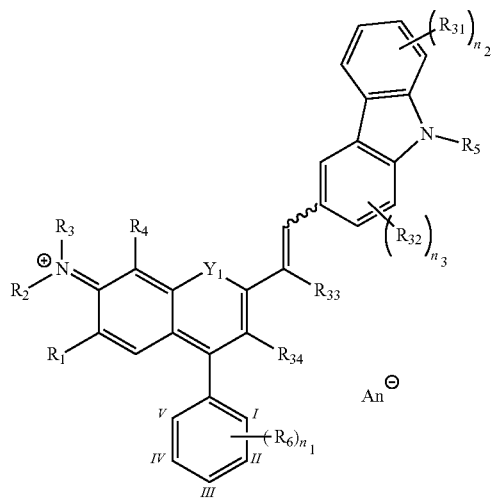

(1-1)

(In the formula, I to V represent a position which can be substituted with $R_6$, and $R_1$ to $R_6$, $R_{31}$ to $R_{34}$, $Y_1$, An$^-$, and $n_1$ to $n_3$ each have the same definition as described above.)

$R_6$ in the general formula (1) represents preferably a group represented by the general formula (2), a carboxy group, an alkoxycarbonyl group having 2 to 13 carbon atoms, a carbamoyl group, a monoalkylaminocarbonyl group having 2 to 7 carbon atoms, a dialkylaminocarbonyl group having 3 to 9 carbon atoms, or an alkylcarbonylamino group having 2 to 7 carbon atoms; more preferably a group represented by any of the general formulae (2'a) to (2'd), a carboxy group, an alkoxycarbonyl group having 2 to 7 carbon atoms, a carbamoyl group, a monoalkylaminocarbonyl group having 2 to 5 carbon atoms, a dialkylaminocarbonyl group having 3 to 5 carbon atoms, or an alkylcarbonylamino group having 2 to 5 carbon atoms; still more preferably a group represented by any of the general formulae (2"a) to (2"d), a carboxy group, or an alkoxycarbonyl group having 2 to 7 carbon atoms; and particularly preferably a group represented by the general formula (2"a), a carboxy group, or an alkoxycarbonyl group having 2 to 5 carbon atoms. Specific examples thereof include a carboxy group, a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, an n-pentyloxycarbonyl group, an n-hexyloxycarbonyl group, a carbamoyl group, a methylaminocarbonyl group, an ethylaminocarbonyl group, a N,N-dimethylaminocarbonyl group, a N,N-diethylaminocarbonyl group, a N,N-ethylmethylaminocarbonyl group, a methylcarbonylamino group, an ethylcarbonylamino group, and groups represented by the following formulae.

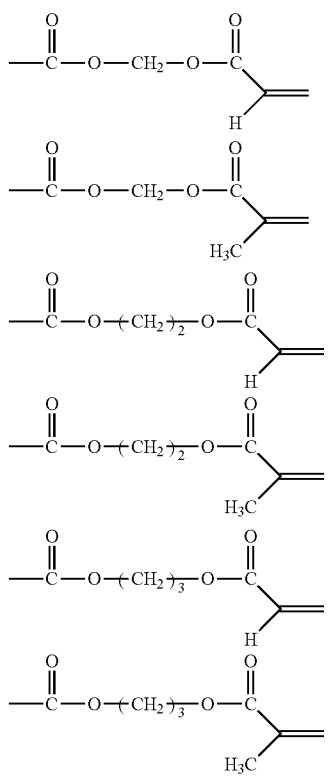

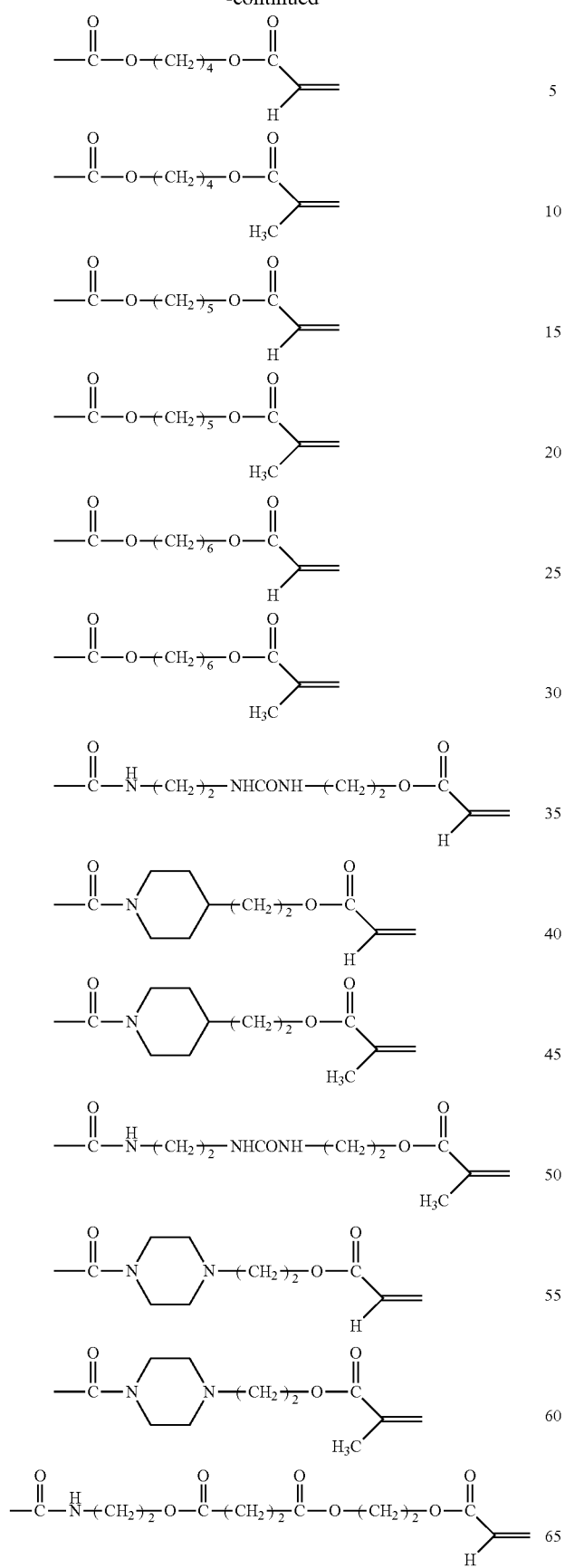
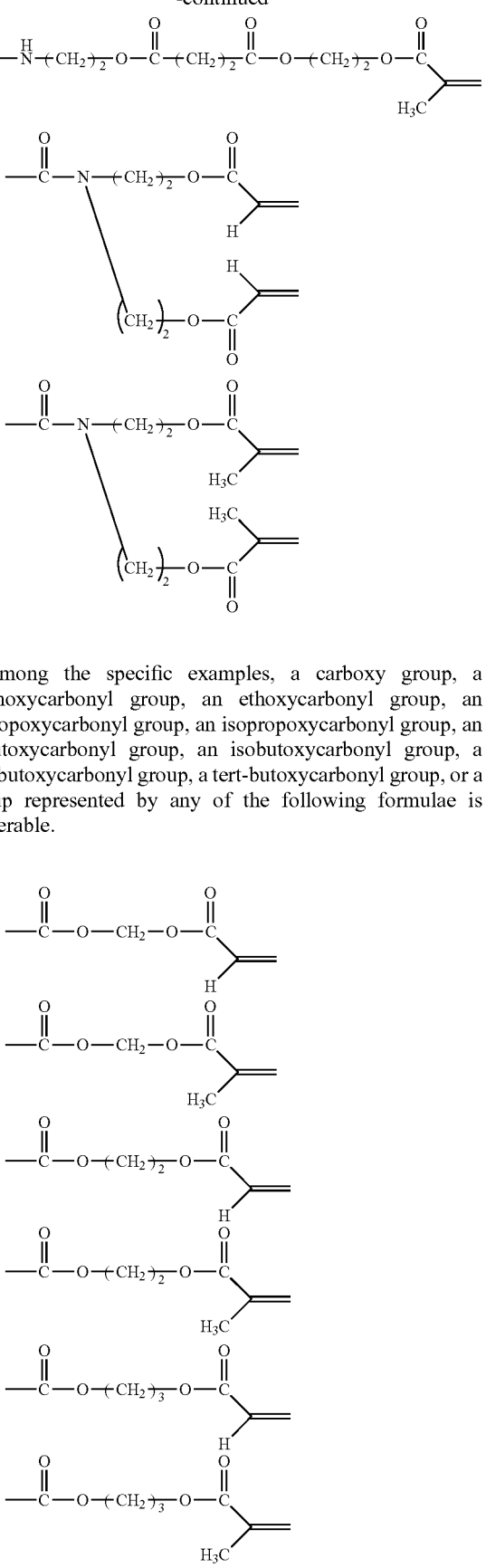
Among the specific examples, a carboxy group, a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, or a group represented by any of the following formulae is preferable.

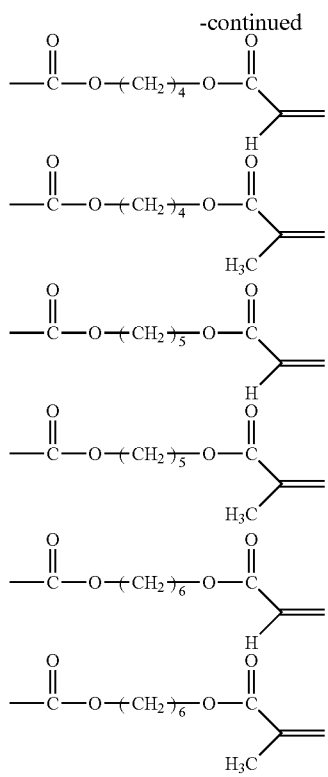

Among the specific examples, a carboxy group, a methoxycarbonyl group, an ethoxycarbonyl group, a group represented by the general formula (2″-1), or a group represented by the general formula (2″-2) is more preferable.

It is preferable that $n_1$ in the general formula (1) represents 1.

Examples of the halogeno group as $R_{31}$ and $R_{32}$ in the general formula (1) include a fluoro group, a chloro group, a bromo group, and an iodo group. Among these, the fluoro group is preferable.

Examples of the alkyl group having 1 to 6 carbon atoms as $R_{31}$ and $R_{32}$ in the general formula (1) are the same as those exemplified as the alkyl group having 1 to 6 carbon atoms as $R_1$ and $R_4$ in the general formula (1), and the preferred examples thereof are the same as described above.

The alkoxy group having 1 to 6 carbon atoms as $R_{31}$ and $R_{32}$ in the general formula (1) may be any of linear, branched, or cyclic. Among these, the alkoxy group is preferably linear or branched and more preferably linear. In addition, among the alkoxy group having 1 to 6 carbon atoms, an alkoxy group having 1 to 4 carbon atoms is preferable. Specific examples thereof include a methoxy group, an ethoxy group, an n-propoxy group, an isopropoxy group, an n-butoxy group, an isobutoxy group, a sec-butoxy group, a tert-butoxy group, a cyclobutoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, and a cyclohexyloxy group. Among these, the methoxy group, the ethoxy group, the n-propoxy group, the isopropoxy group, the n-butoxy group, the isobutoxy group, the sec-butoxy group, or the tert-butoxy group is preferable; the methoxy group or the ethoxy group is more preferable; and the methoxy group is particularly preferable.

The bonding position for $R_{31}$ in the general formula (1) may be any of I- to V-positions in the following general formula (1-2). $R_{31}$ is positioned preferably at the II-position in a case where $n_2$ represents 1; $R_{31}$ is positioned preferably at the II-position and the III-position in a case where $n_2$ represents 2; $R_{31}$ is positioned preferably at the I- to III-positions or the II- to IV-positions in a case where $n_2$ represents 3; and $R_{31}$ is positioned at all the I- to IV-positions in a case where $n_2$ represents 4.

(1-2)

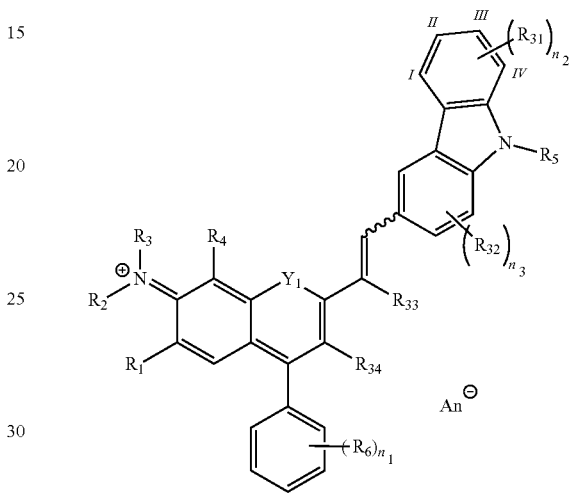

(In the formula, I to IV represent a position which can be substituted with $R_{31}$, and $R_1$ to $R_6$, $R_{31}$ to $R_{34}$, $Y_1$, $An^-$, and $n_1$ to $n_3$ each have the same definition as described above.)

The bonding position for $R_{32}$ in the general formula (1) may be any of I- to III-positions in the following general formula (1-3). $R_{32}$ is positioned preferably at the II-position in a case where $n_3$ represents 1; $R_{32}$ is positioned preferably at the I-position and the II-position or the II-position and the III-position in a case where $n_3$ represents 2; and $R_{32}$ is positioned at all the I- to III-positions in a case where $n_3$ represents 3.

(1-3)

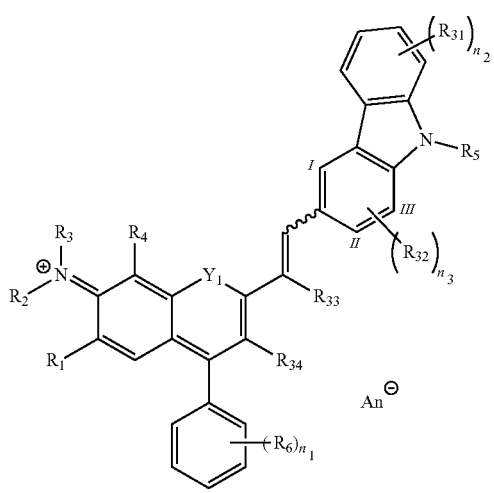

(In the formula, I to V represent a position which can be substituted with $R_6$, and $R_1$ to $R_6$, $R_{31}$ to $R_{34}$, $Y_1$, $An^-$, and $n_1$ to $n_3$ each have the same definition as described above.)

It is preferable that $R_{31}$ and $R_{32}$ in the general formula (1) represent an alkoxy group having 1 to 4 carbon atoms. Specific examples thereof include a hydroxy group, a fluoro group, a methyl group, an ethyl group, a methoxy group, an ethoxy group, an n-propoxy group, an isopropoxy group, an n-butoxy group, an isobutoxy group, a sec-butoxy group, and a tert-butoxy group. Among these, the methoxy group or the ethoxy group is preferable, and the methoxy group is more preferable.

It is preferable that $n_2$ and $n_3$ in the general formula (1) each represent 0 or 1, more preferable that both of $n_2$ and $n_3$ represent 0 or any one of $n_2$ and $n_3$ represents 0 and the other represents 0, and particularly preferable that both of $n_2$ and $n_3$ represent 0.

Examples of the alkyl group having 1 to 6 carbon atoms as $R_{33}$ and $R_{34}$ in the general formula (1) are the same as those exemplified as the alkyl group having 1 to 6 carbon atoms as $R_1$ and $R_4$ in the general formula (1), and the preferred examples thereof are the same as described above.

In the general formula (1), in a case where $R_{33}$ and $R_{34}$ form a linear alkylene group having 2 to 4 carbon atoms which has an alkyl group having 1 to 6 carbon atoms as a substituent or is unsubstituted, examples of the linear alkylene group having 2 to 4 carbon atoms include an ethylene group, a trimethylene group, and a tetramethylene group. Among these, the trimethylene group is preferable.

In the general formula (1), in a case where $R_{33}$ and $R_{34}$ form a linear alkylene group having 2 to 4 carbon atoms which has an alkyl group having 1 to 6 carbon atoms as a substituent, examples of the alkyl group having 1 to 6 carbon atoms as a substituent are the same as those exemplified as the alkyl group having 1 to 6 carbon atoms as $R_1$ and $R_4$ in the general formula (1), and the preferred examples thereof are the same as described above.

In the general formula (1), in a case where $R_{33}$ and $R_{34}$ form a linear alkylene group having 2 to 4 carbon atoms which has an alkyl group having 1 to 6 carbon atoms as a substituent or is unsubstituted, the general formula (1) is represented by the following general formula (9).

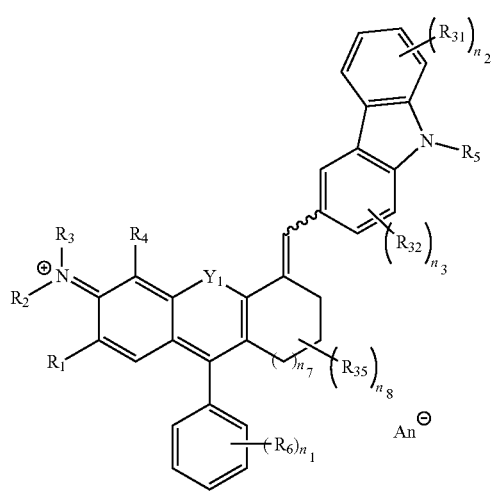

(9)

(In the formula, $R_{35}$ represents an alkyl group having 1 to 6 carbon atoms, $n_7$ represents an integer of 0 to 2, $n_8$ represents an integer of 0 to 2 in a case where $n_7$ represents 0, $n_8$ represents an integer of 0 to 3 in a case where $n_7$ represents 1, $n_8$ represents an integer of 0 to 4 in a case where $n_7$ represents 2, and $R_1$ to $R_6$, $R_{31}$, $R_{32}$, $Y_1$, $An^-$, and $n_1$ to $n_3$ each have the same definition as described above.)

Examples of the alkyl group having 1 to 6 carbon atoms as $R_{35}$ in the general formula (9) are the same as those exemplified as the alkyl group having 1 to 6 carbon atoms as $R_1$ and $R_4$ in the general formula (1), and the preferred examples thereof are the same as described above.

It is preferable that $n_7$ in the general formula (9) represents 1.

It should be noted that $-(CH_2)_{n7}-$ represents a bond in a case where $n_7$ represents 0.

$n_8$ in the general formula (9) represents preferably 0 or 1 and more preferably 0.

The general formula (9) is represented by the following general formula (9-1) in a case where $n_7$ represents 0; the general formula (9) is represented by the following general formula (9-2) in a case where $n_7$ represents 1; and the general formula (9) is represented by the following general formula (9-3) in a case where $n_7$ represents 2.

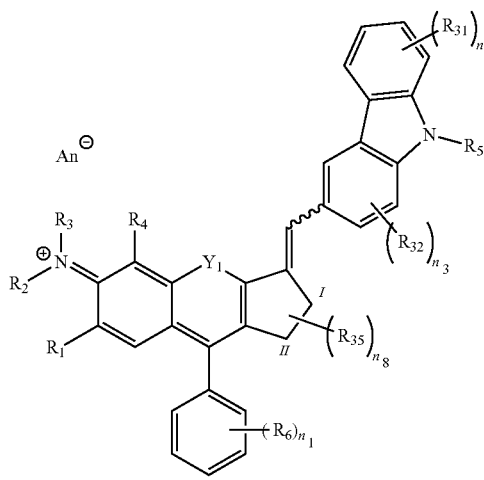

(9-1)

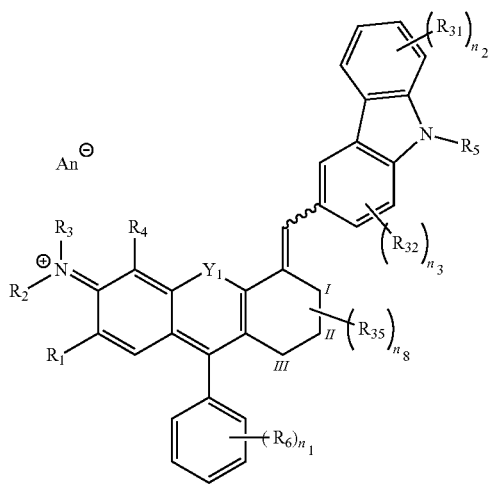

(9-2)

(9-3)

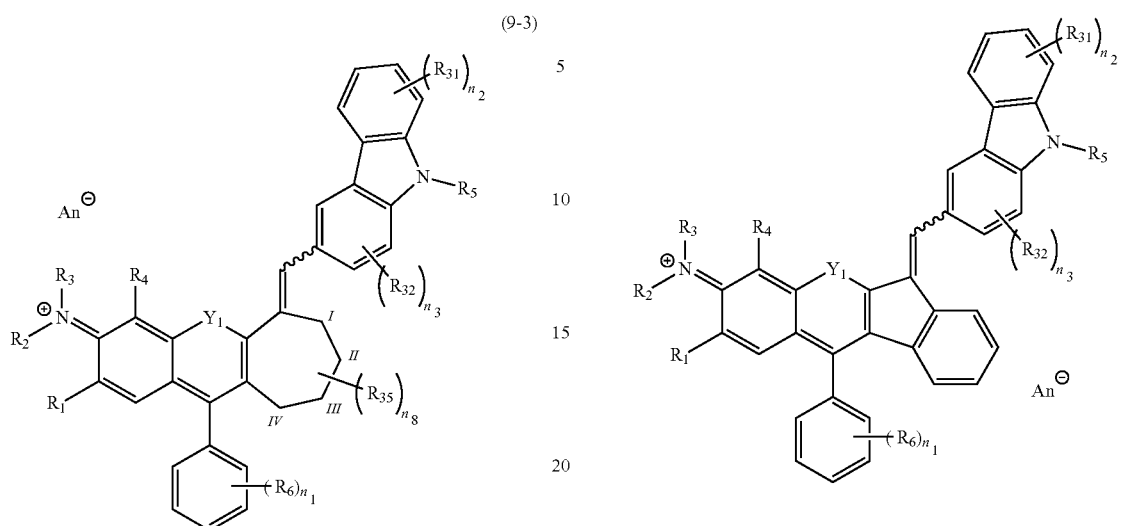

(10)

(In the formulae, the I- to IV-positions represent a position which can be substituted with $R_{35}$, and $R_1$ to $R_6$, $R_{31}$, $R_{32}$, $R_{35}$, $Y_1$, $An^-$, $n_1$ to $n_3$, $n_8$ each have the same definition as described above.)

The bonding position as $R_{35}$ in the general formula (9-1) may be the I-position or the II-position. Further, $R_{35}$ is preferably positioned at the II-position in a case where $n_8$ represents 1, and $R_{35}$ is positioned at the I-position and the II-position in a case where $n_8$ represents 2.

The bonding position as $R_{35}$ in the general formula (9-2) may be any of the I- to III-positions. Further, $R_{35}$ is preferably positioned at the II-position in a case where $n_8$ represents 1; $R_{35}$ is preferably positioned at the II-position and the III-position in a case where $n_8$ represents 2; and $R_{35}$ is positioned at all the I- to III-positions in a case where $n_8$ represents 3.

The bonding position as $R_{35}$ in the general formula (9-3) may be any of the I- to IV-positions. Further, $R_{35}$ is preferably positioned at the II-position or the III-position in a case where $n_8$ represents 1; $R_{35}$ is preferably positioned at the II-position and the III-position in a case where $n_8$ represents 2; $R_{35}$ is preferably positioned at the II- to IV-positions in a case where $n_8$ represents 3; and $R_{35}$ is positioned at all the I- to IV-positions in a case where $n_8$ represents 4.

In the general formula (1), in a case where $R_{33}$ and $R_{34}$ form an unsubstituted phenylene group, the general formula (1) is represented by the following general formula (10).

(In the formula, $R_1$ to $R_6$, $R_{31}$, $R_{32}$, $Y_1$, $An^-$, and $n_1$ to $n_3$ each have the same definition as described above.)

$R_{33}$ and $R_{34}$ in the general formula (1) represent preferably a hydrogen atom, an alkyl group having 1 to 4 carbon atoms, or a linear alkylene group having 2 to 4 carbon atoms or an unsubstituted phenylene group, which has one alkyl group having 1 to 4 carbon atoms as a substituent or is unsubstituted, formed by $R_{33}$ and $R_{34}$; more preferably a hydrogen atom or an unsubstituted linear alkylene group having 2 to 4 carbon atoms or unsubstituted phenylene group, formed by $R_{33}$ and $R_{34}$; still more preferably an unsubstituted linear alkylene group having 2 to 4 carbon atoms formed by $R_{33}$ and $R_{34}$; and particularly preferably a trimethylene group formed by $R_{33}$ and $R_{34}$.

It is preferable that $Y_1$ in the general formula (1) represents an oxygen atom.

Anion Represented by $An^-$ in Compound According to Embodiment of Present Invention $An^-$ in the general formula (1) may typically represent an anion which has been used in the field. Specific examples thereof include an anion containing an aryl group having an electron-withdrawing substituent, a sulfonyl group having an electron-withdrawing substituent, a haloalkyl group, or a halogeno group; a halogen oxo acid anion; and a sulfonic acid anion (hereinafter, also referred to as an anion according to the present invention).

In the anion according to the present invention, examples of the anionic moiety in the anion containing the aryl group having an electron-withdrawing substituent, the sulfonyl group having an electron-withdrawing substituent, or the haloalkyl group include a sulfonic acid anion, a nitrogen anion (N), a quaternary boron anion, a nitric acid ion, and a phosphoric acid ion. Among these, the sulfonic acid anion, the nitrogen anion, or the quaternary boron anion is preferable, and the quaternary boron anion is more preferable.

In the anion according to the present invention, examples of the anionic moiety in the anion containing a halogeno group include a quaternary boron anion, a phosphorus anion, and an antimony anion. Among these, the phosphorus anion or the antimony anion is preferable.

In the anion according to the present invention, examples of the electron-withdrawing substituent in the aryl group having an electron-withdrawing substituent or the sulfonyl group having an electron-withdrawing substituent include a haloalkyl group having 1 to 3 carbon atoms, a halogeno group, and a nitro group. Among these, the haloalkyl group having 1 to 3 carbon atoms or the halogeno group is preferable, and the halogeno group is particularly preferable.

Examples of the haloalkyl group having 1 to 3 carbon atoms as the electron-withdrawing substituent include a chloroalkyl group such as a chloromethyl group, a trichloromethyl group, a 2-chloroethyl group, a 2,2,2-trichloroethyl group, a pentachloroethyl group, a 2-chloropropyl group, a 3-chloropropyl group, a 2-chloro-2-propyl group, or a heptachloropropyl group; a bromoalkyl group such as a bromomethyl group, a tribromomethyl group, a 2-bromoethyl group, a 2,2,2-tribromoethyl group, a pentabromoethyl group, a 2-bromopropyl group, a 3-bromopropyl group, a 2-bromo-2-propyl group, or a heptabromopropyl group; an iodoalkyl group such as an iodomethyl group, a triiodomethyl group, a 2-iodoethyl group, a 2,2,2-triiodoethyl group, a pentaiodoethyl group, a 2-iodopropyl group, a 3-iodopropyl group, a 2-iodo-2-propyl group, or a heptaiodopropyl group; and a fluoroalkyl group such as a fluoromethyl group, a trifluoromethyl group, a 2-fluoroethyl group, a 2,2,2-trifluoroethyl group, a 1,1,2,2-tetrafluoroethyl group, a pentafluoroethyl group, a 3-fluoropropyl group, a 3,3,3-trifluoropropyl group, a 2,2,3,3-tetrafluoropropyl group, or a heptafluoropropyl group. Among these, a perhalogenoalkyl group such as a trichloromethyl group, a pentachloroethyl group, a heptachloropropyl group, a tribromomethyl group, a pentabromoethyl group, a heptabromopropyl group, a triiodomethyl group, a pentaiodoethyl group, a heptaiodopropyl group, a trifluoromethyl group, a pentafluoroethyl group, or a heptafluoropropyl group is preferable; a perfluoroalkyl group such as a trifluoromethyl group, a pentafluoroethyl group, or a heptafluoropropyl group is more preferable; and a trifluoromethyl group is particularly preferable.

Examples of the halogeno group as the electron-withdrawing substituent include a fluoro group, a chloro group, a bromo group, and an iodo group. Among these, a fluoro group is preferable.

In the anion according to the present invention, as the electron-withdrawing substituent in the aryl group having an electron-withdrawing substituent, those with a strong electron-withdrawing force are preferable among the specific examples. Specifically, a trifluoromethyl group, a fluoro group, or a nitro group is preferable, and the fluoro group is more preferable.

In the anion according to the present invention, as the electron-withdrawing substituent in the sulfonyl group having an electron-withdrawing substituent, a trifluoromethyl group, a pentafluoroethyl group, a heptafluoropropyl group, or a fluoro group is preferable among the specific examples.

In the anion according to the present invention, examples of the aryl group in the aryl group having an electron-withdrawing substituent include a phenyl group and a naphthyl group. Among these, the phenyl group is preferable.

Specific examples of the aryl group having an electron-withdrawing substituent in the anion according to the present invention include groups represented by the following general formulae (11) and (12).

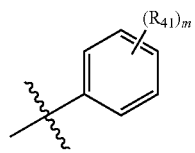

(11)

(In the formula, R$_{41}$ represents a haloalkyl group having 1 to 3 carbon atoms, a halogeno group, or a nitro group, m represents an integer of 1 to 5, and m pieces of R$_{41}$'s may be the same as or different from one another.)

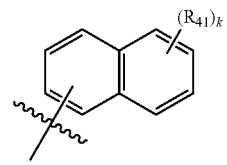

(12)

(In the formula, k represents an integer of 1 to 7, R$_{41}$ has the same definition as described above, and k pieces of R$_{41}$'s may be the same as or different from one another.)

Examples of the haloalkyl group having 1 to 3 carbon atoms as R$_{41}$ in the general formula (11) are the same as those exemplified as the haloalkyl group having 1 to 3 carbon atoms as the electron-withdrawing substituent in the anion according to the present invention, and the preferred examples thereof are the same as described above.

Examples of the halogeno group as R$_{41}$ in the general formula (11) include a fluoro group, a chloro group, a bromo group, and an iodo group. Among these, the fluoro group is preferable.

Specific preferred examples of R$_{41}$ in the general formula (11) are the same as those exemplified as the preferable electron-withdrawing substituent in the aryl group having an electron-withdrawing substituent.

m in the general formula (11) typically represents an integer of 1 to 5. In a case where R$_{41}$ represents a halogeno group, m represents preferably 2 to 5, more preferably 3 to 5, and still more preferably 5. In a case where R$_{41}$ represents a nitro group, m represents preferably 1 to 3 and more preferably 1. In a case where R$_{41}$ represents a haloalkyl group, m represents preferably 1 to 5 and more preferably 1 to 3.

k in the general formula (12) typically represents an integer of 1 to 7. In a case where R$_{41}$ represents a halogeno group, k represents preferably 2 to 7. In a case where R$_{41}$ represents a nitro group, k represents preferably 1 to 3 and more preferably 1. In a case where R$_{41}$ represents a haloalkyl group, k represents preferably 1 to 7 and more preferably 1 to 3.

Specific examples of the group represented by the general formula (11) include a trifluoromethylphenyl group, a di(trifluoromethyl)phenyl group, a tri(trifluoromethyl)phenyl group, a monofluorophenyl group, a difluorophenyl group, a trifluorophenyl group, a perfluorophenyl group, a monochlorophenyl group, a dichlorophenyl group, a trichlorophenyl group, a perchlorophenyl group, a monobromophenyl group, a dibromophenyl group, a tribromophenyl group, a perbromophenyl group, a monoiodophenyl group, a diiodophenyl group, a triiodophenyl group, a periodophenyl group, a nitrophenyl group, a dinitrophenyl group, and a trinitrophenyl group. Among these, the difluorophenyl group, the trifluorophenyl group, or the perfluorophenyl group is preferable, and the perfluorophenyl group is more preferable.

Specific examples of the group represented by the general formula (12) include a trifluoromethylnaphthyl group, a di(trifluoromethyl)naphthyl group, a tri(trifluoromethyl) naphthyl group, a monofluoronaphthyl group, a difluoronaphthyl group, a trifluoronaphthyl group, a perfluoronaphthyl group, a monochloronaphthyl group, a dichloronaphthyl group, a trichloronaphthyl group, a perchloronaphthyl group, a monobromonaphthyl group, a dibromonaphthyl group, a tribromonaphthyl group, a perbromonaphthyl group, a monoiodonaphthyl group, a diiodonaphthyl group, a triiodonaphthyl group, a periodonaphthyl group, a nitronaphthyl group, a dinitronaphthyl group, and a trinitronaphthyl group.

As the aryl group having an electron-withdrawing substituent in the anion according to the present invention, a group represented by the general formula (11) is preferable among the specific examples. Specifically, a trifluoromethylphenyl group, a nitrophenyl group, a dinitrophenyl group, a trinitrophenyl group, a monofluorophenyl group, a difluorophenyl group, a trifluorophenyl group, or a perfluorophenyl group is preferable; the difluorophenyl group, the trifluorophenyl group, the nitrophenyl group, or the perfluorophenyl group is more preferable; and the perfluorophenyl group is more particularly preferable.

Examples of the sulfonyl group having an electron-withdrawing substituent in the anion according to the present invention include —SO$_2$—CF$_3$, —SO$_2$—C$_2$F$_5$, —SO$_2$—C$_3$F$_7$, —SO$_2$—F, —SO$_2$—Cl, —SO$_2$—Br, and —SO$_2$—I.

Examples of the haloalkyl group in the anion according to the present invention include a haloalkyl group having 1 to 3 carbon atoms. Among examples, a perhaloalkyl group is preferable. Specific examples thereof include a trifluoromethyl group, a pentafluoroethyl group, a heptafluoropropyl group, a trichloromethyl group, pentachloroethyl group, a heptachloropropyl group, a tribromomethyl group, a pentabromoethyl group, a heptabromopropyl group, a triiodomethyl group, a pentaiodoethyl group, and a heptaiodopropyl group. Among these, the trifluoromethyl group, the pentafluoroethyl group, or the heptafluoropropyl group is preferable.

Examples of the halogeno group in the anion according to the present invention include a fluoro group, a chloro group, a bromo group, and an iodo group. Among these, the fluoro group is preferable.

In the anion according to the present invention, specific examples of the anion containing the aryl group having an electron-withdrawing substituent, the sulfonyl group having an electron-withdrawing substituent, the haloalkyl group, or the halogeno group include groups represented by the following general formulae (13) to (19).

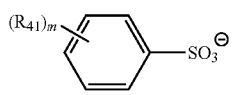
(13)

(In the formula, R$_{41}$ and m each have the same definition as described above, and m pieces of R$_{41}$'s may be the same as or different from one another.)

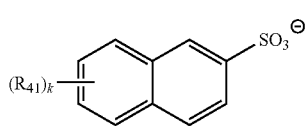
(14)

(In the formula, R$_{41}$ and k each have the same definition as described above, and k pieces of R$_{41}$'s may be the same as or different from one another.)

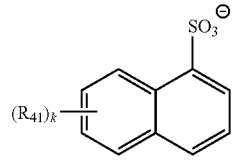
(15)

(In the formula, R$_{41}$ and k each have the same definition as described above, and k pieces of R$_{41}$'s may be the same as or different from one another.)

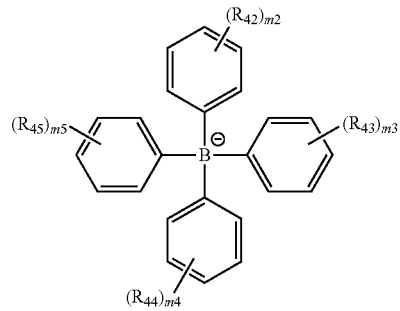
(16)

(In the formula, R$_{42}$ to R$_{45}$ each independently represent a haloalkyl group having 1 to 3 carbon atoms, a halogeno group, or a nitro group, m$_2$ to m$_5$ each independently represent an integer of 1 to 5, m$_2$ pieces of R$_{42}$'s, m$_3$ pieces of R$_{43}$'s, m$_4$ pieces of R$_{44}$'s, and m$_5$ pieces of R$_{45}$'s may be the same as or different from one another respectively.)

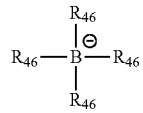
(17)

(In the formula, R$_{46}$ represents a haloalkyl group having 1 to 3 carbon atoms or a halogeno group, and 4 pieces of R$_{46}$'s may be the same as or different from one another.)

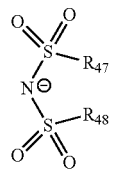
(18)

(In the formula, R$_{47}$ and R$_{48}$ each independently represent a haloalkyl group having 1 to 3 carbon atoms or a halogeno group, and R$_{47}$ and R$_{48}$ may form a halogenated alkylene group having 2 or 3 carbon atoms.)

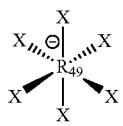
(19)

(In the formula, $R_{49}$ represents a phosphorus atom or an antimony atom, X represents a halogeno group, and 6 pieces of X's are all the same as each other.)

Examples of a combination of $R_{41}$ and m in the general formula (13) include combinations listed in the following table. It should be noted that m pieces of $R_{41}$'s are preferably the same as each other even though $R_{41}$'s are independent of each other.

| $R_{41}$ | m |
|---|---|
| Trifluoromethyl group (—CF$_3$) | 1 to 3 |
| Pentafluoroethyl group (—C$_2$F$_5$) | 1 to 3 |
| Heptafluoropropyl group (—C$_3$F$_7$) | 1 to 3 |
| Nitro group | 1 to 3 |
| Fluoro group | 1 to 5 |
| Chloro group | 1 to 5 |
| Bromo group | 1 to 5 |
| Iodo group | 1 to 5 |

Specific preferred examples of the anion represented by the general formula (13) are as follows.

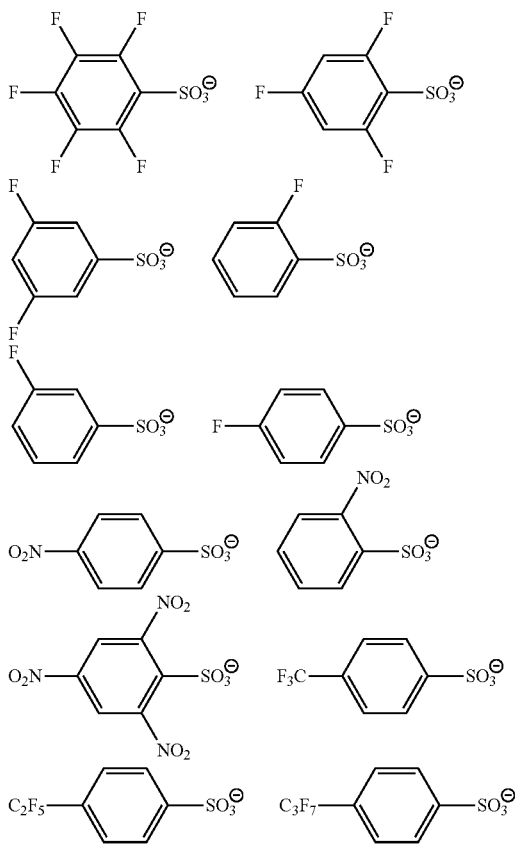

Examples of a combination of $R_{41}$ and k in the general formulae (14) and (15) include combinations listed in the following table. It should be noted that k pieces of $R_{41}$'s are preferably the same as each other even though $R_{41}$'s are independent of each other.

| $R_{41}$ | k |
|---|---|
| Trifluoromethyl group (—CF$_3$) | 1 to 3 |
| Pentafluoroethyl group (—C$_2$F$_5$) | 1 to 3 |
| Heptafluoropropyl group (—C$_3$F$_7$) | 1 to 3 |
| Nitro group | 1 to 3 |
| Fluoro group | 1 to 7 |
| Chloro group | 1 to 7 |
| Bromo group | 1 to 7 |
| Iodo group | 1 to 7 |

Specific preferred examples of the anion represented by the general formulae (14) and (15) are as follows.

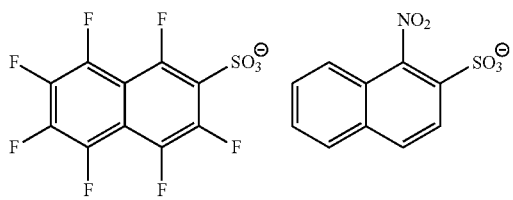

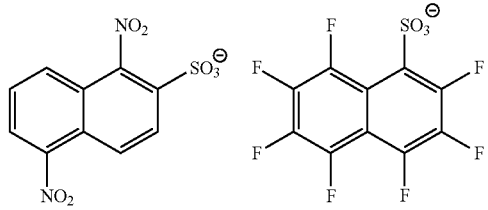

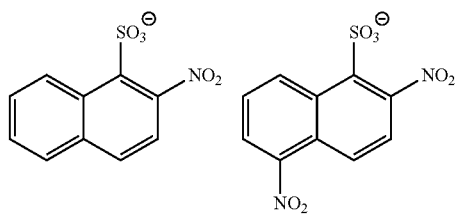

Examples of the haloalkyl group having 1 to 3 carbon atoms as $R_{42}$ to $R_{45}$ in the general formula (16) are the same as those exemplified as the haloalkyl group having 1 to 3 carbon atoms as the electron-withdrawing substituent in the anion according to the present invention, and the preferred examples thereof are the same as described above.

Examples of the halogeno group as $R_{42}$ to $R_{45}$ in the general formula (16) include a fluoro group, a chloro group, a bromo group, and an iodo group. Among these, the fluoro group is preferable.

Examples of a combination of $R_{42}$ to $R_{45}$ and $m_2$ to $m_5$ in the general formula (16) include combinations listed in the following table.

| $R_{42}$ | $m_2$ | $R_{43}$ | $m_3$ | $R_{44}$ | $m_4$ | $R_{45}$ | $m_5$ |
|---|---|---|---|---|---|---|---|
| —$CF_3$ | 1 to 3 | —$CF_3$ | 1 to 3 | —$CF_3$ | 1 to 3 | —$CF_3$ | 1 to 3 |
| —$C_2F_5$ | 1 to 3 | —$C_2F_5$ | 1 to 3 | —$C_2F_5$ | 1 to 3 | —$C_2F_5$ | 1 to 3 |
| —$C_3F_7$ | 1 to 3 | —$C_3F_7$ | 1 to 3 | —$C_3F_7$ | 1 to 3 | —$C_3F_7$ | 1 to 3 |
| Nitro group | 1 to 3 | Nitro group | 1 to 3 | Nitro group | 1 to 3 | Nitro group | 1 to 3 |
| Fluoro group | 1 to 5 | Fluoro group | 1 to 5 | Fluoro group | 1 to 5 | Fluoro group | 1 to 5 |
| Chloro group | 1 to 5 | Chloro group | 1 to 5 | Chloro group | 1 to 5 | Chloro group | 1 to 5 |
| Bromo group | 1 to 5 | Bromo group | 1 to 5 | Bromo group | 1 to 5 | Bromo group | 1 to 5 |
| Iodo group | 1 to 5 | Iodo group | 1 to 5 | Iodo group | 1 to 5 | Iodo group | 1 to 5 |
| Nitro group | 1 to 3 | Fluoro group | 1 to 5 | Fluoro group | 1 to 5 | Fluoro group | 1 to 5 |
| Nitro group | 1 to 3 | Nitro group | 1 to 3 | Fluoro group | 1 to 5 | Fluoro group | 1 to 5 |
| Nitro group | 1 to 3 | Nitro group | 1 to 3 | Nitro group | 1 to 3 | Fluoro group | 1 to 5 |

Specific preferred examples of the anion represented by the general formula (16) are as follows.

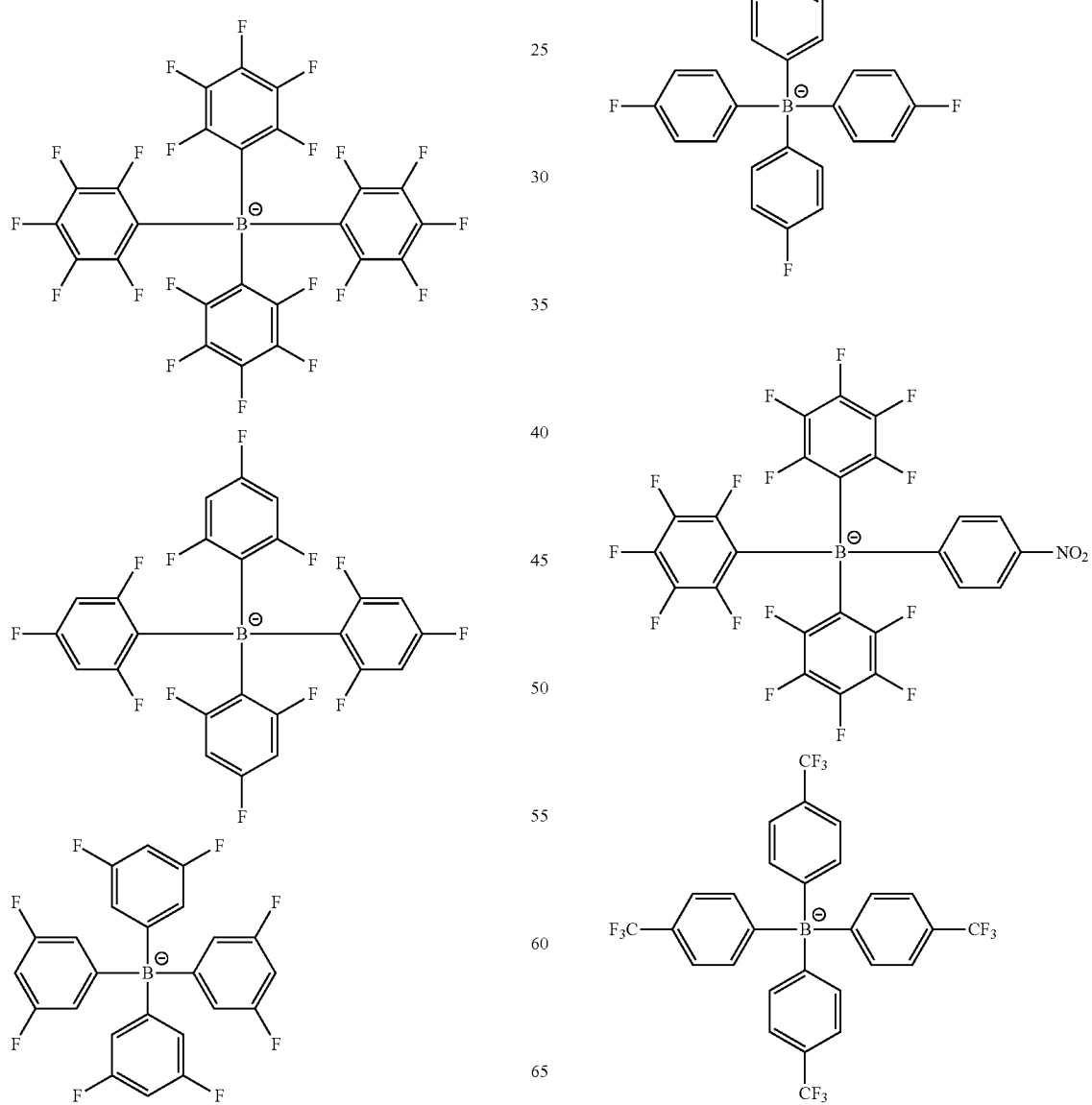

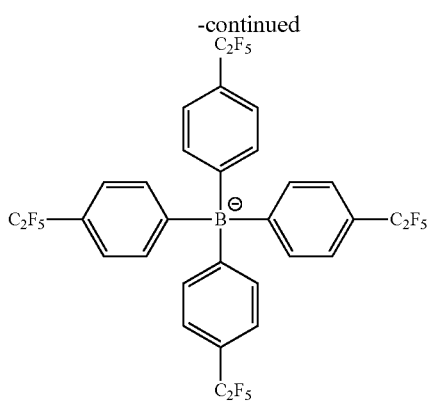

Among the specific example, the following anions are preferable, and a tetrakis(pentafluorophenyl) boron (IV) anion is more preferable.

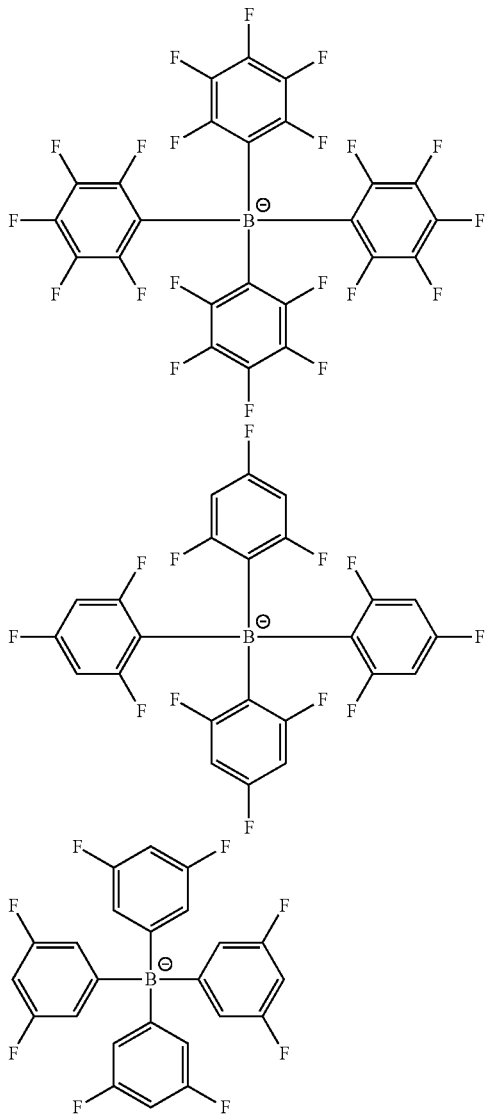 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F ; Fc1cc(F)c([B-](c2c(F)cc(F)cc2F)(c2c(F)cc(F)cc2F)c2c(F)cc(F)cc2F)c(F)c1 ; Fc1cc(F)cc([B-](c2cc(F)cc(F)c2)(c2cc(F)cc(F)c2)c2cc(F)cc(F)c2)c1]

Examples of the haloalkyl group having 1 to 3 carbon atoms as $R_{46}$ in the general formula (17) are the same as those exemplified as the haloalkyl group having 1 to 3 carbon atoms as the electron-withdrawing substituent in the anion according to the present invention, and the preferred examples thereof are the same as described above.

Examples of the halogeno group as $R_{46}$ in the general formula (17) include a fluoro group, a chloro group, a bromo group, and an iodo group. Among these, the fluoro group is preferable.

Specific preferred examples of the anion represented by the general formula (17) include $BF_4^-$, $CF_3BF_3^-$, $C_2F_5BF_3^-$, $C_3F_7BF_3^-$, $(CF_3)_4B^-$, $(C_2F_5)_4B^-$, and $(C_3F_7)_4B^-$.

Examples of the haloalkyl group having 1 to 3 carbon atoms as $R_{47}$ and $R_{48}$ in the general formula (18) are the same as those exemplified as the haloalkyl group having 1 to 3 carbon atoms as the electron-withdrawing substituent in the anion according to the present invention, and the preferred examples thereof are the same as described above.

Examples of the halogeno group as $R_{47}$ and $R_{48}$ in the general formula (18) include a fluoro group, a chloro group, a bromo group, and an iodo group. Among these, the fluoro group is preferable.

Examples of the halogenated alkylene group having 2 or 3 carbon atoms to be formed by $R_{47}$ and $R_{48}$ in the general formula (18) include a tetrafluoroethylene group and a hexafluoropropylene group. Among these, the hexafluoropropylene group is preferable.

Specific preferred examples of the anion represented by the general formula (18) are as follows.

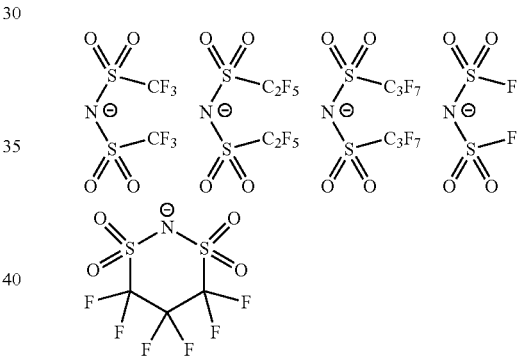

It is preferable that $R_{49}$ in the general formula (19) represents a phosphorus atom.

Examples of the halogeno group as X in the general formula (19) include a fluoro group, a chloro group, a bromo group, and an iodo group. Among these, the fluoro group is preferable.

Specific preferred examples of the anion represented by the general formula (19) include $PF_6^-$ and $SbF_6^-$. Among these, $PF_6^-$ is preferable.

Specific examples of the halogen oxo acid anion in the anion according to the present invention include a hypochlorite anion, a chlorite anion, a chlorate anion, and a perchlorate anion. Among these, the perchlorate anion is preferable.

Specific examples of the sulfonic acid anion in the anion according to the present invention include an alkylsulfonic acid anion having 1 to 20 carbon atoms such as a methanesulfonic acid anion; a halogenated alkylsulfonic acid anion having 1 to 20 carbon atoms such as a trifluoromethanesulfonic acid anion; and a benzenesulfonic acid anion which has a substituent such as a benzenesulfonic acid anion or a toluenesulfonic acid anion or is unsubstituted.

Examples of the anion represented by $An^-$ in the general formula (1) include a halide ion such as a fluoride ion ($F^-$), a chloride ion (Cl⁻), a bromide ion (Br⁻), or an iodide ion (F⁻) in addition to the anion according to the present invention.

As the anion represented by An⁻ in the general formula (1), the anion according to the present invention is preferable, and an anion which contains an aryl group having an electron-withdrawing substituent, a sulfonyl group having an electron-withdrawing substituent, a haloalkyl group, or a halogeno group is more preferable. Specifically, anions represented by the general formulae (16) to (19) are preferable, anions represented by the general formulae (16), (18), and (19) are more preferable, anions represented by the general formulae (16) and (18) are still more preferable, and an anion represented by the general formula (16) is particularly preferable.

Among the specific examples, the following anions are preferable.

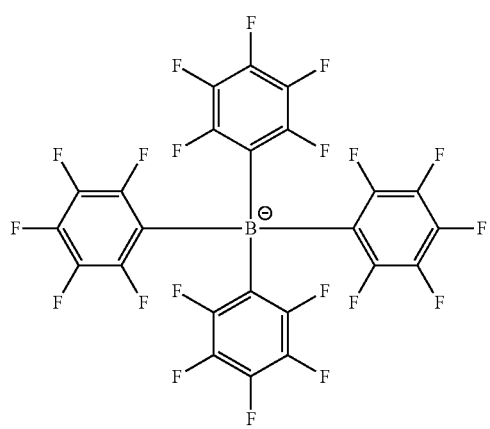

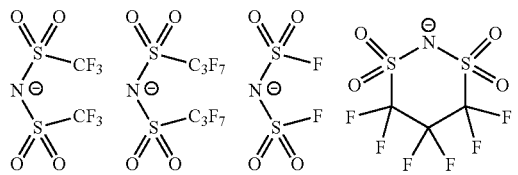

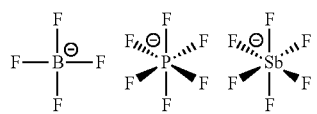

Among the specific examples, a tetrakis(pentafluorophenyl) boron (IV) anion, a bis(trifluoromethanesulfonyl) imide anion, $PF_6^-$, or $SbF_6^-$ is more preferable; a tetrakis(pentafluorophenyl) boron (IV) anion or $PF_6^-$ still more preferable; and a tetrakis(pentafluorophenyl) boron (IV) anion is particularly preferable.

Specific preferred examples of compound according to embodiment of present invention Specific preferred examples of the compound according to the embodiment of the present invention include a compound represented by the following general formula (1-4).

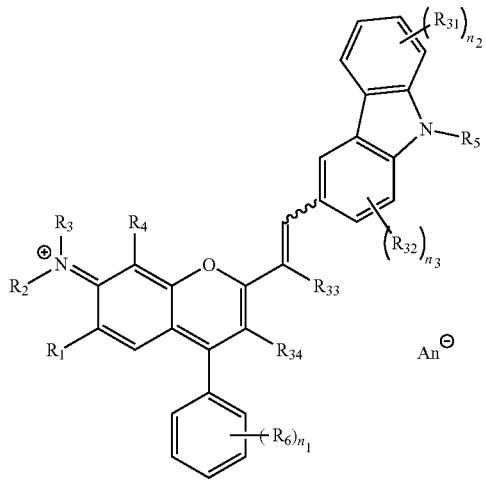

(In the formula, $R_1$ to $R_6$, $R_{31}$ to $R_{34}$, An⁻, and $n_1$ to $n_3$ each have the same definition as described above.)

Specific preferred examples of the compound represented by the general formula (1-4) include a compound represented by the following general formula (1-5).

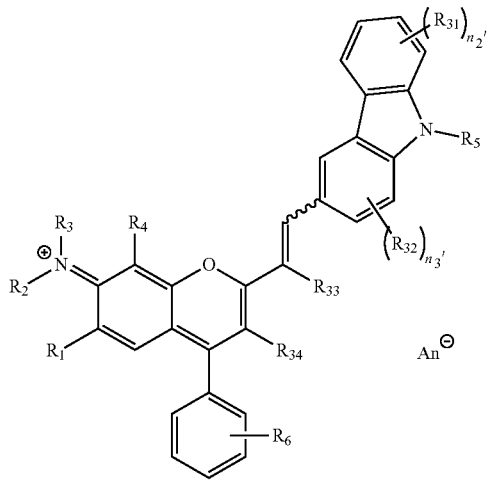

(In the formula, $n_2'$ and $n_3'$ each independently represent 0 or 1, and $R_1$ to $R_6$, $R_{31}$ to $R_{34}$, and An⁻ each have the same definition as described above.)

It is preferable that both of $n_2'$ and $n_3'$ in the general formula (1-5) represent 0 or any of $n_2'$ and $n_3'$ represents 1 and the other represents 0 and more preferable that both of $n_2'$ and $n_3'$ represent 0.

Specific preferred examples of the compound represented by the general formula (1-5) include a compound represented by the following general formula (1-6).

(1-6)

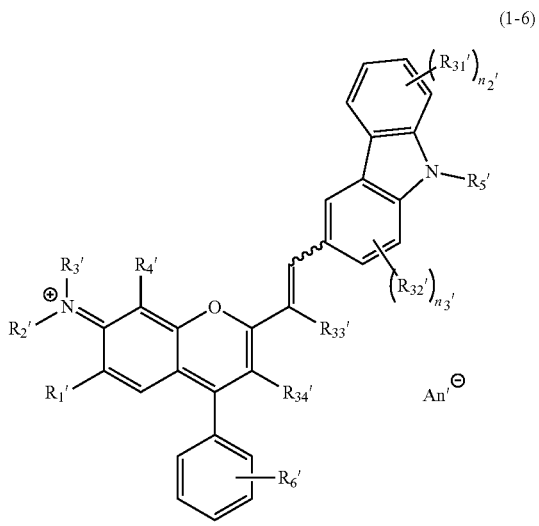

(In the formula, $R_1'$ and $R_4'$ each independently represent a hydrogen atom or an alkyl group having 1 to 4 carbon atoms, $R_2'$ and $R_3'$ each independently represent a group represented by the general formula (2-4), an alkyl group having 1 to 12 carbon atoms, or a phenyl group which has an alkyl group having 1 to 6 carbon atoms or is unsubstituted, $R_5'$ represents a group represented by the general formula (2-4), a formyl group, an alkyl group having 1 to 12 carbon atoms, a haloalkyl group having 1 to 6 carbon atoms, an acyl group having 2 to 7 carbon atoms, or a phenyl group which has an alkyl group having 1 to 6 carbon atoms or is unsubstituted, $R_6'$ represents a group represented by the general formula (2), a carboxy group, an alkoxycarbonyl group having 2 to 13 carbon atoms, a carbamoyl group, a monoalkylaminocarbonyl group having 2 to 7 carbon atoms, a dialkylaminocarbonyl group having 3 to 9 carbon atoms, or an alkylcarbonylamino group having 2 to 7 carbon atoms, $R_{31}'$ and $R_{32}'$ each independently represent an alkoxy group having 1 to 4 carbon atoms, $R_{33}'$ and $R_{34}'$ each independently represent a hydrogen atom or an alkyl group having 1 to 4 carbon atoms, $An'^-$ represents an anion which contains an aryl group having an electron-withdrawing substituent, a sulfonyl group having an electron-withdrawing substituent, a haloalkyl group, or a halogeno group, a halogen oxo acid anion, or an sulfonic acid anion, $R_1'$ and $R_2'$ may form a linear alkylene group having 2 to 4 carbon atoms, $R_3'$ and $R_4'$ may form a linear alkylene group having 2 to 4 carbon atoms, $R_{33}'$ and $R_{34}'$ may form a linear alkylene group having 2 to 4 carbon atoms which has one alkyl group having 1 to 4 carbon atoms as a substituent or is unsubstituted or an unsubstituted phenylene group, and $n_2'$ and $n_3'$ each have the same definition as described above.)

The alkyl group having 1 to 4 carbon atoms as $R_1'$ and $R_4'$ in the general formula (1-6) may be any of linear, branched, or cyclic. Among these, the alkyl group is preferably linear or branched and more preferably linear. In addition, among examples of the alkyl group having 1 to 4 carbon atoms, an alkyl group having 1 or 2 carbon atoms is preferable. Specific examples thereof include a methyl group, an ethyl group, an n-propyl group, an isopropyl group, an n-butyl group, an isobutyl group, a sec-butyl group, and a tert-butyl group. Among these, the methyl group or the ethyl group is preferable.

The group represented by the general formula (2-4) as $R_2'$ and $R_3'$ in the general formula (1-6) has the same definition as the group represented by the general formula (2-4) in the group having a polymerizable unsaturated group in the general formula (1), and the preferred examples thereof are the same as described above.

Examples of the alkyl group having 1 to 12 carbon atoms as $R_2'$ and $R_3'$ in the general formula (1-6) are the same as those exemplified as the alkyl group having 1 to 12 carbon atoms as $R_{10}$ in $A_3$ in the general formula (2), and the preferred examples thereof are the same as described above.

The phenyl group which has an alkyl group having 1 to 6 carbon atoms as $R_2'$ and $R_3'$ in the general formula (1-6) has typically 1 to 5 alkyl groups, preferably 1 to 3 alkyl groups, and more preferably one alkyl group.

Examples of the alkyl group having 1 to 6 carbon atoms in the "phenyl group which has an alkyl group having 1 to 6 carbon atoms" as $R_2'$ and $R_3'$ in the general formula (1-6) are the same as those exemplified as the alkyl group having 1 to 6 carbon atoms as $R_1$ and $R_4$ in the general formula (1), and the preferred examples thereof are the same as described above.

As the phenyl group which has an alkyl group having 1 to 6 carbon atoms as $R_2'$ and $R_3'$ in the general formula (1-6), a phenyl group which has an alkyl group having 1 to 3 carbon atoms is more preferable. Specific examples thereof are the same as those exemplified as the aryl group having 6 to 14 carbon atoms which has a substituent as $R_2$ and $R_3$ in the general formula (1), and the preferred examples thereof are the same as described above.

In the general formula (1-6), in a case where $R_1'$ and $R_2'$ form a linear alkylene group having 2 to 4 carbon atoms or $R_3'$ and $R_4'$ form a linear alkylene group having 2 to 4 carbon atoms, examples of the linear alkylene group having 2 to 4 carbon atoms include an ethylene group, a trimethylene group, and a tetramethylene group. Among these, the trimethylene group is preferable.

In the general formula (1-6), in the case where $R_1'$ and $R_2'$ form a linear alkylene group having 2 to 4 carbon atoms and/or $R_3'$ and $R_4'$ form a linear alkylene group having 2 to 4 carbon atoms, specific examples of the general formula (1-6) include the following general formulae (8'-1) to (8'-9).

(8'-1)

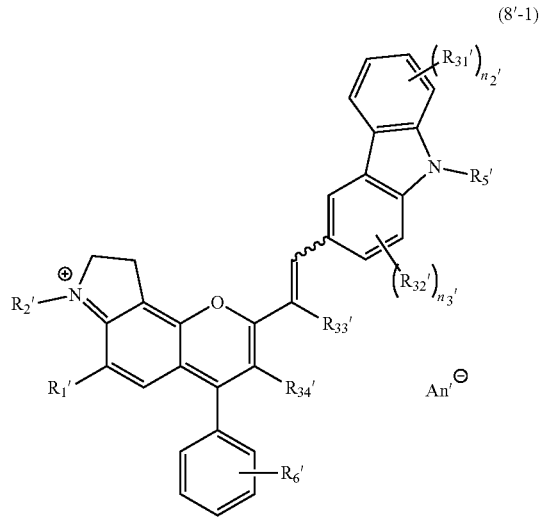

(8'-2)
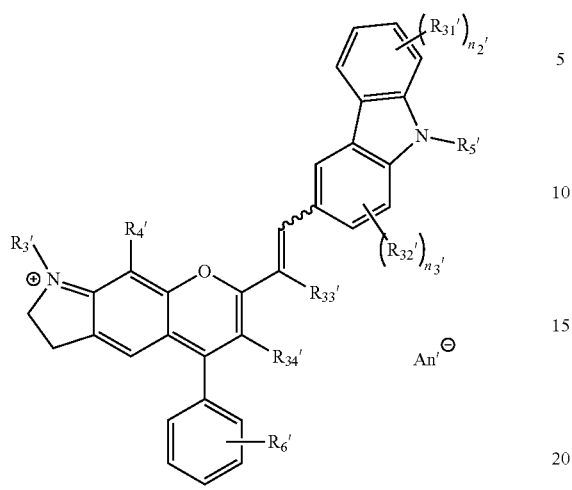
(8'-5)
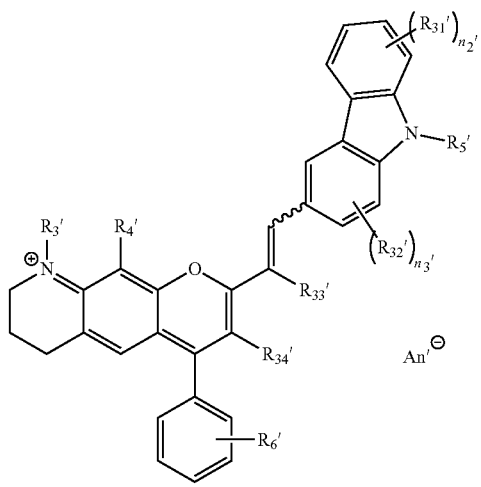
(8'-3)
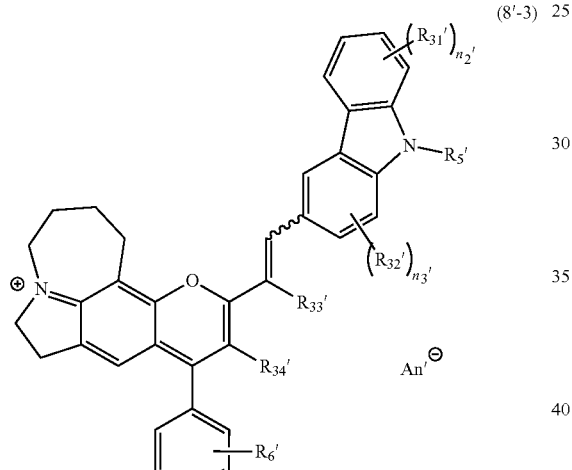
(8'-6)
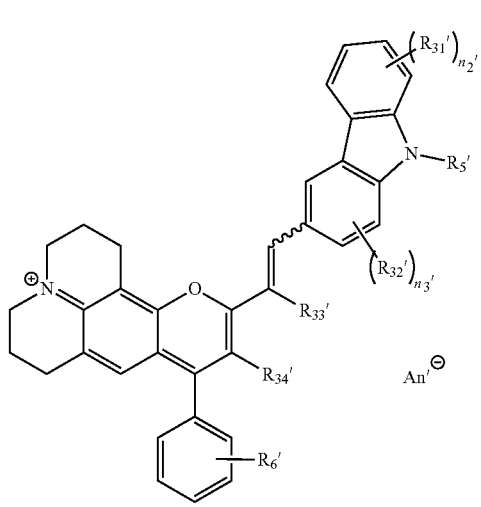
(8'-4)
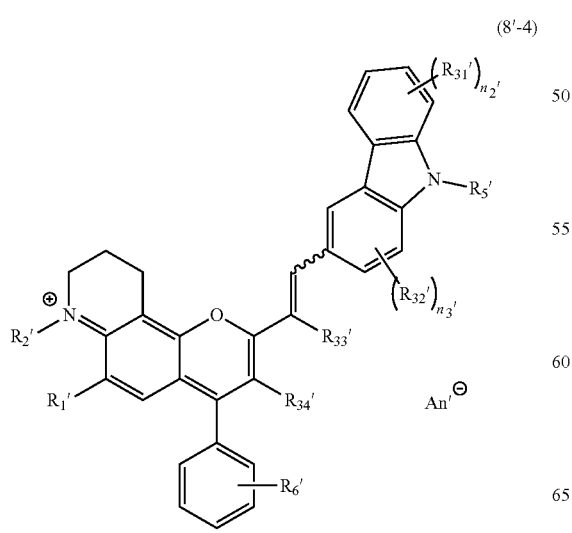
(8'-7)
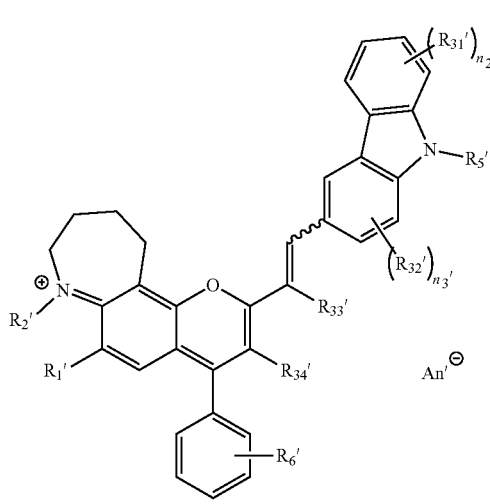

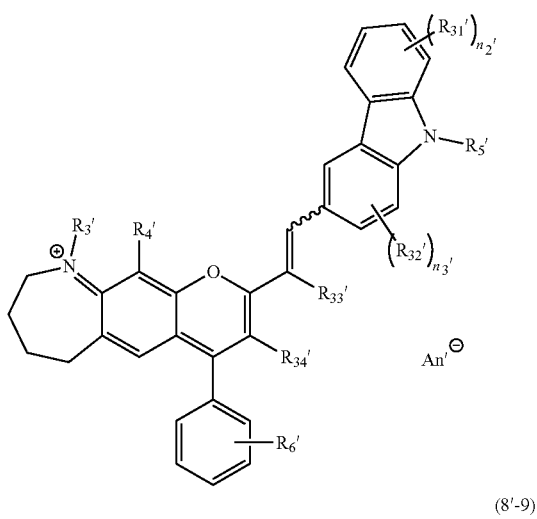

(8'-8)

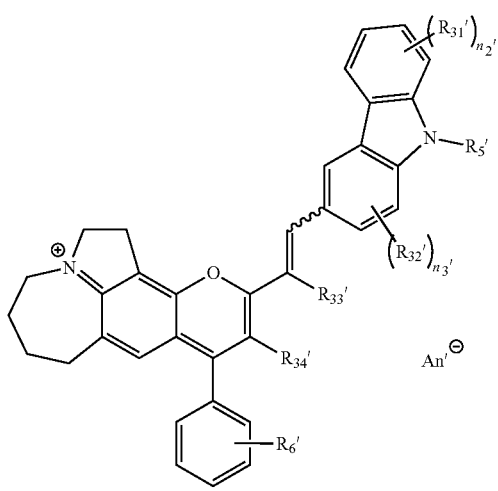

(8'-9)

(In the formulae, $R_1'$ to $R_6'$, $R_{31}'$ to $R_{34}'$, $An'^-$, $n_2'$, and $n_3'$ each have the same definition as described above.)

Among the specific example, the general formulae (8'-4) to (8'-6) are preferable, and the general formula (8'-6) is preferable.

$R_1'$ in the general formula (1-6) represents preferably a hydrogen atom or a trimethylene group formed by $R_1'$ and $R_2'$ and more preferably a hydrogen atom.

$R_2'$ in the general formula (1-6) represents preferably a group represented by the general formula (2-5), an alkyl group having 1 to 6 carbon atoms, a phenyl group which has an alkyl group having 1 to 3 carbon atoms or is unsubstituted, or a linear alkylene group having 2 to 4 carbon atoms which is formed by $R_1'$ and $R_2'$; more preferably an alkyl group having 1 to 6 carbon atoms or a trimethylene group formed by $R_1$ and $R_2$; and still more preferably an alkyl group having 1 to 6 carbon atoms. Specifically, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_1'$ and $R_2'$, a trimethylene group formed by $R_1'$ and $R_2'$, a tetramethylene group formed by $R_1'$ and $R_2'$, a group represented by the general formula (2-5-1), or a group represented by the general formula (2-5-2) is preferable; the methyl group, the ethyl group, the n-propyl group, the isopropyl group, the n-butyl group, the isobutyl group, the sec-butyl group, the tert-butyl group, or the trimethylene group formed by $R_1'$ and $R_2'$ is more preferable; the methyl group, the ethyl group, or the trimethylene group formed by $R_1'$ and $R_2'$ is still more preferable; and the ethyl group is particularly preferable.

$R_3'$ in the general formula (1-6) represents preferably a group represented by the general formula (2-5), an alkyl group having 1 to 6 carbon atoms, a phenyl group which has an alkyl group having 1 to 3 carbon atoms or is unsubstituted, or a linear alkylene group having 2 to 4 carbon atoms which is formed by $R_3'$ and $R_4'$; more preferably an alkyl group having 1 to 6 carbon atoms or a trimethylene group formed by $R_3'$ and $R_4'$; and still more preferably an alkyl group having 1 to 6 carbon atoms. Specifically, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_3'$ and $R_4'$, a trimethylene group formed by $R_3'$ and $R_4'$, a tetramethylene group formed by $R_3'$ and $R_4'$, a group represented by the general formula (2-5-1), or a group represented by the general formula (2-5-2) is preferable; the methyl group, the ethyl group, the n-propyl group, the isopropyl group, the n-butyl group, the isobutyl group, the sec-butyl group, the tert-butyl group, or the trimethylene group formed by $R_3'$ and $R_4'$ is more preferable; the methyl group, the ethyl group, or the trimethylene group formed by $R_3'$ and $R_4'$ is still more preferable; and the ethyl group is particularly preferable.

$R_4'$ in the general formula (1-6) represents preferably a hydrogen atom or a trimethylene group formed by $R_3'$ and $R_4'$ and more preferably a hydrogen atom.

Examples of the alkyl group having 1 to 12 carbon atoms as $R_5'$ in the general formula (1-6) are the same as those exemplified as the alkyl group having 1 to 12 carbon atoms as $R_{10}$ in $A_3$ in the general formula (2), and the preferred examples thereof are the same as described above.

The haloalkyl group having 1 to 6 carbon atoms as $R_5'$ in the general formula (1-6) may be any of linear, branched, or cyclic. Among these, the haloalkyl group is preferably linear or branched and more preferably linear. In addition, among examples of the haloalkyl group having 1 to 6 carbon atoms, a haloalkyl group having 1 to 3 carbon atoms is preferable. Specific examples thereof are the same as those exemplified as the haloalkyl group having 1 to 20 carbon atoms as $R_5$ in the general formula (1), and the preferred examples thereof are the same as described above.

The acyl group having 2 to 7 carbon atoms as $R_5'$ in the general formula (1-6) may be any of linear, branched, or cyclic. Among these, the acyl group is preferably linear or branched and more preferably linear. In addition, among examples of the acyl group having 2 to 7 carbon atoms, an acyl group having 2 to 5 carbon atoms is preferable. Specific examples thereof include an acetyl group, a propionyl group, an n-butyryl group, an isobutyryl group, an n-pentanoyl group, an isopentanoyl group, a sec-pentanoyl group, a tert-pentanoyl group, an n-hexanoyl group, and an n-heptanoyl group. Among these, the acetyl group, the propionyl group, the n-butyryl group, or the n-pentanoyl group is preferable, and the acetyl group or the propionyl group is more preferable.

Examples of the "phenyl group which has an alkyl group having 1 to 6 carbon atoms or is unsubstituted" as $R_5'$ in the general formula (1-6) are the same as those exemplified as the "phenyl group which has an alkyl group having 1 to 6 carbon atoms or is unsubstituted" as $R_2'$ and $R_3'$ in the general formula (1-6), and the preferred examples thereof are the same as described above.

$R_5'$ in the general formula (1-6) represents preferably a group represented by the general formula (2-5), a formyl group, an alkyl group having 1 to 6 carbon atoms, a haloalkyl group having 1 to 3 carbon atoms, an acyl group having 2 to 5 carbon atoms, or a phenyl group which has an alkyl group having 1 to 3 carbon atoms or is unsubstituted; more preferably an alkyl group having 1 to 6 carbon atoms or an unsubstituted phenyl group; and particularly preferably an alkyl group having 1 to 6 carbon atoms. Specifically, a methyl group, an ethyl group, an n-propyl group, an isopropyl group, an n-butyl group, an isobutyl group, a sec-butyl group, a tert-butyl group, or a phenyl group is preferable, the methyl group, the ethyl group, or the phenyl group is more preferable, and the ethyl group is particularly preferable.

The group represented by the general formula (2) as $R_6'$ in the general formula (1-6) has the same definition as the group represented by the general formula (2) in the group having a polymerizable unsaturated group in the general formula (1), and the preferred examples thereof are the same as described above.

The alkoxycarbonyl group having 2 to 13 carbon atoms as $R_6'$ in the general formula (1-6) may be any of linear, branched, or cyclic. Among these, the alkoxycarbonyl group is preferably linear or branched and more preferably linear. In addition, among examples of the alkoxycarbonyl group having 2 to 13 carbon atoms, an alkoxycarbonyl group having 2 to 7 carbon atoms is preferable, and an alkoxycarbonyl group having 2 to 5 carbon atoms is more preferable. Specifically, those which are the same as the specific preferred examples of the alkoxycarbonyl group having 2 to 21 carbon atoms as $R_6$ in the general formula (1) are preferable, and the more preferred examples and still more preferred examples are the same as described above.

The monoalkylaminocarbonyl group having 2 to 7 carbon atoms as $R_6'$ in the general formula (1-6) may be any of linear, branched, or cyclic. Among these, the monoalkylaminocarbonyl group is preferably linear or branched and more preferably linear. In addition, among examples of the monoalkylaminocarbonyl group having 2 to 7 carbon atoms, a monoalkylaminocarbonyl group having 2 to 5 carbon atoms is preferable. Specifically, those which are the same as the specific preferred examples of the monoalkylaminocarbonyl group having 2 to 21 carbon atoms as $R_6$ in the general formula (1) are preferable, and the more preferred examples and still more preferred examples are the same as described above.

In the dialkylaminocarbonyl group having 3 to 9 carbon atoms as $R_6'$ in the general formula (1-6), two alkyl groups at the N-terminal may be any of linear, branched, or cyclic. Among these, it is preferable that at least one alkyl group is linear and more preferable that two alkyl groups are linear. In addition, among examples of the dialkylaminocarbonyl group having 3 to 9 carbon atoms, a dialkylaminocarbonyl group having 3 to 5 carbon atoms is preferable. Specifically, those which are the same as the specific preferred examples of the dialkylaminocarbonyl group having 3 to 41 carbon atoms as $R_6$ in the general formula (1) are preferable, and the more preferred examples are the same as described above.

The alkylcarbonylamino group having 2 to 7 carbon atoms as $R_6'$ in the general formula (1-6) may be any of linear, branched, or cyclic. Among these, the alkylcarbonylamino group is preferably linear or branched and more preferably linear. In addition, among examples of the alkylcarbonylamino group having 2 to 7 carbon atoms, an alkylcarbonylamino group having 2 to 5 carbon atoms is preferable. Specifically, those which are the same as the specific preferred examples of the alkylcarbonylamino group having 2 to 21 carbon atoms as $R_6$ in the general formula (1) are preferable, and the more preferred examples and still more preferred examples are the same as described above.

$R_6'$ in the general formula (1-6) represents more preferably a group represented by any of the general formulae (2'a) to (2'd), a carboxy group, an alkoxycarbonyl group having 2 to 7 carbon atoms, a carbamoyl group, a monoalkylaminocarbonyl group having 2 to 5 carbon atoms, a dialkylaminocarbonyl group having 3 to 5 carbon atoms, or an alkylcarbonylamino group having 2 to 5 carbon atoms; still more preferably a group represented by any of the general formulae (2"a) to (2"d), a carboxy group, or an alkoxycarbonyl group having 2 to 7 carbon atoms; and particularly preferably a group represented by the general formula (2"a), a carboxy group, or an alkoxycarbonyl group having 2 to 5 carbon atoms. Specific preferred examples thereof include a carboxy group, a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, and groups represented by the following formulae.

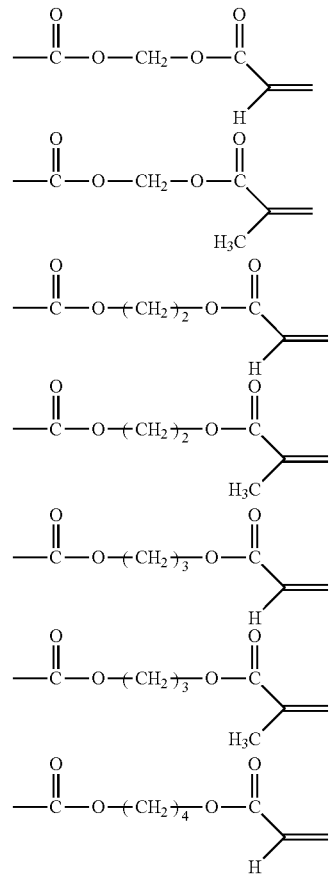

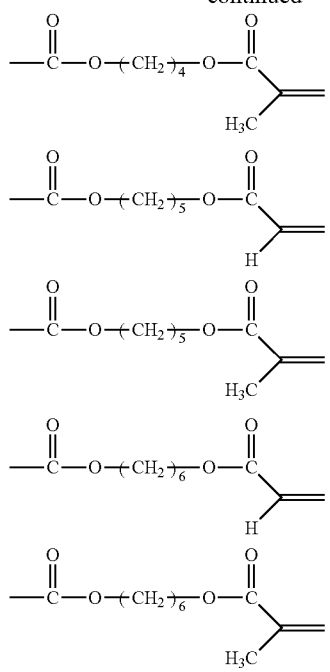

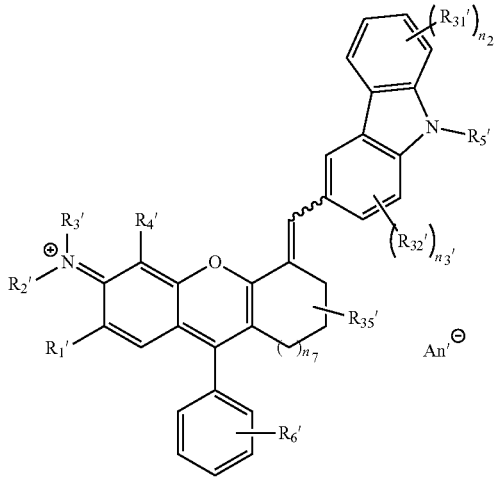

Among the specific examples, a carboxy group, a methoxycarbonyl group, an ethoxycarbonyl group, a group represented by the general formula (2″-1), or a group represented by the general formula (2″-2) is more preferable.

$R_{31}'$ and $R_{32}'$ in the general formula (1-6) represent a methoxy group, an ethoxy group, an n-propoxy group, an isopropoxy group, an n-butoxy group, an isobutoxy group, a sec-butoxy group, or a tert-butoxy group, preferably the methoxy group or the ethoxy group, and more preferably the methoxy group.

Examples of the alkyl group having 1 to 4 carbon atoms as $R_{33}'$ and $R_{34}'$ in the general formula (1-6) are the same as those exemplified as the alkyl group having 1 to 4 carbon atoms as $R_1'$ and $R_4'$ in the general formula (1-6), and the preferred examples thereof are the same as described above.

In the general formula (1-6), in a case where $R_{33}'$ and $R_{34}'$ form a linear alkylene group having 2 to 4 carbon atoms which has one alkyl group having 1 to 4 carbon atoms as a substituent or is unsubstituted, examples of the linear alkylene group having 2 to 4 carbon atoms include an ethylene group, a trimethylene group, and a tetramethylene group. Among these, the trimethylene group is preferable.

In the general formula (1-6), in a case where $R_{33}'$ and $R_{34}'$ form a linear alkylene group having 2 to 4 carbon atoms which has one alkyl group having 1 to 4 carbon atoms as a substituent, examples of the alkyl group having 1 to 4 carbon atoms as a substituent are the same as the those exemplified as the alkyl group having 1 to 4 carbon atoms as $R_1'$ and $R_4'$ in the general formula (1-6), and the preferred examples thereof are the same as described above.

In the general formula (1-6), in a case where $R_{33}'$ and $R_{34}'$ form a linear alkylene group having 2 to 4 carbon atoms which has one alkyl group having 1 to 4 carbon atoms as a substituent or is unsubstituted, the general formula (1) is represented by the following general formula (9').

(In the formula, $R_{35}'$ represents an alkyl group having 1 to 4 carbon atoms, and $R_1'$ to $R_6'$, $R_{31}'$, $R_{32}'$, $An'^-$, $n_2'$, $n_3'$, and $n_7$ each have the same definition as described above.)

Examples of the alkyl group having 1 to 4 carbon atoms as $R_{35}'$ in the general formula (9') are the same as those exemplified as the alkyl group having 1 to 4 carbon atoms as $R_1'$ and $R_4'$ in the general formula (1-6), and the preferred examples thereof are the same as described above.

The general formula (9') is represented by the following general formula (9'-1) in a case where $n_7$ represents 0; the general formula (9') is represented by the following general formula (9'-2) in a case where $n_7$ represents 1; and the general formula (9') is represented by the following general formula (9'-3) in a case where $n_7$ represents 2;

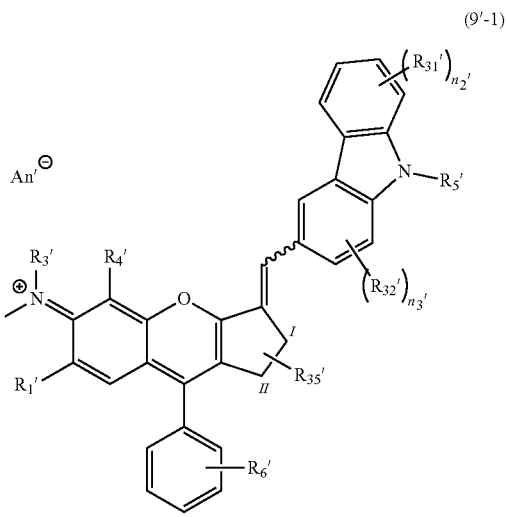

-continued (9'-2)

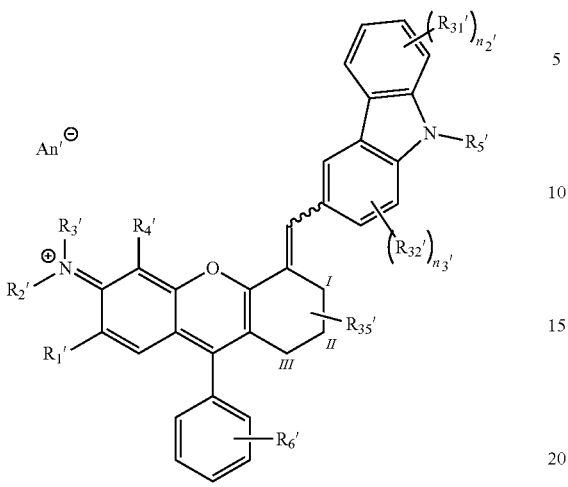

(9'-3)

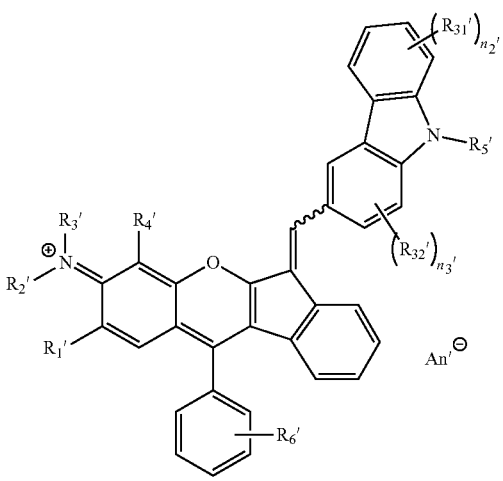

(In the formula, I to IV represent a position which can be substituted with R$_{35}$', and R$_1$' to R$_6$', R$_{31}$', R$_{32}$', R$_{35}$', An'$^-$, n$_2$', and n$_3$' each have the same definition as described above.)

The bonding position as R$_{35}$' in the general formula (9'-1) may be any of the I- or II-position and preferably the II-position.

The bonding position as R$_{35}$' in the general formula (9'-2) may be any of the I- to III-positions and preferably the II-position.

The bonding position as R$_{35}$' in the general formula (9'-3) may be any of the I- to IV-positions and preferably the II-position or the III-position.

In the general formula (1-6), in a case where R$_{33}$' and R$_{34}$' form an unsubstituted phenylene group, the general formula (1) is represented by the following general formula (10').

(10')

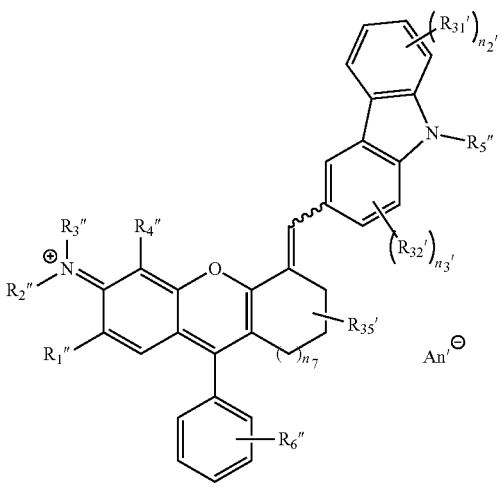

(In the formula, R$_1$' to R$_6$', R$_{31}$', R$_{32}$', An'$^-$, n$_2$', and n$_3$' each have the same definition as described above.)

R$_{33}$' and R$_{34}$' in the general formula (1-6) represents a hydrogen atom. Further, it is preferable that R$_{33}$' and R$_{34}$' form an unsubstituted linear alkylene group having 2 to 4 carbon atoms or an unsubstituted phenylene group, more preferable that R$_{33}$' and R$_{34}$' form an unsubstituted linear alkylene group having 2 to 4 carbon atoms, and particularly preferable that R$_{33}$' and R$_{34}$' form a trimethylene group.

Examples of the anion which contains the aryl group having an electron-withdrawing substituent, a sulfonyl group having an electron-withdrawing substituent, a haloalkyl group, or a halogeno group as An'$^-$ in the general formula (1-6), the halogen oxo acid anion, and the sulfonic acid anion are the same as those exemplified as the anion according to the present invention as An$^-$ in the general formula (1), and the preferred examples thereof are the same as described above.

Specific preferred examples of the compound represented by the general formula (1-6) include a compound represented by the following general formula (1-7).

(1-7)

(In the formula, $R_1''$ and $R_4''$ represent a hydrogen atom, $R_2''$ and $R_3''$ each independently represent an alkyl group having 1 to 6 carbon atoms, $R_5''$ represents an alkyl group having 1 to 6 carbon atoms or an unsubstituted phenyl group, $R_6''$ represents a group represented by the general formula (2''a), a carboxy group, or an alkoxycarbonyl group having 2 to 7 carbon atoms, $R_1''$ and $R_2''$ may form a trimethylene group, $R_3''$ and $R_4''$ may form a trimethylene group, and $R_{31}'$, $R_{32}'$, $An'^-$, $n_2'$, $n_3'$, and $n_7$ each have the same definition as described above.)

Examples of the alkyl group having 1 to 6 carbon atoms as $R_2''$, $R_3''$, and $R_5''$ in the general formula (1-7) are the same as those exemplified as the alkyl group having 1 to 6 carbon atoms as $R_1$ and $R_4$ in the general formula (1), and the preferred examples thereof are the same as described above.

It is preferable that $R_1''$ in the general formula (1-7) represents a hydrogen atom.

It is preferable that $R_2''$ in the general formula (1-7) represents an alkyl group having 1 to 6 carbon atoms. Specific examples thereof include a methyl group, an ethyl group, an n-propyl group, an isopropyl group, an n-butyl group, an isobutyl group, a sec-butyl group, a tert-butyl group, and a trimethylene group formed by $R_1''$ and $R_2''$. Among these, the methyl group, the ethyl group, the trimethylene group formed by $R_1''$ and $R_2''$ is preferable, and the ethyl group is particularly preferable.

It is preferable that $R_3''$ in the general formula (1-7) represents an alkyl group having 1 to 6 carbon atoms. Specific examples thereof include a methyl group, an ethyl group, an n-propyl group, an isopropyl group, an n-butyl group, an isobutyl group, a sec-butyl group, a tert-butyl group, and a trimethylene group formed by $R_3''$ and $R_4''$. Among these, the methyl group, the ethyl group, the trimethylene group formed by $R_3''$ and $R_4''$ is preferable, and the ethyl group is particularly preferable.

It is preferable that $R_4''$ in the general formula (1-7) represents a hydrogen atom.

It is preferable that $R_5''$ in the general formula (1-7) represents an alkyl group having 1 to 6 carbon atoms. Specific examples thereof include a methyl group, an ethyl group, an n-propyl group, an isopropyl group, an n-butyl group, an isobutyl group, a sec-butyl group, a tert-butyl group, and a phenyl group. Among these, the methyl group, the ethyl group, the phenyl group is preferable, and the ethyl group is particularly preferable.

Examples of the group represented by the general formula (2''a) as $R_6''$ in the general formula (1-7) are the same as those exemplified as the group represented by the general formula (2''a) in the group having a polymerizable unsaturated group in the general formula (1), and the preferred examples thereof are the same as described above.

The alkoxycarbonyl group having 2 to 7 carbon atoms as $R_6''$ in the general formula (1-7) may be any of linear, branched, or cyclic. Among these, the alkoxycarbonyl group is preferably linear or branched and more preferably linear. In addition, among examples of the alkoxycarbonyl group having 2 to 7 carbon atoms, an alkoxycarbonyl group having 2 to 5 carbon atoms is preferable. Specific preferred examples thereof are the same as the specific preferred examples described in the section of the alkoxycarbonyl group having 2 to 21 carbon atoms as $R_6$ in the general formula (1), and the more preferred examples and still more preferred examples thereof are the same as described above.

$R_6''$ in the general formula (1-7) represents a carboxy group, a methoxycarbonyl group, an ethoxycarbonyl group, an n-propoxycarbonyl group, an isopropoxycarbonyl group, an n-butoxycarbonyl group, an isobutoxycarbonyl group, a sec-butoxycarbonyl group, a tert-butoxycarbonyl group, or a group represented by any of the following formulae.

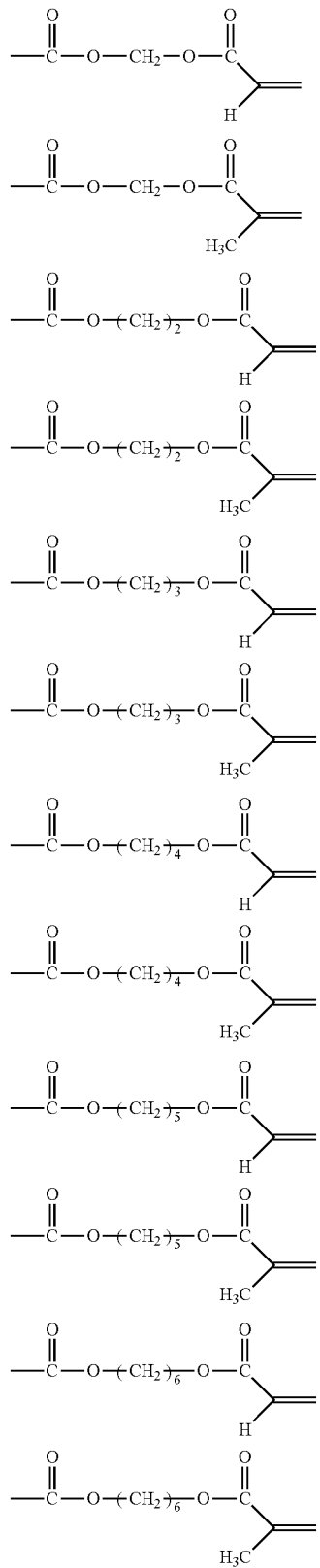

-continued

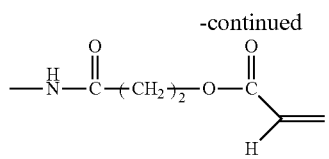

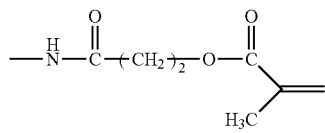

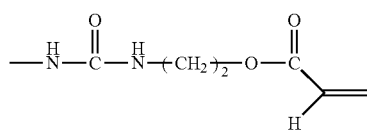

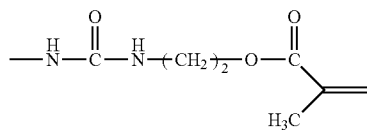

Among the specific examples, a carboxy group, a methoxycarbonyl group, an ethoxycarbonyl group, a group represented by the general formula (2"-1), or a group represented by the general formula (2"-2) is more preferable.

Specific preferred examples of the compound represented by the general formula (1-7) include a compound represented by the following general formula (1-8).

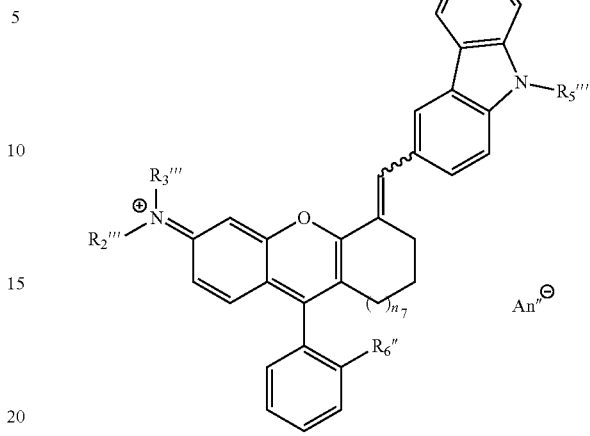

(1-8)

(In the formula, $R_2'''$, $R_3'''$, and $R_5'''$ each independently represent an alkyl group having 1 to 6 carbon atoms, $An''^-$ represents an anion which contains an aryl group having an electron-withdrawing substituent, a sulfonyl group having an electron-withdrawing substituent, a haloalkyl group, or a halogeno group, and $R_6''$ and $n_7$ each have the same definition as described above.)

Examples of the alkyl group having 1 to 6 carbon atoms as $R_2'''$, $R_3'''$, and $R_5'''$ in the general formula (1-8) are the same as those exemplified as the alkyl group having 1 to 6 carbon atoms as $R_1$ and $R_4$ in the general formula (1), and the preferred examples thereof are the same as described above.

Examples of the anion which contains an aryl group having an electron-withdrawing substituent, a sulfonyl group having an electron-withdrawing substituent, a haloalkyl group, or a halogeno group as $An''^-$ in the general formula (1-8) are the same as those exemplified as $An^-$ in the general formula (1), and the preferred examples thereof are the same as described above.

Preferred examples of a combination of $R_2'''$, $R_3'''$, $R_5'''$, $R_6'''$, and $n_7$ in the general formula (1-8) are as follows. Among the examples, the combinations 16 to 20 are preferable.

| | $R_2'''$ | $R_3'''$ | $R_5'''$ | $R_6''$ | $n_7$ |
|---|---|---|---|---|---|
| Combination 1 | Methyl group | Methyl group | Methyl group | Carboxy group | 0 to 2 |
| Combination 2 | Methyl group | Methyl group | Methyl group | Methoxycarbonyl group | |
| Combination 3 | Methyl group | Methyl group | Methyl group | Ethoxycarbonyl group | |
| Combination 4 | Methyl group | Methyl group | Methyl group | General formula (2"-1) | |
| Combination 5 | Methyl group | Methyl group | Methyl group | General formula (2"-2) | |
| Combination 6 | Methyl group | Methyl group | Ethyl group | Carboxy group | |
| Combination 7 | Methyl group | Methyl group | Ethyl group | Methoxycarbonyl group | |
| Combination 8 | Methyl group | Methyl group | Ethyl group | Ethoxycarbonyl group | |
| Combination 9 | Methyl group | Methyl group | Ethyl group | General formula (2"-1) | |
| Combination 10 | Methyl group | Methyl group | Ethyl group | General formula (2"-2) | |
| Combination 11 | Ethyl group | Ethyl group | Methyl group | Carboxy group | |
| Combination 12 | Ethyl group | Ethyl group | Methyl group | Methoxycarbonyl group | |

-continued

| | $R_2'''$ | $R_3'''$ | $R_5'''$ | $R_6''$ | $n_7$ |
|---|---|---|---|---|---|
| Combination 13 | Ethyl group | Ethyl group | Methyl group | Ethoxycarbonyl group | |
| Combination 14 | Ethyl group | Ethyl group | Methyl group | General formula (2"-1) | |
| Combination 15 | Ethyl group | Ethyl group | Methyl group | General formula (2"-2) | |
| Combination 16 | Ethyl group | Ethyl group | Ethyl group | Carboxy group | |
| Combination 17 | Ethyl group | Ethyl group | Ethyl group | Methoxycarbonyl group | |
| Combination 18 | Ethyl group | Ethyl group | Ethyl group | Ethoxycarbonyl group | |
| Combination 19 | Ethyl group | Ethyl group | Ethyl group | General formula (2"-1) | |
| Combination 20 | Ethyl group | Ethyl group | Ethyl group | General formula (2"-2) | |

In addition, examples of $An'''^-$ used with the combination listed in the table include a tetrakis(pentafluorophenyl) boron (IV) anion, a bis(trifluoromethanesulfonyl) imide anion, $PF_6$, and $SbF_6$. Among these, the tetrakis(pentafluorophenyl) boron (IV) anion or $PF_6$ is preferable, and the tetrakis(pentafluorophenyl) boron (IV) anion is more preferable.

The compound according to the embodiment of the present invention exhibits an effect of having a high sensitivity to not only light with a wavelength of 400 to 600 nm but also light with a wavelength of 600 nm or greater which is unlikely to be sensed by a reverse photochromic compound of the related art.

In addition, in a case where the anion represented by $An^-$ is the anion according to the present invention, particularly, a tetrakis(pentafluorophenyl) boron (IV) anion, a bis(trifluoromethanesulfonyl) imide anion, $PF_6$, or $SbF_6$, among examples of the compound according to the embodiment of the present invention, those compounds also exhibit effects of a high solubility in various organic solvents and a high compatibility with resins in addition to the effects described above.

Method of Producing Compound According to Embodiment of Present Invention

For example, a {compound represented by the following general formula (37)} in which the general formula (1) does not have a group having a polymerizable unsaturated group in the formula, $Y_1$ in the general formula (1) represents an oxygen atom, $n_1$ represents 1, and $R_6$ represents a carboxy group among the examples of the compound according to the embodiment of the present invention can be produced by performing the process according to a series of methods shown in the following reactions [I-I] to [III-I], [I-II] to [III-II], or [I-III] to [III-III] and then performing the process according to the method shown in the reaction [IV].

Among examples of the compound represented by the general formula (37), in a case where the carboxy group as $R_6$ in the general formula (1) is positioned at the ortho-position of the benzene ring, first, a compound represented by the following general formula (35-1) may be produced according to a series of methods shown in the following reactions [I-I] to [III-I]. In other words, first, a compound represented by the following general formula (32-1) is obtained by reacting phthalic anhydride with a compound represented by the following general formula (31) (reaction [I-I]). Next, a compound represented by the following general formula (34) is obtained by reacting the compound represented by the following general formula (32-1) with a compound represented by the following general formula (33) (reaction [II-I]). The obtained compound represented by the general formula (34) is subjected to a salt formation reaction to obtain a compound represented by the general formula (35-1) (reaction [III-I]).

In addition, among examples of the compound represented by the general formula (37), in a case where the carboxy group as $R_6$ in the general formula (1) is positioned at the para-position of the benzene ring, first, a compound represented by the following general formula (35-2) may be produced according to a series of methods shown in the following reactions [I-II] to [III-II]. In other words, first, a compound represented by the following general formula (32-2) is obtained by reacting a compound represented by the following general formula (31') with methyl p-(chlorocarbonyl) benzoate (reaction [I-II]). Next, the obtained compound represented by the general formula (32-2) reacts with a compound represented by the following general formula (33) (reaction [II-II]) and is subjected to a salt formation reaction to obtain a compound represented by the general formula (35-2) (reaction [III-II]).

In addition, among examples of the compound represented by the general formula (37), in a case where the carboxy group as $R_6$ in the general formula (1) is positioned at the para-position of the benzene ring, first, a compound represented by the following general formula (35-3) may be produced according to a series of methods shown in the following reactions [I-III] to [III-III]. In other words, first, a compound represented by the following general formula (32-3) is obtained by reacting a compound represented by the following general formula (31') with methyl m-(chlorocarbonyl) benzoate (reaction [I-III]). Next, the obtained compound represented by the general formula (32-3) reacts with a compound represented by the following general formula (33) (reaction [II-III]) and is subjected to a salt formation reaction to obtain a compound represented by the general formula (35-3) (reaction [III-III]).

A compound represented by the general formula (35-1), (35-2), or (35-3) obtained by carrying out the reaction described above {in other words, a compound represented by the following general formula (35)} reacts with a compound represented by the following general formula (36) to obtain a compound represented by the general formula (37) (reaction [IV]).

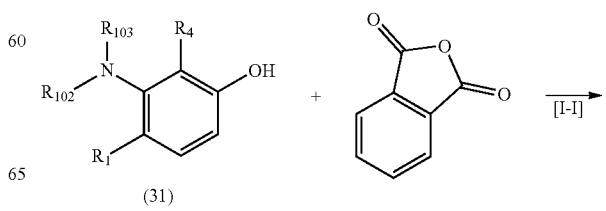

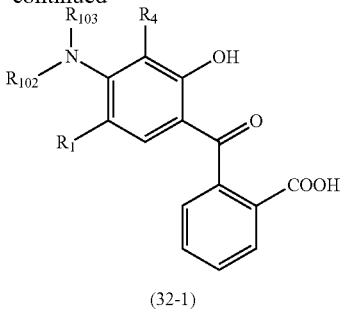

(32-1)

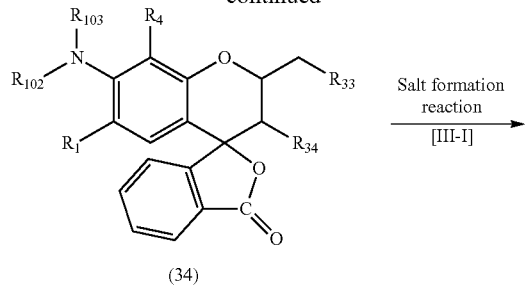

(34)

(In the formulae, $R_{102}$ and $R_{103}$ each independently represent an alkyl group having 1 to 20 carbon atoms or an aryl group having 6 to 14 carbon atoms which has a substituent or is unsubstituted, $R_1$ and $R_4$ each have the same definition as described above, $R_1$ and $R_{102}$ may form an alkylene group having 2 to 4 carbon atoms, and $R_{103}$ and $R_4$ may form an alkylene group having 2 to 4 carbon atoms.)

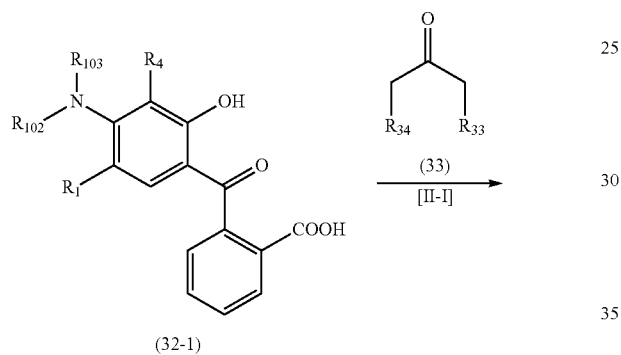

(32-1)    (33)

(35-1)

(In the formulae, $R_1$, $R_{102}$, $R_{103}$, $R_4$, $R_{33}$, $R_{34}$, and $An^-$ each have the same definition as described above.)

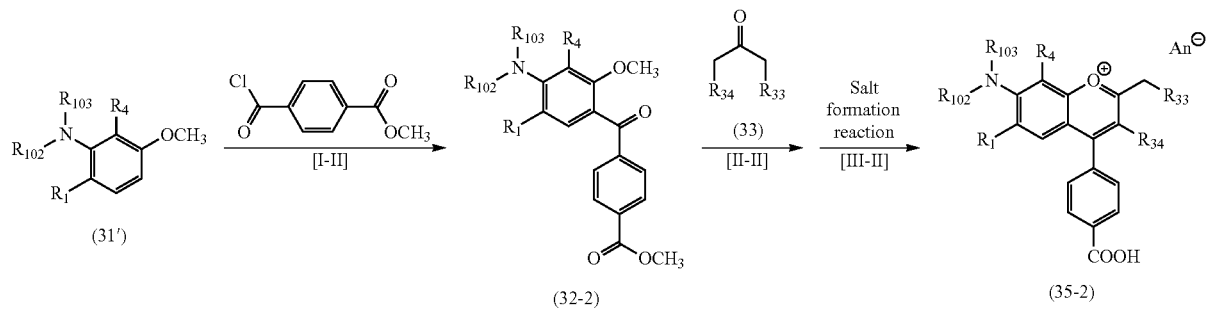

(31')    (32-2)    (35-2)

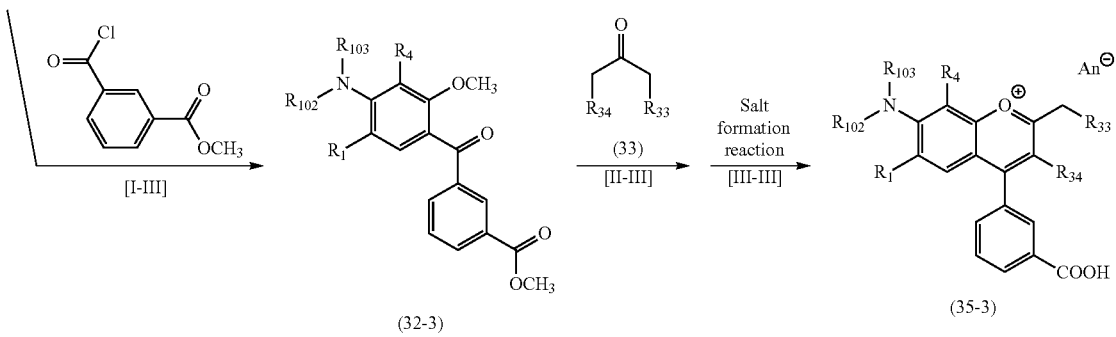

(32-3)    (35-3)

(In the formulae R₁, R₁₀₂, R₁₀, R₄, R₃₃, R₃₄, and An⁻ each have the same definition as described above.)

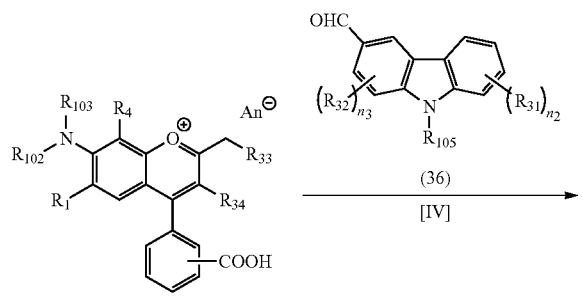

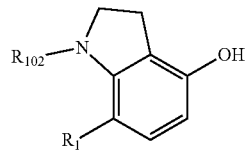

(36)
[IV]

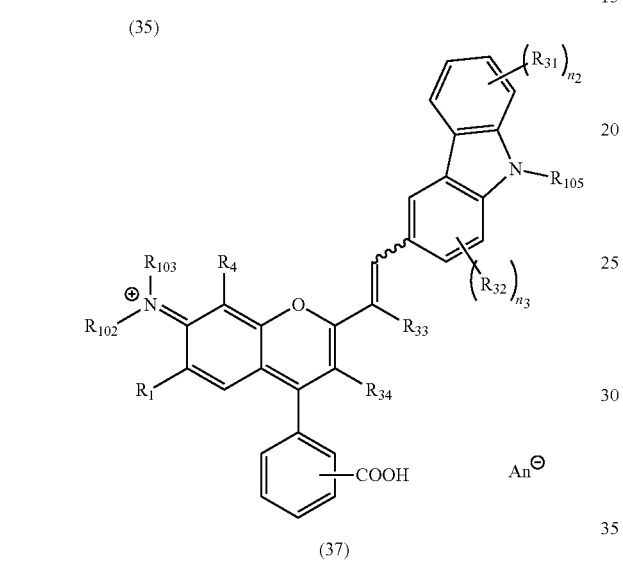

(In the formula, $R_{105}$ represents a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted, and $R_1$, $R_{102}$, $R_{103}$, $R_4$, $R_{31}$ to $R_{34}$, An⁻, $n_2$, and $n_3$ each have the same definition as described above.)

Examples of the alkyl group having 1 to 20 carbon atoms and the aryl group having 6 to 14 carbon atoms which has a substituent or is unsubstituted as $R_{102}$ and $R_{103}$ in the general formula (31) are the same as those exemplified as $R_2$ and $R_3$ in the general formula (1), and the preferred examples thereof are the same as described above.

In the general formula (31), examples of the alkylene group having 2 to 4 carbon atoms in a case where $R_1$ and $R_{102}$ form an alkylene group having 2 to 4 carbon atoms and $R_{103}$ and $R_4$ form an alkylene group having 2 to 4 carbon atoms are the same as those exemplified as the alkylene group having 2 to 4 carbon atoms in a case where $R_1$ and $R_2$ form an alkylene group having 2 to 4 carbon atoms and $R_3$ and $R_4$ form an alkylene group having 2 to 4 carbon atoms in the general formula (1), and the preferred examples thereof are the same as described above.

In the general formula (1), specific examples of the general formula (31) in a case where $R_1$ and $R_{102}$ form an alkylene group having 2 to 4 carbon atoms and $R_{103}$ and $R_4$ form an alkylene group having 2 to 4 carbon atoms include the following general formulae (8-11) to (8-19).

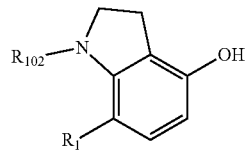
(8-11)

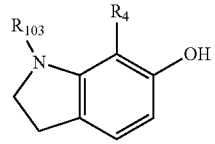
(8-12)

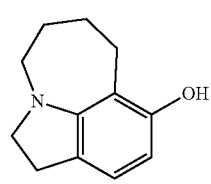
(8-13)

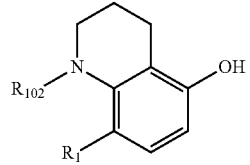
(8-14)

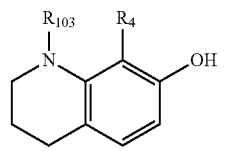
(8-15)

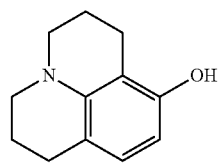
(8-16)

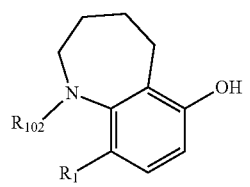
(8-17)

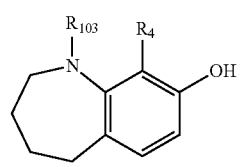
(8-18)

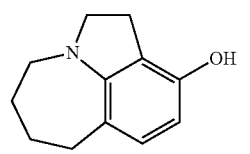
(8-19)

(In the formulae, $R_1$, $R_{102}$, $R_{103}$, and $R_4$ each have the same definition as described above.)

Among the specific examples, the general formulae (8-14) to (8-16) are preferable, and the general formula (8-16) is more preferable.

$R_{102}$ in the general formula (31) represents preferably an alkyl group having 1 to 12 carbon atoms, a phenyl group which has an alkyl group having 1 to 6 carbon atoms or is unsubstituted, or a linear alkylene group having 2 to 4 carbon atoms formed by $R_1$ and $R_{102}$; more preferably an alkyl group having 1 to 6 carbon atoms, a phenyl group which has an alkyl group having 1 to 3 carbon atoms or is unsubstituted, or a linear alkylene group having 2 to 4 carbon atoms formed by $R_1$ and $R_{102}$; still more preferably an alkyl group having 1 to 6 carbon atoms or a trimethylene group formed by $R_1$ and $R_{102}$; and particularly preferably an alkyl group having 1 to 6 carbon atoms. Specific examples thereof include a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, an ethylene group formed by $R_1$ and $R_{102}$, and a trimethylene group formed by $R_1$ and $R_{102}$, a tetramethylene group formed by $R_1$ and $R_{102}$. It should be noted that the alkyl group in the specific examples is not limited to a normal-form and includes all branched forms such as a sec-form, a tert-form, an iso-form, and a neo-form. Among these, a normal-form or an iso-form is preferable, and a normal-form is more preferable.

Among the specific examples, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_1$ and $R_{102}$, a trimethylene group formed by $R_1$ and $R_{102}$, or a tetramethylene group formed by $R_1$ and $R_{102}$ is preferable; the methyl group, the ethyl group, the n-propyl group, the isopropyl group, the n-butyl group, the isobutyl group, the sec-butyl group, the tert-butyl group, or the trimethylene group formed by $R_1$ and $R_{102}$ is more preferable; the methyl group, the ethyl group, or the trimethylene group formed by $R_1$ and $R_{102}$ is still more preferable; and the ethyl group is particularly preferable.

$R_{103}$ in the general formula (31) represents preferably an alkyl group having 1 to 12 carbon atoms, a phenyl group which has an alkyl group having 1 to 6 carbon atoms or is unsubstituted, or a linear alkylene group having 2 to 4 carbon atoms formed by $R_{103}$ and $R_4$; more preferably an alkyl group having 1 to 6 carbon atoms, a phenyl group which has an alkyl group having 1 to 3 carbon atoms or is unsubstituted, or a linear alkylene group having 2 to 4 carbon atoms formed by $R_{103}$ and $R_4$; still more preferably an alkyl group having 1 to 6 carbon atoms or a trimethylene group formed by $R_{103}$ and $R_4$; and particularly preferably an alkyl group having 1 to 6 carbon atoms. Specific examples thereof include a methyl group, an ethyl group, a propyl group, a butyl group, a pentyl group, a hexyl group, a phenyl group, a p-tolyl group, a p-ethylphenyl group, a p-propylphenyl group, a p-butylphenyl group, a p-pentylphenyl group, a p-hexylphenyl group, a 2,4-xylyl group, a 2,6-xylyl group, a 3,5-xylyl group, a mesityl group, an ethylene group formed by $R_{103}$ and $R_4$, a trimethylene group formed by $R_3$ and $R_4$, and a tetramethylene group formed by $R_{103}$ and $R_4$. It should be noted that the alkyl group in the specific examples is not limited to a normal-form and includes all branched forms such as a sec-form, a tert-form, an iso-form, and a neo-form. Among these, the normal-form or the iso-form is preferable, and the normal-form is more preferable.

Among the specific examples, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_{103}$ and $R_4$, a trimethylene group formed by $R_{103}$ and $R_4$, or a tetramethylene group formed by $R_{103}$ and $R_4$ is preferable; the methyl group, the ethyl group, the n-propyl group, the isopropyl group, the n-butyl group, the isobutyl group, the sec-butyl group, the tert-butyl group, or the trimethylene group formed by $R_{103}$ and $R_4$ is more preferable; the methyl group, the ethyl group, or the trimethylene group formed by $R_{103}$ and $R_4$ is still more preferable; and the ethyl group is particularly preferable.

Examples of the alkyl group having 1 to 20 carbon atoms, the haloalkyl group having 1 to 20 carbon atoms, and the acyl group having 2 to 21 carbon atoms as $R_{105}$ in the general formula (36) are the same as those exemplified as $R_5$ in the general formula (1), and the preferred examples thereof are the same as described above.

$R_{105}$ in the general formula (36) represents preferably a formyl group, an alkyl group having 1 to 12 carbon atoms, a haloalkyl group having 1 to 6 carbon atoms, an acyl group having 2 to 7 carbon atoms, an alkyl group having 1 to 6 carbon atoms, or an unsubstituted phenyl group; more preferably a formyl group, an alkyl group having 1 to 6 carbon atoms, a haloalkyl group having 1 to 3 carbon atoms, an acyl group having 2 to 5 carbon atoms, or a phenyl group which has an alkyl group having 1 to 3 carbon atoms or is unsubstituted; still more preferably an alkyl group having 1 to 6 carbon atoms or an unsubstituted phenyl group; and particularly preferably an alkyl group having 1 to 6 carbon atoms. Specific examples thereof include a formyl group, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a trifluoromethyl group, a pentafluoroethyl group, a heptafluoropropyl group, an acetyl group, a propionyl group, an n-butyryl group, an n-pentanoyl group, a p-tolyl group, an p-ethylphenyl group, a p-n-propylphenyl group, a p-isopropylphenyl group, and a phenyl group. Among these, the methyl group, the ethyl group, the n-propyl group, the isopropyl group, the n-butyl group, the isobutyl group, the sec-butyl group, the tert-butyl group, or the phenyl group is preferable, the methyl group, the ethyl group, or the phenyl group is more preferable, and the ethyl group is particularly preferable.

In the reaction [I-I], the compound represented by the general formula (31) may react with phthalic anhydride in a solvent at a temperature of typically 80° C. to 160° C. and preferably 90° C. to 120° C. for typically 1 to 24 hours and preferably 2 to 10 hours.

Examples of the solvent include alcohols such as methanol, ethanol, and isopropyl alcohol; ethers such as diethyl ether, diisopropyl ether, ethyl methyl ether, tetrahydrofuran, 1,4-dioxane, and dimethoxyethane; ketones such as acetone, dimethyl ketone, methyl ethyl ketone, diethyl ketone, 2-hexanone, tert-butyl methyl ketone, cyclopentanone, and cyclohexanone; halogenated hydrocarbons such as chloromethane, chloroform, dichloromethane, dichloroethane, trichloroethane, carbon tetrachloride, and chlorobenzene; hydrocarbons such as n-hexane, benzene, toluene, and xylene; esters such as ethyl acetate, butyl acetate, and methyl propionate; nitriles such as acetonitrile; and amides such as N,N-dimethylformamide. Among these, the alcohols, ethers, the halogenated hydrocarbons, and the hydrocarbons are preferable; and the ethanol, the tetrahydrofuran, the dichloromethane, and the toluene are more preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (31).

The amount of the phthalic anhydride to be used is typically in a range of 1 to 2 equivalents and preferably in a range of 1 to 1.5 equivalents with respect to the mol number of the compound represented by the general formula (31).

Specific examples of the compound represented by the general formula (31) are as follows. A commercially available product may be used as the compound represented by the general formula (31) or the compound may be appropriately synthesized according to a known method.

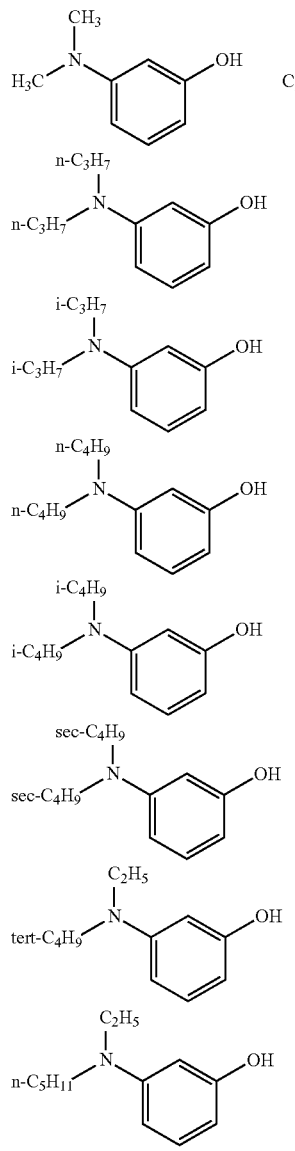

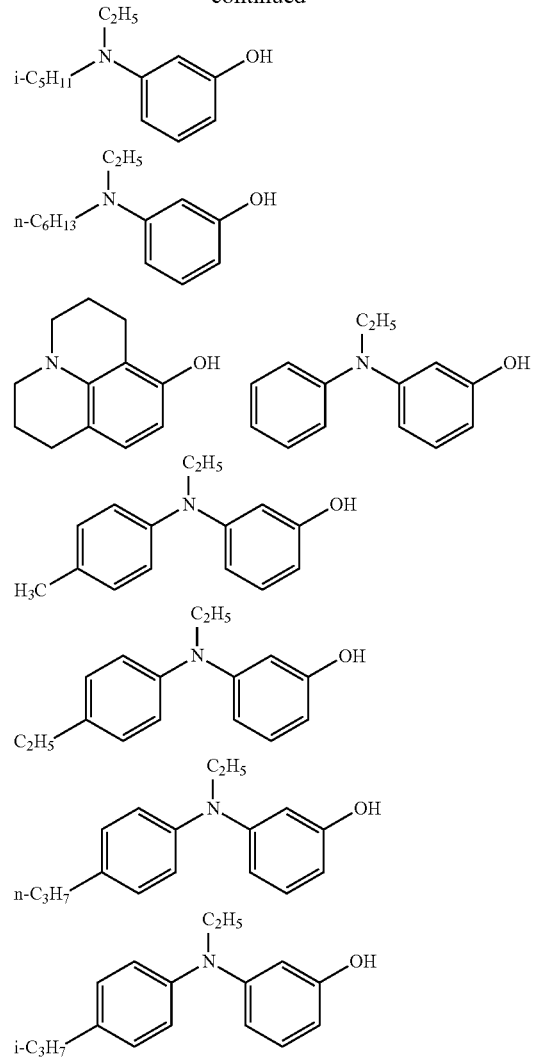

In the reaction [II-I], the compound represented by the general formula (32-1) obtained from the reaction [I-I] may react with the compound represented by the general formula (33) in the presence of an acid at a temperature of typically 70° C. to 140° C. and preferably 80° C. to 120° C. for typically 1 to 24 hours and preferably 2 to 10 hours.

Examples of the acid include sulfuric acid, methanesulfonic acid, trifluoromethanesulfonic acid, p-toluenesulfonic acid, and camphorsulfonic acid. Among these, sulfuric acid is preferable. The amount of the acid to be used is typically in a range of 0.1 to 50 mL and preferably in a range of 0.5 to 10 mL with respect to 1 mmol of the compound represented by the general formula (32-1).

The amount of the compound represented by the general formula (33) to be used is typically in a range of 1 to 5 equivalents and preferably in a range of 1.5 to 3.5 equivalents with respect to the mol number of the compound represented by the general formula (32-1).

Specific examples of the compound represented by the general formula (33) include acetone, methyl ethyl ketone, diethyl ketone, 3-hexanone, 4-heptanone, cyclopentanone, 3-methyl cyclopentanone, 3-ethyl cyclopentanone, cyclohexanone, 3-methyl cyclohexanone, 4-methyl cyclohexanone, 3-ethyl cyclohexanone, 4-ethylcyclohexanone, cycloheptanone, 3-ethyl cyclohexanone, 4-ethylcyclohexanone, 3-methyl cycloheptanone, 4-methyl cycloheptanone, and 2-indanone (β-hydrindon). Among these, the acetone, the cyclopentanone, the cyclohexanone, the cycloheptanone, or the 2-indanone is preferable. A commercially available product may be used as the compound represented by the general formula (33) or the compound may be appropriately synthesized according to a known method.

In the reaction [III-I], the compound represented by the general formula (34) obtained from the reaction [II-I] may be subjected to a salt formation reaction. The salt formation reaction is carried out by bringing a salt of the anion represented by An⁻ into contact with the compound represented by the general formula (34) in a solvent.

The salt formation reaction is carried out at a temperature of typically 0° C. to 80° C. and preferably 10° C. to 50° C. for typically 10 minutes to 24 hours and preferably 30 minutes to 10 hours.

Examples of the solvent in the salt formation reaction include water, methanol, ethanol, isopropyl alcohol, tetrahydrofuran, dioxane, N,N-dimethylformamide, dichloromethane, dichloroethane, and ethyl acetate. Among these, the water and the dichloromethane are preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (34).

Examples of the salt of the anion represented by An⁻ in the salt formation reaction include an alkali metal salt of the anion represented by An⁻ and an inorganic acid.

Examples of the alkali metal salt include salts formed of the anion represented by An⁻ and alkali metals such as sodium, potassium, and lithium. Among these, salts formed of the anion represented by An⁻ and potassium or lithium are preferable. The amount of the alkali metal salts to be used is typically in a range 1 to 2 equivalents and preferably in a range of 1 to 1.5 equivalents with respect to the mol number of the compound represented by the general formula (34).

Examples of the inorganic acid include inorganic acids such as hydrochloric acid, hydrogen bromide, hydrogen iodide, hypochlorous acid, chlorous acid, chloric acid, perchloric acid, hexafluorophosphoric acid, and hexafluoroantimonic acid. Among these, the hydrochloric acid, the perchloric acid, the hexafluorophosphoric acid, or the hexafluoroantimonic acid is preferable, and the perchloric acid is more preferable. The amount of the inorganic acids to be used is typically in a range 1 to 50 equivalents and preferably in a range of 1 to 10 equivalents with respect to the mol number of the compound represented by the general formula (34).

In a case where the salt of the anion represented by An⁻ in the salt formation reaction is an alkali metal salt, it is preferable that the compound represented by the general formula (35-1) is obtained by reacting the compound represented by the general formula (34) with the alkali metal salt of the anion represented by An⁻ in a solvent in the coexistence of hydrochloric acid through a chloro salt. The amount of the hydrochloric acid to be used is typically in a range 1 to 50 equivalents and preferably in a range of 1 to 10 equivalents with respect to the mol number of the compound represented by the general formula (34).

In addition, in a case where the salt of the anion represented by An⁻ in the salt formation reaction is an inorganic acid, the compound represented by the general formula (34) may react with the inorganic acid in a solvent.

In the reaction [I-II], the compound represented by the general formula (31') may react with methyl p-(chlorocarbonyl) benzoate in a solvent in the presence of a catalyst at a temperature of typically 0° C. to 80° C. and preferably 10° C. to 50° C. for typically 1 to 24 hours and preferably 2 to 10 hours.

Examples of the catalyst include aluminum chloride. The amount of the catalyst to be used is typically in a range of 0.1 to 10 equivalents with respect to the mol number of the compound represented by the general formula (31').

Examples of the solvent are the same as those exemplified as the solvent in the reaction [I-I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (31').

The amount of the methyl p-(chlorocarbonyl) benzoate to be used is typically in a range of 1 to 2 equivalents and preferably in a range of 1 to 1.5 equivalents with respect to the mol number of the compound represented by the general formula (31').

Specific examples of the compound represented by the general formula (31') are as follows. A commercially available product may be used as the compound represented by the general formula (31') or the compound may be appropriately synthesized according to a known method.

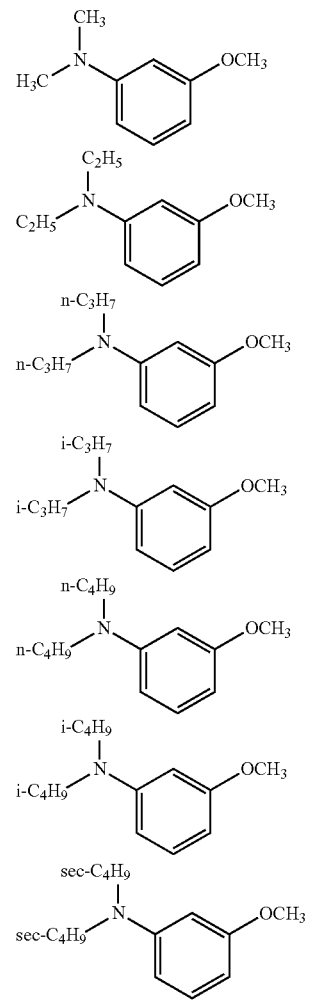

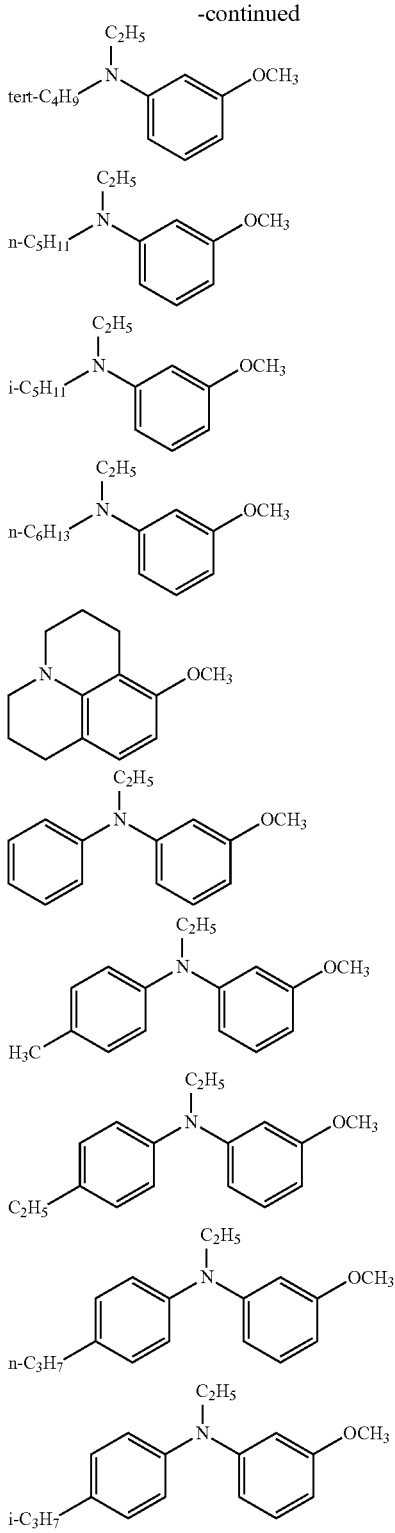

In the reaction [II-II], the compound represented by the general formula (32-2) obtained from the reaction [I-II] may react with lithium hydroxide in a solvent at a temperature of typically 0° C. to 80° C. and preferably 10° C. to 50° C. for typically 1 to 72 hours and preferably 24 to 48 hours, and the obtained compound may react with the compound represented by the general formula (33) in the presence of an acid at a temperature of typically 70° C. to 140° C. and preferably 80° C. to 120° C. for typically 1 to 24 hours and preferably 2 to 10 hours.

Examples of the solvent are the same as those exemplified as the solvent in the reaction [I-I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (31-2).

The amount of the lithium hydroxide to be used is typically in a range of 1 to 5 equivalents and preferably in a range of 2 to 4 equivalents with respect to the mol number of the compound represented by the general formula (32-2). The lithium hydroxide to be used may be hydrate, and water may be further added at the time of use. The amount of water to be used is typically in a range of 0.1 to 50 mL and preferably in a range of 0.5 to 10 mL with respect to 1 mmol of lithium hydroxide.

Examples of the acid include sulfuric acid, methanesulfonic acid, trifluoromethanesulfonic acid, p-toluenesulfonic acid, and camphorsulfonic acid. Among these, the sulfuric acid is preferable. The amount of the acid to be used is typically in a range of 0.1 to 50 mL and preferably in a range of 0.5 to 15 mL with respect to 1 mmol of the compound represented by the general formula (32-1).

The amount of the compound represented by the general formula (33) to be used is typically in a range of 1 to 10 equivalents and preferably in a range of 2 to 5 equivalents with respect to the mol number of the compound represented by the general formula (32-1).

The reaction [III-II] may be carried out under the same reaction conditions (the reaction solvent, the reaction temperature, the reaction time, and each use amount) as those for the reaction [III-I] except that the compound obtained from the reaction [II-II] is used in place of the compound represented by the general formula (34).

The reaction [I-III] may be carried out under the same reaction conditions (the reaction solvent, the reaction temperature, the reaction time, and each use amount) as those for the reaction [I-II] except that methyl m-(chlorocarbonyl)benzoate is used in place of methyl p-(chlorocarbonyl)benzoate.

The reaction [II-III] may be carried out under the same reaction conditions (the reaction solvent, the reaction temperature, the reaction time, and each use amount) as those for the reaction [II-II] except that the compound represented by the general formula (32-3) is used in place of the compound represented by the general formula (32-2).

The reaction [III-III] may be carried out under the same reaction conditions (the reaction solvent, the reaction temperature, the reaction time, and each use amount) as those for the reaction [III-I] except that the compound obtained from the reaction [11-111] is used in place of the compound represented by the general formula (34).

In the reaction [IV], the compound represented by the general formula (35) may react with the compound represented by the general formula (36) in a solvent or without using a solvent in the presence of a dehydration condensation agent at a temperature of typically 40° C. to 100° C. and preferably 50° C. to 80° C. for typically 1 to 24 hours and preferably 2 to 12 hours.

The compound represented by the general formula (35) is shown in a manner that the compound represented by the general formula (35-1) obtained from the reaction [III-I], the compound represented by the general formula (35-2) obtained from the reaction [III-II], and the compound represented by the general formula (35-3) obtained from the reaction [III-III] are collectively shown in one formula.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 15 mL with respect to 1 mmol of the compound represented by the general formula (35).

As the dehydration condensation agent, those which have typically been used as a dehydration condensation agent may be used, and examples thereof include inorganic dehydration agents such as diphosphorous pentaoxide and anhydrous zinc chloride; carbodiimides such as dicyclohexylcarbodiimide, diisopropylcarbodiimide, and 1-ethyl-3-(3-dimethylaminopropylcarbodiimide) hydrochloride; and polyphosphoric acid, acetic anhydride, sulfuric acid, carbonyl diimidazole, and p-toluenesulfonic acid. Among these, the acetic anhydride and the sulfuric acid are preferable. The amount of the dehydration condensation agent to be used is typically in a range 1 to 20 equivalents and preferably in a range of 1 to 10 equivalents with respect to the mol number of the compound represented by the general formula (35).

The amount of the compound represented by the general formula (36) to be used is typically in a range 1 to 2 equivalents and preferably in a range of 1 to 1.5 equivalents with respect to the mol number of the compound represented by the general formula (35).

Specific examples of the compound represented by the general formula (36) are as follows. A commercially available product may be used as the compound represented by the general formula (36) or the compound may be appropriately synthesized according to a known method.

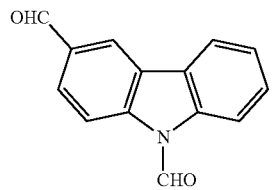
CHO

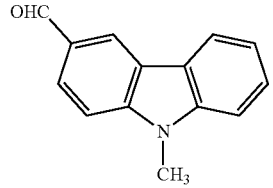
CH$_3$

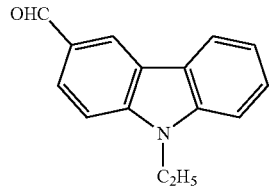
C$_2$H$_5$

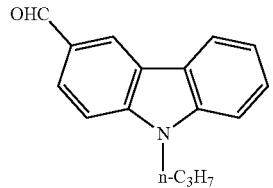
n-C$_3$H$_7$

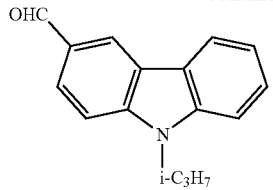
i-C$_3$H$_7$

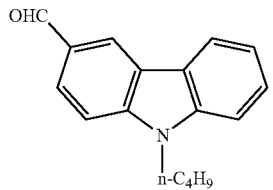
n-C$_4$H$_9$

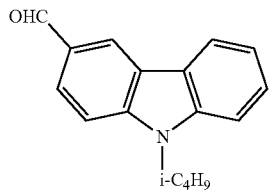
i-C$_4$H$_9$

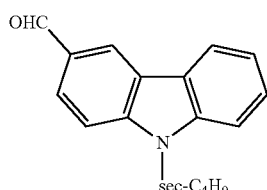
sec-C$_4$H$_9$

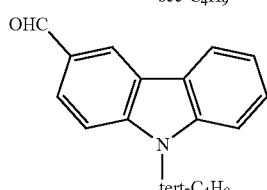
tert-C$_4$H$_9$

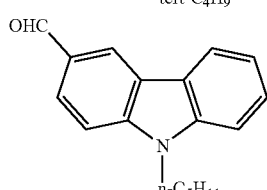
n-C$_5$H$_{11}$

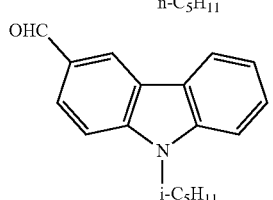
i-C$_5$H$_{11}$

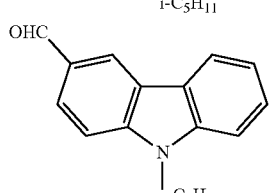
n-C$_6$H$_{13}$

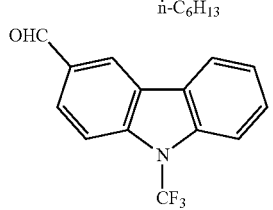
CF$_3$

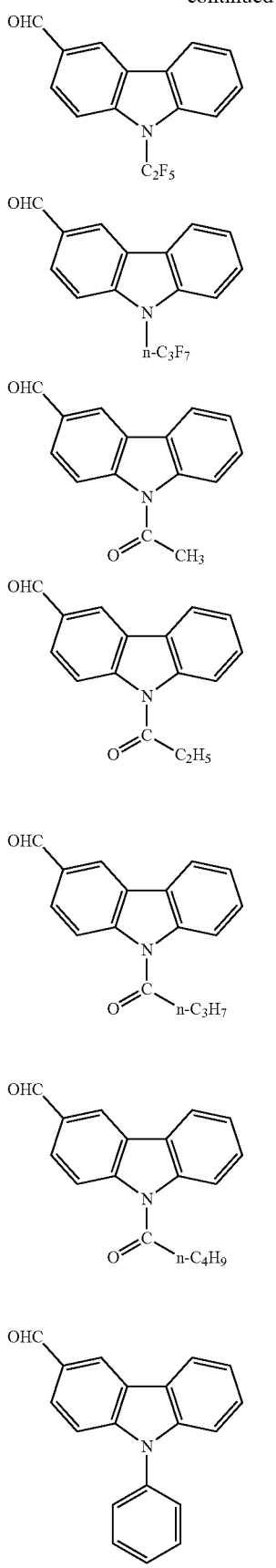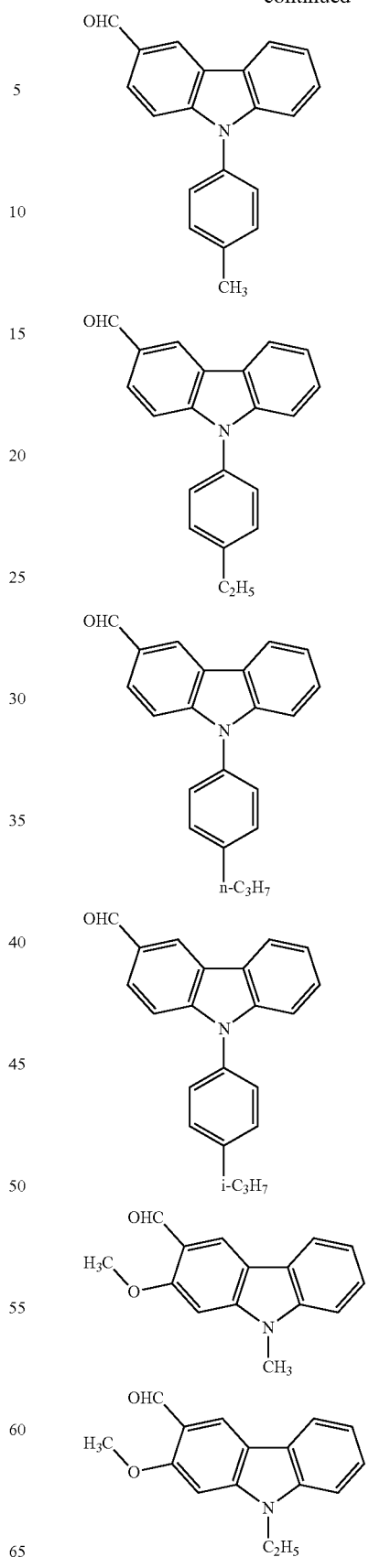

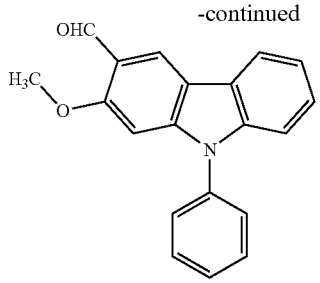

In addition, the compound represented by the general formula (37) obtained from the reactions [I] to [IV] may be further subjected to a salt exchange reaction. The salt exchange reaction is carried out by bringing a salt of the anion represented by An⁻ into contact with the compound represented by the general formula (37) in a solvent.

The salt exchange reaction is carried out at a temperature of typically 0° C. to 80° C. and preferably 10° C. to 50° C. for typically 10 minutes to 24 hours and preferably 30 minutes to 10 hours.

Examples of the solvent in the salt exchange reaction include organic solvents such as methanol, ethanol, isopropyl alcohol, tetrahydrofuran, dioxane, N,N-dimethylformamide, dichloromethane, dichloroethane, and ethyl acetate. Among these, the ethanol, the dichloromethane, and the ethyl acetate are preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (37).

Examples of the salt of the anion represented by An⁻ in the salt exchange reaction are the same as those exemplified as the salt of the anion represented by An⁻ in the salt formation reaction in the reaction [IV], and the preferred examples and the use amounts thereof are the same as described above.

For example, a {compound represented by the following general formula (39-1)} in which the general formula (1) does not have a group having a polymerizable unsaturated group in the formula, $Y_1$ in the general formula (1) represents an oxygen atom, $n_1$ represents 1, and $R_6$ represents an alkoxycarbonyl group having 2 to 21 carbon atoms among the examples of the compound according to the embodiment of the present invention can be produced according to the method shown in the following reaction [V-I]. In other words, a compound represented by the following general formula (39-1) can be obtained by reacting the compound represented by the general formula (37) which has been obtained from the reaction [V] with the compound represented by the general formula (38-1).

In addition, for example, a {compound represented by the following general formula (39-2)} in which the general formula (1) does not have a group having a polymerizable unsaturated group in the formula, $Y_1$ in the general formula (1) represents an oxygen atom, $n_1$ represents 1, and $R_6$ represents a carbamoyl group, a monoalkylaminocarbonyl group having 2 to 21 carbon atoms, or a dialkylaminocarbonyl group having 3 to 41 carbon atoms among the examples of the compound according to the embodiment of the present invention can be produced according to the method shown in the following reaction [V-II]. In other words, a compound represented by the following general formula (39-2) can be obtained by reacting the compound represented by the general formula (37) which has been obtained from the reaction [V] with the compound represented by the general formula (38-2).

In addition, for example, a {compound represented by the following general formula (39-3)} in which only $R_6$ in the general formula (1) represents a group having a polymerizable unsaturated group, $Y_1$ in the general formula (1) represents an oxygen atom, $n_1$ represents 1, $R_6$ represents a group represented by the general formula (2), and $A_1$ in the general formula (2) represents —COO—, —CONH—, or a group represented by the general formula (2-1) among the examples of the compound according to the embodiment of the present invention can be produced according to the method shown in the following reaction [V-III]. In other words, a compound represented by the following general formula (39-3) can be obtained by reacting the compound represented by the general formula (37) which has been obtained from the reaction [V] with the compound represented by the general formula (38-3).

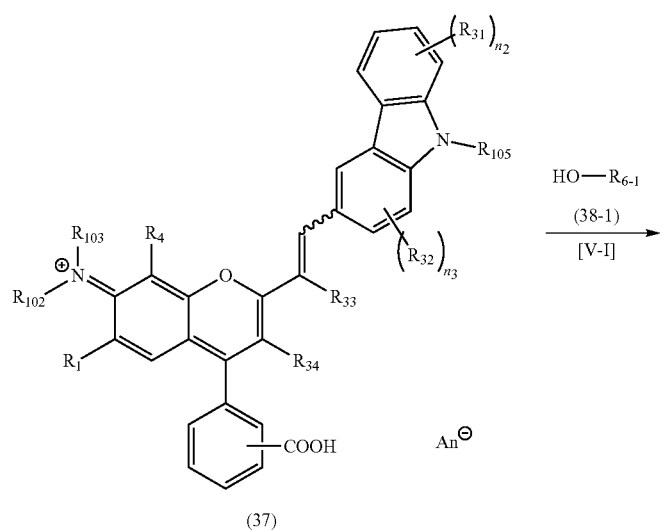
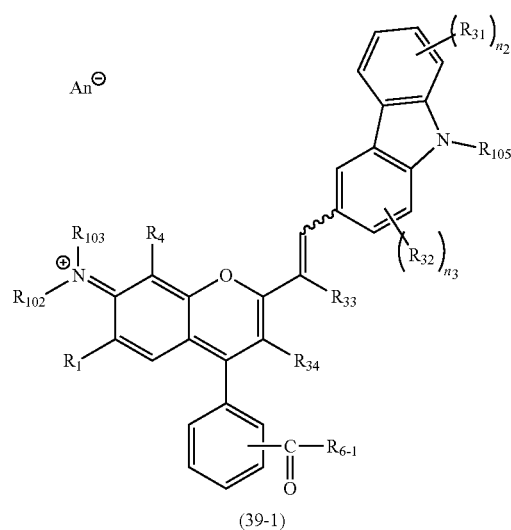
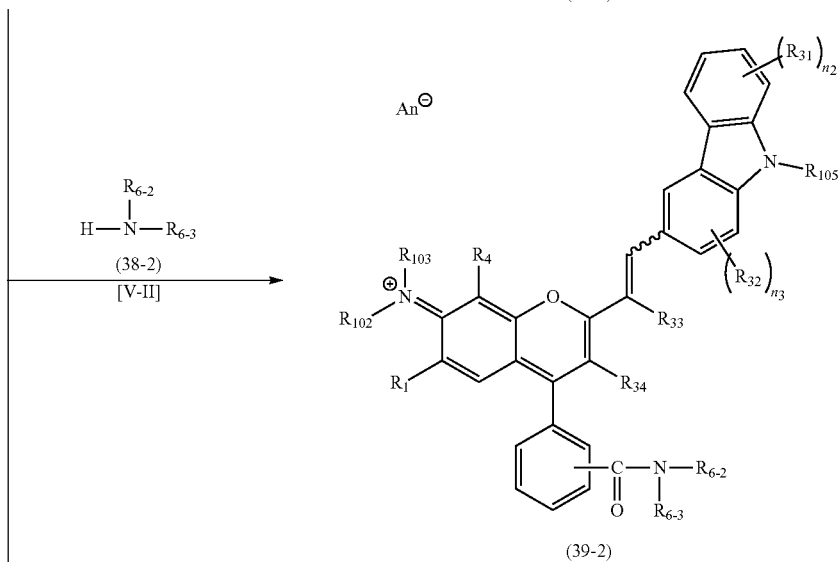
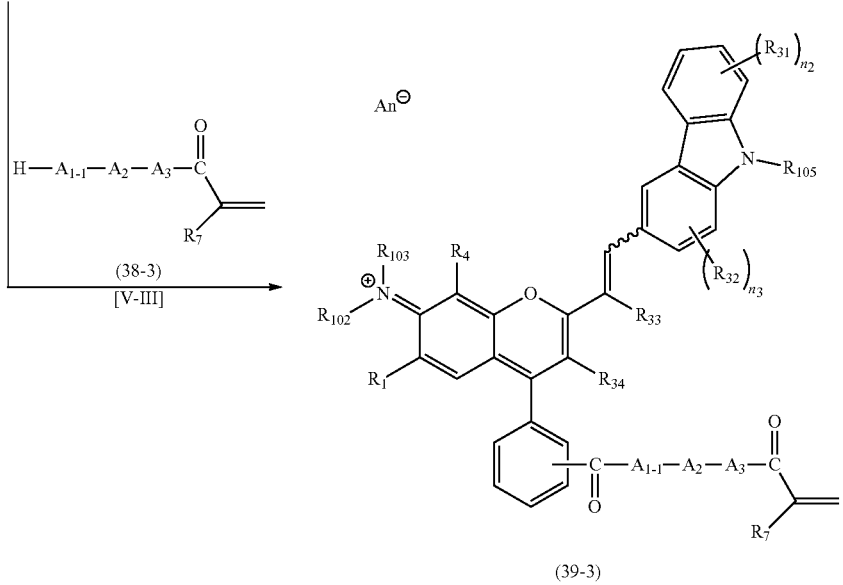

{In the formulae, $R_{6-1}$ represents an alkyl group having 1 to 20 carbon atoms, $R_{6-2}$ and $R_{6-3}$ each independently represent a hydrogen atom or an alkyl group having 1 to 20 carbon atoms, $A_{1-1}$ represents —O—, —NH—, or the following general formula (2-6),

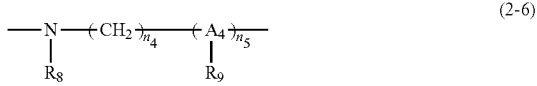

(2-6)

(In the formula, $R_8$, $R_9$, $A_4$, $n_4$, and $n_5$ each have the same definition as described above.) $R_1$, $R_{102}$, $R_{103}$, $R_4$, $R_{105}$, $R_7$, $R_{31}$ to $R_{34}$, $A_2$, $A_3$, $An^-$, $n_2$, and $n_3$ each have the same definition as described above.}

Examples of the alkyl group having 1 to 20 carbon atoms as $R_{6-1}$ in the general formula (38-1) are the same as those exemplified as the alkyl group having 1 to 20 carbon atoms as $R_2$ and $R_3$ in the general formula (1), and the preferred examples thereof are the same as described above.

Examples of the alkyl group having 1 to 20 carbon atoms as $R_{6-2}$ and $R_{6-3}$ in the general formula (38-2) are the same as those exemplified as the alkyl group having 1 to 20 carbon atoms as $R_2$ and $R_3$ in the general formula (1), and the preferred examples thereof are the same as described above.

$R_{6-2}$ and $R_{6-3}$ in the general formula (38-2) represent preferably a hydrogen atom or an alkyl group having 1 to 6 carbon atoms and more preferably a hydrogen atom or an alkyl group having 1 to 4 carbon atoms. Specific examples thereof include a hydrogen atom, a methyl group, an ethyl group, an n-propyl group, an isopropyl group, an n-butyl group, an isobutyl group, a sec-butyl group, and a tert-butyl group. Among these, the hydrogen atom, the methyl group, or the ethyl group is preferable.

$A_{11}$ in the general formula (38-3) represents preferably —O— or —NH— and more preferably —O—.

In the reaction [V-I], the compound represented by the general formula (37) may react with the compound represented by the general formula (38-1) in a solvent in the presence of a dehydration condensation agent at a temperature of typically 0° C. to 80° C. and preferably 10° C. to 50° C. for typically 1 to 24 hours and preferably 2 to 10 hours.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (37).

As the dehydration condensation agent, those which have typically been used as a dehydration condensation agent may be used, and examples thereof include inorganic dehydration agents such as diphosphorous pentaoxide and anhydrous zinc chloride; carbodiimides such as dicyclohexylcarbodiimide, diisopropylcarbodiimide, and 1-ethyl-3-(3-dimethylaminopropylcarbodiimide) hydrochloride; and polyphosphoric acid, acetic anhydride, sulfuric acid, carbonyl diimidazole, and p-toluenesulfonic acid. Among these, the carbodiimides are preferable. The amount of the dehydration condensation agent to be used is typically in a range 1 to 20 equivalents and preferably in a range of 1 to 10 equivalents with respect to the mol number of the compound represented by the general formula (37). In the reaction [V-I], a catalyst such as dimethylaminopyridine may be used in order to improve the efficiency of the dehydration condensation agent. The amount of the catalyst to be used is typically in a range of 0.1 to 10 equivalents with respect to the mol number of the compound represented by the general formula (37).

The amount of the compound represented by the general formula (38-1) to be used is typically in a range 1 to 2 equivalents and preferably in a range of 1 to 1.5 equivalents with respect to the mol number of the compound represented by the general formula (37).

Specific examples of the compound represented by the general formula (38-1) include methanol, ethanol, 1-propanol, 2-propanol, 1-butanol, 2-methyl-1-butanol, 2-butanol, 2-methyl-2-butanol, 1-pentanol, and 1-hexanol. Among these, the methanol or the ethanol is preferable. A commercially available product may be used as the compound represented by the general formula (38-1) or the compound may be appropriately synthesized according to a known method.

In the reaction [V-II], the compound represented by the general formula (37) may react with the compound represented by the general formula (38-2) in a solvent in the presence of a dehydration condensation agent at a temperature of typically 0° C. to 80° C. and preferably 10° C. to 50° C. for typically 1 to 24 hours and preferably 2 to 10 hours.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (37).

Examples of the dehydration condensation agent and the amount of the dehydration condensation agent to be used are the same as those exemplified in the reaction [V-I], and the preferred examples thereof are the same as described above. In addition, similar to the reaction [V-I], a catalyst may be used in the reaction [V-II] in order to improve the efficiency of the dehydration condensation agent. The type of the catalyst and the amount of the catalyst to be used as the same as those in the reaction [V-I].

The amount of the compound represented by the general formula (38-2) to be used is typically in a range 1 to 2 equivalents and preferably in a range of 1 to 1.5 equivalents with respect to the mol number of the compound represented by the general formula (37).

Specific examples of the compound represented by the general formula (38-2) include ammonia, methylamine, ethylamine, n-propylamine, isopropylamine, n-butylamine, isobutylamine, sec-butylamine, tert-butylamine, n-pentylamine, n-hexylamine, N,N-dimethylamine, N,N-diethylamine, N,N-di(n-propyl)amine, N,N-di(n-butyl)amine, N,N-ethylmethylamine, N,N-methyl-n-propylamine, N,N-methyl-n-butylamine, N,N-ethyl-n-propylamine, and N,N-ethyl-n-butylamine. Among these, the ammonia, the methylamine, the ethylamine, the N,N-dimethylamine, the N,N-diethylamine, or the N,N-ethylmethylamine is preferable. A commercially available product may be used as the compound represented by the general formula (38-2) or the compound may be appropriately synthesized according to a known method.

In the reaction [V-III], the compound represented by the general formula (37) may react with the compound represented by the general formula (38-3) in a solvent in the presence of a dehydration condensation agent at a temperature of typically 0° C. to 80° C. and preferably 10° C. to 50° C. for typically 1 to 24 hours and preferably 2 to 10 hours.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (37).

Examples of the dehydration condensation agent and the amount of the dehydration condensation agent to be used are the same as those exemplified in the reaction [V-I], and the preferred examples thereof are the same as described above. In addition, similar to the reaction [V-I], a catalyst may be used in the reaction [V-III] in order to improve the efficiency of the dehydration condensation agent. The type of the catalyst and the amount of the catalyst to be used are also the same as those in the reaction [V-I].

The amount of the compound represented by the general formula (38-3) to be used is typically in a range 1 to 2 equivalents and preferably in a range of 1 to 1.5 equivalents with respect to the mol number of the compound represented by the general formula (37).

Specific examples of the compound represented by the general formula (38-3) are as follows.

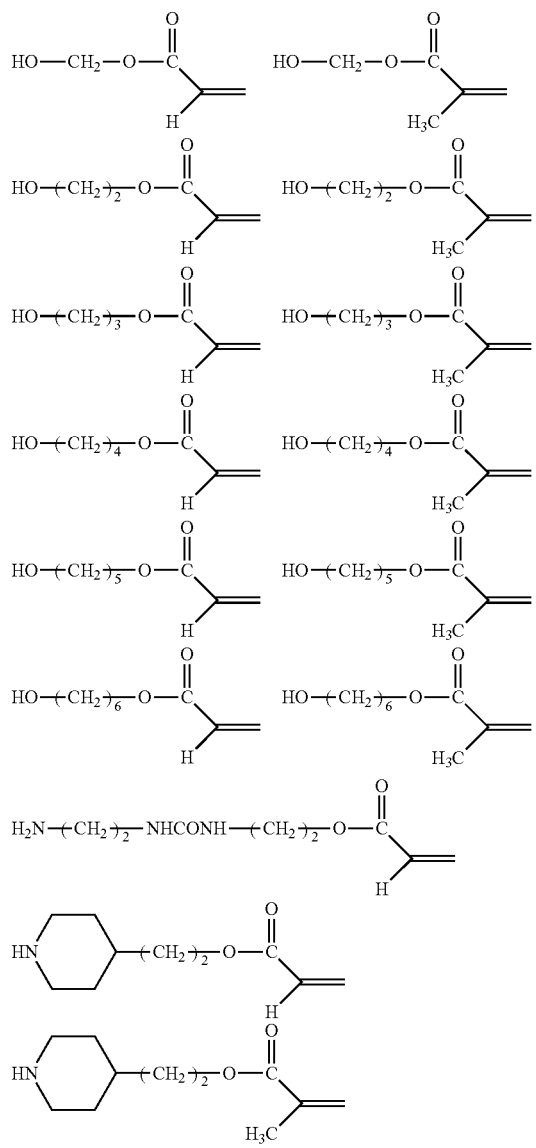

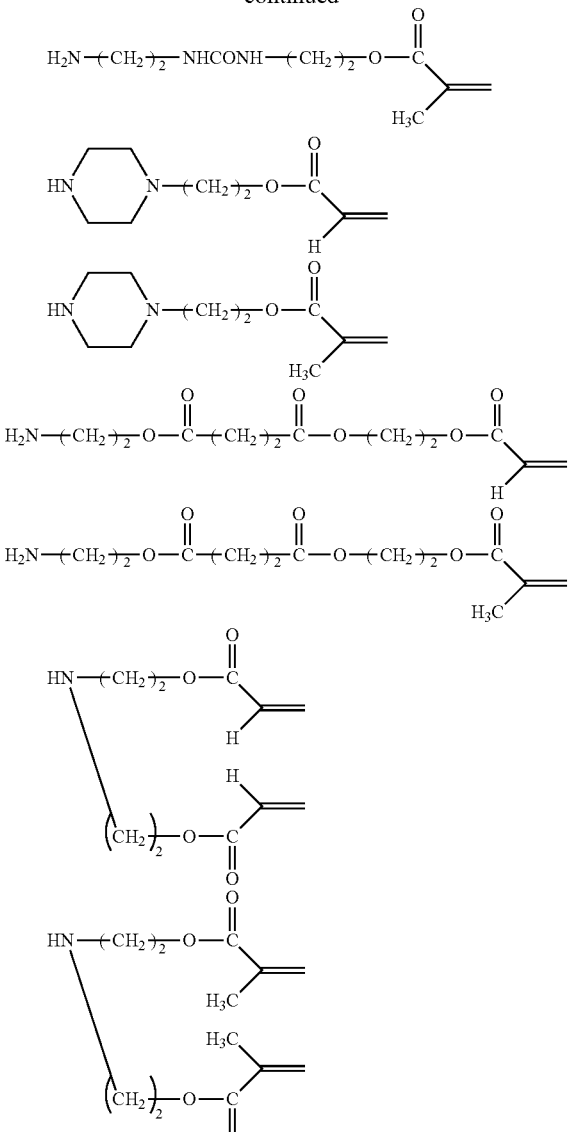

Among the specific examples, hydroxymethyl methacrylate, hydroxymethyl acrylate, 2-hydroxyethyl methacrylate, 2-hydroxyethyl acrylate, 3-hydroxypropyl methacrylate, 3-hydroxypropyl acrylate, 4-hydroxybutyl methacrylate, 4-hydroxybutyl acrylate, 5-hydroxypentyl methacrylate, 5-hydroxypentyl acrylate, 6-hydroxyhexyl methacrylate, or 6-hydroxyhexyl acrylate is preferable, and 2-hydroxyethyl methacrylate or 2-hydroxyethyl acrylate is more preferable. A commercially available product may be used as the compound represented by the general formula (38-3) or the compound may be appropriately synthesized according to a known method.

For example, a {compound represented by the following general formula (44-1)} in which the general formula (1) does not have a group having a polymerizable unsaturated group in the formula, $Y_1$ in the general formula (1) represents an oxygen atom, $n_1$ represents 1, and $R_6$ represents an alkylcarbonylamino group having 2 to 21 carbon atoms among the examples of the compound according to the embodiment of the present invention can be produced by performing the process according to a series of methods shown in the following reactions [VI] to [IX-I].

In other words, first, a compound represented by the following general formula (40) is obtained by reacting a compound represented by the general formula (37) obtained from the reaction [IV] and phosphoryl chloride (reaction [VI]). Next, the obtained compound represented by the general formula (40) reacts with hydroxylamine (reaction [VII]), and the obtained compound further reacts with triethylamine and tosyl chloride (p-toluenesulfonyl chloride) to obtain a compound represented by the following general formula (42) (reaction [VIII]). Thereafter, the obtained compound represented by the general formula (42) may react with a compound represented by the following general formula (43-1) to obtain a compound represented by the general formula (44-1) (reaction [IX-I]).

In addition, for example, a {compound represented by the following general formula (44-2)} in which only $R_6$ in the general formula (1) represents a group having a polymerizable unsaturated group, $Y_1$ in the general formula (1) represents an oxygen atom, $n_1$ represents 1, $R_6$ represents a group represented by the general formula (2), and $A_1$ in the general formula (2) represents —NHCO— among the examples of the compound according to the embodiment of the present invention can be produced by performing the process according to the method shown in the following reaction [IX-II] after the reactions [VI] to [VIII]. In other words, a compound represented by the following general formula (44-2) can be obtained by reacting the compound represented by the general formula (42) which has been obtained from the reaction [VIII] with the compound represented by the general formula (43-2).

In addition, for example, a {compound represented by the following general formula (44-3)} in which only $R_6$ in the general formula (1) represents a group having a polymerizable unsaturated group, $Y_1$ in the general formula (1) represents an oxygen atom, $n_1$ represents 1, $R_6$ represents a group represented by the general formula (2), and $A_1$ in the general formula (2) represents —NHCONH— among the examples of the compound according to the embodiment of the present invention can be produced according to the method shown in the following reaction [IX-III] after the reactions [VI] to [VIII] are carried out. In other words, a compound represented by the following general formula (44-3) can be obtained by reacting the compound represented by the general formula (42) which has been obtained from the reaction [VIII] with the compound represented by the general formula (43-3).

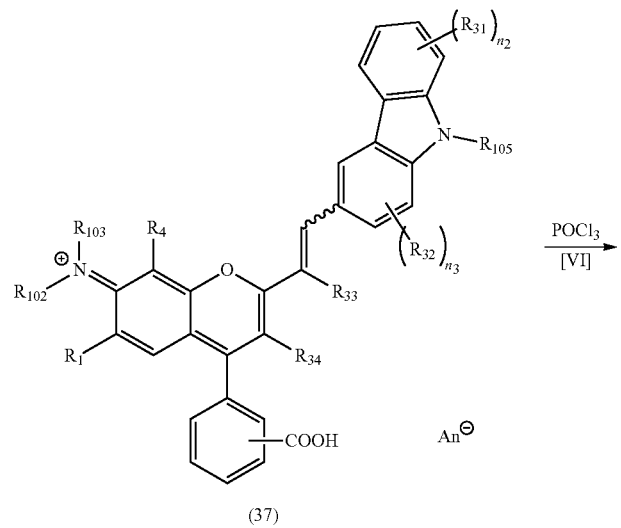

(37)

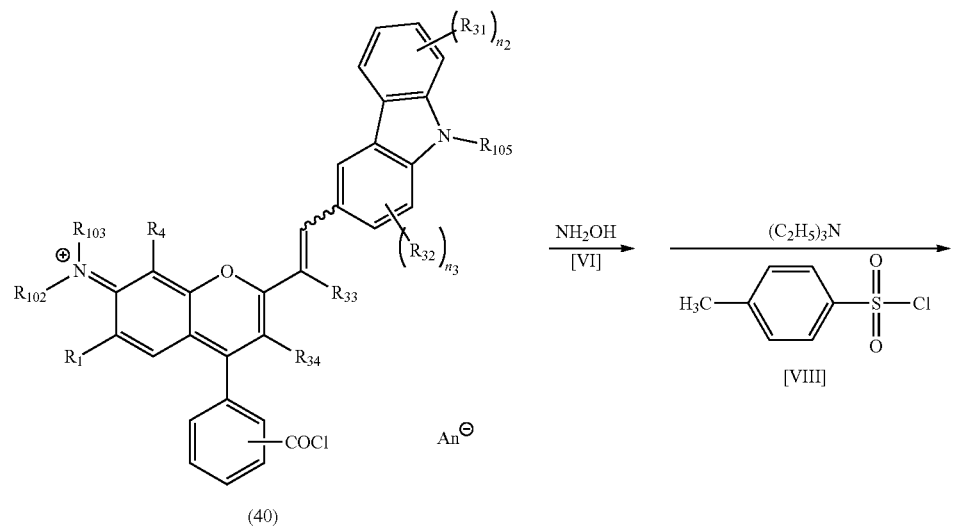

(40)

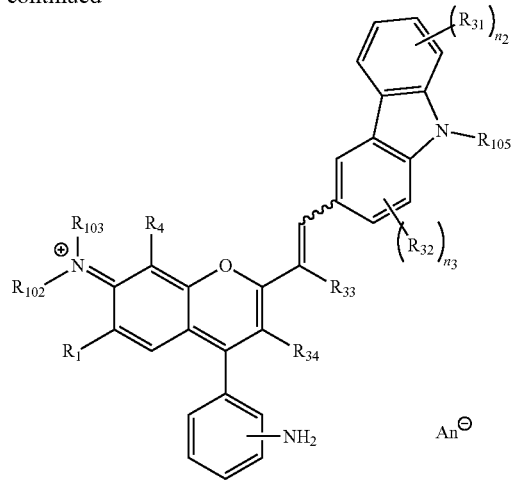
(In the formulae, $R_1$, $R_{102}$, $R_{103}$, $R_4$, $R_{105}$, $R_{31}$ to $R_{34}$, $An^-$, $n_2$, and $n_3$ each have the same definition as described above.)
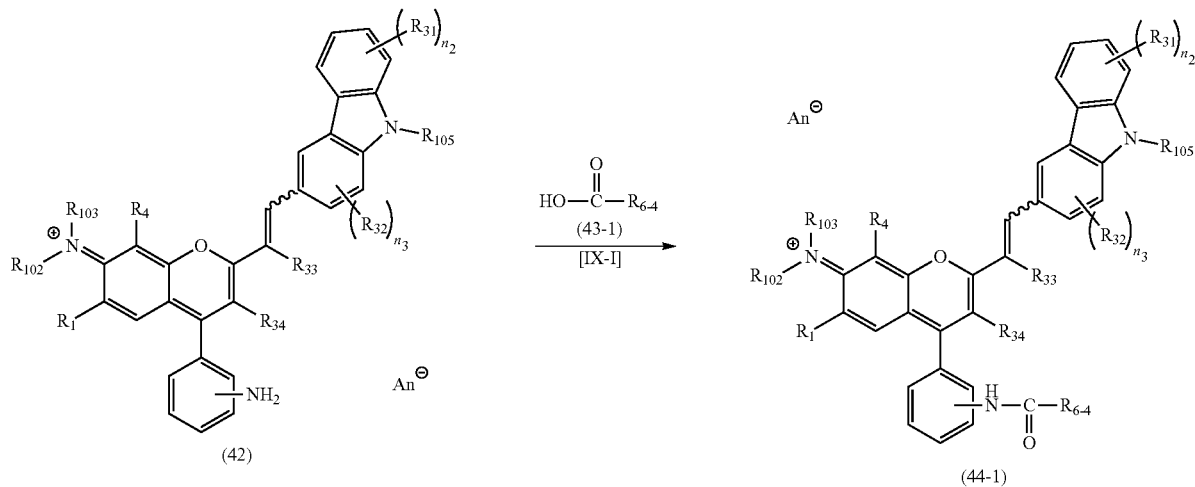

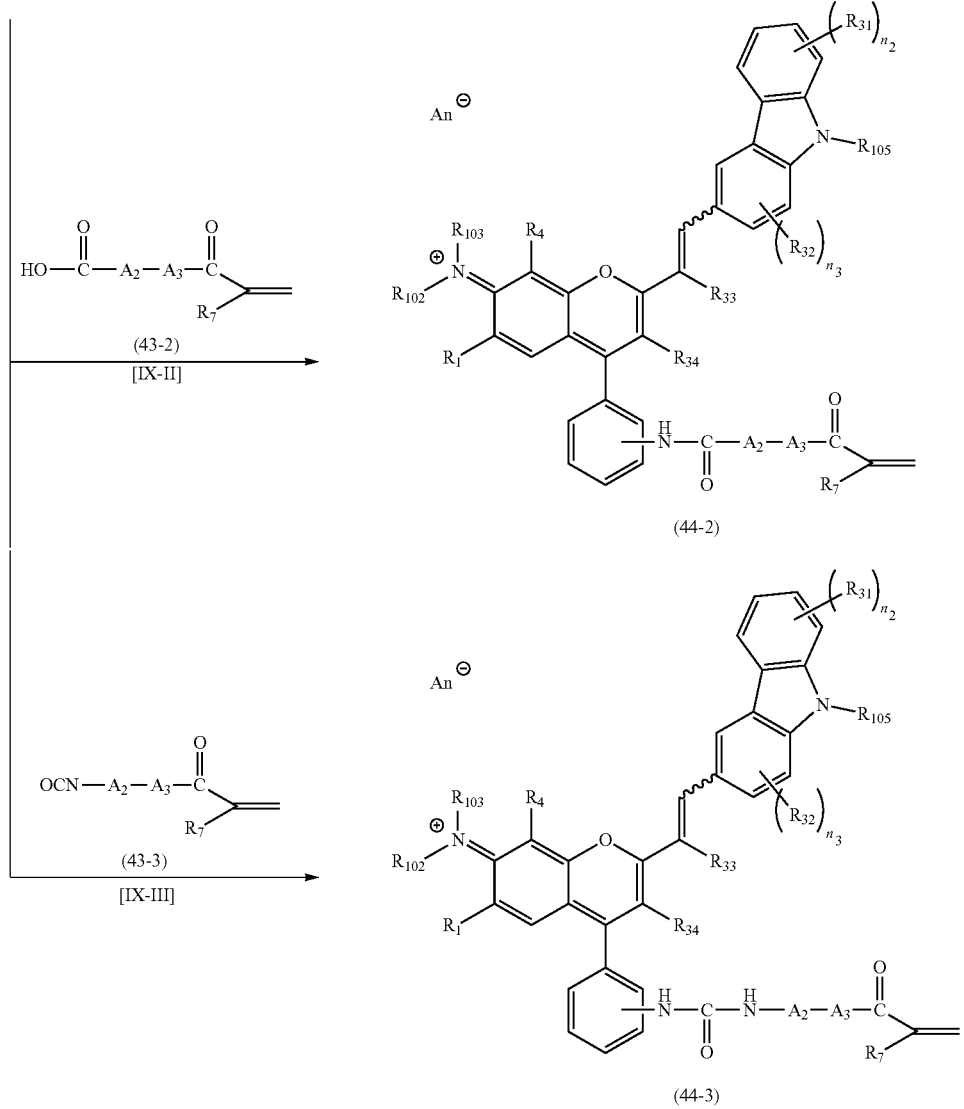

(In the formulae, $R_{6-4}$ represents an alkyl group having 1 to 20 carbon atoms, and $R_1$, $R_{102}$, $R_{103}$, $R_4$, $R_{105}$, $R_7$, $R_{31}$ to $R_{34}$, $A_2$, $A_3$, $An^-$, $n_2$, and $n_3$ each have the same definition as described above.)

Examples of the alkyl group having 1 to 20 carbon atoms as $R_{6-4}$ in the general formula (43-1) are the same as those exemplified as the alkyl group having 1 to 20 carbon atoms as $R_2$ and $R_3$ in the general formula (1), and the preferred examples thereof are the same as described above.

In the reaction [VI], the compound represented by the general formula (37) may react with phosphoryl chloride in a solvent at a temperature of typically 0° C. to 120° C. and preferably 50° C. to 100° C. for typically 1 to 24 hours and preferably 2 to 5 hours.

Examples of the solvent include dichloromethane and dichloroethane. Among these, dichloroethane is preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (37).

The amount of the phosphoryl chloride to be used is typically in a range 1 to 10 equivalents and preferably in a range of 1 to 5 equivalents with respect to the mol number of the compound represented by the general formula (37).

In the reaction [VII], the compound represented by the general formula (40) may react with hydroxylamine in a solvent at a temperature of typically 0° C. to 80° C. and preferably 10° C. to 30° C. for typically 1 to 48 hours and preferably 2 to 24 hours.

Examples of the solvent include tetrahydrofuran, dioxane, N,N-dimethylformamide, and acetonitrile. Among these, the acetonitrile is preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (40).

The amount of the hydroxylamine to be used is typically in a range 1 to 5 equivalents and preferably in a range of 1 to 2 equivalents with respect to the mol number of the compound represented by the general formula (40).

In the reaction [VIII], the compound obtained from the reaction [VII], triethylamine, and tosyl chloride may react in a solvent at a temperature typically 0° C. to 80° C. and preferably 10° C. to 30° C. for typically 1 to 24 hours and preferably 2 to 10 hours.

Examples of the solvent are the same as those exemplified as the solvent in the reaction [VII], and the preferred examples thereof are the same as described above. The amount of the reaction solvent to be used is typically in a range of 0.1 to 50 mL and preferably in a range of 0.5 to 10 mL with respect to 1 mmol of the compound obtained from the reaction [VII].

The amount of the triethylamine to be used is typically in a range 1 to 200 equivalents and preferably in a range of 50 to 100 equivalents with respect to the mol number of the compound obtained from the reaction [VII].

The amount of the tosyl chloride to be used is typically in a range 1 to 5 equivalents and preferably in a range of 1 to 2 equivalents with respect to the mol number of the compound obtained from the reaction [VII].

In the reaction [IX-I], the compound represented by the general formula (42) may react with the compound represented by the general formula (43-1) in a solvent at a temperature typically 0° C. to 150° C. and preferably 10° C. to 80° C. for typically 1 to 24 hours and preferably 2 to 10 hours.

Examples of the solvent include tetrahydrofuran, dioxane, N,N-dimethylformamide, dichloromethane, dichloroethane, and ethyl acetate. Among these, the tetrahydrofuran is preferable. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound represented by the general formula (42).

The amount of the compound represented by the general formula (43-1) to be used is typically in a range 1 to 2 equivalents and preferably in a range of 1 to 1.5 equivalents with respect to the mol number of the compound represented by the general formula (42).

Specific examples of the compound represented by the general formula (43-1) include acetic acid, propionic acid, butyric acid, isobutyric acid, valeric acid (n-pentanoic acid), caproic acid (n-hexanoic acid), and enanthic acid (n-heptanoic acid). Among these, the acetic acid or the propionic acid is preferable. A commercially available product may be used as the compound represented by the general formula (43-1) or the compound may be appropriately synthesized according to a known method.

In the reaction [IX-II], the compound represented by the general formula (42) may react with the compound represented by the general formula (43-2) in a solvent at a temperature of typically 0° C. to 100° C. and preferably 10° C. to 50° C. for typically 1 to 24 hours and preferably 2 to 10 hours.

Examples of the solvent and the amount of the solvent to be used are the same as those exemplified in the reaction [VII], and the preferred examples thereof are the same as described above.

The amount of the compound represented by the general formula (43-2) to be used is typically in a range 1 to 2 equivalents and preferably in a range of 1 to 1.5 equivalents with respect to the mol number of the compound represented by the general formula (42).

Specific examples of the compound represented by the general formula (43-2) are as follows. A commercially available product may be used as the compound represented by the general formula (43-2) or the compound may be appropriately synthesized according to a known method

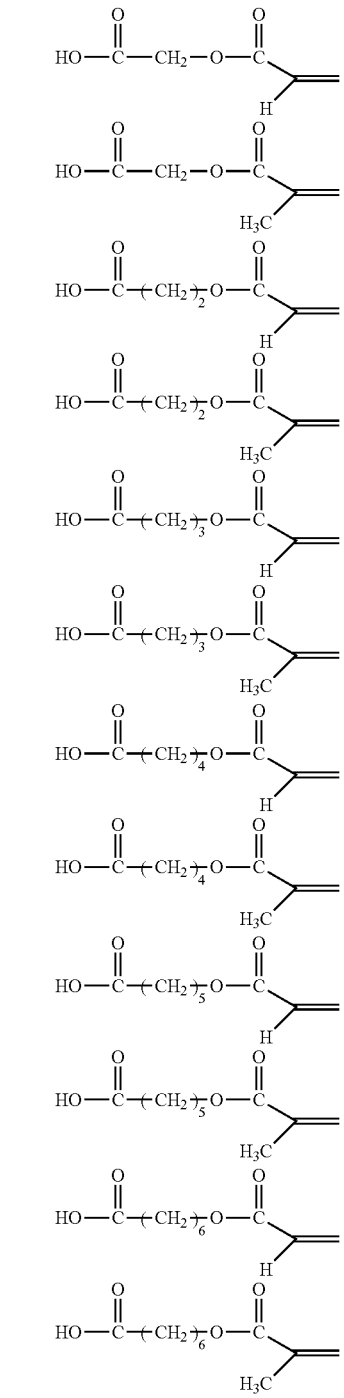

In the reaction [IX-III], the compound represented by the general formula (42) may react with the compound represented by the general formula (43-3) in a solvent at a temperature of typically 0° C. to 80° C. and preferably 10° C. to 50° C. for typically 1 to 24 hours and preferably 2 to 10 hours.

Examples of the solvent are the same as those exemplified as the solvent in the reaction [VII]. Among the examples, the dichloromethane is preferable. These may be used alone or in combination of two or more kinds thereof as appropriate. The amount of the reaction solvent to be used is typically in a range of 0.1 to 50 mL and preferably in a range of 0.5 to 10 mL with respect to 1 mmol of the compound represented by the general formula (42).

The amount of the compound represented by the general formula (43-3) to be used is typically in a range 1 to 2 equivalents and preferably in a range of 1 to 1.5 equivalents with respect to the mol number of the compound represented by the general formula (42).

Specific examples of the compound represented by the general formula (43-3) are as follows. A commercially available product may be used as the compound represented by the general formula (43-3) or the compound may be appropriately synthesized according to a known method.

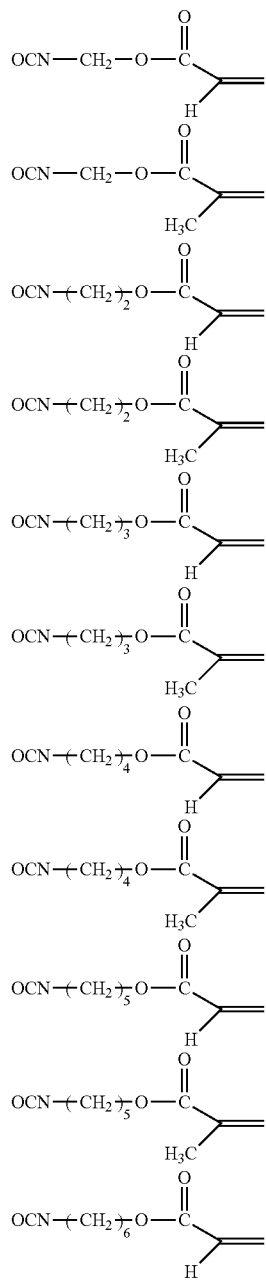

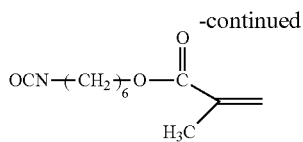

A functional group ($R_2$, $R_3$, and/or $R_5$) other than $R_6$ in the general formula (1) which has a group having a polymerizable unsaturated group among examples of the compound according to the embodiment of the present invention can be produced according to the following method.

In other words, first, in the reactions [I] to [V-III], a compound (hereinafter, also referred to as a compound having a hydroxy terminal or an amino terminal) represented by any of the general formulae (37), (29-1) to (29-3), and (44-1) to (44-3) in which $R_{102}$, $R_{103}$, and/or $R_{105}$ represents a group represented by the general formula (2-7) or (2-8) is obtained by performing the reaction in which $R_{102}$, $R_{103}$, and/or $R_{105}$ represents a group represented by the following general formula (2-7) or (2-8). Next, the obtained compound having a hydroxy terminal or an amino terminal may react with acryloyl chloride, methacryloyl chloride, acrylic anhydride, or methacrylic anhydride to obtain a compound having a group represented by the general formula (2-4) as $R_2$, $R_3$, and/or $R_5$.

(In the formulae, $R_{10}$ and $A_2$ each have the same definition as described above.)

Specific preferred examples of the group represented by the general formula (2-7) include a hydroxymethyl group, a 2-hydroxyethyl group, a 3-hydroxy-n-propyl group, a 4-hydroxy-n-butyl group, a 5-hydroxy-n-pentyl group, and a 6-hydroxy-n-hexyl group. Among these, a 2-hydroxyethyl group is preferable.

Specific preferred examples of the group represented by the general formula (2-8) include an aminomethyl group, a N-methylaminomethyl group, a N-ethylaminomethyl group, a 2-aminoethyl group, a 2-(N-methylamino)ethyl group, a 2-(N-ethylamino)ethyl group, a 3-amino-n-propyl group, a 3-(N-methylamino)-n-propyl group, a 3-(N-ethylamino)-n-propyl group, a 4-amino-n-butyl group, a 4-(N-methylamino)-n-butyl group, a 4-(N-ethylamino)-n-butyl group, a 5-amino-n-pentyl group, a 5-(N-methylamino)-n-pentyl group, a 5-(N-ethylamino)-n-pentyl group, a 6-amino-n-hexyl group, a 6-(N-methylamino)-n-hexyl group, and a 6-(N-ethylamino)-n-hexyl group. Among these, the aminomethyl group, the 2-aminoethyl group, the 3-amino-n-propyl group, the 4-amino-n-butyl group, the 5-amino-n-pentyl group, or the 6-amino-n-hexyl group is preferable, and the 2-aminoethyl group is more preferable.

In a case where $R_{102}$, $R_{103}$, and/or $R_{105}$ represents a group represented by the general formula (2-7), a product obtained after the reaction described above is a product in which $A_3$ as a group represented by the general formula (2-4) represents —O—. In addition, in a case where $R_{102}$, $R_{103}$, and/or $R_{105}$ represents a group represented by the general formula (2-8), a product obtained after the reaction described above is a product in which $A_3$ as a group represented by the general formula (2-4) represents —NR$_{10}$— (R$_{10}$ has the same definition as described above).

In the reaction described above, the compound having a hydroxy terminal or an amino terminal may react with acryloyl chloride, methacryloyl chloride, acrylic anhydride, or methacrylic anhydride in a solvent in the presence of a polymerization inhibitor as necessary at a temperature of typically 0° C. to 80° C. and preferably 10° C. to 50° C. for typically 1 to 72 hours and preferably 2 to 48 hours.

Examples of the solvent include acetonitrile, tetrahydrofuran, dioxane, N,N-dimethylformamide, methylene chloride, chloroform, methacrylic acid, and acrylic acid. These solvents may be used alone or in combination of two or more kinds thereof. The amount of the reaction solvent to be used is typically in a range of 0.1 to 50 mL and preferably in a range of 0.5 to 10 mL with respect to 1 mmol of the compound having a hydroxy terminal.

The amount of the acryloyl chloride, methacryloyl chloride, acrylic anhydride, or methacrylic anhydride to be used is typically in a range 1 to 20 equivalents and preferably in a range of 1 to 10 equivalents with respect to the mol number of the compound having a hydroxy terminal.

In a case where acryloyl chloride or acrylic anhydride is used in the reaction, a product obtained after the reaction described above is a product in which R$_7$ as a group represented by the general formula (2-4) represents a hydrogen atom. In addition, in a case where methacryloyl chloride or methacrylic anhydride is used in the reaction, a product obtained after the reaction described above is a product in which R$_7$ as a group represented by the general formula (2-4) represents a methyl group.

Examples of the polymerization inhibitor used in the reaction include p-methoxyphenol.

The compound having a hydroxy terminal or an amino terminal in the reaction can be produced using a compound represented by any of the following general formulae (45-1) to (45-6) in place of the compound represented by the general formula (31) in the reaction [I] or using a compound represented by the following general formula (45-7) or (45-8) in place of the compound represented by the general formula (36) in the reaction [IV].

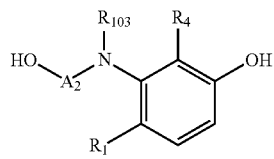
(45-1)

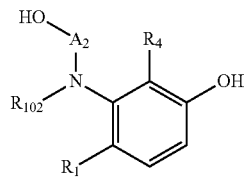
(45-2)

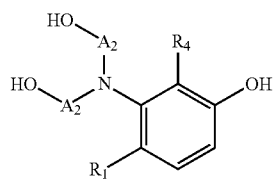
(45-3)

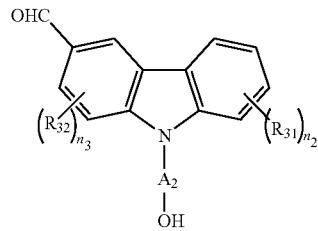
(45-7)

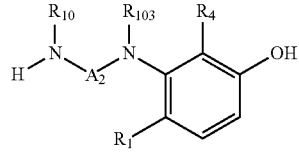
(45-4)

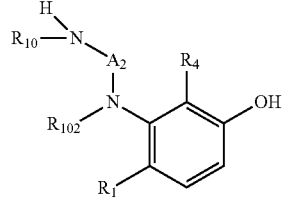
(45-5)

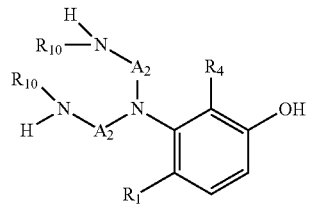
(45-6)

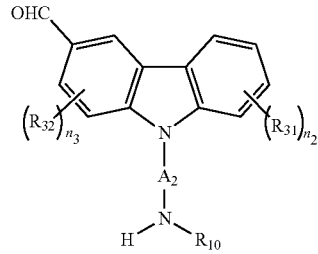
(45-8)

(In the formulae, R$_1$, R$_{102}$, R$_{103}$, R$_4$, R$_{10}$, R$_{31}$, R$_{32}$, A$_2$, n$_2$, and n$_3$ each have the same definition as described above, and two pieces of R$_{10}$'s and two pieces of A$_2$'s may be the same as or different from each other respectively.)

Specific examples of the compound represented by any of the following general formulae (45-1) to (45-6) are as follows. A commercially available product may be used as the compound represented by any of the general formulae (45-1) to (45-6) or the compound may be appropriately synthesized according to a known method.

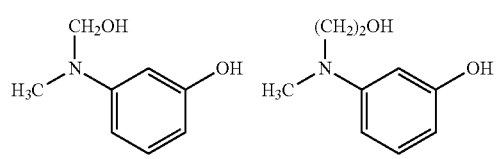

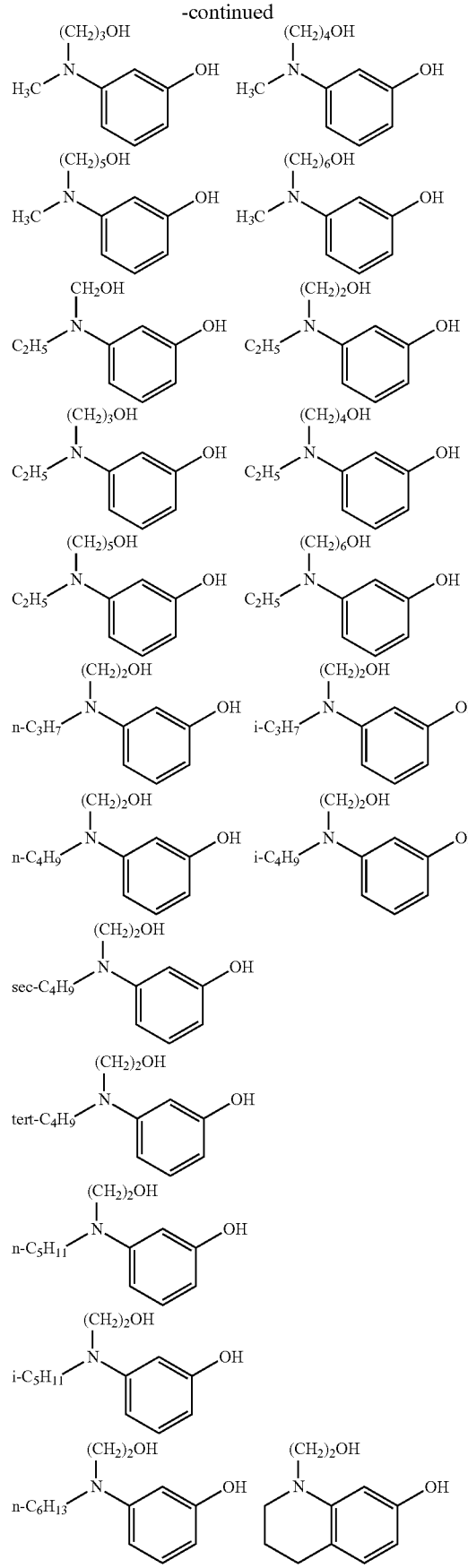
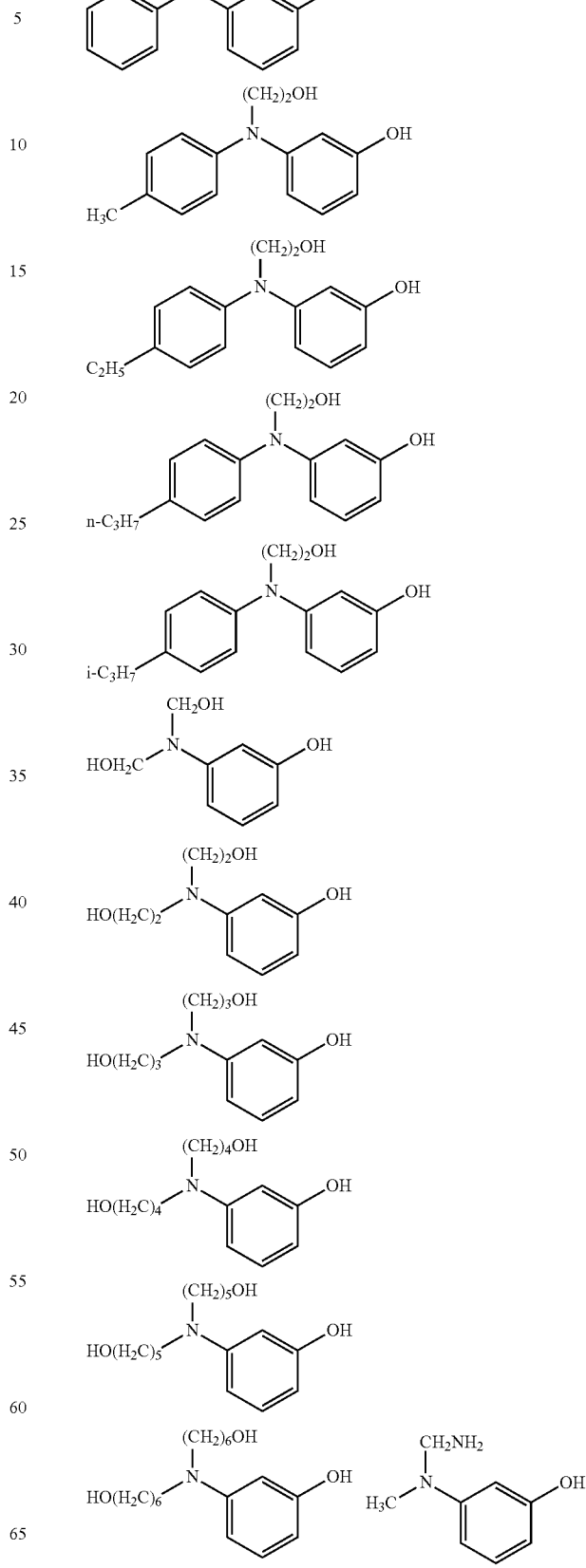

-continued
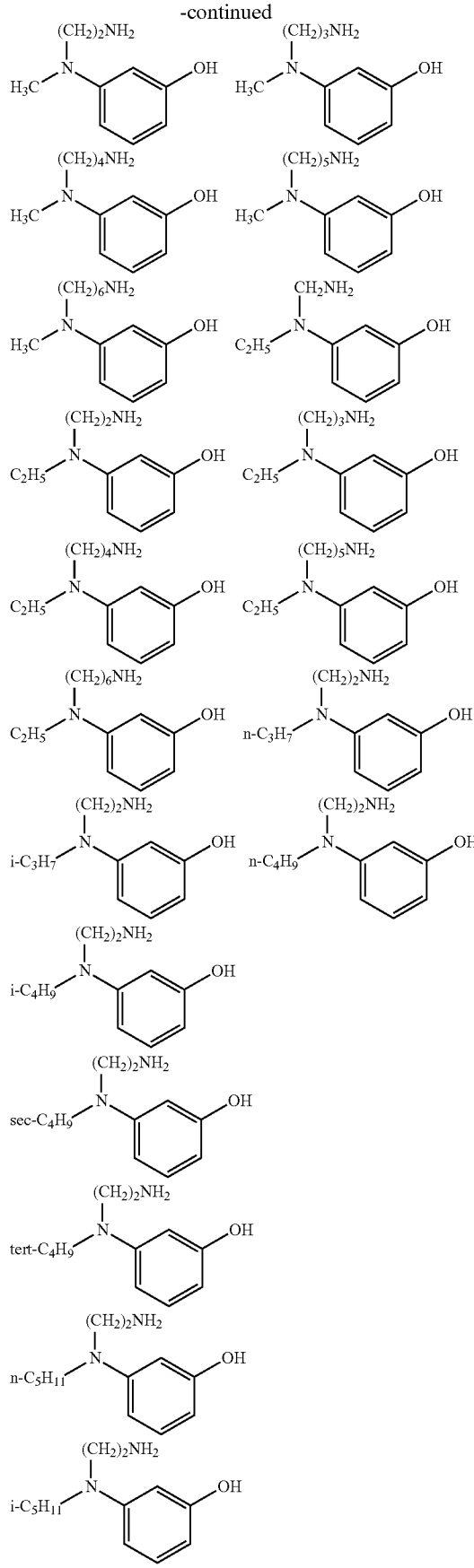
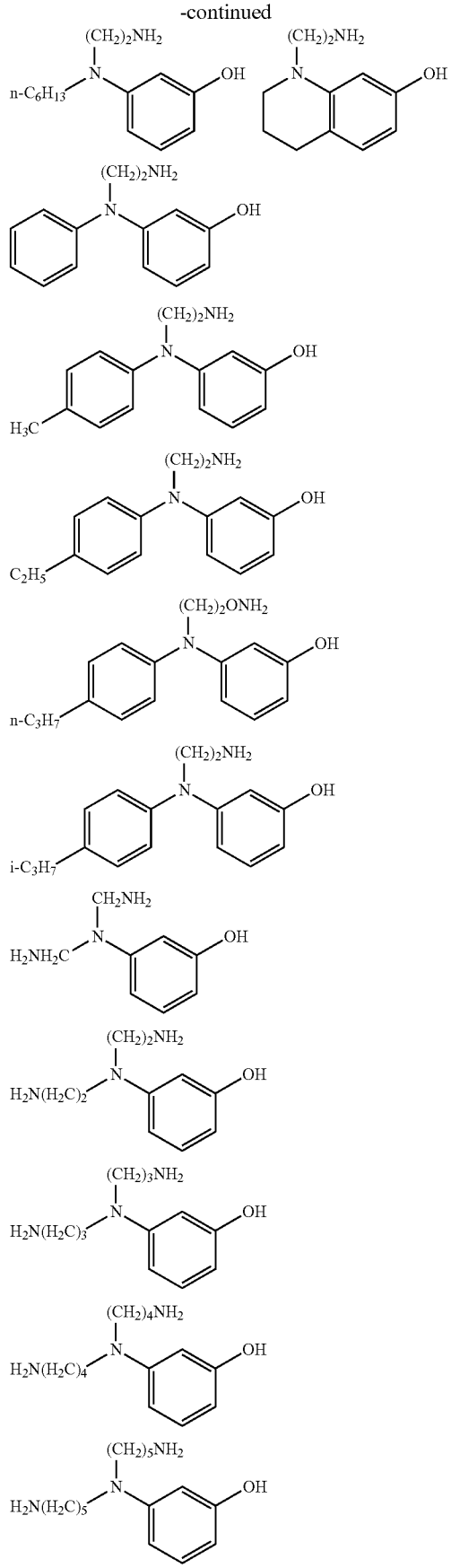

-continued

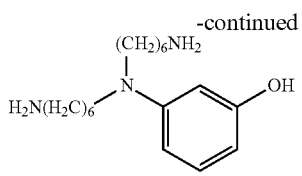

Specific examples of the compound represented by the general formula (45-7) or (45-8) are as follows. A commercially available product may be used as the compound represented by the general formula (45-7) or (45-8) or the compound may be appropriately synthesized according to a known method.

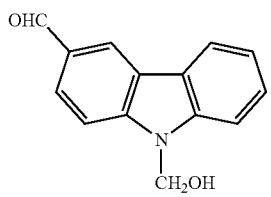

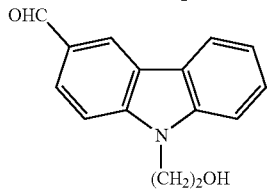

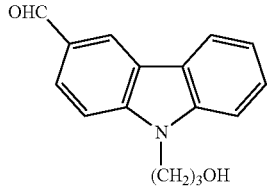

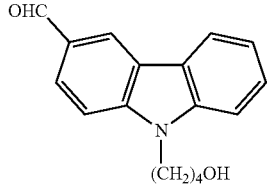

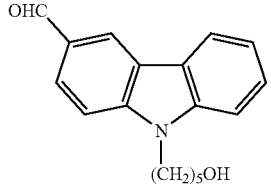

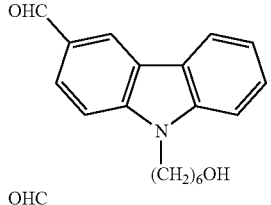

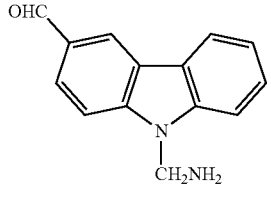

-continued

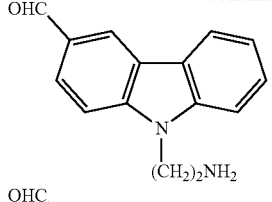

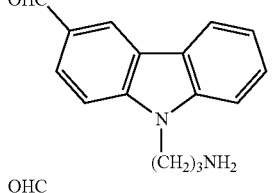

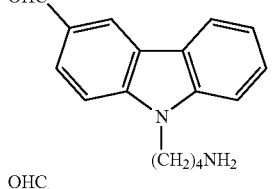

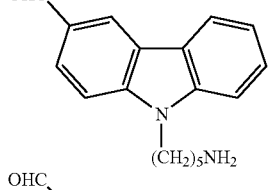

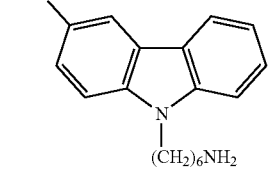

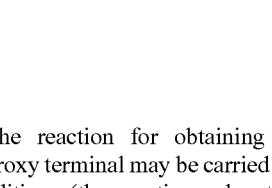

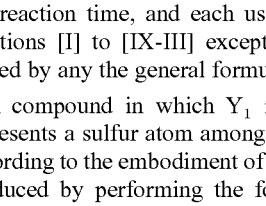

The reaction for obtaining the compound having a hydroxy terminal may be carried out under the same reaction conditions (the reaction solvent, the reaction temperature, the reaction time, and each use amount) as those for the reactions [I] to [IX-III] except that the compound represented by any the general formulae (45-1) to (45-8) is used.

A compound in which $Y_1$ in the general formula (1) represents a sulfur atom among examples of the compound according to the embodiment of the present invention can be produced by performing the following reactions [X] and [XI] in place of the reactions [I] and [II].

In other words, first, a compound represented by the following general formula (46) reacts with a compound represented by the following general formula (47) in the presence of sulfur dichloride ($SCl_2$) (reaction [X]), and then the obtained compound reacts with phthalic anhydride to obtain a compound represented by the following general formula (48) (reaction [XI]). Thereafter, a compound in which an oxygen atom as $Y_1$ in the compound represented by any of the general formulae (37), (29-1) to (29-3), and (44-1) to (44-3) is substituted with a sulfur atom can be produced by using the compound represented by the general formula (48) in place of the compound represented by the general formula (34) in the reaction [III].

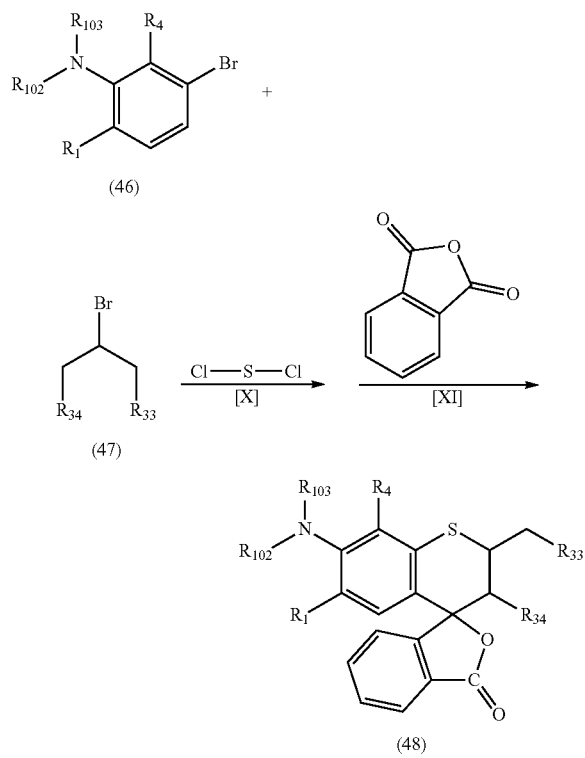

(In the formulae, $R_1$, $R_{102}$, $R_{103}$, $R_4$, $R_{33}$, and $R_{34}$ each have the same definition as described above.)

In the reaction [X], the compound represented by the general formula (46) may react with the compound represented by the general formula (47) in a solvent in the presence of sulfur dichloride at a temperature of typically 80° C. to 160° C. and preferably 90° C. to 120° C. for typically 1 to 24 hours and preferably 3 to 10 hours.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 10 mL with respect to 1 mmol of the compound represented by the general formula (46).

Specific examples of the compound represented by the general formula (46) are as follows. A commercially available product may be used as the compound represented by the general formula (46) or the compound may be appropriately synthesized according to a known method.

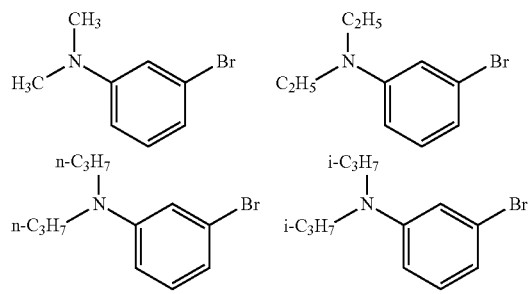

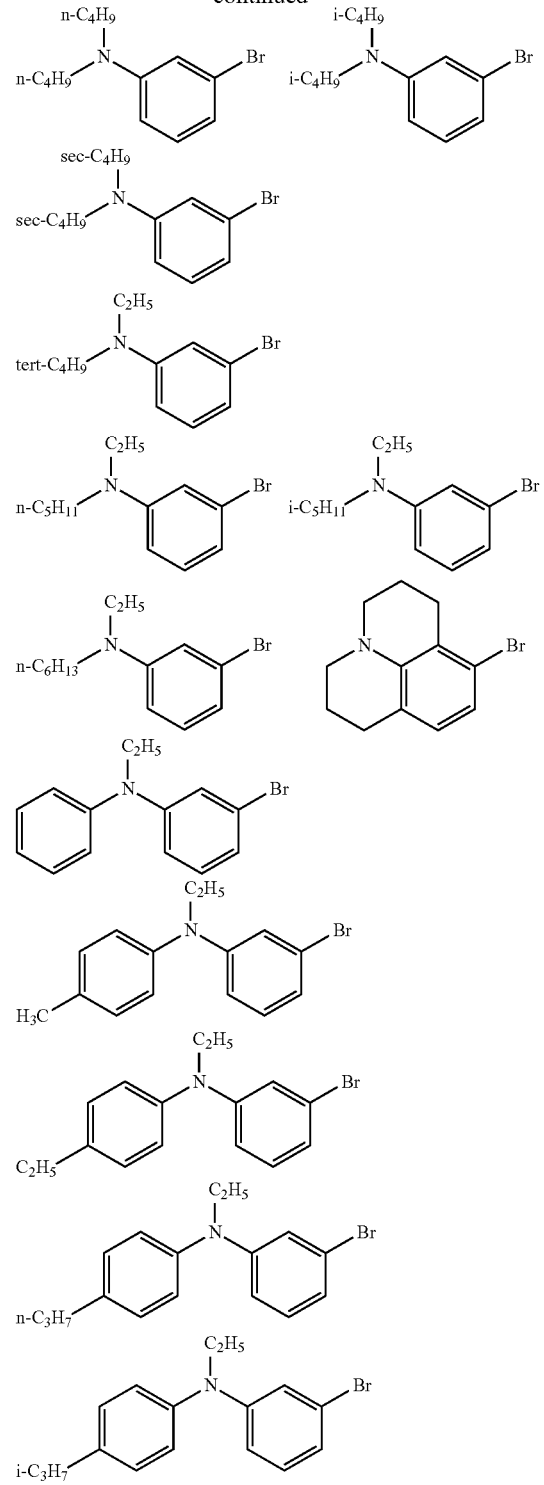

The amount of the compound represented by the general formula (47) to be used is typically in a range 1 to 2 equivalents and preferably in a range of 1 to 1.5 equivalents with respect to the mol number of the compound represented by the general formula (46).

Specific examples of the compound represented by the general formula (47) are as follows. A commercially available product may be used as the compound represented by the general formula (47) or the compound may be appropriately synthesized according to a known method.
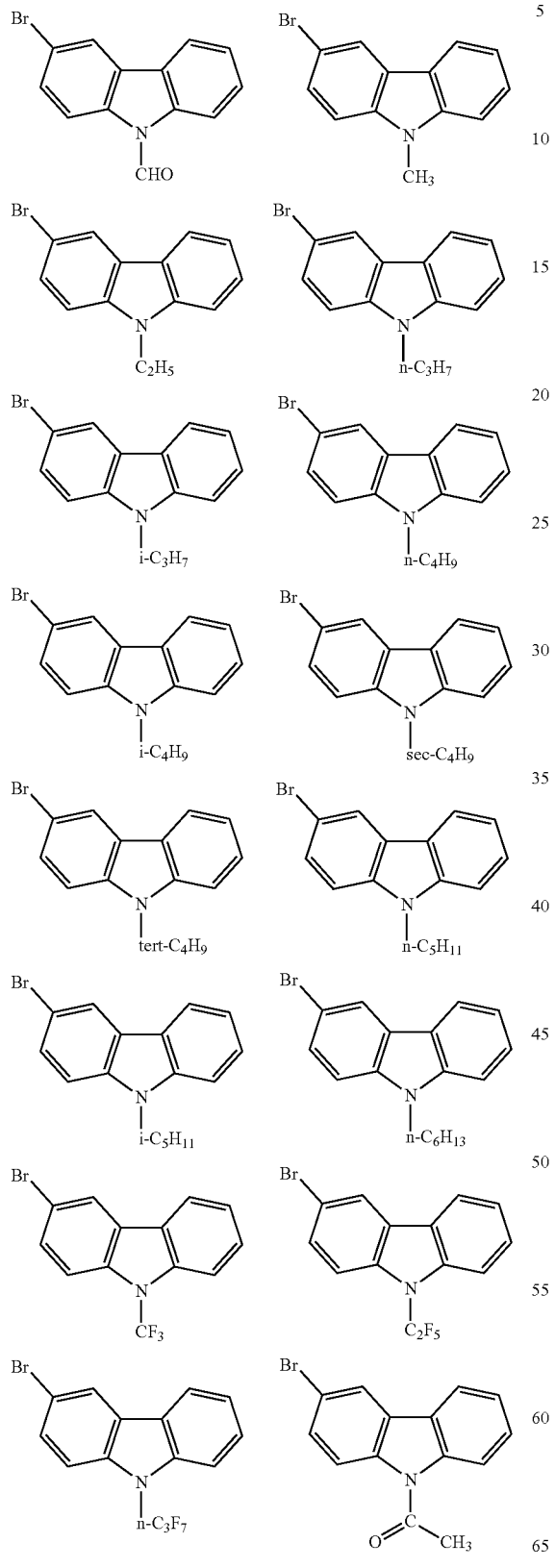
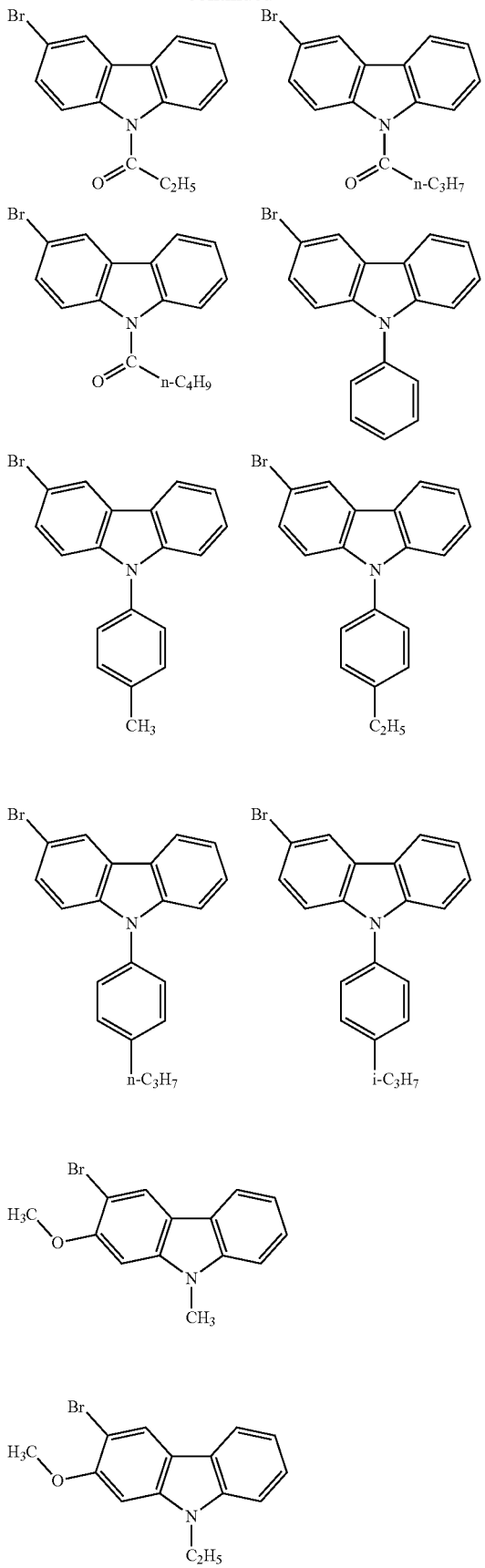

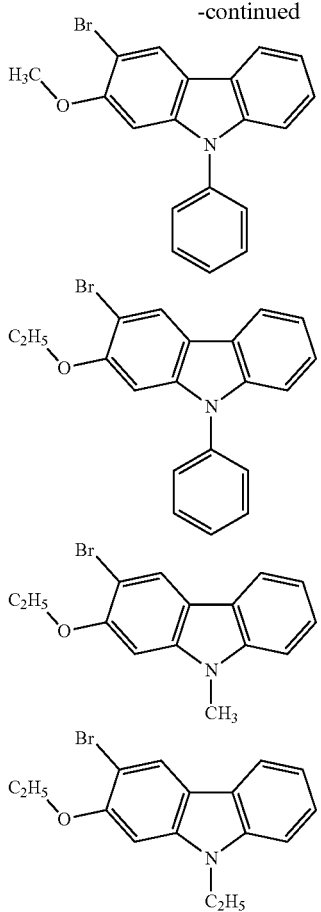

The amount of the sulfur dichloride to be used is typically in a range 1 to 2 equivalents and preferably in a range of 1 to 1.5 equivalents with respect to the mol number of the compound represented by the general formula (46).

In the reaction [XI], the compound obtained from the reaction [X] may react with phthalic anhydride in a solvent at a temperature of typically 80° C. to 160° C. and preferably 90° C. to 120° C. for typically 1 to 24 hours and preferably 3 to 10 hours.

Examples of the solvent are the same as those exemplified as the solvent in the reaction [I], and the preferred examples thereof are the same as described above. The amount of the reaction solvent to be used is typically in a range of 0.1 to 50 mL and preferably in a range of 0.5 to 10 mL with respect to 1 mmol of the compound obtained from the reaction [X].

The amount of the phthalic anhydride to be used is typically in a range 1 to 2 equivalents and preferably in a range of 1 to 1.5 equivalents with respect to the mol number of the compound obtained from the reaction [X].

The reaction for obtaining the compound in which an oxygen atom as $Y_1$ in the compound represented by any of the general formulae (37), (29-1) to (29-3), and (44-1) to (44-3) is substituted with a sulfur atom may be carried out under the same reaction conditions (the reaction solvent, the reaction temperature, the reaction time, and each use amount) as those for the reactions [III] to [IX-III] except that the compound represented by the general formula (48) is used.

The pressure during each reaction carried out using the method of producing the compound according to the embodiment of the present invention is not particularly limited as long as a series of the reactions are smoothly carried out, and the reactions may be carried out, for example, at the normal pressure.

The reactants and the products obtained after each reaction carried out according to the method of producing the compound according to the embodiment of the present invention may be isolated by typical post-treatment operations and purification operations which are performed in this field. Specifically, the obtained reactants and the products may be isolated by performing filtration, washing, extraction, concentration under reduced pressure, recrystallization, distillation, and column chromatography.

Polymer of Present Invention

A polymer of the present invention has a monomer unit derived from a compound represented by the following general formula (3).

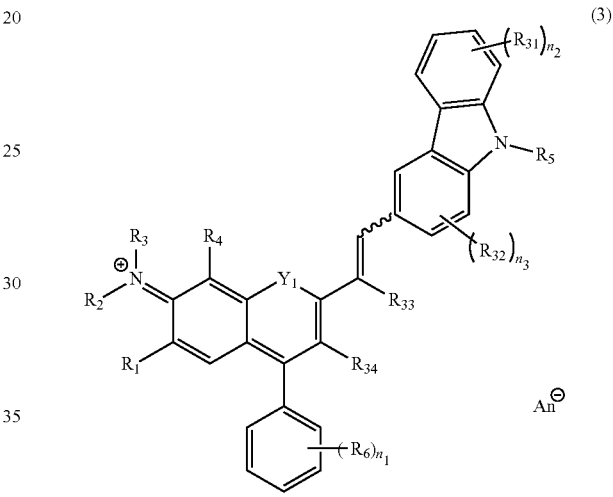

(3)

(In the formula, $R_1$ to $R_6$, $R_{31}$ to $R_{34}$, $Y_1$, $An^-$, $n_1$ to $n_3$ each have the same definition as described above. Here, at least one of $R_2$, $R_3$, $R_5$, or $n_1$ pieces of $R_6$'s represents a group having a polymerizable unsaturated group.)

In the general formula (3), at least one of $R_2$, $R_3$, $R_5$, or $n_1$ pieces of $R_6$'s represents a group having a polymerizable unsaturated group. Examples of the combination thereof include those listed in the following table. Among these, combinations 1 to 4 are preferable, a combination 4 is more preferable, and the combination 4 in which $n_1$ represents 1 among examples of the combination 4 is still more preferable. It should be noted that "other functional groups" in the table indicate functional groups other than the group having a polymerizable unsaturated group as $R_2$, $R_3$, $R_5$, or $R_6$ in the general formula (3). In other words, "other functional groups" in the table indicate an alkyl group having 1 to 20 carbon atoms or an aryl group having 6 to 14 carbon atoms which has a substituent or is unsubstituted as $R_2$ or $R_3$; a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted as $R_5$; and a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms as $R_6$.

| | $R_2$ | $R_3$ | $R_5$ | $R_6$ | $n_1$ |
|---|---|---|---|---|---|
| Combination 1 | Group having polymerizable unsaturated group | Other functional groups | Other functional groups | Other functional groups | 1 to 5 |
| Combination 2 | Other functional groups | Group having polymerizable unsaturated group | Other functional groups | Other functional groups | |
| Combination 3 | Other functional groups | Other functional groups | Group having polymerizable unsaturated group | Other functional groups | |
| Combination 4 | Other functional groups | Other functional groups | Other functional groups | Group having polymerizable unsaturated group | |
| Combination 5 | Group having polymerizable unsaturated group | Group having polymerizable unsaturated group | Other functional groups | Other functional groups | |
| Combination 6 | Group having polymerizable unsaturated group | Other functional groups | Group having polymerizable unsaturated group | Other functional groups | |
| Combination 7 | Group having polymerizable unsaturated group | Other functional groups | Other functional groups | Group having polymerizable unsaturated group | |
| Combination 8 | Other functional groups | Group having polymerizable unsaturated group | Group having polymerizable unsaturated group | Other functional groups | |
| Combination 9 | Other functional groups | Group having polymerizable unsaturated group | Other functional groups | Group having polymerizable unsaturated group | |
| Combination 10 | Other functional groups | Other functional groups | Group having polymerizable unsaturated group | Group having polymerizable unsaturated group | |
| Combination 11 | Group having polymerizable unsaturated group | Group having polymerizable unsaturated group | Group having polymerizable unsaturated group | Other functional groups | |
| Combination 12 | Group having polymerizable unsaturated group | Group having polymerizable unsaturated group | Other functional groups | Group having polymerizable unsaturated group | |
| Combination 13 | Group having polymerizable unsaturated group | Other functional groups | Group having polymerizable unsaturated group | Group having polymerizable unsaturated group | |
| Combination 14 | Other functional groups | Group having polymerizable unsaturated group | Group having polymerizable unsaturated group | Group having polymerizable unsaturated group | |
| Combination 15 | Group having polymerizable unsaturated group | Group having polymerizable unsaturated group | Group having polymerizable unsaturated group | Group having polymerizable unsaturated group | |

Specific preferred examples of the compound represented by the general formula (3) include a compound represented by the following general formula (3-1).

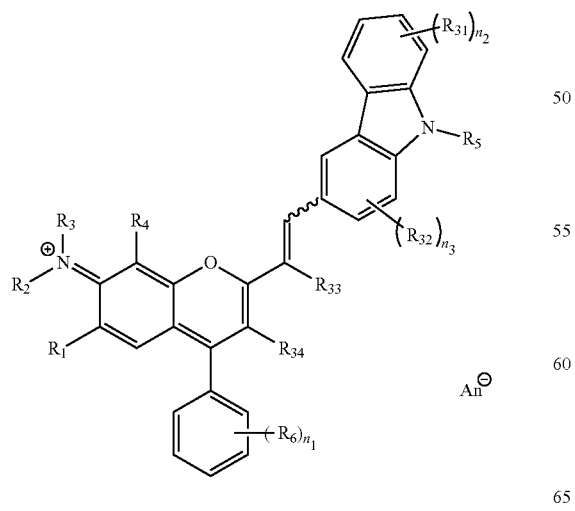

(3-1)

(In the formula, $R_1$ to $R_6$, $R_{31}$ to $R_{34}$, $An^-$, $n_1$ to $n_3$ each have the same definition as described above. Here, at least one of $R_2$, $R_3$, $R_5$, or $n_1$ pieces of $R_6$'s represents a group having a polymerizable unsaturated group.)

Specific preferred examples of the compound represented by the general formula (3-1) include a compound represented by the following general formula (3-2).

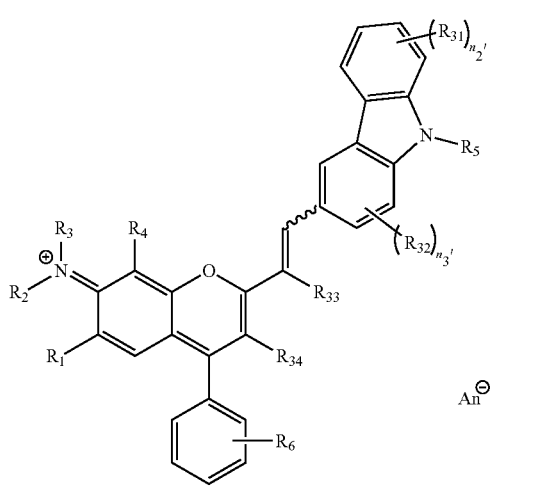

(3-2)

(In the formula, $R_1$ to $R_6$, $R_{31}$ to $R_{34}$, $An^-$, $n_2'$ and $n_3'$ each have the same definition as described above. Here, at least one of $R_2$, $R_3$, $R_5$, or $R_6$ represents a group having a polymerizable unsaturated group.)

Specific preferred examples of the compound represented by the general formula (3-2) include a compound represented by the following general formula (3-3).

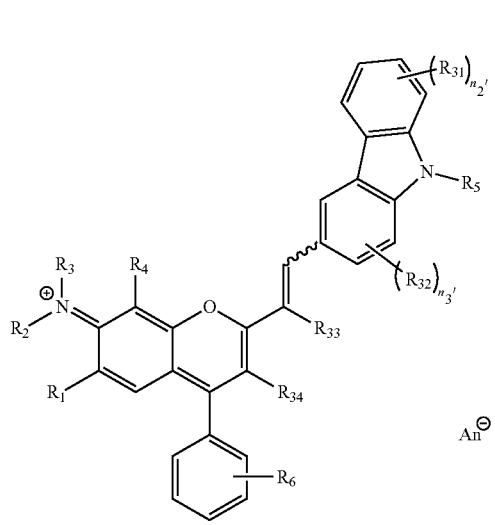

(3-3)

(In the formula, $R_1$ to $R_6$, $R_{31}$ to $R_{34}$, $An^-$, $n_2'$ and $n_3'$ each have the same definition as described above. Here, at least one of $R_2$, $R_3$, $R_5$, or $R_6$ represents a group having a polymerizable unsaturated group.)

In the general formula (3-3), any one of $R_2$, $R_3$, $R_5$, and $R_6$ represents a group having a polymerizable unsaturated group, and other three represent a functional group other than the group having a polymerizable unsaturated group.

In the general formula (3-3), it is preferable that only $R_6$ represents a group having a polymerizable unsaturated group. In other words, the following general formula (3-4) is preferable in the form of the general formula (3-3).

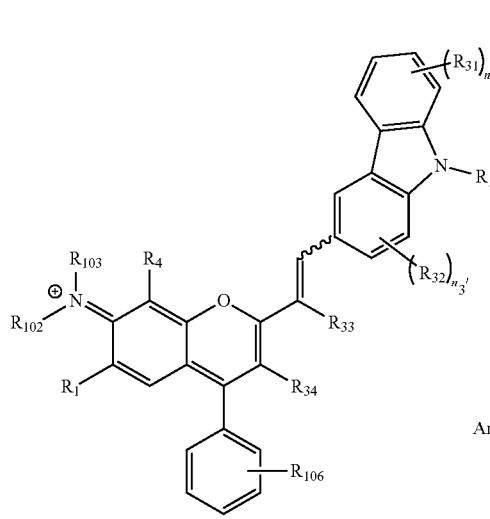

(3-4)

(In the formula, $R_{106}$ represents a group having a polymerizable unsaturated group, and $R_1$, $R_{102}$, $R_{103}$, $R_4$, $R_{105}$, $R_{31}$ to $R_{34}$, $An^-$, $n_2'$, and $n_3'$ each have the same definition as described above.)

Examples of the group having a polymerizable unsaturated group as $R_{106}$ in the general formula (3-4) are the same as those exemplified as the group having a polymerizable unsaturated group as $R_6$ in the general formula (1), and the preferred examples thereof are the same as described above.

Specific preferred examples of the compound represented by the general formula (3-4) include a compound represented by the following general formula (3-5).

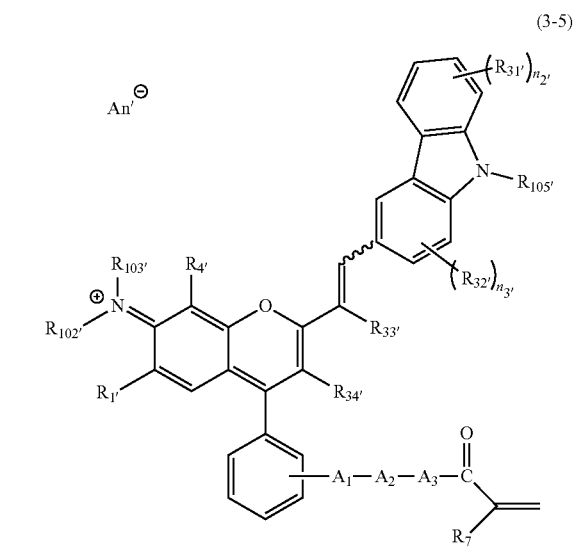

(3-5)

(In the formula, $R_{102}'$ and $R_{103}'$ each independently represent an alkyl group having 1 to 12 carbon atoms or a phenyl group which has an alkyl group having 1 to 6 carbon atoms or is unsubstituted, $R_{105}'$ represents a formyl group, an alkyl group having 1 to 12 carbon atoms, a haloalkyl group having 1 to 6 carbon atoms, an acyl group having 2 to 7 carbon atoms, or a phenyl group which has an alkyl group having 1 to 6 carbon atoms or is unsubstituted, $R_1'$, $R_4'$, $R_7$, $R_{31}'$ to $R_{34}'$, $A_1$ to $A_3$, $An'^-$, $n_2'$, and $n_3'$ each have the same definition as described above, $R_1'$ and $R_{102}'$ may form a linear alkylene group having 2 to 4 carbon atoms, and $R_{103}'$ and $R_4'$ may form a linear alkylene group having 2 to 4 carbon atoms.)

Examples of the alkyl group having 1 to 12 carbon atoms and the phenyl group which has an alkyl group having 1 to 6 carbon atoms as $R_{102}'$ and $R_{103}'$ in the general formula (3-5) are the same as those exemplified as $R_2'$ and $R_3'$ in the general formula (1-6), and the preferred examples thereof are the same as described above.

In the general formula (3-5), the linear alkylene group having 2 to 4 carbon atoms in a case where $R_1'$ and $R_{102}'$ form a linear alkylene group having 2 to 4 carbon atoms and $R_{103}'$ and $R_4'$ form a linear alkylene group having 2 to 4 carbon atoms is an ethylene group, a trimethylene group, or a tetramethylene group. Among these, the trimethylene group is preferable.

In the general formula (3-5), specific examples of the general formula (3-5) in a case where $R_1'$ and $R_{102}'$ form a linear alkylene group having 2 to 4 carbon atoms and/or $R_{103}'$ and $R_4'$ form a linear alkylene group having 2 to 4 carbon atoms include the following general formulae (8-21) to (8-29).

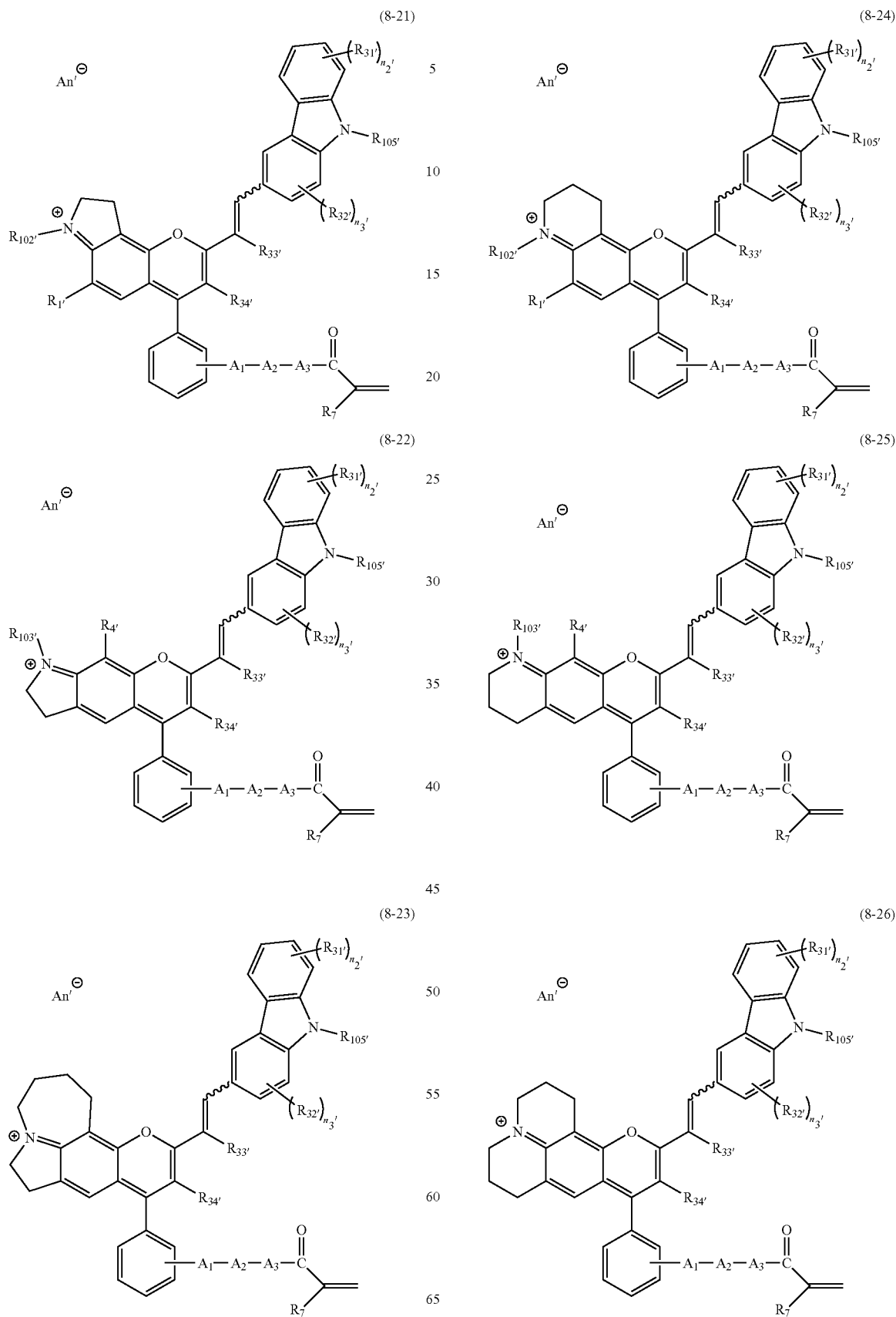

(8-27)

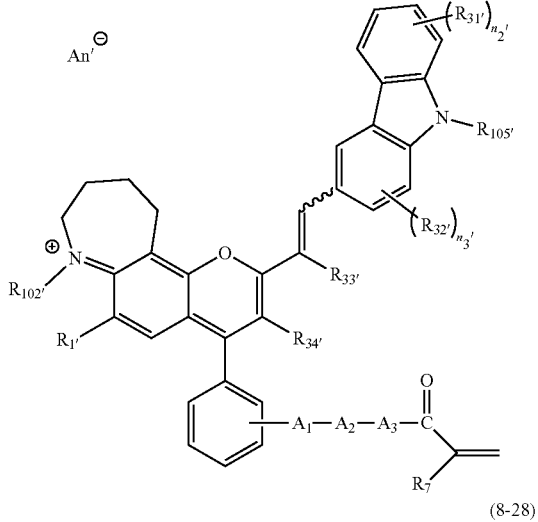

(8-28)

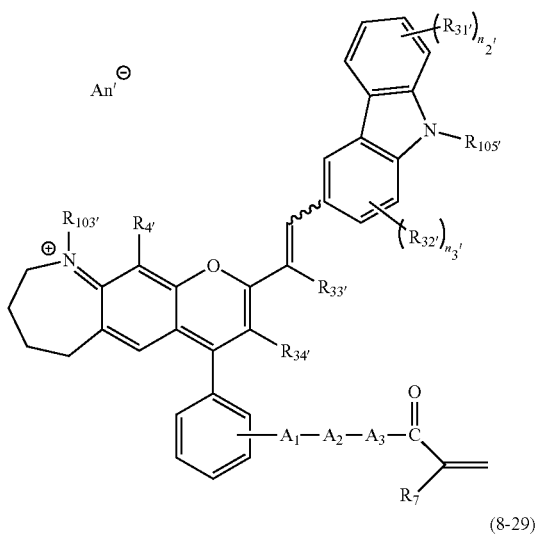

(8-29)

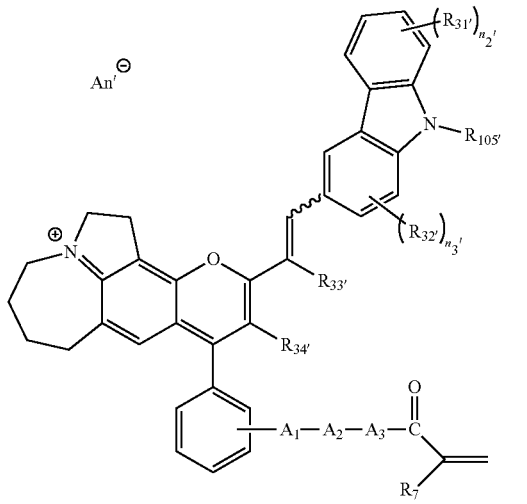

(In the formulae, $R_1'$, $R_{102}'$, $R_{103}'$, $R_4'$, $R_{105}'$, $R_7$, $R_{31}'$ to $R_{34}'$, $A_1$ to $A_3$, $An'^-$, $n_2'$, and $n_3'$ each have the same definition as described above.)

Among the specific examples described above, the general formulae (8-24) to (8-26) are preferable, and the general formula (8-26) is preferable.

$R_1'$ in the general formula (3-5) represents preferably a hydrogen atom or a trimethylene group formed by $R_1'$ and $R_{102}'$ and more preferably a hydrogen atom.

$R_{102}'$ in the general formula (3-5) represents preferably an alkyl group having 1 to 6 carbon atoms, a phenyl group which has an alkyl group having 1 to 3 carbon atoms or is unsubstituted, or a linear alkylene group having 2 to 4 carbon atoms formed by $R_1'$ and $R_{102}'$; more preferably an alkyl group having 1 to 6 carbon atoms or a trimethylene group formed by $R_1'$ and $R_{102}'$; and still more preferably an alkyl group having 1 to 6 carbon atoms. Specifically, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_1'$ and $R_{102}'$, a trimethylene group formed by $R_1'$ and $R_{102}'$, and a tetramethylene group formed by $R_1'$ and $R_{102}'$ are preferable; the methyl group, the ethyl group, the n-propyl group, the isopropyl group, the n-butyl group, the isobutyl group, the sec-butyl group, the tert-butyl group, and the trimethylene group formed by $R_1'$ and $R_{102}'$ are more preferable; the methyl group, the ethyl group, and the trimethylene group formed by $R_1'$ and $R_{102}'$ are still more preferable; and the ethyl group is particularly preferable.

$R_{103}'$ in the general formula (3-5) represents preferably an alkyl group having 1 to 6 carbon atoms, a phenyl group which has an alkyl group having 1 to 3 carbon atoms or is unsubstituted, or a linear alkylene group having 2 to 4 carbon atoms formed by $R_{103}'$ and $R_4'$; more preferably an alkyl group having 1 to 6 carbon atoms or a trimethylene group formed by $R_{103}'$ and $R_4'$; and still more preferably an alkyl group having 1 to 6 carbon atoms. Specifically, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a phenyl group, a p-tolyl group, a p-ethylphenyl group, a p-n-propylphenyl group, a p-isopropylphenyl group, an ethylene group formed by $R_{103}'$ and $R_4'$, a trimethylene group formed by $R_{103}'$ and $R_4'$, and a tetramethylene group formed by $R_{103}'$ and $R_4'$ are preferable; the methyl group, the ethyl group, the n-propyl group, the isopropyl group, the n-butyl group, the isobutyl group, the sec-butyl group, the tert-butyl group, and the trimethylene group formed by $R_{103}'$ and $R_4'$ are more preferable; the methyl group, the ethyl group, and the trimethylene group formed by $R_{103}'$ and $R_4'$ are still more preferable; and the ethyl group is particularly preferable.

$R_4'$ in the general formula (3-5) represents preferably a hydrogen atom or a trimethylene group formed by $R_{103}'$ and $R_4'$ and more preferably a hydrogen atom.

Examples of the formyl group, the alkyl group having 1 to 12 carbon atoms, the haloalkyl group having 1 to 6 carbon atoms, the acyl group having 2 to 7 carbon atoms, or the phenyl group which has an alkyl group having 1 to 6 carbon atoms or is unsubstituted as $R_{105}'$ in the general formula (3-5) include those exemplified as $R_5'$ in the general formula (1-6), and the preferred examples thereof are the same as described above.

$R_{105}'$ in the general formula (3-5) represents preferably a formyl group, an alkyl group having 1 to 6 carbon atoms, a haloalkyl group having 1 to 3 carbon atoms, an acyl group having 2 to 5 carbon atoms, or a phenyl group which has an alkyl group having 1 to 3 carbon atoms or is unsubstituted; more preferably an alkyl group having 1 to 6 carbon atoms or an unsubstituted phenyl group; and particularly preferably an alkyl group having 1 to 6 carbon atoms. Specific examples thereof include a formyl group, a methyl group, an ethyl group, an n-propyl group, an isopropyl group, an n-butyl group, an isobutyl group, a sec-butyl group, a tert-butyl group, an n-pentyl group, an isopentyl group, an n-hexyl group, a trifluoromethyl group, a pentafluoroethyl group, a heptafluoropropyl group, an acetyl group, a propionyl group, an n-butyryl group, an n-pentanoyl group, a p-tolyl group, a p-ethylphenyl group, a p-n-propylphenyl group, a p-isopropylphenyl group, and a phenyl group. Among these, the methyl group, the ethyl group, the n-propyl group, the isopropyl group, the n-butyl group, the isobutyl group, the sec-butyl group, the tert-butyl group, and the phenyl group are preferable; the methyl group, the ethyl group, and the phenyl group are more preferable; and the ethyl group is particularly preferable.

Specific preferred examples of the compound represented by the general formula (3-5) include a compound represented by the following general formula (3-6).

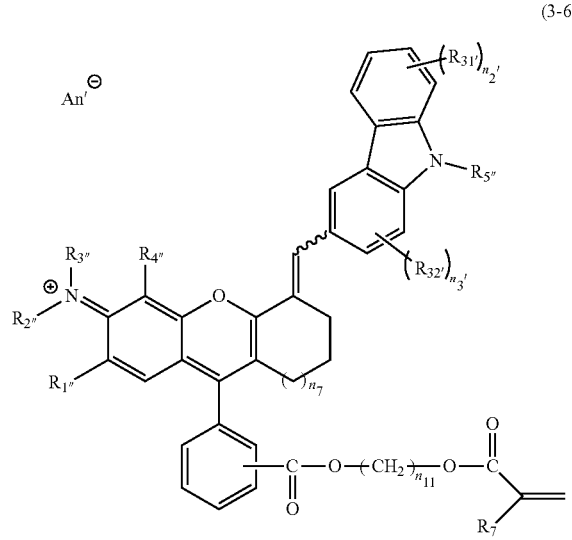

(3-6)

(In the formula, $R_1''$ to $R_5''$, $R_7$, $R_{31}'$, $R_{32}'$, $An'^-$, $n_2'$, $n_3'$, $n_7$, and $n_{11}$ each have the same definition as described above.)

Specific preferred examples of the compound represented by the general formula (3-6) include a compound represented by the following general formula (3-7).

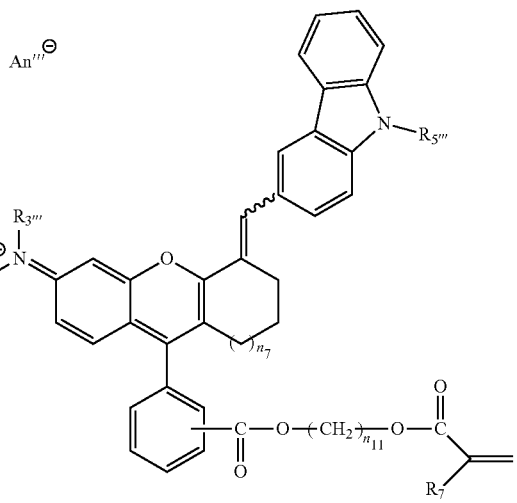

(3-7)

(In the formula, $R_2'''$, $R_3'''$, $R_5'''$, $R_7$, $An''^-$, $n_7$, and $n_{11}$ each have the same definition as described above.)

Preferred examples of a combination of $R_2'''$, $R_3'''$, $R_5'''$, $R_7$, $n_7$, and $n_{11}$ in the general formula (3-6) are as follows. Among the examples, the combinations 10 to 17 are preferable.

|  | $R_2'''$ | $R_3'''$ | $R_5'''$ | $R_7$ | $n_7$ | $n_{11}$ |
|---|---|---|---|---|---|---|
| Combination 1 | Methyl group | Methyl group | Methyl group | Methyl group or ethyl group | 0 | 2 |
| Combination 2 | Methyl group | Methyl group | Methyl group | Methyl group or ethyl group | 1 | 2 |
| Combination 3 | Methyl group | Methyl group | Methyl group | Methyl group or ethyl group | 2 | 2 |
| Combination 4 | Methyl group | Methyl group | Ethyl group | Methyl group or ethyl group | 0 | 2 |
| Combination 5 | Methyl group | Methyl group | Ethyl group | Methyl group or ethyl group | 1 | 2 |
| Combination 6 | Methyl group | Methyl group | Ethyl group | Methyl group or ethyl group | 2 | 2 |
| Combination 7 | Ethyl group | Ethyl group | Methyl group | Methyl group or ethyl group | 0 | 2 |
| Combination 8 | Ethyl group | Ethyl group | Methyl group | Methyl group or ethyl group | 1 | 2 |
| Combination 9 | Ethyl group | Ethyl group | Methyl group | Methyl group or ethyl group | 2 | 2 |
| Combination 10 | Ethyl group | Ethyl group | Ethyl group | Methyl group or ethyl group | 0 | 2 |

| | $R_2'''$ | $R_3'''$ | $R_5'''$ | $R_7$ | $n_7$ | $n_{11}$ |
|---|---|---|---|---|---|---|
| Combination 11 | Ethyl group | Ethyl group | Ethyl group | Methyl group or ethyl group | 1 | 1 |
| Combination 12 | Ethyl group | Ethyl group | Ethyl group | Methyl group or ethyl group | 1 | 2 |
| Combination 13 | Ethyl group | Ethyl group | Ethyl group | Methyl group or ethyl group | 1 | 3 |
| Combination 14 | Ethyl group | Ethyl group | Ethyl group | Methyl group or ethyl group | 1 | 4 |
| Combination 15 | Ethyl group | Ethyl group | Ethyl group | Methyl group or ethyl group | 1 | 5 |
| Combination 16 | Ethyl group | Ethyl group | Ethyl group | Methyl group or ethyl group | 1 | 6 |
| Combination 17 | Ethyl group | Ethyl group | Ethyl group | Methyl group or ethyl group | 2 | 2 |

In addition, examples of $An'''^-$ used with the combination listed in the table above include a tetrakis(pentafluorophenyl) boron (IV) anion, a bis(trifluoromethanesulfonyl)imide anion, $PF_6-$, and $SbF_6-$. Among these, a tetrakis(pentafluorophenyl) boron (IV) anion or PF is preferable, and a tetrakis(pentafluorophenyl) boron (IV) anion is more preferable.

The weight-average molecular weight (Mw) of the polymer of the present invention is typically in a range of 2000 to 100000, preferably in a range of 2000 to 50000, and more preferably in a range of 2000 to 30000. In addition, the dispersity (Mw/Mn) thereof is typically in a range of 1.00 to 5.00 and preferably in a range of 1.00 to 3.00.

The polymer of the present invention may be a homopolymer or a copolymer as long as the polymer has a monomer unit derived from the compound represented by the general formula (3), but a copolymer which is highly effective in the heat resistance is preferable.

Examples of the copolymer include copolymers having one or two kinds of monomer units derived from a compound represented by the following general formula (4), (5), (6), or (7) and a monomer unit derived from the compound represented by the general formula (3) as constituent components (hereinafter, also referred to as a copolymer of the present invention).

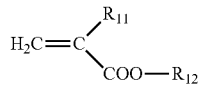

(4)

[In the formula, $R_{11}$ represents a hydrogen atom or a methyl group, and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms together with an oxygen atom, a dialkylaminoalkyl group having 3 to 9 carbon atoms, a fluoroalkyl group having 1 to 18 carbon atoms, a N-alkylenephthalimide group having 9 to 14 carbon atoms, a group represented by the following general formula (4-1), a group represented by the following general formula (4-2), or a group represented by the following general formula (4-3),

(4-1)

(In the formula, q pieces of $R_{21}$'s each independently represent an alkylene group having 1 to 3 carbon atoms which has a hydroxy group as a substituent or is unsubstituted, $R_{22}$ represents a phenyl group which has a hydroxy group as a substituent or is unsubstituted or an alkyl group having 1 to 3 carbon atoms, and q represents an integer of 1 to 3.)

(4-2)

(In the formula, $R_{23}$ to $R_{25}$ each independently represent an alkyl group having 1 to 3 carbon atoms, and $R_{26}$ represents an alkylene group having 1 to 3 carbon atoms.)

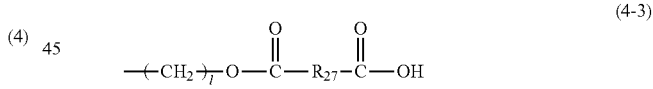

(4-3)

(In the formula, l represents an integer of 1 to 6, and $R_{27}$ represents a phenylene group or a cyclohexylene group.)]

(5)

(In the formula, $R_{11}$ has the same definition as described above, $R_{13}$ represents a hydrogen atom or an alkyl group having 1 to 3 carbon atoms, $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms, and $R_{13}$ and $R_{14}$ may form a morpholino group together with a nitrogen atom adjacent to these.)

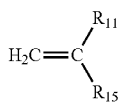

(6)

(In the formula, $R_{15}$ represents a phenyl group or a pyrrolidino group, and $R_{11}$ has the same definition as described above.)

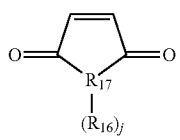

(7)

(In the formula, $R_{17}$ represents a nitrogen atom or an oxygen atom, j represents 0 in a case where $R_{17}$ represents an oxygen atom and represents 1 in a case where $R_{17}$ represents a nitrogen atom, and $R_{16}$ represents a hydrogen atom, an alkyl group having 1 to 20 carbon atoms, a hydroxyalkyl group having 1 to 10 carbon atoms, a haloalkyl group having 1 to 10 carbon atoms, an aryl group having 6 to 10 carbon atoms, or an aryl group having 6 to 10 carbon atoms which has an alkyl group having 1 to 6 carbon atoms or a halogeno group as a substituent.)

It is preferable that $R_{11}$ in the general formula (4) represents a methyl group.

The alkyl group having 1 to 18 carbon atoms as $R_{12}$ in the general formula (4) may be any of linear, branched, or cyclic. Specific examples thereof include a methyl group, an ethyl group, an n-propyl group, an isopropyl group, an n-butyl group, an isobutyl group, a sec-butyl group, a tert-butyl group, an n-pentyl group, a isopentyl group, a sec-pentyl group, a tert-pentyl group, a neopentyl group, a 2-methylbutyl group, a 1,2-dimethylpropyl group, a 1-ethylpropyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a cyclotetradecyl group, a cyclooctadecyl group, an isobornyl group, an adamantyl group, and a dicyclopentanyl group. Among these, the methyl group or the ethyl group is preferable.

Examples of the hydroxyalkyl group having 1 to 10 carbon atoms as $R_{12}$ in the general formula (4) and $R_{16}$ in the general formula (7) include a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, a hydroxynonyl group, and a hydroxydecyl group.

Examples of the aryl group having 6 to 10 carbon atoms as $R_{12}$ in the general formula (4) and $R_{16}$ in the general formula (7) include a phenyl group and a naphthyl group.

Examples of the arylalkyl group having 7 to 13 carbon atoms as $R_{12}$ in the general formula (4) include a benzyl group, a phenylethyl group, a phenylpropyl group, a naphthylmethyl group, a naphthylethyl group, and a naphthylpropyl group. Among these, the benzyl group is preferable.

Examples of the alkoxyalkyl group having 2 to 9 carbon atoms as $R_{12}$ in the general formula (4) include a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxypropyl group, an ethoxybutyl group, an ethoxypentyl group, an ethoxyhexyl group, an ethoxyheptyl group, a propoxymethyl group, a propoxyethyl group, a propoxypropyl group, a propoxybutyl group, a propoxypentyl group, and a propoxyhexyl group.

Examples of the alkoxyalkoxyalkyl group having 3 to 9 carbon atoms as $R_{12}$ in the general formula (4) include a methoxymethoxymethyl group, a methoxymethoxyethyl group, a methoxymethoxypropyl group, an ethoxymethoxymethyl group, an ethoxymethoxyethyl group, an ethoxymethoxypropyl group, a propoxymethoxymethyl group, a propoxymethoxyethyl group, a propoxymethoxypropyl group, an ethoxyethoxymethyl group, an ethoxyethoxyethyl group, an ethoxyethoxypropyl group, a propoxyethoxymethyl group, a propoxyethoxyethyl group, a propoxyethoxypropyl group, a propoxypropoxymethyl group, a propoxypropoxyethyl group, and a propoxypropoxypropyl group.

Examples of the aryloxyalkyl group having 7 to 13 carbon atoms as $R_{12}$ in the general formula (4) include a phenoxymethyl group, a phenoxyethyl group, a phenoxypropyl group, a naphthyloxymethyl group, a naphthyloxyethyl group, and a naphthyloxypropyl group.

Examples of the morpholinoalkyl group having 5 to 7 carbon atoms as $R_{12}$ in the general formula (4) include a morpholinomethyl group, a morpholinoethyl group, and a morpholinopropyl group.

Examples of the trialkylsilyl group having 3 to 9 carbon atoms as $R_{12}$ in the general formula (4) include a trimethylsilyl group, a triethylsilyl group, a tripropylsilyl group, a dimethylethylsilyl group, and a diethylmethylsilyl group.

Examples of the alicyclic hydrocarbon group having 6 to 12 carbon atoms together with an oxygen atom as $R_{12}$ in the general formula (4) include a dicyclopentenyloxyethyl group.

Examples of the dialkylaminoalkyl group having 3 to 9 carbon atoms as $R_{12}$ in the general formula (4) and $R_{14}$ in the general formula (5) include a N,N-dimethylaminomethyl group, a N,N-dimethylaminoethyl group, a N,N-dimethylaminopropyl group, a N,N-diethylaminomethyl group, a N,N-diethylaminoethyl group, a N,N-diethylaminopropyl group, a N,N-dipropylaminomethyl group, a N,N-dipropylaminoethyl group, and a N,N-dipropylaminopropyl group.

Examples of the fluoroalkyl group having 1 to 18 carbon atoms as $R_{12}$ in the general formula (4) include a 2,2,2-trifluoroethyl group, a 2,2,3,3-tetrafluoropropyl group, a 2,2,3,3,4,4-hexafluorobutyl group, a 2,2,3,3,4,4,5,5-octafluoropentyl group, a 3,3,4,4,5,5,6,6,7,7,8,8,9,9,10,10,10-heptadecafluorodecyl group, and a 2-(heptadecafluorooctyl)ethyl group.

Examples of the N-alkylenephthalimide group having 9 to 14 carbon atoms as $R_{12}$ in the general formula (4) include a 2-phthalimidoethyl group and a 2-tetrahydrophthalimidoethyl group.

Examples of the alkylene group having 1 to 3 carbon atoms which has a hydroxy group as a substituent or is unsubstituted as $R_{21}$ in the general formula (4-1) include a methylene group, an ethylene group, a trimethylene group, a hydroxymethylene group, a hydroxyethylene group, a 1-hydroxytrimethylene group, and a 2-hydroxytrimethylene group. Among these, the ethylene group, the trimethylene group, or the 2-hydroxytrimethylene group is preferable.

Examples of the phenyl group which has a hydroxy group as a substituent or is unsubstituted as $R_{22}$ in the general formula (4-1) include a hydroxyphenyl group and a phenyl group.

Examples of the alkyl group having 1 to 3 carbon atoms as $R_{22}$ in the general formula (4-1), $R_{23}$ to $R_{25}$ in the general formula (4-2), and $R_{13}$ and $R_{14}$ in the general formula (5) include a methyl group, an ethyl group, an n-propyl group, an isopropyl group.

Specific examples of the group represented by the general formula (4-1) include a (4-hydroxyphenoxy)methyl group, a (4-hydroxyphenoxy)ethyl group, a (4-hydroxyphenoxy)propyl group, a 1-hydroxy-1-phenoxymethyl group, a 1-hydroxy-2-phenoxyethyl group, a 2-hydroxy-3-phenoxypropyl group, a methyltrimethylene glycol group, a methyltriethylene glycol group, and a methyltripropylene glycol group. Among these, a (4-hydroxyphenoxy)propyl group, a 2-hydroxy-3-phenoxypropyl group, a methyltripropylene glycol group, or a methyltriethylene glycol group is preferable.

Specific examples of the group represented by the general formula (4-2) include a trimethylammonium methyl group, a trimethylammonium ethyl group, a triethylammonium methyl group, and a triethylammonium ethyl group.

Specific preferred examples of the group represented by the general formula (4-3) are as follows.

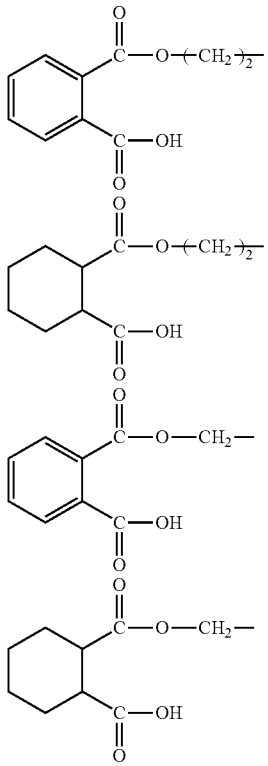

$R_{12}$ in the general formula (4) represents preferably a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an aryloxyalkyl group having 7 to 13 carbon atoms, a group represented by the general formula (4-1), or a group represented by the general formula (4-3); more preferably the hydrogen atom, the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, or the alkoxyalkyl group having 2 to 9 carbon atoms; still more preferably the hydrogen atom, the alkyl group having 1 to 18 carbon atoms, or the arylalkyl group having 7 to 13 carbon atoms, and particularly preferably the hydrogen atom or the alkyl group having 1 to 18 carbon atoms.

Specific preferred examples of the structure represented by the general formula (4) include acrylic acid, benzyl acrylate, methacrylic acid, benzyl methacrylate, hydroxyethyl methacrylate, and methyl methacrylate. Among these, the acrylic acid, the benzyl acrylate, the methacrylic acid, the benzyl methacrylate, or the methyl methacrylate is preferable, and the methacrylic acid or the methyl methacrylate is more preferable.

Examples of the hydroxyalkyl group having 1 to 6 carbon atoms as $R_{14}$ in the general formula (5) include a hydroxymethyl group, a hydroxyethyl group, a hydroxypropyl group, a hydroxybutyl group, a hydroxypentyl group, and a hydroxyhexyl group. Among these, the hydroxyethyl group is preferable.

Specific preferred examples of the structure represented by the general formula (5) include (meth)acrylamide, N,N-dimethylacrylamide, N,N-diethylacrylamide, hydroxyethyl (meth)acrylamide, and 4-acryloyl morpholine. Among these, the (meth)acrylamide, N,N-dimethylacrylamide, or the N,N-diethylacrylamide is preferable, and the N,N-diethylacrylamide is more preferable.

Specific preferred examples of the structure represented by the general formula (6) include styrene, a-methylstyrene, and N-vinylpyrrolidone. Among these, the styrene or the a-methylstyrene is preferable, and the styrene is more preferable.

Examples of the alkyl group having 1 to 20 carbon atoms as $R_{16}$ in the general formula (7) are the same as those exemplified as the alkyl group having 1 to 20 carbon atoms as $R_2$ and $R_3$ in the general formula (1).

Examples of the haloalkyl group having 1 to 10 carbon atoms as $R_{16}$ in the general formula (7) include a fluoromethyl group, a fluoroethyl group, a fluoro-n-propyl group, a fluoroisopropyl group, a fluoro-n-butyl group, a fluoro-tert-butyl group, a fluoro-n-pentyl group, a fluoro-n-hexyl group, a fluoro-n-heptyl group, a fluoro-n-octyl group, a fluoro-n-nonyl group, a fluoro-n-decyl group, a fluorocyclohexyl group, a fluorocycloheptyl group, a chloromethyl group, a chloroethyl group, a chloro-n-propyl group, a chloroisopropyl group, a chloro-n-butyl group, a chloro-tert-butyl group, a chloro-n-pentyl group, a chloro-n-hexyl group, a chloro-n-heptyl group, a chloro-n-octyl group, a chloro-n-nonyl group, a chloro-n-decyl group, a chlorocyclohexyl group, and a chlorocycloheptyl group.

Examples of the aryl group having 6 to 10 carbon atoms which has an alkyl group having 1 to 6 carbon atoms or a halogeno group as a substituent as $R_{16}$ in the general formula (7) include a methylphenyl group, an ethylphenyl group, an n-propylphenyl group, an n-butylphenyl group, an n-pentylphenyl group, an n-hexylphenyl group, a chlorophenyl group, a fluorophenyl group, a methylnaphthyl group, an ethylnaphthyl group, an n-propylnaphthyl group, a chloronaphthyl group, and a fluoronaphthyl group.

Specific preferred examples of the structure represented by the general formula (7) include maleic anhydride, maleimide, N-methylmaleimide, N-ethylmaleimide, N-butylmaleimide, N-octylmaleimide, N-dodecylmaleimide, N-(2-ethylhexyl)maleimide, N-(2-hydroxyethyl)maleimide, N-(2-chlorohexyl)maleimide, N-cyclohexylmaleimide, N-(2-methylcyclohexyl)maleimide, N-(2-ethylcyclohexyl) maleimide, N-(2-chlorocyclohexyl)maleimide, N-phenylmaleimide, N-(2-methylphenyl)maleimide, N-(2-ethylphenyl)maleimide, and N-(2-chlorophenyl)maleimide. Among these, the N-phenylmaleimide is preferable.

Specific examples of the copolymer of the present invention include combinations of monomer units listed in the following table. Among these, the combinations 1 and 5 to 7 are preferable, and the combination 1 is more preferable. In addition, a combination of the compound represented by the general formula (3) and two kinds of the compounds represented by the general formula (4) is preferable among examples of the combination 1.

| | Compound derived from monomer unit | | |
|---|---|---|---|
| Combination 1 | General formula (3) | General formula (4) | — |
| Combination 2 | General formula (3) | General formula (5) | — |
| Combination 3 | General formula (3) | General formula (6) | — |
| Combination 4 | General formula (3) | General formula (7) | — |
| Combination 5 | General formula (3) | General formula (4) | General formula (5) |
| Combination 6 | General formula (3) | General formula (4) | General formula (6) |
| Combination 7 | General formula (3) | General formula (4) | General formula (7) |

The weight ratio between the monomer unit derived from the compound represented by the general formula (3) and the monomer unit derived from the compound represented by the general formula (4), (5), (6), or (7) may be appropriately set depending on the kind of the compound to be used, but the amount of the monomer unit derived from the compound represented by the general formula (3) is typically in a range of 1% to 90% by weight and preferably in a range of 5% to 85% by weight with respect to the total weight of the polymer to be obtained.

Specific preferred examples of the copolymer of the present invention include a polymer which has a monomer unit derived from the compound represented by the general formula (3) and one or two kinds of monomer units derived from a compound represented by the following general formula (4').

(4')

(In the formula, $R'_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, or an alkoxyalkyl group having 2 to 9 carbon atoms, and $R_{11}$ has the same definition as described above.)

Examples of the alkyl group having 1 to 18 carbon atoms, the hydroxyalkyl group having 1 to 10 carbon atoms, the aryl group having 6 to 10 carbon atoms, the arylalkyl group having 7 to 13 carbon atoms, and the alkoxyalkyl group having 2 to 9 carbon atoms as $R'_{12}$ in the general formula (4') are the same as those exemplified as $R_{12}$ in the general formula (4), and the preferred examples thereof are the same as described above.

$R'_{12}$ in the general formula (4') represents preferably a hydrogen atom, an alkyl group having 1 to 18 carbon atoms, or an arylalkyl group having 7 to 13 carbon atoms, more preferably a hydrogen atom or an arylalkyl group having 7 to 13 carbon atoms, and particularly preferably a hydrogen atom or an alkyl group having 1 to 18 carbon atoms.

Specific preferred examples of the structure represented by the general formula (4') include acrylic acid, benzyl acrylate, methacrylic acid, benzyl methacrylate, and methyl methacrylate. Among these, the methacrylic acid or the methyl methacrylate is preferable.

The polymer of the present invention exhibits an effect of having a high sensitivity to not only light with a wavelength of 400 to 600 nm but also light with a wavelength of 600 nm or greater which is unlikely to be sensed by a reverse photochromic compound of the related art. Further, the polymer of the present invention also has excellent elution resistance with respect to a solvent in addition to the effects.

Method of Producing Polymer of Present Invention

The polymer of the present invention is produced, for example, in the following manner. In other words, the compound represented by the general formula (3) is obtained using the method of producing the compound according to the embodiment of the present invention, and the obtained compound represented by the general formula (3) is subjected to a known polymerization reaction, thereby obtaining the polymer of the present invention. In a case where the polymer of the present invention is a copolymer, the polymerization is carried out after the compound represented by the general formula (3) is mixed with one or two kinds of the compounds represented by the general formula (4), (5), (6), or (7) during the polymerization reaction such that the ratio of the monomer unit derived from each monomer in the polymer to be finally obtained is set to the value described above.

The polymerization reaction is carried out, for example, in the following manner. In other words, the compound represented by the general formula (3) or the compound represented by the general formula (3) and one or two kinds of the compounds represented by the general formula (4), (5), (6), or (7) are dissolved in an appropriate solvent having a volume one to ten times the total volume thereof, and examples of the solvent include toluene, 1,4-dioxane, tetrahydrofuran, isopropanol, methyl ethyl ketone, and propylene glycol monomethyl ether acetate. Next, the polymerization reaction is carried out by causing a reaction in a temperature range of 50° C. to 150° C. for 1 to 48 hours in the presence of 0.01% to 30% by weight of a polymerization initiator with respect to the total amount of the dissolved compound, and examples of the polymerization initiator include azobisisobutyronitrile, 2,2'-azobis(2,4-dimethylvaleronitrile), 2,2'-azobis(methyl 2-methylpropionate), 2,2-azobis(2-methylbutyronitrile), benzoyl peroxide, and lauroyl peroxide. After the reaction, the treatment may be performed according to a known method of acquiring a polymer.

Hereinafter, the present invention will be described in more detail based on examples, but the present invention is not limited to these examples.

EXAMPLES

Example 1: Synthesis of Carboxylic Acid Product (Compound 6)

(1) Synthesis of Carboxylic Acid Product (Compound 3)

First, 15.7 g (50.0 mmol) of 2-(4-diethylamino-2-hydroxybenzoyl) benzoic acid (compound 1: manufactured by Tokyo Chemical Industry Co., Ltd.) was added to 56 mL of concentrated sulfuric acid (manufactured by Wako Pure Chemical Industries, Ltd.) in a round bottom flask provided with a stirrer and dissolved therein, and 9.8 g (100.0 mmol) of cyclohexanone (compound 2: manufactured by Wako Pure Chemical Industries, Ltd.) was added thereto for the reaction at 90° C. for 4 hours. After the reaction, the reaction solution was added dropwise to ice water, and 27 mL of perchloric acid (manufactured by Wako Pure Chemical Industries, Ltd.) was added dropwise thereto for the reaction at room temperature for 1 hour. The deposited solid was collected by filtration, dissolved in dichloromethane, and washed with water. The solvent was distilled off by concentration under reduced pressure, thereby obtaining 17.3 g of a carboxylic acid product (compound 3) (73% yield) as a black solid.

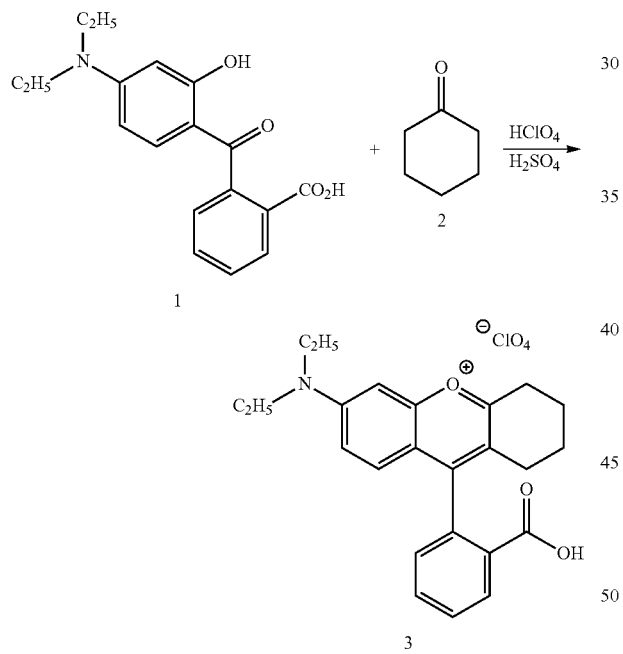

(2) Synthesis of Carboxylic Acid Product (Compound 5)

First, 3.8 g (8.0 mmol) of the carboxylic acid product (compound 3) obtained in the synthesis (1) was added to 23 mL of acetic anhydride (manufactured by Wako Pure Chemical Industries, Ltd.) in a round bottom flask provided with a stirrer and dissolved therein, and 1.9 g (8.4 mmol) of N-ethylcarbazole-3-carboxyaldehyde (compound 4: manufactured by Tokyo Chemical Industry Co., Ltd.) was added thereto for the reaction at 60° C. for 4 hours. After the reaction, the acetic anhydride was distilled off from the reaction solution by concentration under reduced pressure, thereby obtaining 5.5 g of a carboxylic acid product (compound 5) (100% yield) as a black solid.

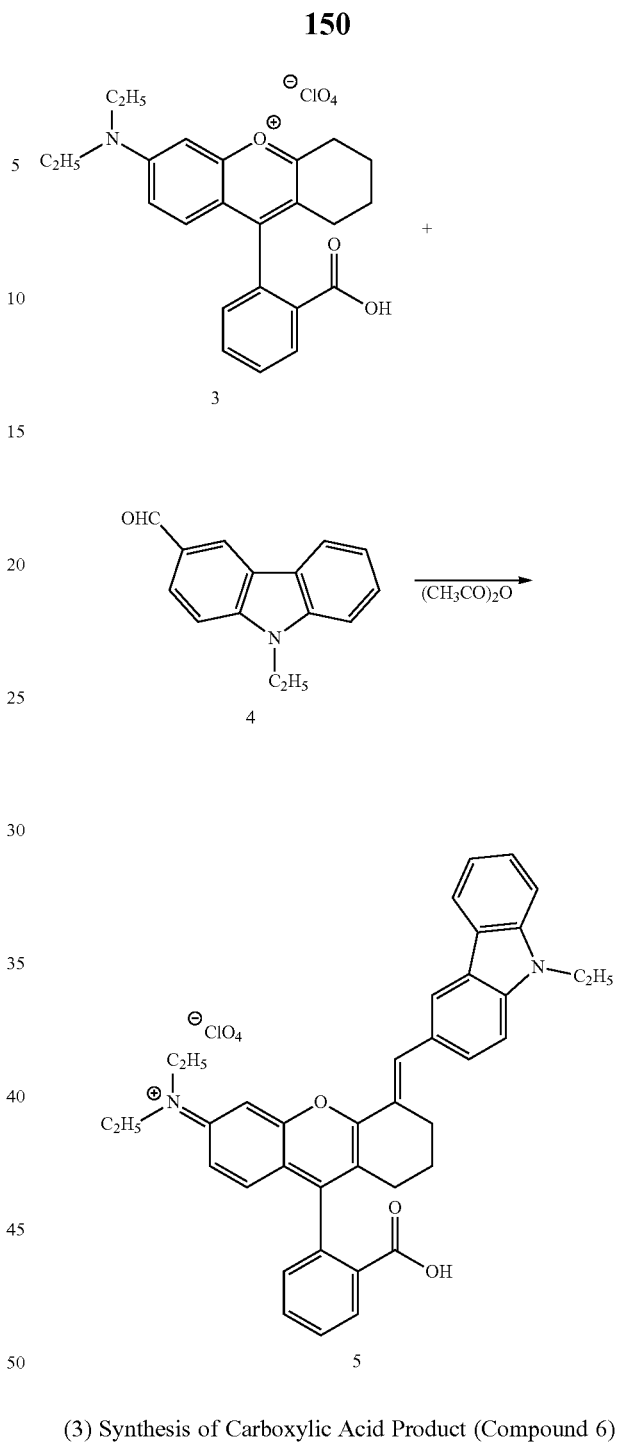

(3) Synthesis of Carboxylic Acid Product (Compound 6)

First, 5.5 g (8.0 mmol) of the carboxylic acid product (compound 5) obtained in the synthesis (2) was added to 51 mL of dichloromethane in a round bottom flask provided with a stirrer and dissolved therein, and 6.1 g (8.0 mmol) of a lithium salt (LiFABA) of tetrakis(pentafluorophenyl) boron (IV) (manufactured by Tosoh Finechem Corporation) was added thereto for the reaction at room temperature for 2 hours. After the reaction, the reaction solution was washed with water, the solvent was distilled off from the reaction solution by concentration under reduced pressure, thereby obtaining as a black solid. The solid was purified by a silica gel column chromatography so that 5.1 g of a carboxylic acid product (compound 6) (51% yield) as a dark blue solid having a tetrakis(pentafluorophenyl) boron (IV) anion was obtained.

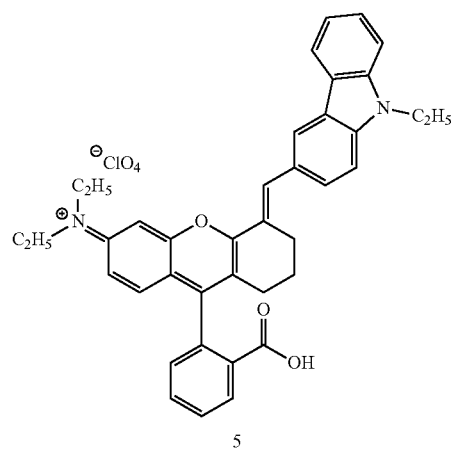

5

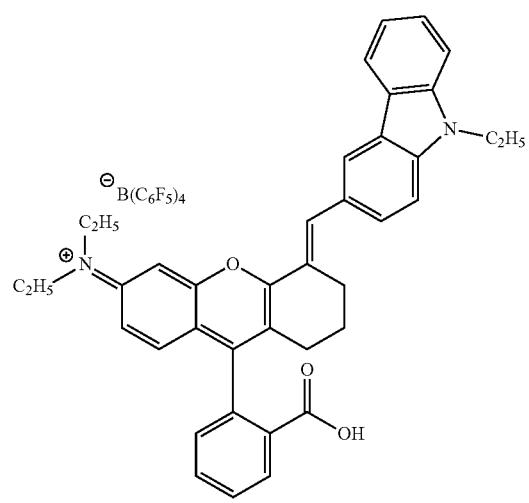

6

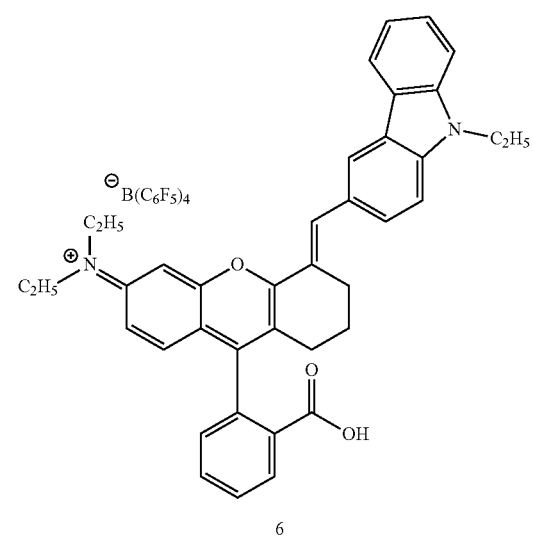

6

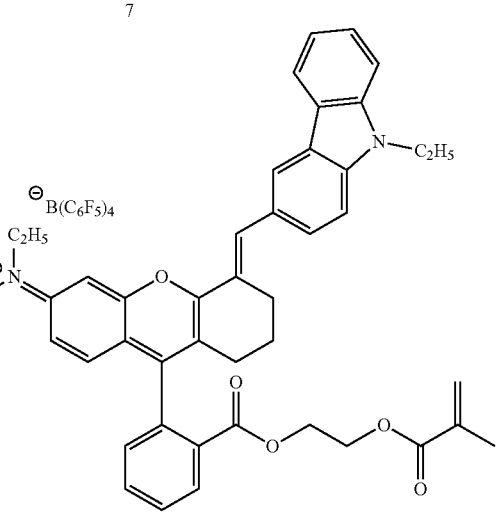

8

Example 2: Synthesis of Monomer Having Polymerizable Unsaturated Group (Compound 8)

First, 5.1 g (4.1 mmol) of the carboxylic acid product (compound 6) obtained in Example 1 was added to 34 mL of dichloromethane in a round bottom flask provided with a stirrer and dissolved therein, and 0.6 g (4.9 mmol) of 2-hydroxyethyl methacrylate (compound 7, manufactured by Wako Pure Chemical Industries, Ltd.), 50 mg (0.4 mmol) of 4-dimethylaminopyridine (DMAP) (manufactured by Wako Pure Chemical Industries, Ltd.), and 1.3 g (6.9 mmol) of 1-ethyl-3-(3-dimethylaminopropyl)carbodiimide hydrochloride (WSC) (manufactured by Toyobo Co., Ltd.) were added thereto for the reaction at room temperature for 5 hours. After the reaction, the reaction solution was washed with water, the solvent was distilled off from the reaction solution by concentration under reduced pressure, thereby obtaining a dark blue solid. The solid was purified by a silica gel column chromatography so that 1.2 g of a monomer having a polymerizable unsaturated group (compound 8) (21% yield) as a dark blue solid was obtained.

Example 3: Synthesis of Ester Product (Compound 9)

First, 0.6 g (0.5 mmol) of the carboxylic acid product (compound 3) obtained in Example 1 was added to 6 mL of dichloromethane in a round bottom flask provided with a stirrer and dissolved therein, and 20 mg (0.6 mmol) of methanol, 10 mg (0.05 mmol) of DMAP (manufactured by Wako Pure Chemical Industries, Ltd.), 0.2 g (0.9 mmol) of WSC (manufactured by Toyobo Co., Ltd.) were added thereto for the reaction at room temperature for 7 hours. After the reaction, the reaction solution was washed with water, the solvent was distilled off from the reaction solution by concentration under reduced pressure, thereby obtaining a dark blue solid. The solid was purified by a silica gel column chromatography so that 0.1 g of an ester product (compound 9) (17% yield) as a dark blue solid was obtained.

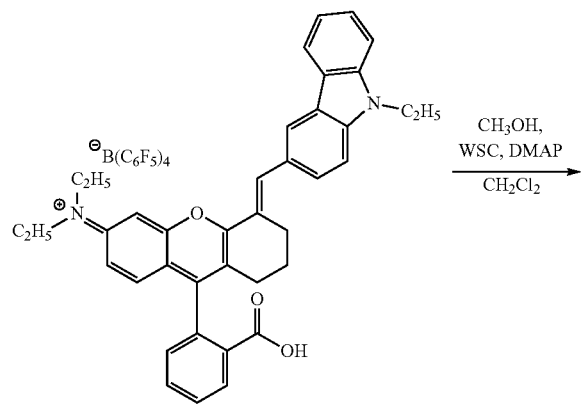

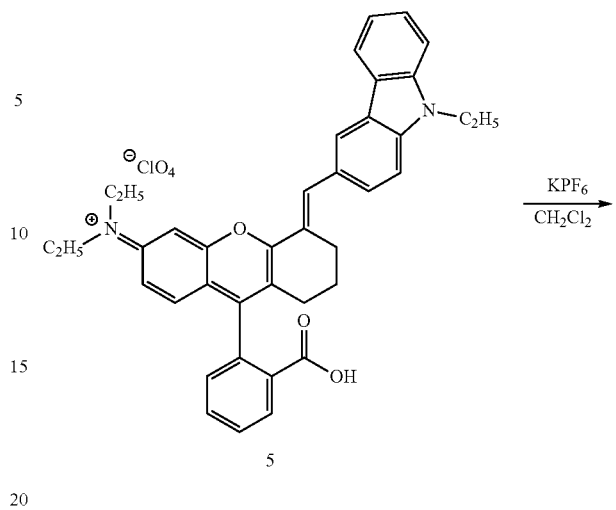

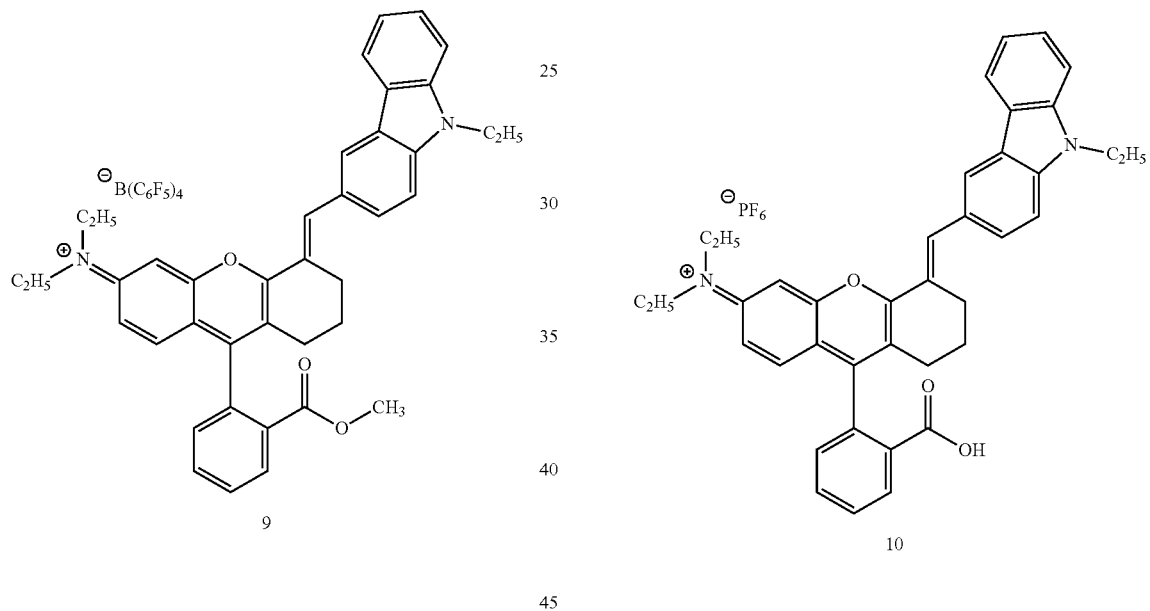

Example 4: Synthesis of Ester Product (Compound 11)

(1) Synthesis of carboxylic acid product (compound 10)

First, 2.7 g (4.0 mmol) of the carboxylic acid product (compound 5) obtained in the synthesis (2) of Example 1 was added to 46 mL of dichloromethane in a round bottom flask provided with a stirrer and dissolved therein, and 0.7 g (4.0 mmol) of potassium hexafluorophosphate (manufactured by Wako Pure Chemical Industries, Ltd.) was added thereto for the reaction at room temperature for 4 hours. After the reaction, the reaction solution was diluted with dichloromethane and washed with water. The solvent was distilled off from the reaction solution by concentration under reduced pressure, thereby obtaining 1.8 g of a carboxylic acid product (compound 10) (62% yield) as a black solid having a hexafluorophosphoric acid anion.

(2) Synthesis of Ester Product (Compound 11)

First, 0.6 g (0.8 mmol) of the carboxylic acid product (compound 10) obtained in the synthesis (1) was added to 5 mL of dichloromethane in a round bottom flask provided with a stirrer and dissolved therein, and 30 mg (0.9 mmol) of methanol, 10 mg (0.08 mmol) of DMAP (manufactured by Wako Pure Chemical Industries, Ltd.), 0.2 g (1.3 mmol) of WSC (manufactured by Toyobo Co., Ltd.) were added thereto for the reaction at room temperature for 7 hours. After the reaction, the reaction solution was washed with water, the solvent was distilled off from the reaction solution by concentration under reduced pressure, thereby obtaining a reddish brown solid. The solid was purified by a silica gel column chromatography so that 0.2 g of an ester product (compound 11) (32% yield) as a blue solid was obtained.

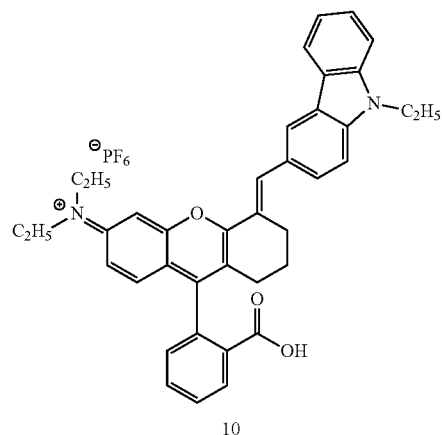
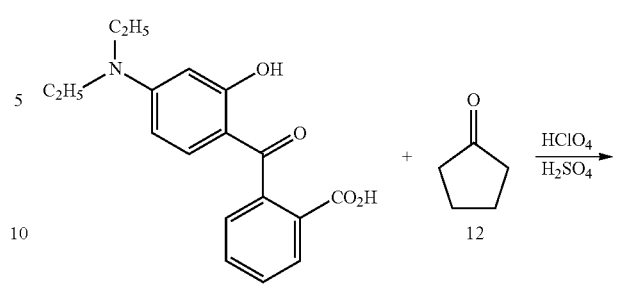
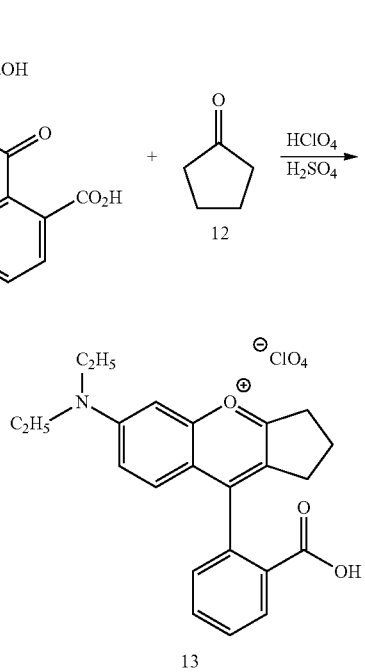
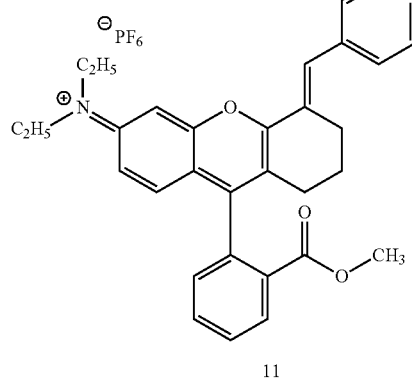

Example 5: Synthesis of Carboxylic Acid Product (Compound 15)

(1) Synthesis of Carboxylic Acid Product (Compound 13)

First, 9.4 g (30.0 mmol) of 2-(4-diethylamino-2-hydroxybenzoyl) benzoic acid (compound 1: manufactured by Tokyo Chemical Industry Co., Ltd.) was added to 38 mL of concentrated sulfuric acid (manufactured by Wako Pure Chemical Industries, Ltd.) in a round bottom flask provided with a stirrer and dissolved therein, and 7.7 g (90.0 mmol) of cyclopentanone (compound 12: manufactured by Wako Pure Chemical Industries, Ltd.) was added thereto for the reaction at 90° C. for 4 hours. After the reaction, the reaction solution was added dropwise to ice water, and 25 mL of perchloric acid (manufactured by Wako Pure Chemical Industries, Ltd.) was added dropwise thereto for the reaction at room temperature for 1 hour. The deposited solid was collected by filtration, dissolved in dichloromethane, and washed with water. The solvent was distilled off by concentration under reduced pressure, thereby obtaining 6.4 g of a carboxylic acid product (compound 13) (46% yield) as a black solid.

(2) Synthesis of Carboxylic Acid Product (Compound 14)

First, 4.6 g (10.0 mmol) of the carboxylic acid product (compound 13) obtained in the synthesis (1) was added to 23 mL of acetic anhydride (manufactured by Wako Pure Chemical Industries, Ltd.) in a round bottom flask provided with a stirrer and dissolved therein, and 2.3 g (10.5 mmol) of N-ethylcarbazole-3-carboxyaldehyde (compound 4: manufactured by Tokyo Chemical Industry Co., Ltd.) was added thereto for the reaction at 60° C. for 4 hours. After the reaction, the acetic anhydride was distilled off from the reaction solution by concentration under reduced pressure, thereby obtaining 6.7 g of a carboxylic acid product (compound 14) (100% yield) as a black solid.

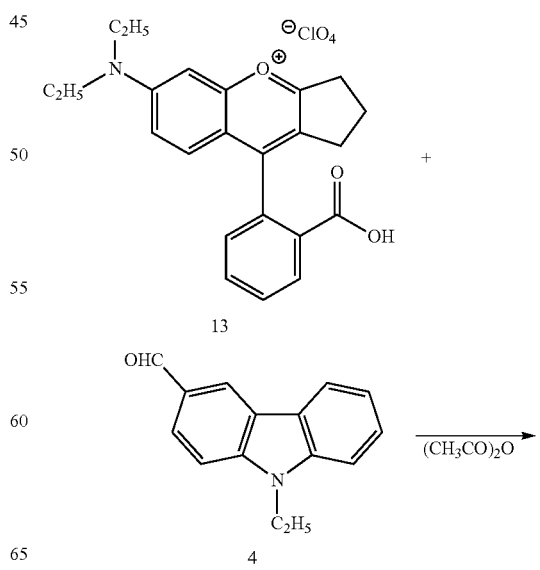

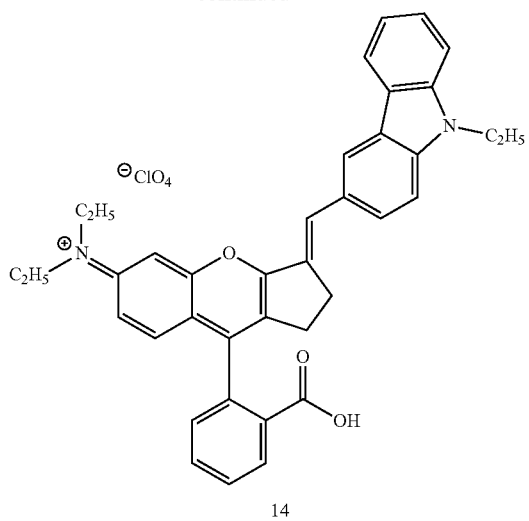

14

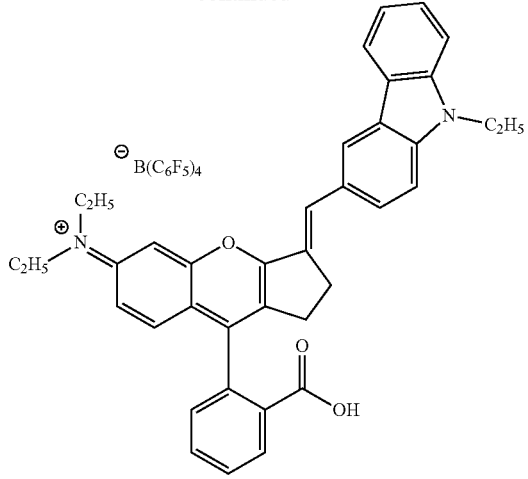

15

(3) Synthesis of Carboxylic Acid Product (Compound 15)

First, 7.7 g (11.5 mmol) of the carboxylic acid product (compound 14) obtained in the synthesis (2) was added to 130 mL of dichloromethane in a round bottom flask provided with a stirrer and dissolved therein, and 8.8 g (11.5 mmol) of LiFABA (manufactured by Tosoh Finechem Corporation) was added thereto for the reaction at room temperature for 2 hours. After the reaction, the reaction solution was washed with water, the solvent was distilled off from the reaction solution by concentration under reduced pressure, thereby obtaining a black solid. The solid was purified by a silica gel column chromatography so that 4.3 g of a carboxylic acid product (compound 15) (30% yield) as a dark blue solid having a tetrakis(pentafluorophenyl) boron (IV) anion was obtained.

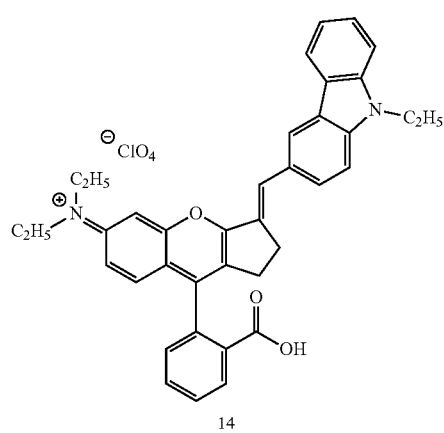

14

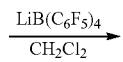

Example 6: Synthesis of Carboxylic Acid Product (Compound 19)

(1) Synthesis of Carboxylic Acid Product (Compound 17)

First, 9.4 g (30.0 mmol) of 2-(4-diethylamino-2-hydroxybenzoyl) benzoic acid (compound 1: manufactured by Tokyo Chemical Industry Co., Ltd.) was added to 38 mL of concentrated sulfuric acid (manufactured by Wako Pure Chemical Industries, Ltd.) in a round bottom flask provided with a stirrer and dissolved therein, and 5.2 g (90.0 mmol) of acetone (compound 16: manufactured by Wako Pure Chemical Industries, Ltd.) was added thereto for the reaction at 90° C. for 4 hours. After the reaction, the reaction solution was added dropwise to ice water, and 20 mL of perchloric acid (manufactured by Wako Pure Chemical Industries, Ltd.) was added dropwise thereto for the reaction at room temperature for 1 hour. The deposited solid was collected by filtration, dissolved in dichloromethane, and washed with water. The solvent was distilled off by concentration under reduced pressure, thereby obtaining 8.8 g of a carboxylic acid product (compound 17) (67% yield) as a black solid.

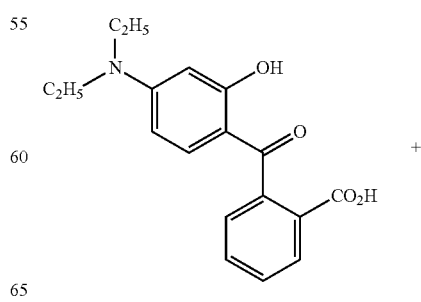

1

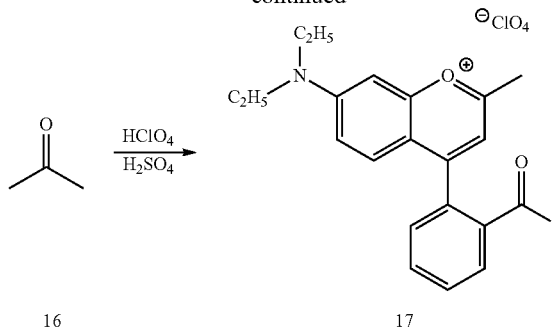

(2) Synthesis of Carboxylic Acid Product (Compound 18)

First, 4.4 g (10.0 mmol) of the carboxylic acid product (compound 17) obtained in the synthesis (1) was added to 22 mL of acetic anhydride (manufactured by Wako Pure Chemical Industries, Ltd.) in a round bottom flask provided with a stirrer and dissolved therein, and 2.3 g (10.5 mmol) of N-ethylcarbazole-3-carboxyaldehyde (compound 4: manufactured by Tokyo Chemical Industry Co., Ltd.) was added thereto for the reaction at 60° C. for 4 hours. After the reaction, the acetic anhydride was distilled off from the reaction solution by concentration under reduced pressure, thereby obtaining 6.4 g of a carboxylic acid product (compound 18) (100% yield) as a black solid.

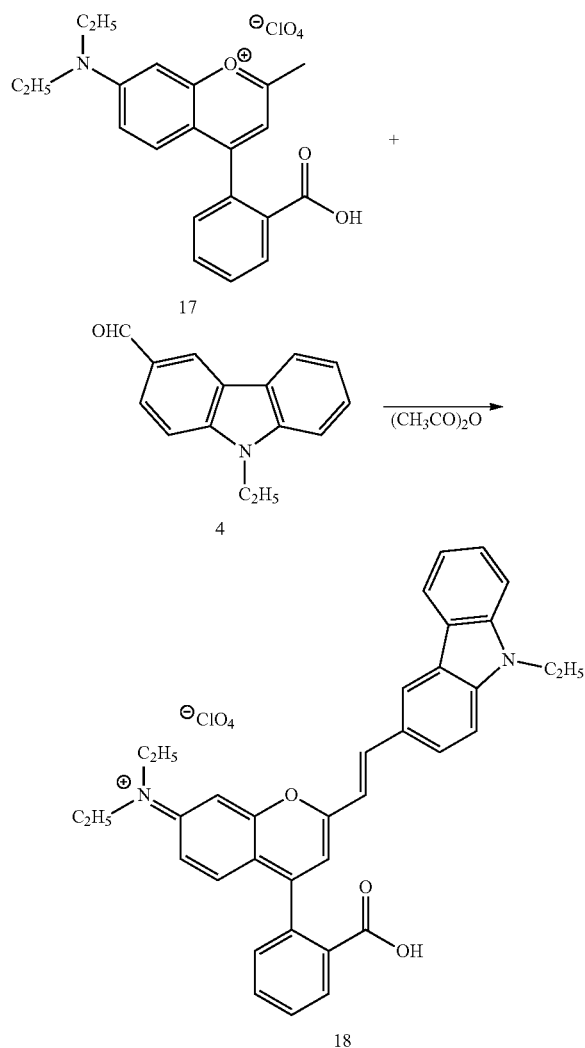

(3) Synthesis of Carboxylic Acid Product (Compound 19)

First, 8.0 g (12.5 mmol) of the carboxylic acid product (compound 18) obtained in the synthesis (2) was added to 145 mL of dichloromethane in a round bottom flask provided with a stirrer and dissolved therein, and 9.5 g (12.5 mmol) of LiFABA (manufactured by Tosoh Finechem Corporation) was added thereto for the reaction at room temperature for 2 hours. After the reaction, the reaction solution was washed with water, the solvent was distilled off from the reaction solution by concentration under reduced pressure, thereby obtaining a black solid. The solid was purified by a silica gel column chromatography so that 4.1 g of a carboxylic acid product (compound 19) (27% yield) as a dark blue solid having a tetrakis(pentafluorophenyl) boron (IV) anion.

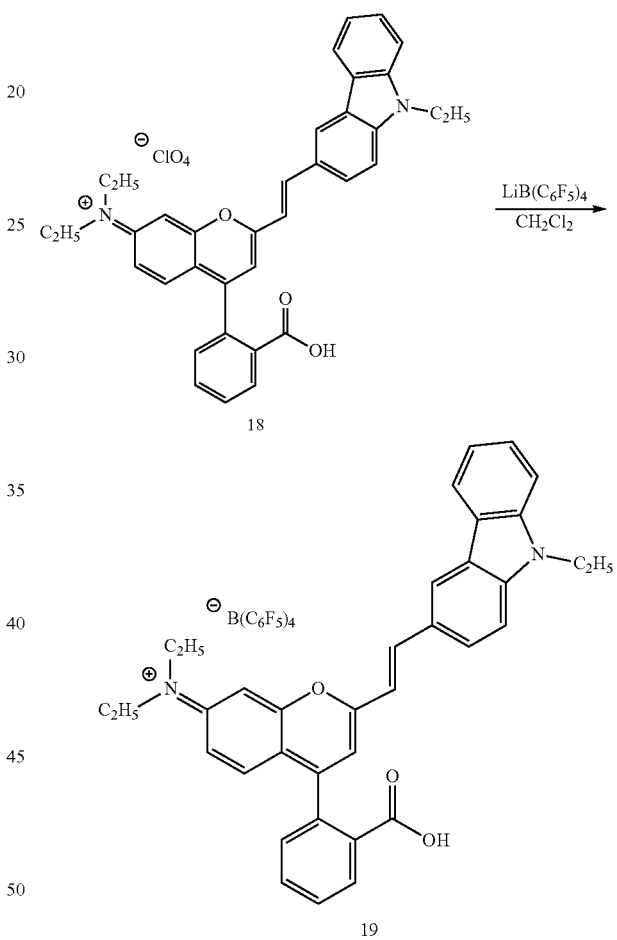

Experiment Example 1: Evaluation of Reverse Photochromic Characteristics of Compound 8

The reverse photochromic characteristics of the compound 8 were evaluated in the following manner.

In other words, 1.2 mg ($8.7 \times 10^{-7}$ mol) of the compound 8 obtained in Example 2 was weighed in a vial bottle (glass bottle), and 9 mL of methanol was added thereto to prepare a solution having a concentration of $1.0 \times 10^{-4}$ mol/L. The obtained solution was poured into another vial bottle (glass bottle) and further diluted with methanol to prepare a methanol solution containing the compound 8 with a concentration of $5.6 \times 10^{-5}$ mol/L. The obtained methanol solution was put into a quartz cell having an optical path length of 1 cm together with a stirring bar, and the absorbance was measured using a spectrophotometer (product name: V-670, manufactured by Jasco Corporation). Thereafter, the solution was irradiated with light while being stirred for 1 minute under a condition of an irradiation intensity of 1 SUN (AM 1.5, 1000 W/m$^2$) using a solar simulator (product name: LAX-C100, manufactured by Asahi Spectra Co., Ltd.), and the absorbance was measured. Further, the quartz cell after the irradiation with light was stored in a dark place for 310 minutes, and the absorbance was measured again.

The results of Experiment Example 1 are shown in FIG. 1. It should be noted that the vertical axis in FIG. 1 indicates the absorbance and the horizontal axis (nm) indicates the wavelength. In addition, the broken line in FIG. 1 shows the measurement result before the irradiation with light, the one dot chain line shows the measurement result immediately after the irradiation with light for 1 minute, and the solid line shows the measurement result after the storage in a dark place for 310 minutes after the irradiation with light.

Experiment Example 2: Evaluation of Reverse Photochromic Characteristics of Compound 6

The reverse photochromic characteristics of the compound 6 were evaluated in the following manner.

In other words, 1.5 mg ($1.2 \times 10^{0.6}$ mol) of the compound 6 obtained in Example 1 was weighed in a vial bottle (glass bottle), and 10 mL of methanol was added thereto to prepare a methanol solution containing the compound 6 with a concentration of $1.2 \times 10^{-4}$ mol/L. The obtained methanol solution was put into a quartz cell having an optical path length of 1 cm together with a stirring bar, and the absorbance was measured using a spectrophotometer (product name: V-670, manufactured by Jasco Corporation). Thereafter, the solution was irradiated with light while being stirred for 5 minutes under a condition of an irradiation intensity of 1 SUN (AM 1.5, 1000 W/m$^2$) using a solar simulator (product name: LAX-C100, manufactured by Asahi Spectra Co., Ltd.), and the absorbance was measured. Further, the quartz cell after the irradiation with light was stored in a dark place for a night, and the absorbance was measured again.

Figure 2:
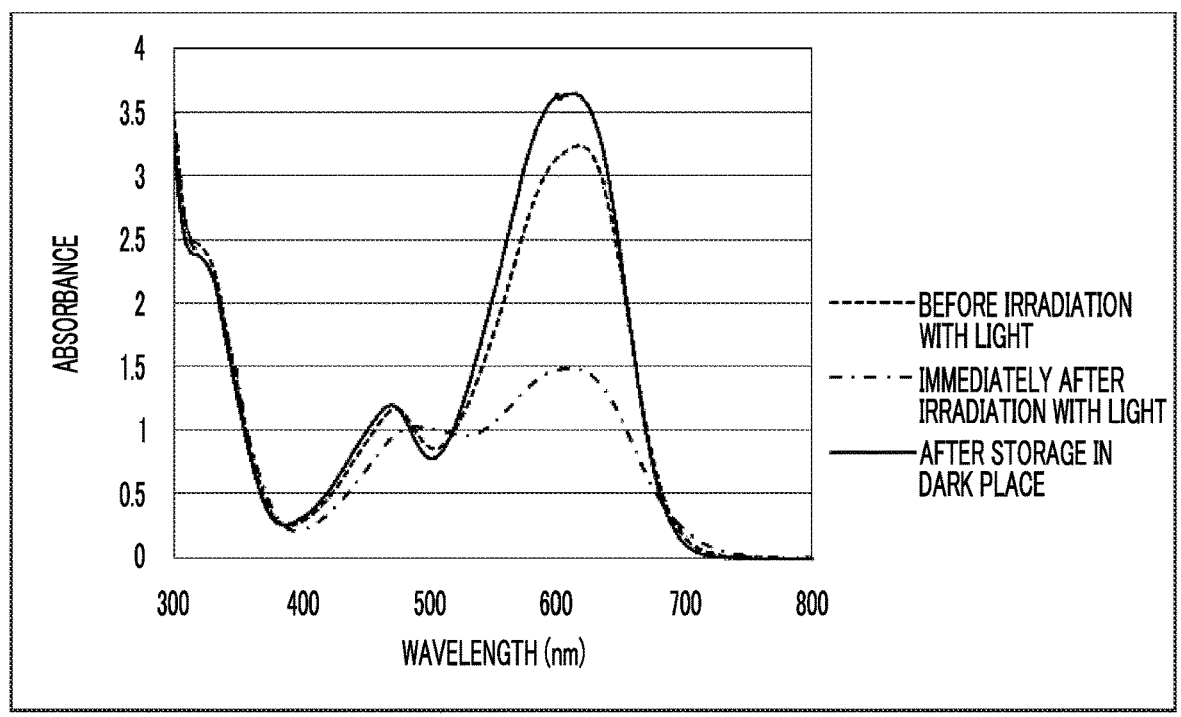
FIG. 2 is a graph showing the results obtained from measurement of the absorbance of a compound (a carboxylic acid product: compound 6) according to the embodiment of the present invention, which is obtained in Experiment Example 2.

The results of Experiment Example 2 are shown in FIG. 2. It should be noted that the vertical axis in FIG. 2 indicates the absorbance and the horizontal axis (nm) indicates the wavelength. In addition, the broken line in FIG. 2 shows the measurement result before the irradiation with light, the one dot chain line shows the measurement result immediately after the irradiation with light for 5 minutes, and the solid line shows the measurement result after the storage in a dark place for a night after the irradiation with light.

Experiment Example 3: Evaluation of Reverse Photochromic Characteristics of Compound 9

The reverse photochromic characteristics were evaluated using the same method as described above except that a methanol solution containing the compound 9 obtained in the following manner was used in place of the methanol solution containing the compound 6 in Experiment Example 2.

In other words, 1.1 mg ($8.5 \times 10^7$ mol) of the compound 9 obtained in Example 3 was weighed in a vial bottle (glass bottle), and 10 mL of methanol was added thereto to prepare a methanol solution containing the compound 9 with a concentration of $8.5 \times 10^{-5}$ mol/L.

Figure 3:
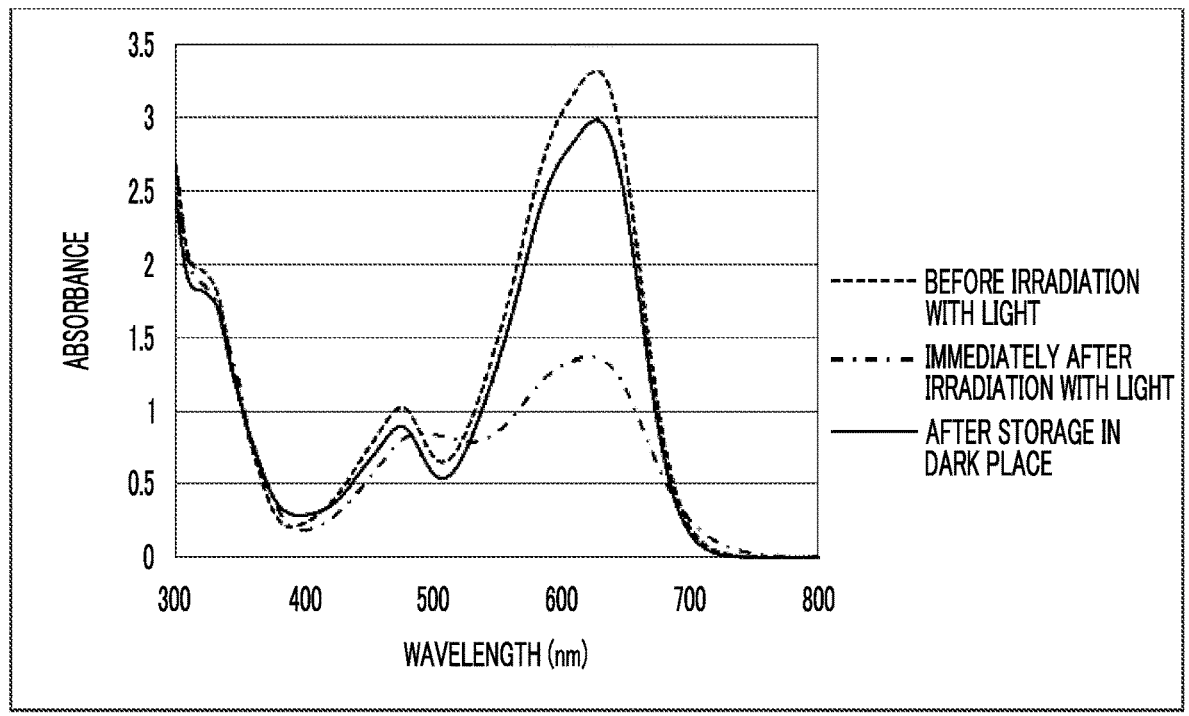
FIG. 3 is a graph showing the results obtained from measurement of the absorbance of a compound (an ester product: compound 9) according to the embodiment of the present invention, which is obtained in Experiment Example 3.

The results of Experiment Example 3 are shown in FIG. 3. It should be noted that the vertical axis in FIG. 3 indicates the absorbance and the horizontal axis (nm) indicates the wavelength. In addition, the broken line in FIG. 3 shows the measurement result before the irradiation with light, the one dot chain line shows the measurement result immediately after the irradiation with light for 5 minutes, and the solid line shows the measurement result after the storage in a dark place for a night after the irradiation with light.

Experiment Example 4: Evaluation of Reverse Photochromic Characteristics of Compound 11

The reverse photochromic characteristics were evaluated using the same method as described above except that a methanol solution containing the compound 11 obtained in the following manner was used in place of the methanol solution containing the compound 6 in Experiment Example 2.

In other words, 2.0 mg ($2.7 \times 10^{0.6}$ mol) of the compound 11 obtained in Example 4 was weighed in a vial bottle (glass bottle), and 10 mL of methanol was added thereto to prepare a solution with a concentration of $2.7 \times 10^{-4}$ mol/L. The obtained solution was poured into another vial bottle (glass bottle) and further diluted with methanol to prepare a methanol solution containing the compound 11 with a concentration of $5.4 \times 10^{-4}$ mol/L.

Figure 4:
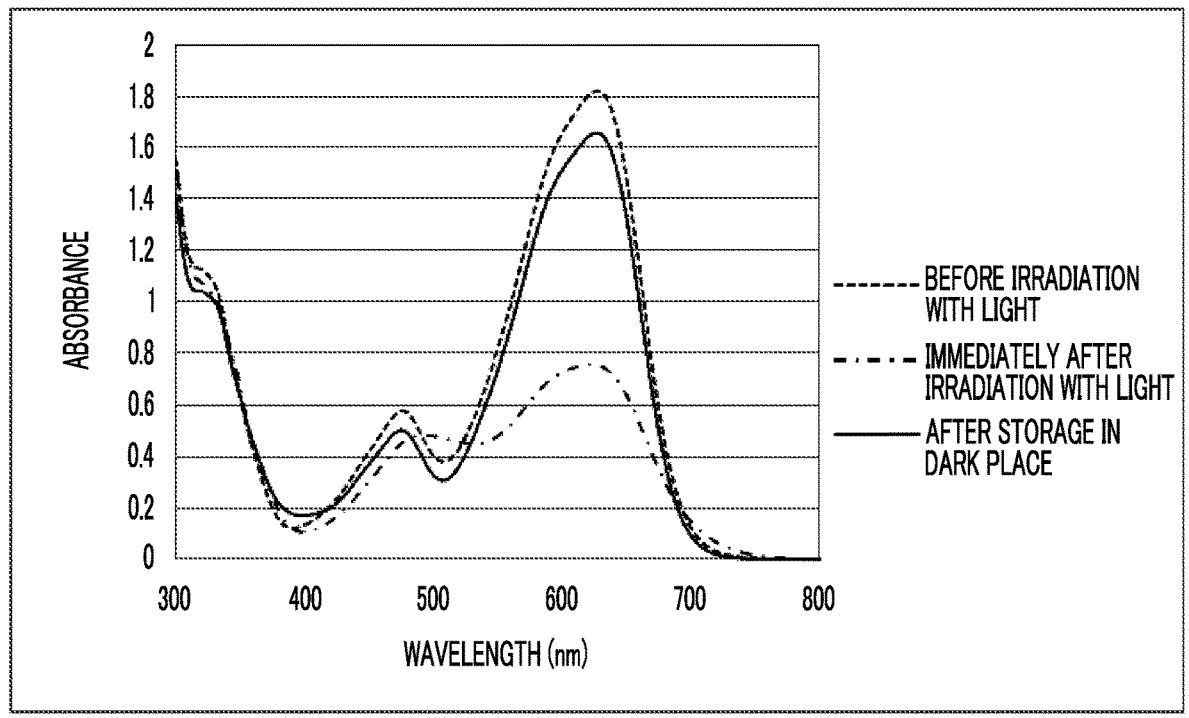
FIG. 4 is a graph showing the results obtained from measurement of the absorbance of a compound (an ester product: compound 11) according to the embodiment of the present invention, which is obtained in Experiment Example 4.

The results of Experiment Example 4 are shown in FIG. 4. It should be noted that the vertical axis in FIG. 4 indicates the absorbance and the horizontal axis (nm) indicates the wavelength. In addition, the broken line in FIG. 4 shows the measurement result before the irradiation with light, the one dot chain line shows the measurement result immediately after the irradiation with light for 5 minutes, and the solid line shows the measurement result after the storage in a dark place for a night after the irradiation with light.

Based on the results of Experiment Examples 1 to 4, it was found that in a case where the compound according to the embodiment of the present invention in a colored state of exhibiting a blue color was irradiated with light, the blue color faded and the colored state of the compound was changed to a light color or a colorless state. Further, it was found that in a case where the compound having a light color or in a colorless state was stored in a dark place (light shielding), the compound according to the embodiment of the present invention was developed to the almost original blue color and returned to the colored state. Therefore, it was found that the compound according to the embodiment of the present invention shows the reverse change of color fading that occurs at the time of irradiation with light and color development that occurs at the time of light shielding, in other words, the compound has reverse photochromic characteristics. In addition, it was found that the reverse photochromic characteristics exhibit regardless of the kind of the counter anion, the functional group such as carboxylic acid or an ester bond, and the length of the carbon chain in the compound according to the embodiment of the present invention.

Experiment Example 5: Evaluation of Solvent Dependence of Reverse Photochromic Characteristics of Compound 8

The solvent dependence of the reverse photochromic characteristics of the compound 8 was evaluated in the following manner.

(1) Preparation of Various Solutions of Compound 8

Various solutions of the compound 8 obtained in Example 2 were prepared using the following methods (1-1) to (1-7).

(1-1) Preparation of Methanol Solution

First, 1.2 mg ($8.7 \times 10^{-7}$ mol) of the compound 8 was weighed in a vial bottle (glass bottle), and 9 mL of methanol was added thereto to prepare a solution having a concentration of $1.0 \times 10^{-4}$ mol/L. The obtained solution was poured into another vial bottle (glass bottle) and further diluted with methanol to prepare a methanol solution containing the compound 8 with a concentration of $5.6 \times 10^{0.5}$ mol/L.

(1-2) Preparation of Toluene Solution

First, 1.2 mg ($8.7 \times 10^{-7}$ mol) of the compound 8 was weighed in a vial bottle (glass bottle), and 9 mL of toluene was added thereto to prepare a solution having a concentration of $9.3 \times 10^{-5}$ mol/L. The obtained solution was poured into another vial bottle (glass bottle) and further diluted with toluene to prepare a toluene solution containing the compound 8 with a concentration of $1.9 \times 10^{-5}$ mol/L.

(1-3) Preparation of Acetonitrile Solution

First, 1.2 mg ($8.7 \times 10^{-7}$ mol) of the compound 8 was weighed in a vial bottle (glass bottle), and 10 mL of acetonitrile was added thereto to prepare a solution having a concentration of $8.7 \times 10^{-5}$ mol/L. The obtained solution was poured into another vial bottle (glass bottle) and further diluted with acetonitrile to prepare an acetonitrile solution containing the compound 8 with a concentration of $2.2 \times 10^{-5}$ mol/L.

(1-4) Preparation of Chloroform Solution

First, 1.1 mg ($8.0 \times 10^{7'}$ mol) of the compound 8 was weighed in a vial bottle (glass bottle), and 10 mL of chloroform was added thereto to prepare a solution having a concentration of $8.0 \times 10^{-5}$ mol/L. The obtained solution was poured into another vial bottle (glass bottle) and further diluted with chloroform to prepare a chloroform solution containing the compound 8 with a concentration of $1.8 \times 10^{-5}$ mol/L.

(1-5) Preparation of o-Dichlorobenzene Solution

First, 1.5 mg ($1.1 \times 10^{0.6}$ mol) of the compound 8 was weighed in a vial bottle (glass bottle), and 10 mL of o-dichlorobenzene was added thereto to prepare a solution having a concentration of $1.1 \times 10^{-4}$ mol/L. The obtained solution was poured into another vial bottle (glass bottle) and further diluted with o-dichlorobenzene to prepare an o-dichlorobenzene solution containing the compound 8 with a concentration of $2.2 \times 10^{-5}$ mol/L.

(1-6) Preparation of 2-Propanol Solution

First, 1.3 mg ($9.7 \times 10^{-7}$ mol) of the compound 8 was weighed in a vial bottle (glass bottle), and 10 mL of 2-propanol was added thereto to prepare a saturated solution. The supernatant of the obtained saturated solution was poured into another vial bottle (glass bottle) and further diluted with 2-propanol by three times to prepare a 2-propanol solution containing the compound 8.

(1-7) Preparation of Chlorobenzene Solution

First, 1.4 mg ($1.0 \times 10^{0.6}$ mol) of the compound 8 was weighed in a vial bottle (glass bottle), and 10 mL of chlorobenzene was added thereto to prepare a solution having a concentration of $1.0 \times 10^{-4}$ mol/L. The obtained solution was poured into another vial bottle (glass bottle) and further diluted with chlorobenzene to prepare a chlorobenzene solution containing the compound 8 with a concentration of $2.0 \times 10^{-5}$ mol/L.

(2) Evaluation of Solvent Dependence of Reverse Photochromic Characteristics

Various solutions containing the compound 8 obtained in the preparation (1) were put into a quartz cell having an optical path length of 1 cm together with a stirring bar, the solutions were irradiated with light while being stirred for 5 minutes under a condition of an irradiation intensity of 1 SUN (AM 1.5, 1000 W/m$^2$) using a solar simulator (product name: LAX-C100, manufactured by Asahi Spectra Co., Ltd.), and the absorbance of each solution at the maximum absorption wavelength was measured using a spectrophotometer (product name: V-670, manufactured by Jasco Corporation). Thereafter, the quartz cell was stored in a dark place, the absorbance at every fixed interval time was measured, and the temporal change of the absorbance of each solution at the maximum absorption wavelength was confirmed.

It should be noted that the maximum absorption wavelength of various solutions during the measurement were 632 nm in a case of the methanol solution, 653 nm in a case of the toluene solution, 626 nm in a case of the acetonitrile solution, 650 nm in a case of the chloroform solution, 659 nm in a case of the o-dichlorobenzene solution, 639 nm in a case of the 2-propanol solution, and 659 nm in a case of the chlorobenzene solution.

Figure 5:
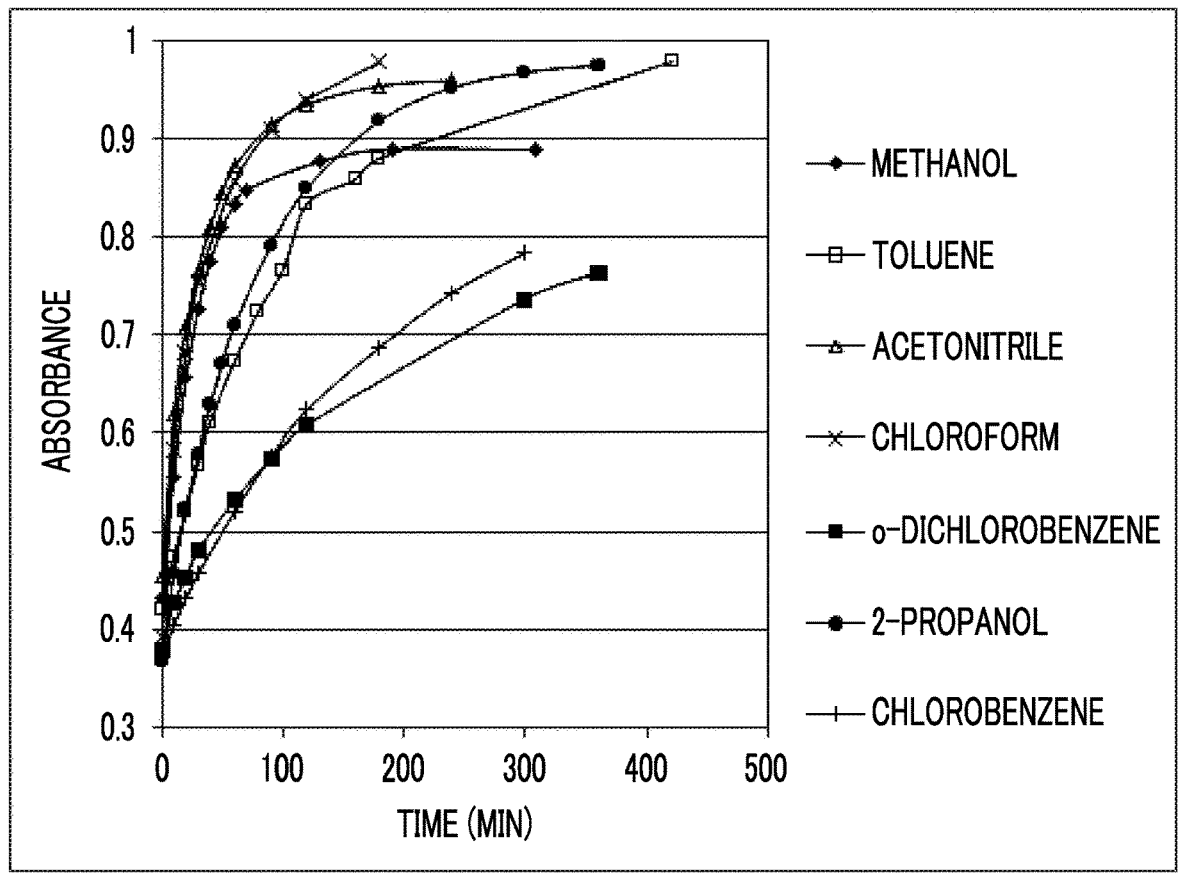
FIG. 5 is a graph showing the results of a temporal change in the absorbance of the compound (the monomer having a polymerizable unsaturated group: compound 8) according to the embodiment of the present invention at a maximum absorption wavelength, which has been stored in a dark place after irradiation with light for 5 minutes and is obtained in Experiment Example 5.

The results of Experiment Example 5 are shown in FIG. 5. It should be noted that the vertical axis in FIG. 5 indicates the absorbance at the maximum absorption wavelength of each solution and the horizontal axis (min) indicates the storage time in a dark place. In addition, in FIG. 5, "♦" shows the measurement result at the time of using methanol as a solvent, "□" shows the measurement result at the time of using toluene as a solvent, "Δ" shows the measurement result at the time of using acetonitrile as a solvent, "x" shows the measurement result at the time of using chloroform as a solvent, "■" shows the measurement result at the time of using o-dichlorobenzene as a solvent, "●" shows the measurement result at the time of using 2-propanol as a solvent, and "+" shows the measurement result at the time of using chlorobenzene as a solvent.

Based on the results of Experiment Example 5, it was found that the compound according to the embodiment of the present invention exhibits the reverse photochromic characteristics in a case of using any solvent, but exhibits different responsiveness depending on the kind of the solvent at the time of change from the colorless state after the irradiation with light to the colored state. In addition, acetonitrile and chloroform among various organic solvents show rapid responsiveness, and thus the results were preferable.

Experiment Example 6: Evaluation of Temperature Dependence of Reverse Photochromic Characteristics of Compound 8

The temperature dependence of the reverse photochromic characteristics of the compound 8 was evaluated in the following manner.

In other words, 1.1 mg ($8.0 \times 10^{-7}$ mol) of the compound 8 obtained in Example 2 was weighed in a vial bottle (glass bottle), and 9 mL of toluene was added thereto to prepare a solution with a concentration of $8.5 \times 10^{-5}$ mol/L. The obtained solution was poured into another vial bottle (glass bottle) and further diluted with toluene to prepare a toluene solution containing the compound 8 with a concentration of $2.3 \times 10^{-5}$ mol/L. The obtained toluene solution was put into a quartz cell having an optical path length of 1 cm together with a stirring bar, and the quartz cell was inserted into an electronic cooling cell positioner (product name: CPS-240A, manufactured by Shimadzu Corporation). After the quartz cell was allowed to stand for 30 minutes or longer in order to adjust the temperature thereof to a set temperature (20° C., 40° C., or 60° C.), the absorbance at a wavelength of 651 nm was measured using a spectrophotometer (product name: UV-2450, manufactured by Shimadzu Corporation). Thereafter, the cell was taken out from the electronic cooling cell positioner, and the solution was irradiated with light while being stirred for 1 minute under a condition of an irradiation intensity of 1 SUN (AM 1.5, 1000 W/m$^2$) using a solar simulator (product name: LAX-C100, manufactured by Asahi Spectra Co., Ltd.). The quartz cell was inserted into the electronic cooling cell positioner again, the absorbance was measured at every fixed interval time while the set temperature was maintained, and the temporal change of the absorbance at a wavelength of 651 nm was confirmed.

Figure 6:
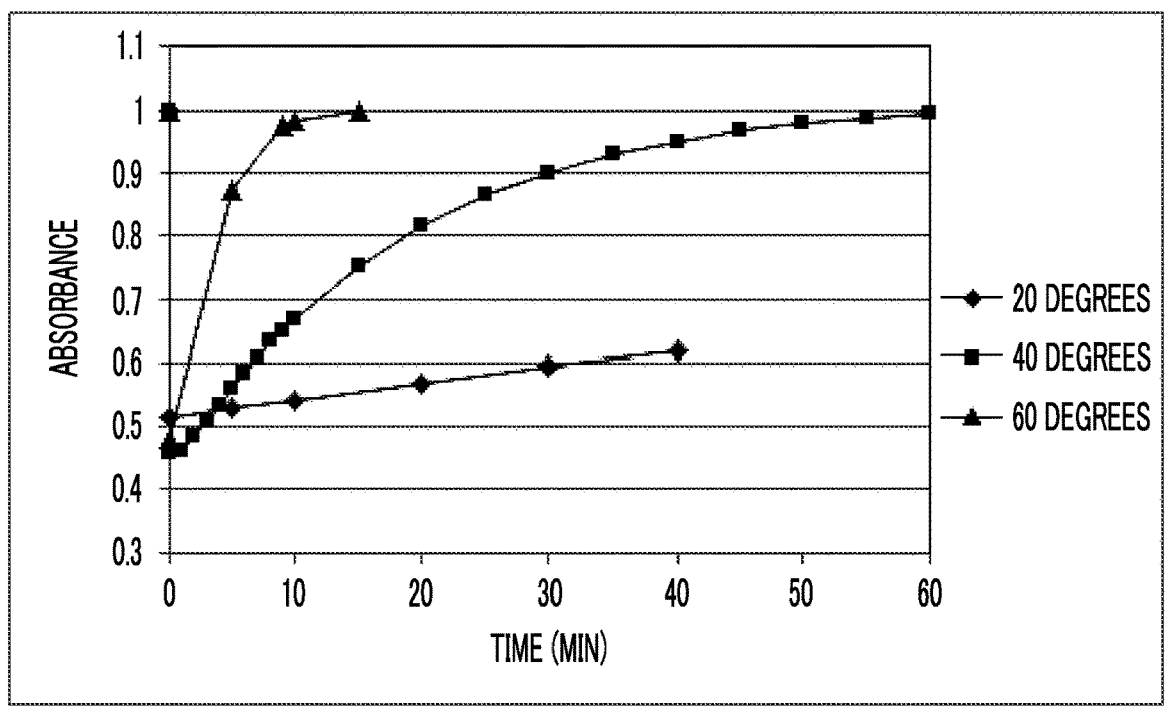
FIG. 6 is a graph showing the results of a temporal change in the absorbance of the compound (the monomer having a polymerizable unsaturated group: compound 8) according to the embodiment of the present invention at a wavelength of 651 nm, which has been stored in a dark place after irradiation with light for 1 minute while the temperature is maintained to a set temperature and is obtained in Experiment Example 6.

The results of Experiment Example 6 are shown in FIG. 6. It should be noted that the vertical axis in FIG. 6 indicates the absorbance at a wavelength of 651 nm and the horizontal axis (min) indicates the storage time in the electronic cooling cell positioner after the irradiation with light. In addition, in FIG. 6, "♦" shows the measurement result at the time of setting the temperature to 20° C., "■" shows the measurement result at the time of setting the temperature to 40° C., and "▲" shows the measurement result at the time of setting the temperature to 60° C.

Based on the results of Experiment Example 6, it was found that the compound according to the embodiment of the present invention exhibits the reverse photochromic characteristics in a case of any temperature setting. However, the compound exhibits high responsiveness in a case where a high temperature was maintained at the time of change from the colorless state after the irradiation with light to the colored state, and the colorless state is changed to a colored state in approximately 10 minutes.

Experiment Example 7: Evaluation of Repeated Durability of Reverse Photochromic Characteristics of Compound 8

The repeated durability of the reverse photochromic characteristics of the compound 8 was evaluated in the following manner.

In other words, 1.1 mg ($8.0 \times 10^{7t}$ mol) of the compound 8 obtained in Example 2 was weighed in a vial bottle (glass bottle), and 9 mL of toluene was added thereto to prepare a solution with a concentration of $8.5 \times 10^{-5}$ mol/L. The obtained solution was poured into another vial bottle (glass bottle) and further diluted with toluene to prepare a toluene solution containing the compound 8 with a concentration of $2.3 \times 10^{-5}$ mol/L. The obtained toluene solution was put into a quartz cell having an optical path length of 1 cm together with a stirring bar, and the quartz cell was inserted into an electronic cooling cell positioner (product name: CPS-240A, manufactured by Shimadzu Corporation). After the quartz cell was allowed to stand for 30 minutes or longer in order to adjust the temperature thereof to a set temperature (60° C.), the absorbance at a wavelength of 651 nm was measured using a spectrophotometer (product name: UV-2450, manufactured by Shimadzu Corporation). Thereafter, the cell was taken out from the electronic cooling cell positioner, the solution was irradiated with light while being stirred for 1 minute under a condition of an irradiation intensity of 1 SUN (AM 1.5, 1000 W/m$^2$) using a solar simulator (product name: LAX-C100, manufactured by Asahi Spectra Co., Ltd.), and the absorbance thereof at a wavelength of 651 nm was measured using a spectrophotometer. The quartz cell was inserted into the electronic cooling cell positioner again, the absorbance at a wavelength of 651 nm was measured after 15 minutes at a set temperature of 60° C. The absorbance at every time the operation (the irradiation with light and the storage in the electronic cooling cell positioner) described above was repeated ten times was measured.

Figure 7:
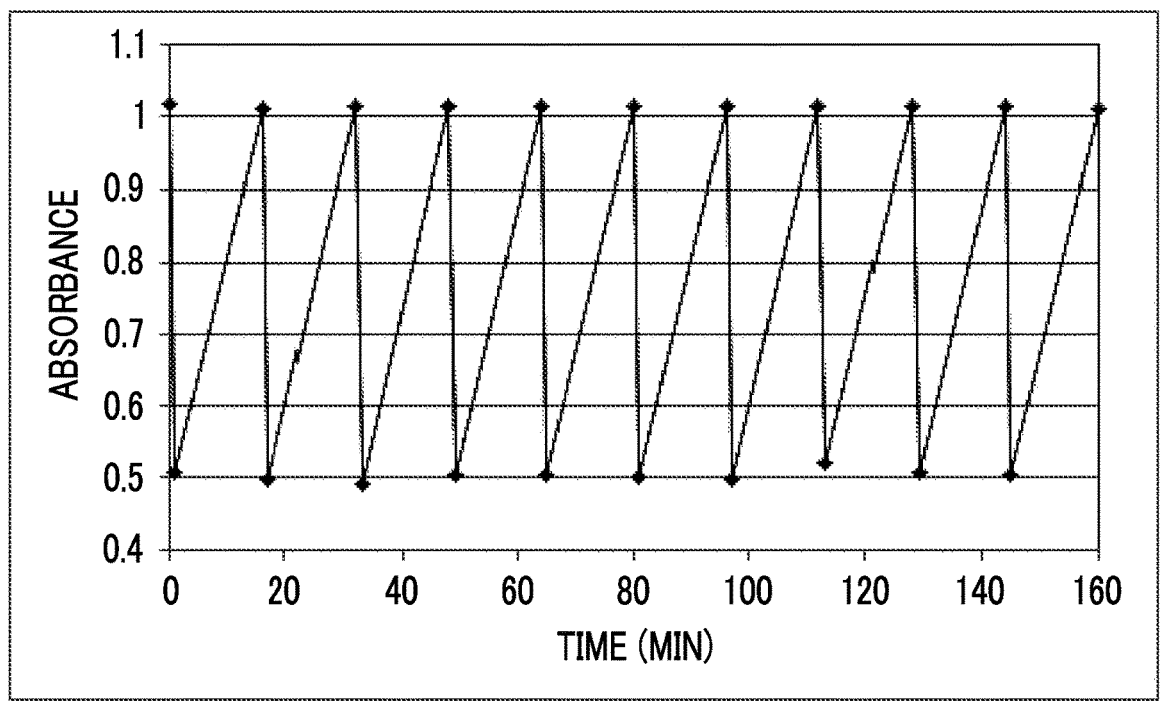
FIG. 7 is a graph showing the results obtained from measurement of the absorbance of the compound (the monomer having a polymerizable unsaturated group: compound 8) according to the embodiment of the present invention at a wavelength of 651 nm for 1 to 10 cycles immediately after irradiation with light for 1 minute and after storage in a dark place for 15 minutes after irradiation with light, which is obtained in Experiment Example 7.

The results of Experiment Example 7 are shown in FIG. 7. It should be noted that the vertical axis in FIG. 7 indicates the absorbance at a wavelength of 651 nm and the horizontal axis (min) indicates the elapsed time from the measurement of the initial absorbance. In addition, in FIG. 7, the solid line shows the measurement results (1 to 10 cycles) immediately after irradiation with light for 1 minute and after storage in the electronic cooling cell positioner for 15 minutes after irradiation with light.

Based on the results of Experiment Example 7, it was found that the compound according to the embodiment of the present invention has excellent repeated durability and the reverse photochromic behavior thereof was not changed even in a case where the irradiation with light and the storage in a dark place were repeated ten times.

Experiment Example 8: Evaluation of Solubility and Compatibility of Compound 8

The solubility and the compatibility of the compound 8 obtained in Example 2 were evaluated in the following manner.

In other words, 100 mg of the compound 8 was weighed in a glass container (manufactured by NICHIDEN RIKA GLASS CO., LTD.), 10 mg of various organic solvents were added thereto in a state in which the temperature thereof was maintained to 20° C., and the solution was stirred for 10 minutes. In a case where the solid content remained, the operation of adding 10 mg of the organic solvents and stirring the solution for 10 minutes was repeated, and the amount (A mg) of the organic solvents to be used at the time of complete dissolution of the compound 8 was measured. The solubility (%) was acquired based on the value of A mg using the following equation. The results are listed in Table 1.

Solubility (%)=100 mg/(100 mg+$A$ mg)×100

TABLE 1

| Organic solvent | Solubility (%) |
| --- | --- |
| Toluene | 50 |
| Ethyl acetate (AcOEt) | 50 |
| Methyl ethyl ketone (MEK) | 50 |
| Methyl methacrylate (MMA) | 50 |
| 1-Methoxy-2-propanol (PGME) | 38 |
| Triethyl phosphate (TEP) | 31 |
| Dibutyl sebacate (DBS) | 20 |
| Epoxy resin (jER ®) | 11 |

Based on the results of Experiment Example 8, it was found that a compound having a tetrakis(pentafluorophenyl) boron (IV) anion as a counter anion, among examples of the compound according to the embodiment of the present invention, shows a high solubility in various organic solvents. Further, it was found that the compound shows a high compatibility with a plasticizer such as triethyl phosphate or dibutyl sebacate and also shows a compatibility with an epoxy resin without being separated therefrom.

Example 7: Synthesis of Carboxylic Acid Product (Compound 23)

(1) Synthesis of Dimethyl Product (Compound 21)

First, 1.0 g (5.5 mmol) of 2-hydroxycarbazole (compound 20: manufactured by Wako Pure Chemical Industries, Ltd.), 3.8 g (27 mmol) of potassium carbonate (manufactured by Wako Pure Chemical Industries, Ltd.), 3.9 g (27 mmol) of methyl iodide (manufactured by Wako Pure Chemical Industries, Ltd.), and 100 mL of N,N-dimethylformamide (DMF) (manufactured by Wako Pure Chemical Industries, Ltd.) were added to a round bottom flask provided with a stirrer, and the reaction was carried out at room temperature for 14 hours. After the reaction, ethyl acetate and water were added thereto, an organic layer obtained by liquid separation was washed with water, and the solvent was distilled off by concentration under reduced pressure, thereby obtaining a white solid. The solid was purified by a silica gel column so that 0.45 g of a dimethyl product (compound 21) (39% yield) as a white solid was obtained.

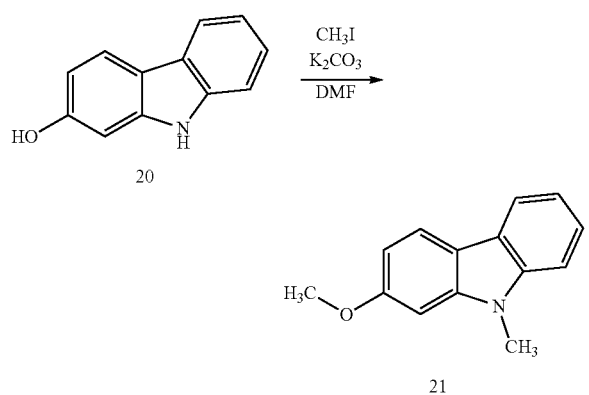

(2) Synthesis of Aldehyde Product (Compound 22)

First, 2.0 g (9.5 mmol) of the dimethyl product (compound 21) obtained in the synthesis (1) and 19 mL of DMF (manufactured by Wako Pure Chemical Industries, Ltd.) were added to a round bottom flask provided with a stirrer in a nitrogen atmosphere and dissolved therein. The solution was cooled to 0° C., and 1.8 mL (19 mmol) of phosphorus oxychloride (manufactured by Wako Pure Chemical Industries, Ltd.) was added thereto for the reaction at 60° C. for 3 hours. After the reaction, the reaction solution was added dropwise to 100 mL of a saturated aqueous solution containing potassium acetate (manufactured by Wako Pure Chemical Industries, Ltd.) and subjected to liquid separation using ethyl acetate. An organic layer obtained by liquid separation was washed with water three times, and the solvent was distilled off by concentration under reduced pressure, thereby obtaining a yellow solid. The solid was purified by a silica gel column chromatography so that 1.8 g of an aldehyde product (compound 22) (77% yield) as a white solid was obtained.

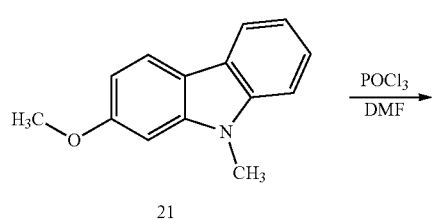

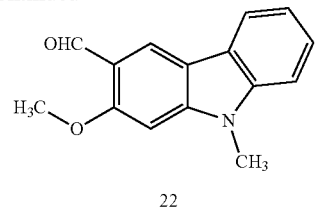

(3) Synthesis of Carboxylic Acid Product (Compound 23)

First, 0.10 g (0.21 mmol) of the carboxylic acid product (compound 3) obtained in the synthesis (1) of Example 1 and 1.0 mL of ethanol (manufactured by Wako Pure Chemical Industries, Ltd.) were added to a round bottom flask provided with a stirrer and dissolved therein, and 0.23 g (0.23 mmol) of the aldehyde product (compound 22) obtained in the synthesis (2) and two drops of concentrated sulfuric acid (manufactured by Wako Pure Chemical Industries, Ltd.) were added thereto using Pasteur pipettes for the reaction at 65° C. for 2 hours. After the reaction, ethanol was distilled off by concentration under reduced pressure. After the concentration, 10 mL of dichloromethane and 10 mL of water were added thereto, 0.18 g (0.23 mmol) of LiFABA (manufactured by Tosoh Finechem Corporation) was added thereto, and the solution was stirred at room temperature for 1 hour. After the stirring, the water layer was removed, and concentration under reduced pressure, thereby obtaining 0.28 g of a carboxylic acid product (compound 23) (100% yield) as a dark blue solid having a tetrakis(pentafluorophenyl) boron (IV) anion.

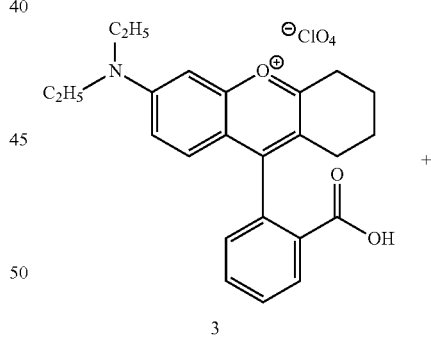

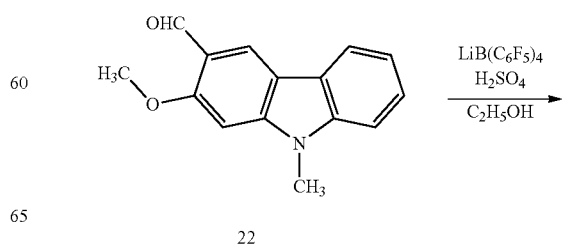

-continued

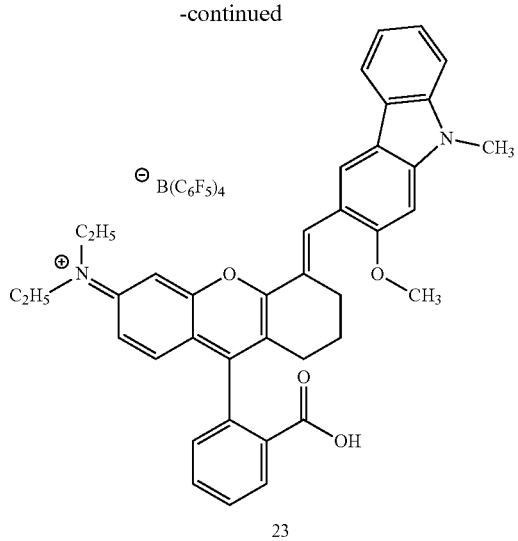

23

Example 8: Synthesis of Carboxylic Acid Product (Compound 25)

First, 0.20 g (0.42 mmol) of the carboxylic acid product (compound 3) obtained in the synthesis (1) of Example 1 and 2.0 mL of ethanol (manufactured by Wako Pure Chemical Industries, Ltd.) were added to a round bottom flask provided with a stirrer and dissolved therein, and 0.13 g (0.46 mmol) of N-phenylcarbazole-3-carboxyaldehyde (compound 24: manufactured by Tokyo Chemical Industry Co., Ltd.) and three drops of concentrated sulfuric acid (manufactured by Wako Pure Chemical Industries, Ltd.) were added thereto using Pasteur pipettes for the reaction at 65° C. for 2 hours. After the reaction, ethanol was distilled off by concentration under reduced pressure. After the concentration, 10 mL of dichloromethane and 10 mL of water were added thereto, 0.35 g (0.46 mmol) of LiFABA (manufactured by Tosoh Finechem Corporation) was added thereto, and the solution was stirred at room temperature for 1 hour. After the stirring, the water layer was removed, concentration under reduced pressure, thereby obtaining 0.51 g of a carboxylic acid product (compound 25) (93% yield) as a dark blue solid having a tetrakis(pentafluorophenyl) boron (IV) anion.

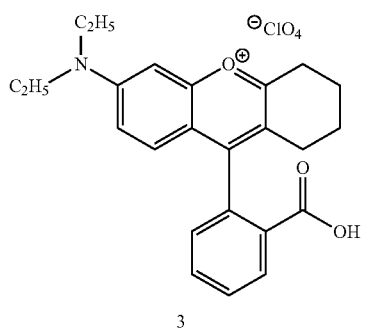

3

-continued

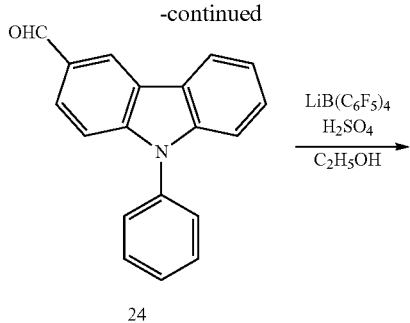

24

25

Example 9: Synthesis of Carboxylic Acid Product (Compound 30)

(1) Synthesis of Benzoic Acid Derivative (Compound 28)

First, 1.9 g (9.8 mmol) of 2,3,6,7-tetrahydro-1,5-benzo [ij]quinolizin-8-ol (compound 26: manufactured by Wako Pure Chemical Industries, Ltd.), 1.6 g (9.8 mmol) of phthalic anhydride (compound 27: manufactured by Wako Pure Chemical Industries, Ltd.), and 30 mL of toluene were added to a round bottom flask provided with a stirrer for the reaction at 100° C. for 6 hours. After the reaction, the solution was cooled to room temperature, and the deposited crystals were collected by filtration, washed with methanol, and dried, thereby obtaining 2.3 g of a benzoic acid derivative (compound 28) (70% yield) as a white solid.

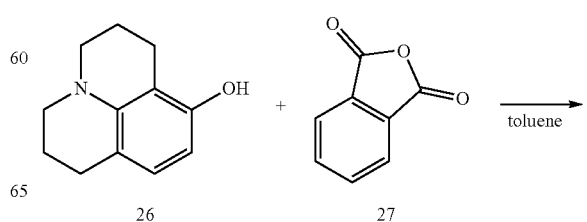

26   27

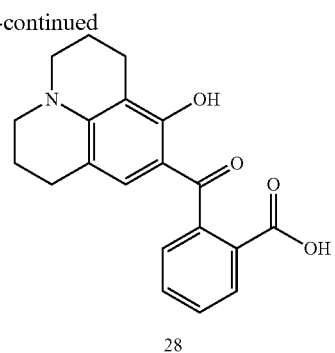

28

(2) Synthesis of Carboxylic Acid Product (Compound 29)

First, 5.0 g (15 mmol) of the benzoic acid derivative (compound 28) obtained in the synthesis (1) and 25 mL of concentrated sulfuric acid (manufactured by Wako Pure Chemical Industries, Ltd.) were added to a round bottom flask provided with a stirrer and dissolved therein, and 2.9 g (30 mmol) of cyclohexanone (compound 2: manufactured by Wako Pure Chemical Industries, Ltd.) was further added thereto for the reaction at 90° C. for 4 hours. After the reaction, the reaction solution was added dropwise to ice water, and 100 mL of dichloromethane and 12 g (16 mmol) of LiFABA (manufactured by Tosoh Finechem Corporation) were added thereto, and the solution was stirred at room temperature for 1 hour. After the water layer was removed, the solvent was distilled off by concentration under reduced pressure, thereby obtaining 15 g of a carboxylic acid product (compound 29) (96% yield) as a red solid.

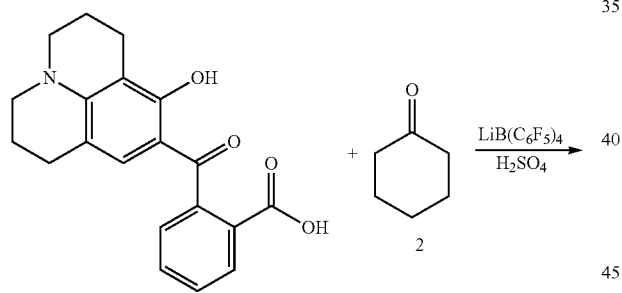

28

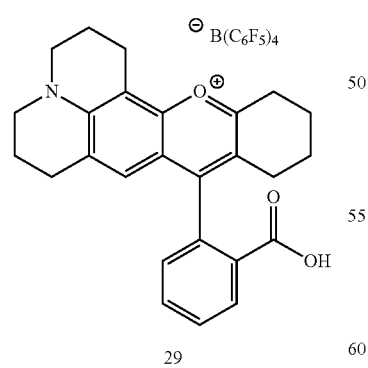

29

(3) Synthesis of Carboxylic Acid Product (Compound 30)

First, 0.50 g (0.46 mmol) of the carboxylic acid product (compound 29) obtained in the synthesis (2) and 5.0 mL of ethanol (manufactured by Wako Pure Chemical Industries, Ltd.) were added to a round bottom flask provided with a stirrer and dissolved therein, and 0.11 g (0.51 mmol) of N-ethylcarbazole-3-carboxyaldehyde (compound 4: manufactured by Tokyo Chemical Industry Co., Ltd.) and four drops of concentrated sulfuric acid (manufactured by Wako Pure Chemical Industries, Ltd.) were added thereto using Pasteur pipettes for the reaction at 80° C. for 12 hours. After the reaction, ethanol was distilled off by concentration under reduced pressure. After the concentration, 20 mL of dichloromethane and 20 mL of water were added thereto, and the solution was stirred at room temperature for 1 hour. After the stirring, the water layer was removed, and the solvent was distilled off by concentration under reduced pressure, thereby obtaining a dark blue solid. The solid was purified by a silica gel column chromatographyso that 0.080 g of a carboxylic acid product (compound 30) (13% yield) as a dark blue solid having a tetrakis(pentafluorophenyl) boron (IV) anion.

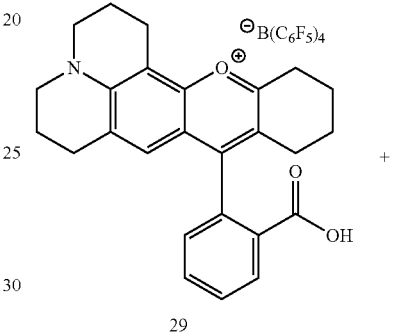

29

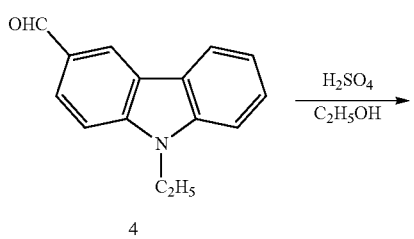

4

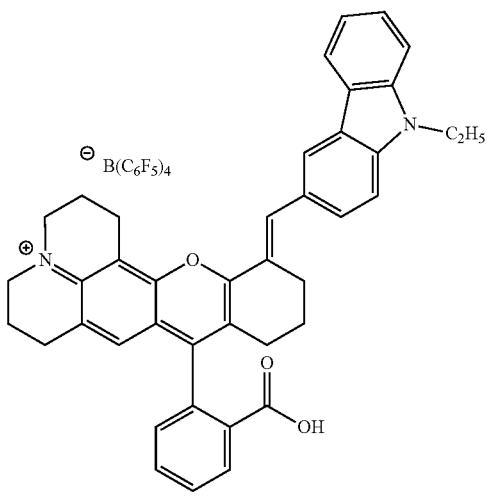

30

Example 10: Synthesis of Carboxylic Acid Product (Compound 35)

(1) Synthesis of Benzophenone Derivative (Compound 33)

First, 0.50 g (3.3 mmol) of N,N-dimethyl-m-anisidine (compound 31: manufactured by Wako Pure Chemical Industries, Ltd.), 0.88 g (6.6 mmol) of aluminum chloride (manufactured by Wako Pure Chemical Industries, Ltd.), and 20 mL of dichloromethane were added to a round bottom flask provided with a stirrer in a nitrogen atmosphere and then dissolved therein. The solution was cooled to 0° C., and a 10 mL dichloromethane solution containing 0.79 g (4.0 mmol) of methyl p-(chlorocarbonyl) benzoate (manufactured by Wako Pure Chemical Industries, Ltd.) was added thereto for the reaction at room temperature for 3 hours. After the reaction, the reaction solution was added dropwise to ice water, an organic layer obtained by liquid separation was washed with water, and the solvent was distilled off by concentration under reduced pressure, thereby obtaining a green solid. The solid was purified by a silica gel column chromatography so that 0.17 g of a benzophenone product (compound 33) (16% yield) as a yellow solid was obtained.

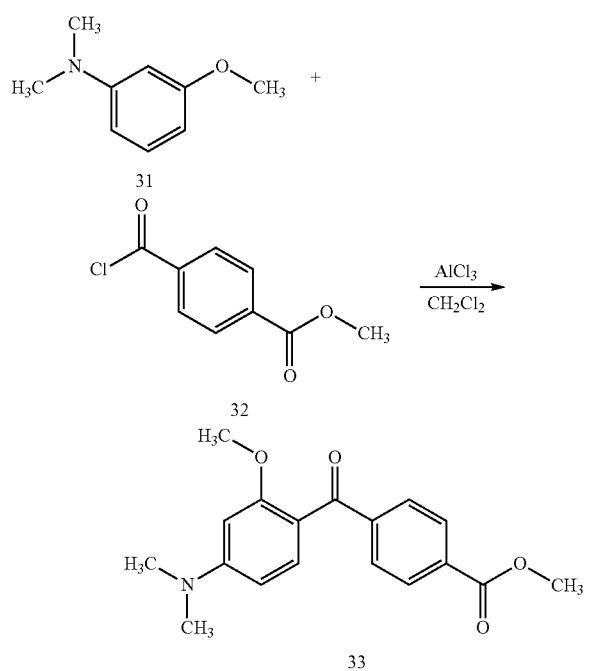

(2) Synthesis of Carboxylic Acid Product (Compound 34)

First, 63 mg (0.20 mmol) of the benzophenone derivative (compound 33) obtained in the synthesis (1) and 1.0 mL of methanol were added to a round bottom flask provided with a stirrer and dissolved therein, and 25 mg (0.60 mmol) of a lithium hydroxide monohydrate (manufactured by Wako Pure Chemical Industries, Ltd.) and 3.0 mL of water were added thereto for the reaction at room temperature for 48 hours. After the reaction, 0.5 mol/L of hydrochloric acid (manufactured by Wako Pure Chemical Industries, Ltd.) was added thereto for neutralization, and the solvent was distilled off by concentration under reduced pressure, thereby obtaining a yellow solid. The solid was dissolved in 2.0 mL of concentrated sulfuric acid (manufactured by Wako Pure Chemical Industries, Ltd.), and 78 mg (0.80 mmol) of cyclohexanone (compound 2: manufactured by Wako Pure Chemical Industries, Ltd.) was added thereto for the reaction at 90° C. for 10 hours. After the reaction, the reaction solution was added dropwise to ice water, and 1.0 mL of perchloric acid (manufactured by Wako Pure Chemical Industries, Ltd.) was added dropwise thereto for the reaction at room temperature for 1 hour. The deposited solid was collected by filtration and recrystallized using methanol and diisopropyl ether, thereby obtaining 11 mg of a carboxylic acid product (compound 34) (12% yield) as a red solid.

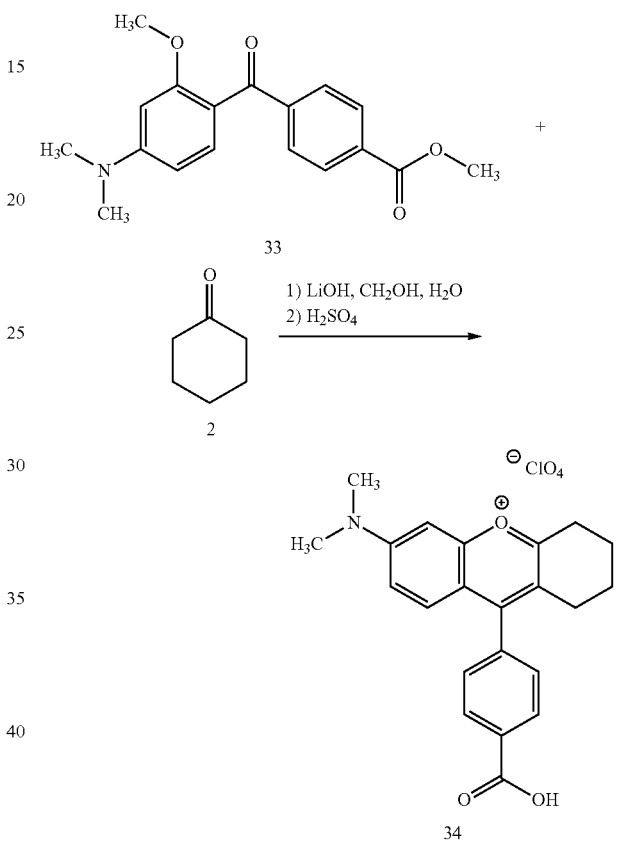

(3) Synthesis of Carboxylic Acid Product (Compound 35)

First, 11 mg (0.025 mmol) of the carboxylic acid product (compound 34) obtained in the synthesis (2) and 1.0 mL of ethanol (manufactured by Wako Pure Chemical Industries, Ltd.) were added to a round bottom flask provided with a stirrer and dissolved therein, and 6.0 mg (0.027 mmol) of N-ethylcarbazole-3-carboxyaldehyde (compound 4: manufactured by Tokyo Chemical Industry Co., Ltd.) and one drop of concentrated sulfuric acid (manufactured by Wako Pure Chemical Industries, Ltd.) were added thereto using Pasteur pipettes for the reaction at 70° C. for 5 hours. After the reaction, ethanol was distilled off by concentration under reduced pressure. After the concentration, liquid separation into dichloromethane and water was carried out, and the solvent was distilled off from the obtained organic layer by concentration under reduced pressure, thereby obtaining a dark blue solid. The solid was purified by a silica gel column chromatography so that 1.8 mg of a carboxylic acid product (compound 35) (11% yield) as a green solid having a perchloric acid anion was obtained.

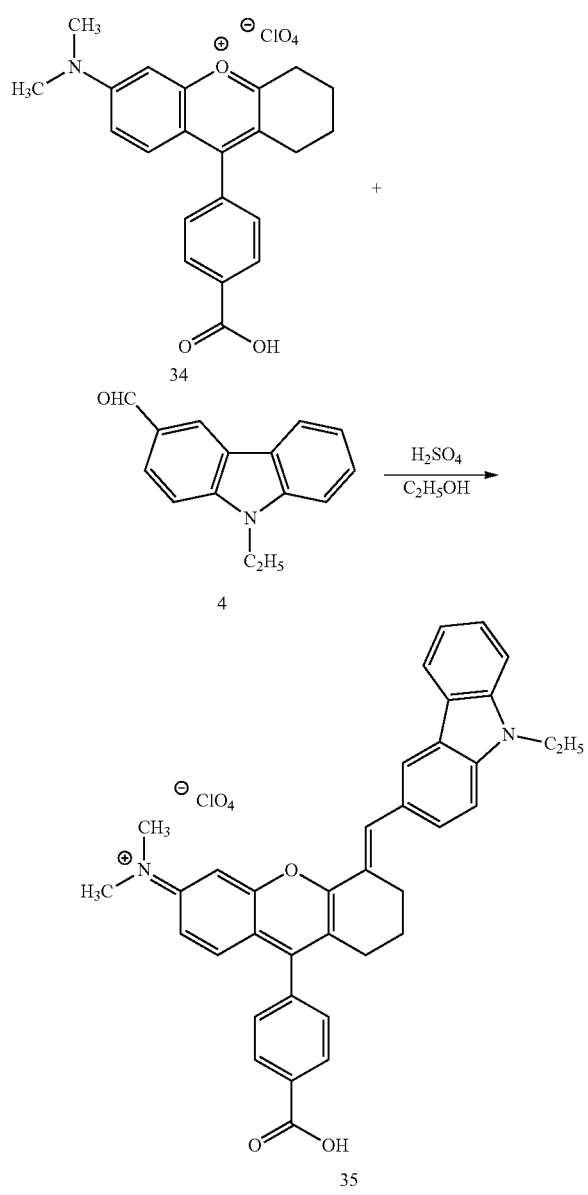

Experiment Example 9: Evaluation of Reverse Photochromic Characteristics of Compound 23

The reverse photochromic characteristics of the compound 23 were evaluated in the following manner.

In other words, 1.04 mg (8.1×10⁷ mol) of the compound 23 obtained in Example 7 was weighed in a vial bottle (glass bottle), and 3 mL of toluene was added thereto and the solution was diluted by 10 times to prepare a toluene solution containing the compound 23 with a concentration of $2.68 \times 10^{-5}$ mol/L. The obtained toluene solution was put into a quartz cell having an optical path length of 1 cm together with a stirring bar, and the absorbance thereof was measured using a spectrophotometer (product name: V-670, manufactured by Jasco Corporation). Thereafter, the solution was irradiated with light while being stirred for 1 minute under a condition of an irradiation intensity of 1 SUN (AM 1.5, 1000 W/m²) using a solar simulator (product name: LAX-C100, manufactured by Asahi Spectra Co., Ltd.), and the absorbance thereof was measured. Further, the quartz cell after the irradiation with light was stored in a dark place for 10 minutes, and the absorbance thereof was measured again.

Figure 8:
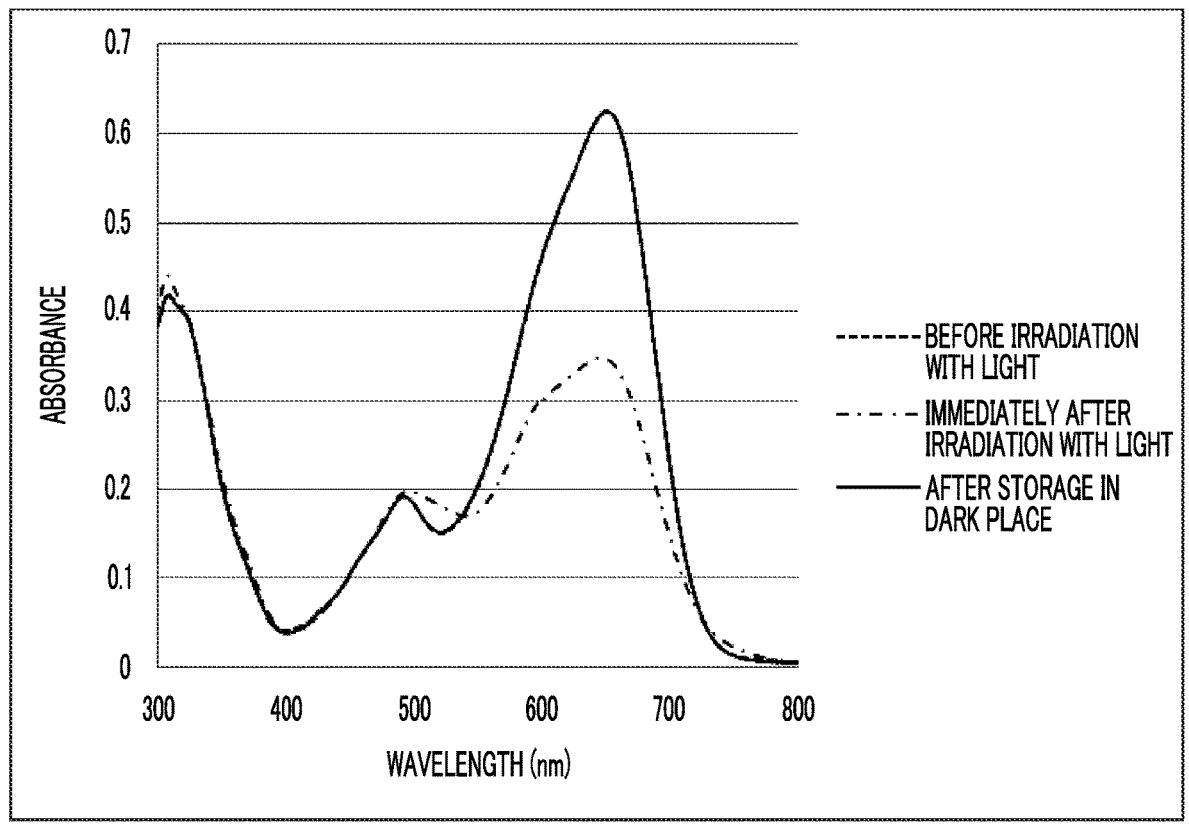
FIG. 8 is a graph showing the results obtained from measurement of the absorbance of a compound (a carboxylic acid product: compound 23) according to the embodiment of the present invention which is obtained in Experiment Example 9.

The results of Experiment Example 9 are shown in FIG. 8. It should be noted that the vertical axis in FIG. 8 indicates the absorbance and the horizontal axis (nm) indicates the wavelength. In addition, the broken line in FIG. 8 shows the measurement result before the irradiation with light, the one dot chain line shows the measurement result immediately after the irradiation with light for 10 minutes, and the solid line shows the measurement result after the storage in a dark place for 10 minutes after the irradiation with light.

Experiment Example 10: Evaluation of Reverse Photochromic Characteristics of Compound 25

The reverse photochromic characteristics of the compound 25 were evaluated in the following manner.

In other words, 1.28 mg (9.8×10⁷ mol) of the compound 25 obtained in Example 8 was weighed in a vial bottle (glass bottle), and 3 mL of toluene was added thereto and the solution was diluted by 15 times to prepare a toluene solution containing the compound 25 with a concentration of $2.17 \times 10^{-5}$ mol/L. The obtained toluene solution was put into a quartz cell having an optical path length of 1 cm together with a stirring bar, and the absorbance thereof was measured using a spectrophotometer (product name: V-670, manufactured by Jasco Corporation). Thereafter, the solution was irradiated with light while being stirred for 1 minute under a condition of an irradiation intensity of 1 SUN (AM 1.5, 1000 W/m²) using a solar simulator (product name: LAX-C100, manufactured by Asahi Spectra Co., Ltd.), and the absorbance thereof was measured. Further, the quartz cell after the irradiation with light was stored in a dark place for 138 hours, and the absorbance thereof was measured again.

Figure 9:
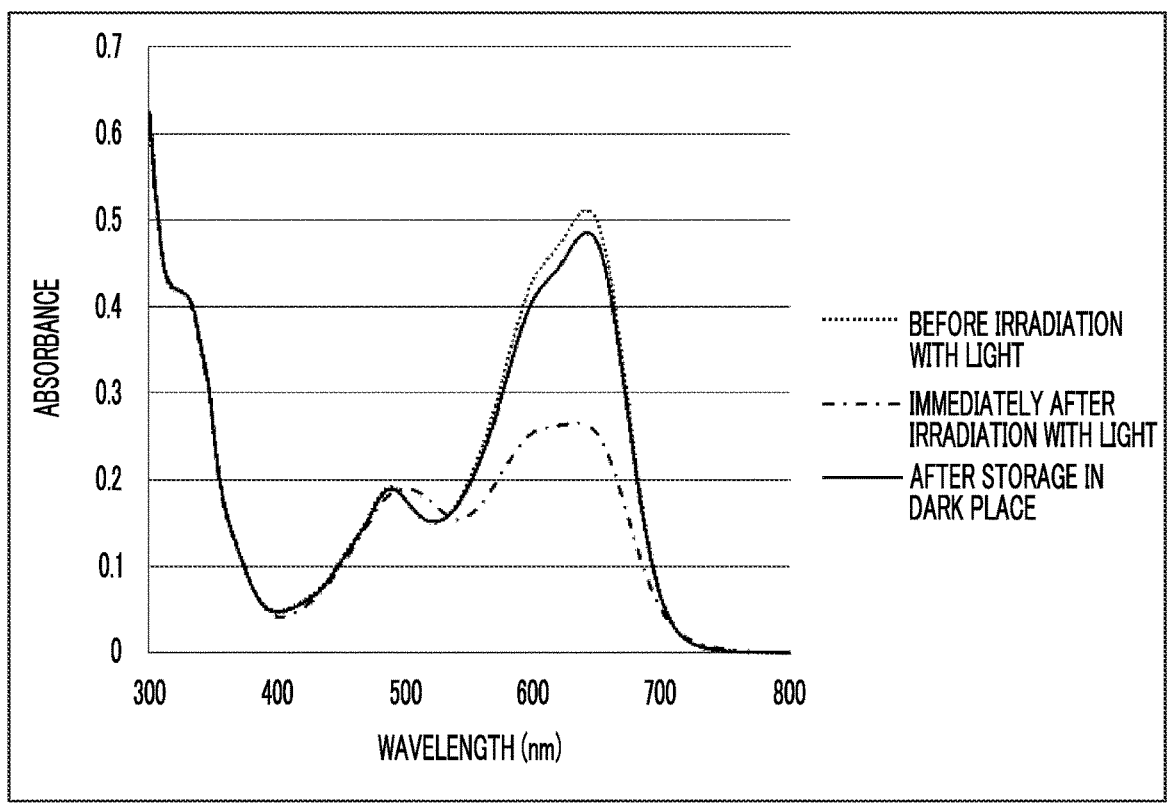
FIG. 9 is a graph showing the results obtained from measurement of the absorbance of a compound (a carboxylic acid product: compound 25) according to the embodiment of the present invention which is obtained in Experiment Example 10.

The results of Experiment Example 10 are shown in FIG. 9. It should be noted that the vertical axis in FIG. 9 indicates the absorbance and the horizontal axis (nm) indicates the wavelength. In addition, the broken line in FIG. 9 shows the measurement result before the irradiation with light, the one dot chain line shows the measurement result immediately after the irradiation with light for 1 minute, and the solid line shows the measurement result after the storage in a dark place for 138 hours after the irradiation with light.

Example 11: Synthesis of Polymer 1 (MMA: Compound 8=95:5)

(1) Synthesis of Carboxylic Acid Product (Compound 3)

First, 0.25 g (0.18 mmol) of the monomer (compound 8) having a polymerizable unsaturated group obtained in Example 2, 4.75 g (47.44 mol) of methyl methacrylate (MMA) (manufactured by Wako Pure Chemical Industries, Ltd.), 0.25 g (1.09 mmol) of 2,2'-azobis(methyl 2-methylpropionate) (product name V-601: manufactured by Wako Pure Chemical Industries, Ltd.), and 3.50 g of propylene glycol monomethyl ether acetate (manufactured by Daicel Corporation) were added to a round bottom flask provided with a stirrer and dissolved therein, nitrogen substitution was carried out, and the solution was heated to 95° C. After the solution was heated, the reaction was carried out at 95° C. for 4 hours. After the reaction, 20 g of ethyl acetate was added thereto, and the resulting solution was added dropwise to a mixed solvent of 100 mL of hexane and 10 mL of ethyl acetate for reprecipitation. The reprecipitated polymer was collected by filtration and dried under reduced pressure, thereby obtaining 4.72 g of a blue polymer (MMA/derived from compound 8, MMA:compound 8=95:5) (90% yield).

Experiment Example 11: Evaluation of Reverse Photochromic Characteristics of Polymer 1 (MMA:Compound 8=95:5)

The reverse photochromic characteristics of the polymer 1 were evaluated in the following manner.

In other words, 1.5 mg ($1.2 \times 10^{-6}$ mol) of the polymer 1 obtained in Example 11 was weighed in a vial bottle (glass bottle), and 10 mL of acetonitrile was added thereto to prepare an acetonitrile solution containing the polymer 1 with a concentration of $1.2 \times 10^{-4}$ mol/L. The obtained acetonitrile solution was put into a quartz cell having an optical path length of 1 cm together with a stirring bar, and the absorbance thereof was measured using a spectrophotometer (product name: V-670, manufactured by Jasco Corporation). Thereafter, the solution was irradiated with light while being stirred for 2 minutes under a condition of an irradiation intensity of 1 SUN (AM 1.5, 1000 W/m$^2$) using a solar simulator (product name: LAX-C100, manufactured by Asahi Spectra Co., Ltd.), and the absorbance thereof was measured. Further, the quartz cell after the irradiation with light was stored in a dark place for 1 hour, and the absorbance thereof was measured again.

Figure 10:
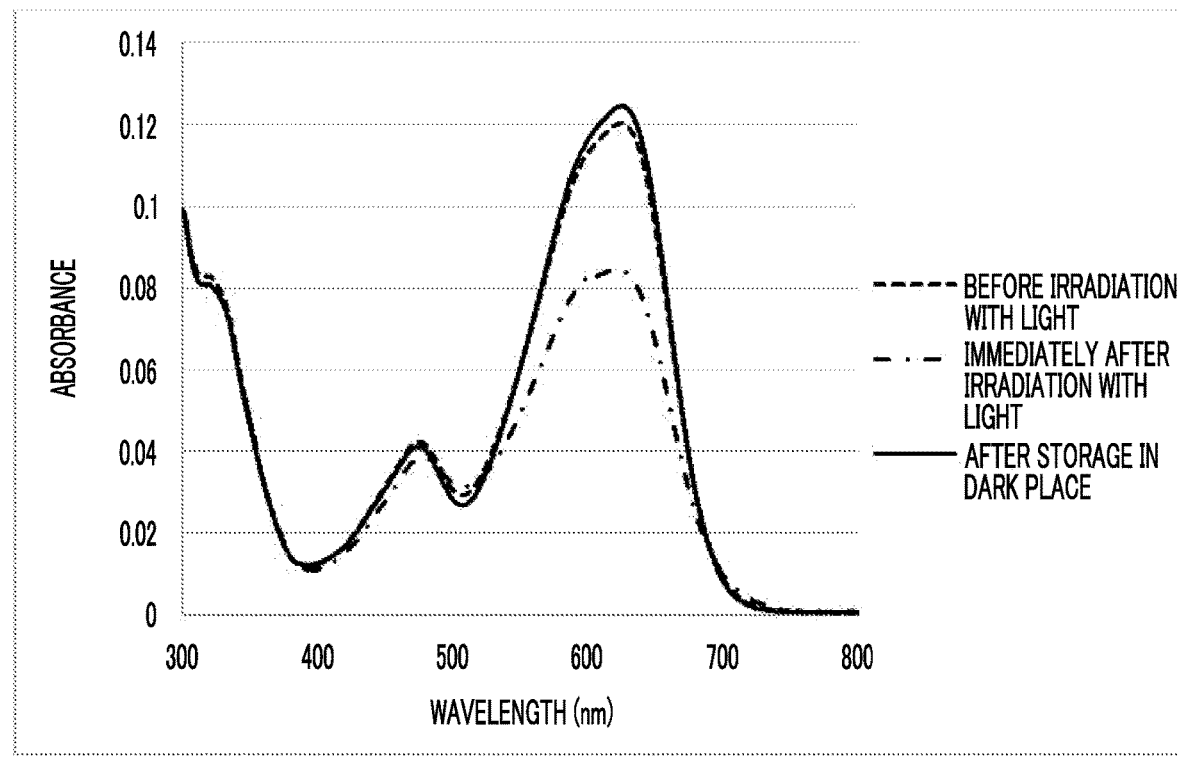
FIG. 10 is a graph showing the results obtained from measurement of the absorbance of a polymer (a polymer 1) of the present invention which is obtained in Experiment Example 11.

The results of Experiment Example 11 are shown in FIG. 10. It should be noted that the vertical axis in FIG. 10 indicates the absorbance and the horizontal axis (nm) indicates the wavelength. In addition, the broken line in FIG. 10 shows the measurement result before the irradiation with light, the one dot chain line shows the measurement result immediately after the irradiation with light for 2 minutes, and the solid line shows the measurement result after the storage in a dark place for 1 hour after the irradiation with light.

Based on the results of Experiment Example 11, it was found that in a case where the polymer of the present invention (in a colored state of) exhibiting a blue color was irradiated with light, the blue color faded to a light color or the colored state of the polymer was changed to a colorless state, similar to the compound according to the embodiment of the present invention. Further, it was found that in a case where the polymer having a light color or in a colorless state was stored in a dark place (light shielding), the polymer of the present invention was developed to the almost original blue color and returned to the colored state. Therefore, it was found that the polymer of the present invention shows the reverse change of color fading that occurs at the time of irradiation with light and color development that occurs at the time of light shielding, in other words, the polymer has reverse photochromic characteristics.

The invention claimed is:

1. A compound represented by the following general formula (1),

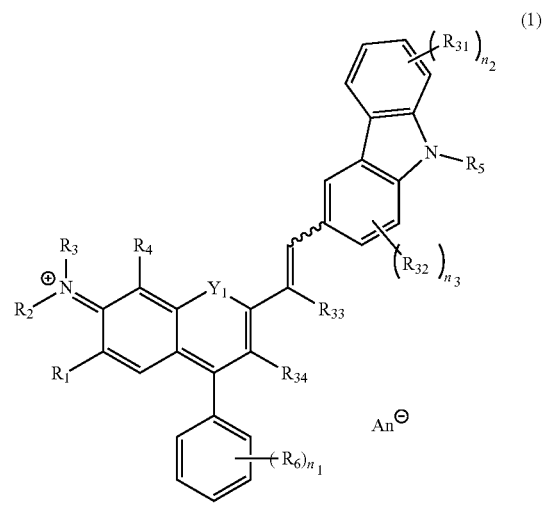

in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, An$^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted or may form an unsubstituted phenylene group.

2. The compound according to claim 1, wherein $Y_1$ represents an oxygen atom.
3. The compound according to claim 1, wherein $n_1$ represents 1, and $n_2$ and $n_3$ represent 0 or 1.
4. The compound according to claim 1, wherein $R_2$, $R_3$, and $R_5$ represent an alkyl group having 1 to 6 carbon atoms or an unsubstituted phenyl group.
5. The compound according to claim 1, wherein $R_{33}$ and $R_{34}$ form an unsubstituted linear alkylene group having 2 to 4 carbon atoms.

6. The compound according to claim 1, which fades in a case of being irradiated with light having a wavelength of 600 to 750 nm.

7. A polymer comprising:
a monomer unit derived from a compound represented by the following general formula (3),

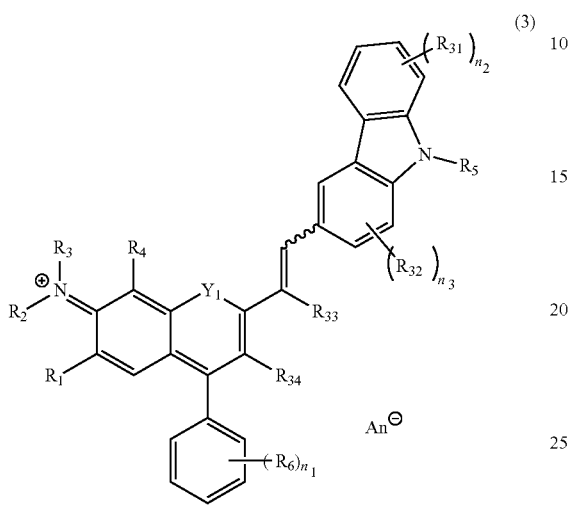

in the formula, $R_1$ and $R_4$ each independently represent a hydrogen atom or an alkyl group having 1 to 6 carbon atoms, $R_2$ and $R_3$ each independently represent a group having a polymerizable unsaturated group, an alkyl group having 1 to 20 carbon atoms, or an aryl group having 6 to 14 carbon atoms which has a substituent or is unsubstituted, $R_5$ represents a group having a polymerizable unsaturated group, a formyl group, an alkyl group having 1 to 20 carbon atoms, a haloalkyl group having 1 to 20 carbon atoms, an acyl group having 2 to 21 carbon atoms, or an aryl group having 6 to 14 carbon atoms which has a substituent or is unsubstituted, $R_6$ represents a group having a polymerizable unsaturated group, a carboxy group, an alkoxycarbonyl group having 2 to 21 carbon atoms, a carbamoyl group, a monoalkylaminocarbonyl group having 2 to 21 carbon atoms, a dialkylaminocarbonyl group having 3 to 41 carbon atoms, or an alkylcarbonylamino group having 2 to 21 carbon atoms, $R_{31}$ and $R_{32}$ each independently represent a hydroxy group, a halogeno group, an alkyl group having 1 to 6 carbon atoms, or an alkoxy group having 1 to 6 carbon atoms, $R_{33}$ and $R_{34}$ each independently represent a hydrogen atom or an alkyl group having 1 to 6 carbon atoms, $Y_1$ represents an oxygen atom or a sulfur atom, $An^-$ represents an anion, $n_1$ represents an integer of 0 to 5, $n_2$ represents an integer of 0 to 4, $n_3$ represents an integer of 0 to 3, $R_1$ and $R_2$ may form an alkylene group having 2 to 4 carbon atoms, $R_3$ and $R_4$ may form an alkylene group having 2 to 4 carbon atoms, and $R_{33}$ and $R_{34}$ may form a linear alkylene group having 2 to 4 carbon atoms which has an alkyl group having 1 to 6 carbon atoms as a substituent or is unsubstituted or may form an unsubstituted phenylene group, where at least one of $R_2$, $R_3$, $R_5$, or $n_1$ pieces of $R_6$'s represents a group having a polymerizable unsaturated group.

8. The polymer according to claim 7,
wherein $Y_1$ represents an oxygen atom.

9. The polymer according to claim 7,
wherein $n_1$ represents 1, and
$n_2$ and $n_3$ represent 0 or 1.

10. The polymer according to claim 7,
wherein $R_2$, $R_3$, and $R_5$ represent an alkyl group having 1 to 6 carbon atoms or an unsubstituted phenyl group.

11. The polymer according to claim 7,
wherein $R_{33}$ and $R_{34}$ form an unsubstituted linear alkylene group having 2 to 4 carbon atoms.

12. The polymer according to claim 7, which fades in a case of being irradiated with light having a wavelength of 600 to 750 nm.

13. The polymer according to claim 7,
wherein the polymer is a copolymer.

14. The polymer according to claim 13,
wherein the copolymer has one or two kinds of monomer units derived from a compound represented by the following general formula (4), (5), (6), or (7) and a monomer unit derived from a compound represented by the general formula (3) as constituent components,

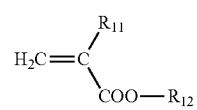

in the formula, $R_{11}$ represents a hydrogen atom or a methyl group, and $R_{12}$ represents a hydrogen atom, an alkyl group having 1 to 18 carbon atoms, a hydroxyalkyl group having 1 to 10 carbon atoms, an aryl group having 6 to 10 carbon atoms, an arylalkyl group having 7 to 13 carbon atoms, an alkoxyalkyl group having 2 to 9 carbon atoms, an alkoxyalkoxyalkyl group having 3 to 9 carbon atoms, an aryloxyalkyl group having 7 to 13 carbon atoms, a morpholinoalkyl group having 5 to 7 carbon atoms, a trialkylsilyl group having 3 to 9 carbon atoms, an alicyclic hydrocarbon group having 6 to 12 carbon atoms together with an oxygen atom, a dialkylaminoalkyl group having 3 to 9 carbon atoms, a fluoroalkyl group having 1 to 18 carbon atoms, a N-alkylenephthalimide group having 9 to 14 carbon atoms, a group represented by the following general formula (4-1)

in the formula, q pieces of $R_{21}$'s each independently represent an alkylene group having 1 to 3 carbon atoms which has a hydroxy group as a substituent or is unsubstituted, $R_{22}$ represents a phenyl group which has a hydroxy group as a substituent or is unsubstituted or an alkyl group having 1 to 3 carbon atoms, and q represents an integer of 1 to 3, a group represented by the following general formula (4-2)

in the formula, $R_{23}$ to $R_{25}$ each independently represent an alkyl group having 1 to 3 carbon atoms, and $R_{26}$ represents an alkylene group having 1 to 3 carbon atoms, or a group represented by the following general formula (4-3)

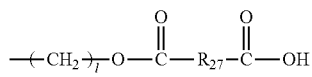
(4-3)

in the formula, l represents an integer of 1 to 6, and $R_{27}$ represents a phenylene group or a cyclohexylene group,

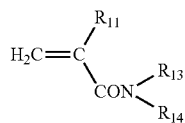
(5)

in the formula, $R_{11}$ has the same definition as described above, $R_{13}$ represents a hydrogen atom or an alkyl group having 1 to 3 carbon atoms, $R_{14}$ represents a hydrogen atom, an alkyl group having 1 to 3 carbon atoms, a dialkylaminoalkyl group having 3 to 9 carbon atoms, or a hydroxyalkyl group having 1 to 6 carbon atoms, and $R_{13}$ and $R_{14}$ may form a morpholino group together with a nitrogen atom adjacent to these,

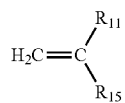
(6)

in the formula, $R_{15}$ represents a phenyl group or a pyrrolidino group, and $R_{11}$ has the same definition as described above, and

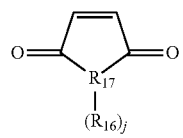
(7)

in the formula, $R_{17}$ represents a nitrogen atom or an oxygen atom, j represents 0 in a case where $R_{17}$ represents an oxygen atom and represents 1 in a case where $R_{17}$ represents a nitrogen atom, and $R_{16}$ represents a hydrogen atom, an alkyl group having 1 to 20 carbon atoms, a hydroxyalkyl group having 1 to 10 carbon atoms, a haloalkyl group having 1 to 10 carbon atoms, an aryl group having 6 to 10 carbon atoms, or an aryl group having 6 to 10 carbon atoms which has an alkyl group having 1 to 6 carbon atoms or a halogeno group as a substituent.

* * * * *